US010988520B2

(12) United States Patent
Schuch

(10) Patent No.: US 10,988,520 B2
(45) Date of Patent: Apr. 27, 2021

(54) LYSIN-ANTIMICROBIAL PEPTIDE (AMP) POLYPEPTIDE CONSTRUCTS, LYSINS, ISOLATED POLYNUCLEOTIDES ENCODING SAME AND USES THEREOF

(71) Applicant: ContraFect Corporation, Yonkers, NY (US)

(72) Inventor: Raymond Schuch, Mountain Lakes, NJ (US)

(73) Assignee: CONTRAFECT CORPORATION, Yonkers, NY (US)

( * ) Notice: Subject to any disclaimer, the term of this patent is extended or adjusted under 35 U.S.C. 154(b) by 0 days.

(21) Appl. No.: 16/777,154

(22) Filed: Jan. 30, 2020

(65) Prior Publication Data

US 2020/0157160 A1 May 21, 2020

Related U.S. Application Data

(63) Continuation-in-part of application No. PCT/US2019/047916, filed on Aug. 23, 2019, which is a continuation-in-part of application No. PCT/US2019/024912, filed on Mar. 29, 2019.

(60) Provisional application No. 62/935,479, filed on Nov. 14, 2019, provisional application No. 62/860,836, filed on Jun. 13, 2019, provisional application No. 62/849,320, filed on May 17, 2019, provisional application No. 62/721,969, filed on Aug. 23, 2018, provisional application No. 62/650,235, filed on Mar. 29, 2018, provisional application No. 62/722,793, filed on Aug. 24, 2018.

(51) Int. Cl.

| A61P 31/04 | (2006.01) |
|---|---|
| C07K 14/47 | (2006.01) |
| C12N 15/64 | (2006.01) |
| A61K 9/00 | (2006.01) |
| A61K 45/06 | (2006.01) |
| A61K 9/107 | (2006.01) |
| A61K 38/00 | (2006.01) |

(52) U.S. Cl.
CPC ......... *C07K 14/4723* (2013.01); *A61P 31/04* (2018.01); *C12N 15/64* (2013.01); *A61K 9/0073* (2013.01); *A61K 9/107* (2013.01); *A61K 38/00* (2013.01); *A61K 45/06* (2013.01)

(58) Field of Classification Search
None
See application file for complete search history.

(56) References Cited

U.S. PATENT DOCUMENTS

| 8,846,865 B2 | 9/2014 | Briers et al. |
| 2017/0130214 A1 | 5/2017 | Fischetti et al. |

FOREIGN PATENT DOCUMENTS

| CA | 2998484 A1 * | 3/2017 | ............ A61K 38/46 |
|---|---|---|---|
| CN | 102861324 | 1/2013 | |
| KR | 20130129326 | 1/2013 | |
| WO | 2017049233 | 3/2017 | |
| WO | 2019118632 | 6/2019 | |

OTHER PUBLICATIONS

Heselpoth et al. 2019 (Lysocins: Bioengineered Antimicrobials That Deliver Lysins across the Outer Membrane of Gram-Negative Bacteria; vol. 63 Issue 6 e00342-19) (Year: 2019).*
International Search Report and Written Opinion for PCT Application No. PCT/US2019/024912, dated Oct. 1, 2019, pp. 1-19.
International Search Report and Written Opinion for PCT Application No. PCT/US2019/047916, dated Jan. 13, 2020, pp. 1-17.
Briers, Y. et al., Art-175 Is a Highly Efficient Antibacterial against Multidrug-Resistant Strains and Persisters of Pseudomonas aeruginosa, Antimicrob. Agents. Chemo. 2014; 58(7):3774-3784.
Briers, Y. et al., Engineered Endolysin-Based 'Artilysins' to Combat Multidrug-Resistant Gram-Negative Pathogens, mBio Jul./Aug. 2014; 5(4):e01379-14.
Daniels, D.S., et al., Intrinsically Cell-Permeable Miniature Proteins Based on a Minimal Cationic PPII Motif, J. Am. Chem. Soc. 2007; 129:14578-14579.
Dassanayake, R. P. et al., Antimicrobial activity of bovine NK-lysin-derived peptides on Mycoplasma bovis, Plos One 2018; 13(5): e0197677.
Goerke, J., Pulmonary Surfactant: functions and molecular composition, Biochimica et Biophysica Acta 1998; 1408:79-89.
Jung, D. et al., Structural Transitions as Determinants of the Action of the Calcium-Dependent Antibiotic Daptomycin, Chem. Bio. 2004; 11:949-967.
Koplowicz, Y. B. et al., Development of Daptomycin-Susceptible, Methicillin-Resistant *Staphylococcus aureus* Pneumonia during High-Dose Daptomycin Therapy, CID 2009; 49: 1286-87.
Lakey, J.H. et al., Fluorescence Indicates a Calcium-Dependent Interaction between the Lipopeptide Antibiotic LY146032 and Phospholipid Membrane, Biochem. 1988; 27:4639-4645.
Yu, Y. et al., Antimicrobial activity, improved cell selectivity and mode of action of short PMAP-36-derived peptides against bacteria and Candida, Scientific Reports 2016; 6, 27258, pp. 1-12.

(Continued)

*Primary Examiner* — Mary Maille Lyons
(74) *Attorney, Agent, or Firm* — Natalie Bogdanos

(57) ABSTRACT

The present disclosure is directed to a lysin-AMP polypeptide construct comprising: (a) a first component comprising the polypeptide sequence of: (i) SEQ ID NO: 118 (GN202); or (ii) a polypeptide having lysin activity and having at least 80% sequence identity with the polypeptide sequence of SEQ ID NO: 118 (GN202); or (iii) an active fragment of SEQ ID NO: 118 (GN202); and (b) a second component comprising the polypeptide sequence of at least one antimicrobial peptide (AMP), wherein the at least one AMP comprises SEQ ID NO: 114 (FIRL). Exemplary lysin-AMP polypeptides, such as GN370 (SEQ ID NO: 44) as well as methods of treating bacterial infections using the present lysin-AMP polypeptide constructs are also disclosed.

20 Claims, 6 Drawing Sheets

Specification includes a Sequence Listing.

(56) References Cited

OTHER PUBLICATIONS

Manabe, T. et al., D-form KLKLLLLLKLK-NH2 peptide exerts higher antimicrobial properties than its L-form counterpart via an association with bacterial cell wall components, Scientific Reports 2017; 7, 43384, pp. 1-10.

Melvin, J. A. et al., Simultaneous Antibiofilm and Antiviral Activities of an Engineered Antimicrobial Peptide during Virus-Bacterium Coinfection, mSphere 2016; 1(3):e00083-16, pp. 1-11.

Nguyen, K.T., et al., Genetically Engineered Lipopeptide Antibiotics Related to A54145 and Daptomycin with Improved Properties, Antimicrob. Agents Chemo. 2010; 54(4):1404-1413.

Oliveira, H. et al., Structural and Enzymatic Characterization of ABgp46, a Novel Phage Endolysin with Broad Anti-Gram-Negative Bacterial Activity, Frontiers in Microbio. 2016; 7(208), pp. 1-9.

Schwameis, R. et al., Effect of Pulmonary Surfactant on Antimicrobial Activity in Vitro, Antimicrob. Agents Chemo. 2013; 57(10):5151-5154.

Silverman, J.A. et al., Inhibition of Daptomycin by Pulmonary Surfactant: In Vitro Modeling and Clinical Impact, J. Infect. Dis. 2005; 191:2149-2152.

Storey, C.C. et al., Analysis of the Complete Nucleotide Sequence of Chp1, a Phage which Infects Avian Chlamydia psittaci, J. Gen. Virol. 1989; 70:3381-3390.

Thandar, M. et al., Novel Engineered Peptides of a Phage Lysin as Effective Antimicrobials against Multidrug-Resistant Acinetobacter baumannii, Antimicrob. Agents Chemo. 2016; 60(5):2671-2679.

Vaara, M. et al., Group of Peptides That Act Synergistically with Hydrophobic Antibiotics against Gram-Negative Enteric Bacteria, Antimicrob. Agents Chemo. 1996; 40(8): 1801-1805.

Van't Veen, A., et al., Influence of Pulmonary Surfactant on In Vitro Bactericidal Activities of Amoxicillin, Ceftazidine, and Tobramycin, Antimicrob. Agents Chem. 1995; 39(2):329-333.

Yang, H. et al., Antibacterial Activity of a Novel Peptide-Modified Lysin Against Acinetobacter baumannii and Pseudomonas aeruginosa, Frontiers in Microbio. 2015; 6(1471); pp. 1-10.

GenBank submission J_BPCHP DNA Binding Protein ORF8, Accession No. P19188.1, Jul. 5, 2017.

NCBI Reference Sequence NP_044319.1, hypothetical protein chp1p08 [Chlamydia virus Chp1], Aug. 13, 2018.

Mori, N. et al., A peptide based on homologous sequences of the β-barrel assembly machinery component BamD potentiates antibiotic susceptibility of Pseudomonas aeruginosa, J. Antimicrob. Chemother. 2012; 67:2173-2181.

International Preliminary Report on Patentability for corresponding International Patent Application No. PCT/US2019/024912, dated Sep. 29, 2020 (10 pages).

Li, S. et al, Therapeutic Potential of the Antimicrobial Peptide OH-CATH30 for Antibiotic-Resistant Pseudomonas aeruginosa Keratitis, Antimicrobial Agents Chemother. 2014; 58(6)3144-3150.

International Preliminary Report on Patentability for corresponding International Patent Application No. PCT/US2019/047916, dated Feb. 23, 2021 (13 pages).

\* cited by examiner

SEQUENCE LISTING

<160> NUMBER OF SEQ ID NOS: 226

<210> SEQ ID NO 1
<211> LENGTH: 636
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (28)..(162)
<223> OTHER INFORMATION: GN168 lysin
<220> FEATURE:
<221> NAME/KEY: CDS
<222> LOCATION: (28)..(612)

<400> SEQUENCE: 1

```
gtttaacttt aagaaggaga attcacc atg agg tta aaa atg gca cga aga aga         54
                               Met Arg Leu Lys Met Ala Arg Arg Arg
                                1               5 tac aga ctt ccg cga cgt aga agt cga aga ctt ttt tca aga act gca         102
Tyr Arg Leu Pro Arg Arg Arg Ser Arg Arg Leu Phe Ser Arg Thr Ala
 10              15                  20                  25 ttg agg atg cat cca aga aat agg ctt cga aga att atg cgt ggc ggc         150
Leu Arg Met His Pro Arg Asn Arg Leu Arg Arg Ile Met Arg Gly Gly
                 30                  35                  40 att agg ttc acc gcg ggc ggc acc gcg ggc ggc cgt aca tcc caa cga         198
Ile Arg Phe Thr Ala Gly Gly Thr Ala Gly Gly Arg Thr Ser Gln Arg
             45                  50                  55 ggc atc gac ctc atc aaa tcc ttc gag ggc ctg cgc ctg tcc gct tac         246
Gly Ile Asp Leu Ile Lys Ser Phe Glu Gly Leu Arg Leu Ser Ala Tyr
         60                  65                  70 cag gac tcg gtg ggt gtc tgg acc ata ggt tac ggc acc act cgg ggc         294
Gln Asp Ser Val Gly Val Trp Thr Ile Gly Tyr Gly Thr Thr Arg Gly
 75                  80                  85 gtc acc cgc tac atg acg atc acc gtc gag cag gcc gag cgg atg ctg         342
Val Thr Arg Tyr Met Thr Ile Thr Val Glu Gln Ala Glu Arg Met Leu
 90                  95                 100                 105 tcg aac gac att cag cgc ttc gag cca gag cta gac agg ctg gcg aag         390
Ser Asn Asp Ile Gln Arg Phe Glu Pro Glu Leu Asp Arg Leu Ala Lys
                110                 115                 120 gtg cca ctg aac cag aac cag tgg gat gcc ctg atg agc ttc gtg tac         438
Val Pro Leu Asn Gln Asn Gln Trp Asp Ala Leu Met Ser Phe Val Tyr
            125                 130                 135 aac ctg ggc gcg gcc aat ctg gcg tcg tcc acg ctg ctc gac ctg ctg         486
Asn Leu Gly Ala Ala Asn Leu Ala Ser Ser Thr Leu Leu Asp Leu Leu
        140                 145                 150 aac aag ggt gac tac cag gga gca gcg gac cag ttc ccg cat tgg gtg         534
Asn Lys Gly Asp Tyr Gln Gly Ala Ala Asp Gln Phe Pro His Trp Val
    155                 160                 165 aat gcg ggc ggt aag cgc ttg gat ggt ctg gtt aag cgt cga gca gcc         582
Asn Ala Gly Gly Lys Arg Leu Asp Gly Leu Val Lys Arg Arg Ala Ala
170                 175                 180                 185 gag cgt gcg ctg ttc ctg gag cca cta tcg tgataaaagc ttggctgttt          632
Glu Arg Ala Leu Phe Leu Glu Pro Leu Ser
                190                 195 tggc                                                                    636

<210> SEQ ID NO 2
<211> LENGTH: 195
<212> TYPE: PRT
<213> ORGANISM: Artificial Sequence
<220> FEATURE:
<223> OTHER INFORMATION: Synthetic Construct

<400> SEQUENCE: 2

Met Arg Leu Lys Met Ala Arg Arg Arg Tyr Arg Leu Pro Arg Arg Arg
 1               5                  10                  15

Ser Arg Arg Leu Phe Ser Arg Thr Ala Leu Arg Met His Pro Arg Asn
             20                  25                  30

Arg Leu Arg Arg Ile Met Arg Gly Gly Ile Arg Phe Thr Ala Gly Gly
         35                  40                  45

Thr Ala Gly Gly Arg Thr Ser Gln Arg Gly Ile Asp Leu Ile Lys Ser
     50                  55                  60

Phe Glu Gly Leu Arg Leu Ser Ala Tyr Gln Asp Ser Val Gly Val Trp
 65                  70                  75                  80
```

```
Thr Ile Gly Tyr Gly Thr Thr Arg Gly Val Thr Arg Tyr Met Thr Ile
                85                  90                  95

Thr Val Glu Gln Ala Glu Arg Met Leu Ser Asn Asp Ile Gln Arg Phe
            100                 105                 110

Glu Pro Glu Leu Asp Arg Leu Ala Lys Val Pro Leu Asn Gln Asn Gln
        115                 120                 125

Trp Asp Ala Leu Met Ser Phe Val Tyr Asn Leu Gly Ala Ala Asn Leu
130                 135                 140

Ala Ser Ser Thr Leu Leu Asp Leu Leu Asn Lys Gly Asp Tyr Gln Gly
145                 150                 155                 160

Ala Ala Asp Gln Phe Pro His Trp Val Asn Ala Gly Gly Lys Arg Leu
                165                 170                 175

Asp Gly Leu Val Lys Arg Arg Ala Ala Glu Arg Ala Leu Phe Leu Glu
            180                 185                 190

Pro Leu Ser
        195

<210> SEQ ID NO 3
<211> LENGTH: 567
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (28)..(543)
<220> FEATURE:
<221> NAME/KEY: misc_feature
<222> LOCATION: (29)..(543)
<223> OTHER INFORMATION: GN 176 lysin

<400> SEQUENCE: 3
gtttaacttt aagaaggaga attcacc atg agc ttt aac gtg acc ccg aaa ttt      54
                               Met Ser Phe Asn Val Thr Pro Lys Phe
                                 1               5 aaa cgc tgg cag ctg tat ttt cgc ggc cgc atg tgg acc gcg ggc ggc      102
Lys Arg Trp Gln Leu Tyr Phe Arg Gly Arg Met Trp Thr Ala Gly Gly
 10              15                  20                  25 acc gcg ggc ggc cgt aca tcc caa cga ggc atc gac ctc atc aaa tcc      150
Thr Ala Gly Gly Arg Thr Ser Gln Arg Gly Ile Asp Leu Ile Lys Ser
                 30                  35                  40 ttc gag ggc ctg cgc ctg tcc gct tac cag gac tcg gtg ggt gtc tgg      198
Phe Glu Gly Leu Arg Leu Ser Ala Tyr Gln Asp Ser Val Gly Val Trp
             45                  50                  55 acc ata ggt tac ggc acc act cgg ggc gtc acc cgc tac atg acg atc      246
Thr Ile Gly Tyr Gly Thr Thr Arg Gly Val Thr Arg Tyr Met Thr Ile
         60                  65                  70 acc gtc gag cag gcc gag cgg atg ctg tcg aac gac att cag cgc ttc      294
Thr Val Glu Gln Ala Glu Arg Met Leu Ser Asn Asp Ile Gln Arg Phe
 75                  80                  85 gag cca gag cta gac agg ctg gcg aag gtg cca ctg aac cag aac cag      342
Glu Pro Glu Leu Asp Arg Leu Ala Lys Val Pro Leu Asn Gln Asn Gln
 90                  95                 100                 105 tgg gat gcc ctg atg agc ttc gtg tac aac ctg ggc gcg gcc aat ctg      390
Trp Asp Ala Leu Met Ser Phe Val Tyr Asn Leu Gly Ala Ala Asn Leu
                110                 115                 120 gcg tcg tcc acg ctg ctc gac ctg ctg aac aag ggt gac tac cag gga      438
Ala Ser Ser Thr Leu Leu Asp Leu Leu Asn Lys Gly Asp Tyr Gln Gly
            125                 130                 135
```

```
gca gcg gac cag ttc ccg cat tgg gtg aat gcg ggt ggt aag cgc ttg      486
Ala Ala Asp Gln Phe Pro His Trp Val Asn Ala Gly Gly Lys Arg Leu
        140                 145                 150 gat ggt ctg gtt aag cgt cga gca gcc gag cgt gcg ctg ttc ctg gag      534
Asp Gly Leu Val Lys Arg Arg Ala Ala Glu Arg Ala Leu Phe Leu Glu
155                 160                 165 cca cta tcg tgataaaagc ttggctgttt tggc                               567
Pro Leu Ser
170
```

```
<210> SEQ ID NO 4
<211> LENGTH: 172
<212> TYPE: PRT
<213> ORGANISM: Artificial Sequence
<220> FEATURE:
<223> OTHER INFORMATION: Synthetic Construct

<400> SEQUENCE: 4

Met Ser Phe Asn Val Thr Pro Lys Phe Lys Arg Trp Gln Leu Tyr Phe
1               5                   10                  15

Arg Gly Arg Met Trp Thr Ala Gly Gly Thr Ala Gly Gly Arg Thr Ser
            20                  25                  30

Gln Arg Gly Ile Asp Leu Ile Lys Ser Phe Glu Gly Leu Arg Leu Ser
        35                  40                  45

Ala Tyr Gln Asp Ser Val Gly Val Trp Thr Ile Gly Tyr Gly Thr Thr
    50                  55                  60

Arg Gly Val Thr Arg Tyr Met Thr Ile Thr Val Glu Gln Ala Glu Arg
65                  70                  75                  80

Met Leu Ser Asn Asp Ile Gln Arg Phe Glu Pro Glu Leu Asp Arg Leu
                85                  90                  95

Ala Lys Val Pro Leu Asn Gln Asn Gln Trp Asp Ala Leu Met Ser Phe
            100                 105                 110

Val Tyr Asn Leu Gly Ala Ala Asn Leu Ala Ser Ser Thr Leu Leu Asp
        115                 120                 125

Leu Leu Asn Lys Gly Asp Tyr Gln Gly Ala Ala Asp Gln Phe Pro His
    130                 135                 140

Trp Val Asn Ala Gly Gly Lys Arg Leu Asp Gly Leu Val Lys Arg Arg
145                 150                 155                 160

Ala Ala Glu Arg Ala Leu Phe Leu Glu Pro Leu Ser
                165                 170
```

```
<210> SEQ ID NO 5
<211> LENGTH: 582
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (28)..(558)
<223> OTHER INFORMATION: GN178 lysin
<220> FEATURE:
<221> NAME/KEY: CDS
<222> LOCATION: (28)..(558)

<400> SEQUENCE: 5
gtttaacttt aagaaggaga attcacc atg cca cca att ttt agc aaa ctg gcg      54
                                Met Pro Pro Ile Phe Ser Lys Leu Ala
                                1               5 ggc aaa aaa att aaa aac ctg ctg att agc ggc ctg aaa ggc ggt agc      102
Gly Lys Lys Ile Lys Asn Leu Leu Ile Ser Gly Leu Lys Gly Gly Ser
```

```
                   10                  15                  20                  25 ggc agc ggt agc ggt agc ggc agc ccg cgt aca tcc caa cga ggc atc              150
  Gly Ser Gly Ser Gly Ser Gly Ser Pro Arg Thr Ser Gln Arg Gly Ile
              30                  35                  40 gac ctc atc aaa tcc ttc gag ggc ctg cgc ctg tcc gct tac cag gac              198
  Asp Leu Ile Lys Ser Phe Glu Gly Leu Arg Leu Ser Ala Tyr Gln Asp
          45                  50                  55 tcg gtg ggt gtc tgg acc ata ggt tac ggc acc act cgg ggc gtc acc              246
  Ser Val Gly Val Trp Thr Ile Gly Tyr Gly Thr Thr Arg Gly Val Thr
      60                  65                  70 cgc tac atg acg atc acc gtc gag cag gcc gag cgg atg ctg tcg aac              294
  Arg Tyr Met Thr Ile Thr Val Glu Gln Ala Glu Arg Met Leu Ser Asn
  75                  80                  85 gac att cag cgc ttc gag cca gag cta gac agg ctg gcg aag gtg cca              342
  Asp Ile Gln Arg Phe Glu Pro Glu Leu Asp Arg Leu Ala Lys Val Pro
  90                  95                  100                 105 ctg aac cag aac cag tgg gat gcc ctg atg agc ttc gtg tac aac ctg              390
  Leu Asn Gln Asn Gln Trp Asp Ala Leu Met Ser Phe Val Tyr Asn Leu
                  110                 115                 120 ggc gcg gcc aat ctg gcg tcg tcc acg ctg ctc gac ctg ctg aac aag              438
  Gly Ala Ala Asn Leu Ala Ser Ser Thr Leu Leu Asp Leu Leu Asn Lys
              125                 130                 135 ggt gac tac cag gga gca gcg gac cag ttc ccg cat tgg gtg aat gcg              486
  Gly Asp Tyr Gln Gly Ala Ala Asp Gln Phe Pro His Trp Val Asn Ala
          140                 145                 150 ggc ggt aag cgc ttg gat ggt ctg gtt aag cgt cga gca gcc gag cgt              534
  Gly Gly Lys Arg Leu Asp Gly Leu Val Lys Arg Arg Ala Ala Glu Arg
      155                 160                 165 gcg ctg ttc ctg gag cca cta tcg tgataaaagc ttggctgttt tggc                   582
  Ala Leu Phe Leu Glu Pro Leu Ser
  170                 175

<210> SEQ ID NO 6
<211> LENGTH: 177
<212> TYPE: PRT
<213> ORGANISM: Artificial Sequence
<220> FEATURE:
<223> OTHER INFORMATION: Synthetic Construct

<400> SEQUENCE: 6

Met Pro Pro Ile Phe Ser Lys Leu Ala Gly Lys Lys Ile Lys Asn Leu
1               5                   10                  15

Leu Ile Ser Gly Leu Lys Gly Gly Ser Gly Ser Gly Ser Gly Ser Gly
            20                  25                  30

Ser Pro Arg Thr Ser Gln Arg Gly Ile Asp Leu Ile Lys Ser Phe Glu
        35                  40                  45

Gly Leu Arg Leu Ser Ala Tyr Gln Asp Ser Val Gly Val Trp Thr Ile
    50                  55                  60

Gly Tyr Gly Thr Thr Arg Gly Val Thr Arg Tyr Met Thr Ile Thr Val
65                  70                  75                  80

Glu Gln Ala Glu Arg Met Leu Ser Asn Asp Ile Gln Arg Phe Glu Pro
                85                  90                  95

Glu Leu Asp Arg Leu Ala Lys Val Pro Leu Asn Gln Asn Gln Trp Asp
            100                 105                 110

Ala Leu Met Ser Phe Val Tyr Asn Leu Gly Ala Ala Asn Leu Ala Ser
        115                 120                 125

Ser Thr Leu Leu Asp Leu Leu Asn Lys Gly Asp Tyr Gln Gly Ala Ala
    130                 135                 140
```

```
Asp Gln Phe Pro His Trp Val Asn Ala Gly Gly Lys Arg Leu Asp Gly
145                 150                 155                 160

Leu Val Lys Arg Arg Ala Ala Glu Arg Ala Leu Phe Leu Glu Pro Leu
            165                 170                 175

Ser
```

```
<210> SEQ ID NO 7
<211> LENGTH: 429
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (28)..(405)
<223> OTHER INFORMATION: GN217 lysin
<220> FEATURE:
<221> NAME/KEY: CDS
<222> LOCATION: (28)..(405)

<400> SEQUENCE: 7
```

```
gtttaacttt aagaaggaga attcacc atg acc tac acc ctg tct aaa cgt tct      54
                            Met Thr Tyr Thr Leu Ser Lys Arg Ser
                             1               5 ctg gac aac ctg aaa ggt gtt cac ccg gac ctg gtt gct gtt gtt cac       102
Leu Asp Asn Leu Lys Gly Val His Pro Asp Leu Val Ala Val Val His
10                  15                  20                  25 cgt gct atc cag ctg acc ccg gtt gac ttc gct gtt atc gaa ggt ctg       150
Arg Ala Ile Gln Leu Thr Pro Val Asp Phe Ala Val Ile Glu Gly Leu
                30                  35                  40 cgt tct gtt tct cgt cag aaa gaa ctg gtt gct gct ggt gct tct aaa       198
Arg Ser Val Ser Arg Gln Lys Glu Leu Val Ala Ala Gly Ala Ser Lys
            45                  50                  55 acc atg aac tct cgt cac ctg acc ggt cac gct gtt gac ctg gct gct       246
Thr Met Asn Ser Arg His Leu Thr Gly His Ala Val Asp Leu Ala Ala
        60                  65                  70 tac gtt aac ggt atc cat tgg gac tgg ccg ctg tac gac gct atc gct       294
Tyr Val Asn Gly Ile His Trp Asp Trp Pro Leu Tyr Asp Ala Ile Ala
    75                  80                  85 gtt gct gtt aaa gct gct gct aaa gaa ctg ggt gtt gct atc gtt tgg       342
Val Ala Val Lys Ala Ala Ala Lys Glu Leu Gly Val Ala Ile Val Trp
90                  95                 100                 105 ggt ggt gac tgg acc acc ttc aaa gac ggt ccg cac ttc gaa ctg gac       390
Gly Gly Asp Trp Thr Thr Phe Lys Asp Gly Pro His Phe Glu Leu Asp
                110                 115                 120 cgt tct aaa tac cgt taataaaagc ttggctgttt tggc                        429
Arg Ser Lys Tyr Arg
            125
```

```
<210> SEQ ID NO 8
<211> LENGTH: 126
<212> TYPE: PRT
<213> ORGANISM: Artificial Sequence
<220> FEATURE:
<223> OTHER INFORMATION: Synthetic Construct

<400> SEQUENCE: 8
```

```
Met Thr Tyr Thr Leu Ser Lys Arg Ser Leu Asp Asn Leu Lys Gly Val
1               5                   10                  15

His Pro Asp Leu Val Ala Val Val His Arg Ala Ile Gln Leu Thr Pro
            20                  25                  30

Val Asp Phe Ala Val Ile Glu Gly Leu Arg Ser Val Ser Arg Gln Lys
```

```
                    35                  40                  45
Glu Leu Val Ala Ala Gly Ala Ser Lys Thr Met Asn Ser Arg His Leu
 50                  55                  60

Thr Gly His Ala Val Asp Leu Ala Ala Tyr Val Asn Gly Ile His Trp
 65                  70                  75                  80

Asp Trp Pro Leu Tyr Asp Ala Ile Ala Val Lys Ala Ala
                     85                  90                  95

Lys Glu Leu Gly Val Ala Ile Val Trp Gly Asp Trp Thr Thr Phe
                100                 105                 110

Lys Asp Gly Pro His Phe Glu Leu Asp Arg Ser Lys Tyr Arg
                115                 120                 125

<210> SEQ ID NO 9
<211> LENGTH: 501
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<223> OTHER INFORMATION: GN218 lysin
<220> FEATURE:
<221> NAME/KEY: CDS
<222> LOCATION: (28)..(477)

<400> SEQUENCE: 9
gtttaacttt aagaaggaga attcacc atg acc tac acc ctg tct aaa cgt tct       54
                                Met Thr Tyr Thr Leu Ser Lys Arg Ser
                                  1               5 ctg gac aac ctg aaa ggt gtt cac ccg gac ctg gtt gct gtt gtt cac      102
Leu Asp Asn Leu Lys Gly Val His Pro Asp Leu Val Ala Val Val His
 10                  15                  20                  25 cgt gct atc cag ctg acc ccg gtt gac ttc gct gtt atc gaa ggt ctg      150
Arg Ala Ile Gln Leu Thr Pro Val Asp Phe Ala Val Ile Glu Gly Leu
                 30                  35                  40 cgt tct gtt tct cgt cag aaa gaa ctg gtt gct gct ggt gct tct aaa      198
Arg Ser Val Ser Arg Gln Lys Glu Leu Val Ala Ala Gly Ala Ser Lys
             45                  50                  55 acc atg aac tct cgt cac ctg acc ggt cac gct gtt gac ctg gct gct      246
Thr Met Asn Ser Arg His Leu Thr Gly His Ala Val Asp Leu Ala Ala
         60                  65                  70 tac gtt aac ggt atc cgt tgg gac tgg ccg ctg tac gac gct atc gct      294
Tyr Val Asn Gly Ile Arg Trp Asp Trp Pro Leu Tyr Asp Ala Ile Ala
     75                  80                  85 gtt gct gtt aaa gct gct gct aaa gaa ctg ggt gtt gct atc gtt tgg      342
Val Ala Val Lys Ala Ala Ala Lys Glu Leu Gly Val Ala Ile Val Trp
 90                  95                 100                 105 ggt ggt gac tgg acc acc ttc aaa gac ggt ccg cac ttc gaa ctg gac      390
Gly Gly Asp Trp Thr Thr Phe Lys Asp Gly Pro His Phe Glu Leu Asp
                110                 115                 120 cgt tct aaa tac ggc ggt ggc tct gga ggt ggt ggg tcc ggt ggt ggc      438
Arg Ser Lys Tyr Gly Gly Gly Ser Gly Gly Gly Gly Ser Gly Gly Gly
            125                 130                 135 tct cgc ctg aaa aaa att ggc aaa gtg ctg aaa tgg att taataaaagc      487
Ser Arg Leu Lys Lys Ile Gly Lys Val Leu Lys Trp Ile
        140                 145                 150 ttggctgttt tggc                                                      501

<210> SEQ ID NO 10
<211> LENGTH: 150
```

<212> TYPE: PRT
<213> ORGANISM: Artificial Sequence
<220> FEATURE:
<223> OTHER INFORMATION: Synthetic Construct

<400> SEQUENCE: 10

```
Met Thr Tyr Thr Leu Ser Lys Arg Ser Leu Asp Asn Leu Lys Gly Val
1               5                   10                  15

His Pro Asp Leu Val Ala Val Val His Arg Ala Ile Gln Leu Thr Pro
            20                  25                  30

Val Asp Phe Ala Val Ile Glu Gly Leu Arg Ser Val Ser Arg Gln Lys
        35                  40                  45

Glu Leu Val Ala Ala Gly Ala Ser Lys Thr Met Asn Ser Arg His Leu
50                  55                  60

Thr Gly His Ala Val Asp Leu Ala Ala Tyr Val Asn Gly Ile Arg Trp
65                  70                  75                  80

Asp Trp Pro Leu Tyr Asp Ala Ile Ala Val Ala Val Lys Ala Ala Ala
                85                  90                  95

Lys Glu Leu Gly Val Ala Ile Val Trp Gly Gly Asp Trp Thr Thr Phe
            100                 105                 110

Lys Asp Gly Pro His Phe Glu Leu Asp Arg Ser Lys Tyr Gly Gly Gly
        115                 120                 125

Ser Gly Gly Gly Gly Ser Gly Gly Gly Ser Arg Leu Lys Lys Ile Gly
    130                 135                 140

Lys Val Leu Lys Trp Ile
145                 150
```

<210> SEQ ID NO 11
<211> LENGTH: 573
<212> TYPE: DNA
<213> ORGANISM: Artificial Sequence
<220> FEATURE:
<223> OTHER INFORMATION: Description of Artificial Sequence: Synthetic
    polynucleotide
<220> FEATURE:
<221> NAME/KEY: misc_feature
<222> LOCATION: (28)..(549)
<223> OTHER INFORMATION: GN223 lysin
<220> FEATURE:
<221> NAME/KEY: CDS
<222> LOCATION: (28)..(549)

<400> SEQUENCE: 11

```
gtttaacttt aagaaggaga attcacc atg acc tac acc ctg tct aaa cgt tct      54
                            Met Thr Tyr Thr Leu Ser Lys Arg Ser
                              1               5 ctg gac aac ctg aaa ggt gtt cac ccg gac ctg gtt gct gtt gtt cac       102
Leu Asp Asn Leu Lys Gly Val His Pro Asp Leu Val Ala Val Val His
 10                  15                  20                  25 cgt gct atc cag ctg acc ccg gtt gac ttc gct gtt atc gaa ggt ctg       150
Arg Ala Ile Gln Leu Thr Pro Val Asp Phe Ala Val Ile Glu Gly Leu
                 30                  35                  40 cgt tct gtt tct cgt cag aaa gaa ctg gtt gct gct ggt gct tct aaa       198
Arg Ser Val Ser Arg Gln Lys Glu Leu Val Ala Ala Gly Ala Ser Lys
             45                  50                  55 acc atg aac tct cgt cac ctg acc ggt cac gct gtt gac ctg gct gct       246
Thr Met Asn Ser Arg His Leu Thr Gly His Ala Val Asp Leu Ala Ala
         60                  65                  70 tac gtt aac ggt atc cgt tgg gac tgg ccg ctg tac gac gct atc gct       294
Tyr Val Asn Gly Ile Arg Trp Asp Trp Pro Leu Tyr Asp Ala Ile Ala
     75                  80                  85
```

```
gtt gct gtt aaa gct gct gct aaa gaa ctg ggt gtt gct atc gtt tgg      342
Val Ala Val Lys Ala Ala Ala Lys Glu Leu Gly Val Ala Ile Val Trp
 90              95                 100                 105 ggt ggt gac tgg acc acc ttc aaa gac ggt ccg cac ttc gaa ctg gac      390
Gly Gly Asp Trp Thr Thr Phe Lys Asp Gly Pro His Phe Glu Leu Asp
            110                 115                 120 cgt tct aaa tac cgt cca cca ggc ggt ggc tct gga ggt ggt ggg tcc      438
Arg Ser Lys Tyr Arg Pro Pro Gly Gly Gly Ser Gly Gly Gly Gly Ser
                125                 130                 135 ggc ggt ggc tct tcg aag aag gcg tcg agg aag agt ttt act aag ggt      486
Gly Gly Gly Ser Ser Lys Lys Ala Ser Arg Lys Ser Phe Thr Lys Gly
            140                 145                 150 gcc gtt aag gtt cat aag aaa aat gtt cct act cgt gtt cct atg cgt      534
Ala Val Lys Val His Lys Lys Asn Val Pro Thr Arg Val Pro Met Arg
155                 160                 165 ggc ggt att agg ctt taataaaagc ttggctgttt tggc                       573
Gly Gly Ile Arg Leu
170

<210> SEQ ID NO 12
<211> LENGTH: 174
<212> TYPE: PRT
<213> ORGANISM: Artificial Sequence
<220> FEATURE:
<223> OTHER INFORMATION: Synthetic Construct

<400> SEQUENCE: 12

Met Thr Tyr Thr Leu Ser Lys Arg Ser Leu Asp Asn Leu Lys Gly Val
 1               5                  10                  15

His Pro Asp Leu Val Ala Val Val His Arg Ala Ile Gln Leu Thr Pro
            20                  25                  30

Val Asp Phe Ala Val Ile Glu Gly Leu Arg Ser Val Ser Arg Gln Lys
        35                  40                  45

Glu Leu Val Ala Ala Gly Ala Ser Lys Thr Met Asn Ser Arg His Leu
 50                  55                  60

Thr Gly His Ala Val Asp Leu Ala Ala Tyr Val Asn Gly Ile Arg Trp
 65                  70                  75                  80

Asp Trp Pro Leu Tyr Asp Ala Ile Ala Val Ala Val Lys Ala Ala Ala
                85                  90                  95

Lys Glu Leu Gly Val Ala Ile Val Trp Gly Gly Asp Trp Thr Thr Phe
            100                 105                 110

Lys Asp Gly Pro His Phe Glu Leu Asp Arg Ser Lys Tyr Arg Pro Pro
        115                 120                 125

Gly Gly Gly Ser Gly Gly Gly Gly Ser Gly Gly Gly Ser Ser Lys Lys
    130                 135                 140

Ala Ser Arg Lys Ser Phe Thr Lys Gly Ala Val Lys Val His Lys Lys
145                 150                 155                 160

Asn Val Pro Thr Arg Val Pro Met Arg Gly Gly Ile Arg Leu
                165                 170

<210> SEQ ID NO 13
<211> LENGTH: 519
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (28)..(495)
<223> OTHER INFORMATION: GN239 lysin
```

```
<220> FEATURE:
<221> NAME/KEY: CDS
<222> LOCATION: (28)..(495)

<400> SEQUENCE: 13
gtttaacttt aagaaggaga attcacc atg acc tac acc ctg tct aaa cgt tct         54
                                Met Thr Tyr Thr Leu Ser Lys Arg Ser
                                 1               5 ctg gac aac ctg aaa ggt gtt cac ccg gac ctg gtt gct gtt gtt cac          102
Leu Asp Asn Leu Lys Gly Val His Pro Asp Leu Val Ala Val Val His
 10                  15                  20                  25 cgt gct atc cag ctg acc ccg gtt gac ttc gct gtt atc gaa ggt ctg          150
Arg Ala Ile Gln Leu Thr Pro Val Asp Phe Ala Val Ile Glu Gly Leu
                 30                  35                  40 cgt tct gtt tct cgt cag aaa gaa ctg gtt gct gct ggt gct tct aaa          198
Arg Ser Val Ser Arg Gln Lys Glu Leu Val Ala Ala Gly Ala Ser Lys
             45                  50                  55 acc atg aac tct cgt cac ctg acc ggt cac gct gtt gac ctg gct gct          246
Thr Met Asn Ser Arg His Leu Thr Gly His Ala Val Asp Leu Ala Ala
         60                  65                  70 tac gtt aac ggt atc cgt tgg gac tgg ccg ctg tac gac gct atc gct          294
Tyr Val Asn Gly Ile Arg Trp Asp Trp Pro Leu Tyr Asp Ala Ile Ala
 75                  80                  85 gtt gct gtt aaa gct gct gct aaa gaa ctg ggt gtt gct atc gtt tgg          342
Val Ala Val Lys Ala Ala Ala Lys Glu Leu Gly Val Ala Ile Val Trp
 90                  95                 100                 105 ggt ggt gac tgg acc acc ttc aaa gac ggt ccg cac ttc gaa ctg gac          390
Gly Gly Asp Trp Thr Thr Phe Lys Asp Gly Pro His Phe Glu Leu Asp
                110                 115                 120 cgt tct aaa tac ggc ggt ggc tct gga ggt ggt ggg tcc ggc ggt ggc          438
Arg Ser Lys Tyr Gly Gly Gly Ser Gly Gly Gly Gly Ser Gly Gly Gly
                125                 130                 135 tct cgt aaa aaa acc cgt aaa cgt ctg aaa aaa atc ggt aaa gtt ctg          486
Ser Arg Lys Lys Thr Arg Lys Arg Leu Lys Lys Ile Gly Lys Val Leu
                140                 145                 150 aaa tgg atc taataaaagc ttggctgttt tggc                                   519
Lys Trp Ile
    155

<210> SEQ ID NO 14
<211> LENGTH: 156
<212> TYPE: PRT
<213> ORGANISM: Artificial Sequence
<220> FEATURE:
<223> OTHER INFORMATION: Synthetic Construct

<400> SEQUENCE: 14

Met Thr Tyr Thr Leu Ser Lys Arg Ser Leu Asp Asn Leu Lys Gly Val
 1               5                  10                  15

His Pro Asp Leu Val Ala Val Val His Arg Ala Ile Gln Leu Thr Pro
             20                  25                  30

Val Asp Phe Ala Val Ile Glu Gly Leu Arg Ser Val Ser Arg Gln Lys
         35                  40                  45

Glu Leu Val Ala Ala Gly Ala Ser Lys Thr Met Asn Ser Arg His Leu
     50                  55                  60

Thr Gly His Ala Val Asp Leu Ala Ala Tyr Val Asn Gly Ile Arg Trp
 65                  70                  75                  80

Asp Trp Pro Leu Tyr Asp Ala Ile Ala Val Ala Val Lys Ala Ala Ala
                 85                  90                  95

Lys Glu Leu Gly Val Ala Ile Val Trp Gly Gly Asp Trp Thr Thr Phe
```

100                 105                 110
Lys Asp Gly Pro His Phe Glu Leu Asp Arg Ser Lys Tyr Gly Gly Gly
        115                 120                 125

Ser Gly Gly Gly Gly Ser Gly Gly Gly Ser Arg Lys Lys Thr Arg Lys
    130                 135                 140

Arg Leu Lys Lys Ile Gly Lys Val Leu Lys Trp Ile
145                 150                 155

<210> SEQ ID NO 15
<211> LENGTH: 570
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (28)..(546)
<223> OTHER INFORMATION: GN243 lysin
<220> FEATURE:
<221> NAME/KEY: CDS
<222> LOCATION: (28)..(546)

<400> SEQUENCE: 15
gtttaacttt aagaaggaga attcacc atg acc tac acc ctg tct aaa cgt tct    54
                             Met Thr Tyr Thr Leu Ser Lys Arg Ser
                               1               5 ctg gac aac ctg aaa ggt gtt cac ccg gac ctg gtt gct gtt gtt cac    102
Leu Asp Asn Leu Lys Gly Val His Pro Asp Leu Val Ala Val Val His
 10                  15                  20                  25 cgt gct atc cag ctg acc ccg gtt gac ttc gct gtt atc gaa ggt ctg    150
Arg Ala Ile Gln Leu Thr Pro Val Asp Phe Ala Val Ile Glu Gly Leu
                 30                  35                  40 cgt tct gtt tct cgt cag aaa gaa ctg gtt gct gct ggt gct tct aaa    198
Arg Ser Val Ser Arg Gln Lys Glu Leu Val Ala Ala Gly Ala Ser Lys
             45                  50                  55 acc atg aac tct cgt cac ctg acc ggt cac gct gtt gac ctg gct gct    246
Thr Met Asn Ser Arg His Leu Thr Gly His Ala Val Asp Leu Ala Ala
         60                  65                  70 tac gtt aac ggt atc cgt tgg gac tgg ccg ctg tac gac gct atc gct    294
Tyr Val Asn Gly Ile Arg Trp Asp Trp Pro Leu Tyr Asp Ala Ile Ala
 75                  80                  85 gtt gct gtt aaa gct gct gct aaa gaa ctg ggt gtt gct atc gtt tgg    342
Val Ala Val Lys Ala Ala Ala Lys Glu Leu Gly Val Ala Ile Val Trp
 90                  95                 100                 105 ggt ggt gac tgg acc acc ttc aaa gac ggt ccg cac ttc gaa ctg gac    390
Gly Gly Asp Trp Thr Thr Phe Lys Asp Gly Pro His Phe Glu Leu Asp
                110                 115                 120 cgt tct aaa tac cgt aaa aaa acc cgt aaa cgt ctg aaa aaa atc ggt    438
Arg Ser Lys Tyr Arg Lys Lys Thr Arg Lys Arg Leu Lys Lys Ile Gly
            125                 130                 135 aaa gtt ctg aaa tgg atc cca cca ggc ggt ggc tct gga ggt ggt ggg    486
Lys Val Leu Lys Trp Ile Pro Pro Gly Gly Gly Ser Gly Gly Gly Gly
        140                 145                 150 tcc ggc ggt ggc tct acc cgc aaa cgc ctg aaa aaa att ggc aaa gtg    534
Ser Gly Gly Gly Ser Thr Arg Lys Arg Leu Lys Lys Ile Gly Lys Val
    155                 160                 165 ctg aaa tgg att taataaaagc ttggctgttt tggc                          570
Leu Lys Trp Ile
170

<210> SEQ ID NO 16

<211> LENGTH: 173
<212> TYPE: PRT
<213> ORGANISM: Artificial Sequence
<220> FEATURE:
<223> OTHER INFORMATION: Synthetic Construct

<400> SEQUENCE: 16

```
Met Thr Tyr Thr Leu Ser Lys Arg Ser Leu Asp Asn Leu Lys Gly Val
1               5                   10                  15

His Pro Asp Leu Val Ala Val Val His Arg Ala Ile Gln Leu Thr Pro
            20                  25                  30

Val Asp Phe Ala Val Ile Glu Gly Leu Arg Ser Val Ser Arg Gln Lys
        35                  40                  45

Glu Leu Val Ala Ala Gly Ala Ser Lys Thr Met Asn Ser Arg His Leu
50                  55                  60

Thr Gly His Ala Val Asp Leu Ala Ala Tyr Val Asn Gly Ile Arg Trp
65                  70                  75                  80

Asp Trp Pro Leu Tyr Asp Ala Ile Ala Val Ala Val Lys Ala Ala Ala
                85                  90                  95

Lys Glu Leu Gly Val Ala Ile Val Trp Gly Gly Asp Trp Thr Thr Phe
            100                 105                 110

Lys Asp Gly Pro His Phe Glu Leu Asp Arg Ser Lys Tyr Arg Lys Lys
        115                 120                 125

Thr Arg Lys Arg Leu Lys Lys Ile Gly Lys Val Leu Lys Trp Ile Pro
130                 135                 140

Pro Gly Gly Gly Ser Gly Gly Gly Ser Gly Gly Gly Ser Thr Arg
145                 150                 155                 160

Lys Arg Leu Lys Lys Ile Gly Lys Val Leu Lys Trp Ile
                165                 170
```

<210> SEQ ID NO 17
<211> LENGTH: 528
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: misc_feature
<222> LOCATION: (28)..(504)
<223> OTHER INFORMATION: GN280 lysin
<220> FEATURE:
<221> NAME/KEY: CDS
<222> LOCATION: (28)..(504)

<400> SEQUENCE: 17

```
gtttaacttt aagaaggaga attcacc atg aaa ctc agc gaa aaa cga gca ctg      54
                                Met Lys Leu Ser Glu Lys Arg Ala Leu
                                1               5 ttc acc cag ctg ctt gcc cag tta att ctt tgg gca gga act cag gat      102
Phe Thr Gln Leu Leu Ala Gln Leu Ile Leu Trp Ala Gly Thr Gln Asp
10              15                  20                  25 cga gtg tca gta gcc ttg gat caa gtg aaa agg aca cag gct gaa gct      150
Arg Val Ser Val Ala Leu Asp Gln Val Lys Arg Thr Gln Ala Glu Ala
                30                  35                  40 gat gcc aat gct aag tct gga gca ggc att agg aac tct ctc cat cta      198
Asp Ala Asn Ala Lys Ser Gly Ala Gly Ile Arg Asn Ser Leu His Leu
            45                  50                  55 ctg gga tta gcc ggt gat ctt atc ctc tac aag gat ggt aaa tac atg      246
Leu Gly Leu Ala Gly Asp Leu Ile Leu Tyr Lys Asp Gly Lys Tyr Met
        60                  65                  70
```

```
gat aag agc gag gat tat aag ttc ctg gga gat tac tgg aag agt ctc      294
Asp Lys Ser Glu Asp Tyr Lys Phe Leu Gly Asp Tyr Trp Lys Ser Leu
 75                  80                  85 cat cct ctt tgt cgg tgg ggc gga gat ttt aaa agc cgt cct gat ggt      342
His Pro Leu Cys Arg Trp Gly Gly Asp Phe Lys Ser Arg Pro Asp Gly
 90                  95                 100                 105 aat cat ttc tcc ttg gaa cac gaa gga gtg caa cgt aaa aaa acc cgt      390
Asn His Phe Ser Leu Glu His Glu Gly Val Gln Arg Lys Lys Thr Arg
                110                 115                 120 aaa cgt ctg aaa aaa atc ggt aaa gtt ctg aaa tgg atc cca cca acc      438
Lys Arg Leu Lys Lys Ile Gly Lys Val Leu Lys Trp Ile Pro Pro Thr
            125                 130                 135 gcg ggc ggc acc gcg ggc ggc acc cgc aaa cgc ctg aaa aaa att ggc      486
Ala Gly Gly Thr Ala Gly Gly Thr Arg Lys Arg Leu Lys Lys Ile Gly
        140                 145                 150 aaa gtg ctg aaa tgg att taataaaagc ttggctgttt tggc                   528
Lys Val Leu Lys Trp Ile
    155
```

<210> SEQ ID NO 18
<211> LENGTH: 159
<212> TYPE: PRT
<213> ORGANISM: Artificial Sequence
<220> FEATURE:
<223> OTHER INFORMATION: Synthetic Construct

<400> SEQUENCE: 18

```
Met Lys Leu Ser Glu Lys Arg Ala Leu Phe Thr Gln Leu Leu Ala Gln
 1               5                  10                  15

Leu Ile Leu Trp Ala Gly Thr Gln Asp Arg Val Ser Val Ala Leu Asp
             20                  25                  30

Gln Val Lys Arg Thr Gln Ala Glu Ala Asp Ala Asn Ala Lys Ser Gly
         35                  40                  45

Ala Gly Ile Arg Asn Ser Leu His Leu Gly Leu Ala Gly Asp Leu
     50                  55                  60

Ile Leu Tyr Lys Asp Gly Lys Tyr Met Asp Lys Ser Glu Asp Tyr Lys
 65                  70                  75                  80

Phe Leu Gly Asp Tyr Trp Lys Ser Leu His Pro Leu Cys Arg Trp Gly
                 85                  90                  95

Gly Asp Phe Lys Ser Arg Pro Asp Gly Asn His Phe Ser Leu Glu His
            100                 105                 110

Glu Gly Val Gln Arg Lys Lys Thr Arg Lys Arg Leu Lys Lys Ile Gly
        115                 120                 125

Lys Val Leu Lys Trp Ile Pro Pro Thr Ala Gly Thr Ala Gly Gly
    130                 135                 140

Thr Arg Lys Arg Leu Lys Lys Ile Gly Lys Val Leu Lys Trp Ile
145                 150                 155
```

<210> SEQ ID NO 19
<211> LENGTH: 543
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: misc_feature
<223> OTHER INFORMATION: GN281 lysin
<220> FEATURE:
<221> NAME/KEY: CDS
<222> LOCATION: (28)..(519)

<400> SEQUENCE: 19

```
gtttaacttt aagaaggaga attcacc atg aaa ctc agc gaa aaa cga gca ctg        54
                            Met Lys Leu Ser Glu Lys Arg Ala Leu
                              1               5 ttc acc cag ctg ctt gcc cag tta att ctt tgg gca gga act cag gat          102
Phe Thr Gln Leu Leu Ala Gln Leu Ile Leu Trp Ala Gly Thr Gln Asp
 10              15                  20                  25 cga gtg tca gta gcc ttg gat caa gtg aaa agg aca cag gct gaa gct          150
Arg Val Ser Val Ala Leu Asp Gln Val Lys Arg Thr Gln Ala Glu Ala
             30                  35                  40 gat gcc aat gct aag tct gga gca ggc att agg aac tct ctc cat cta          198
Asp Ala Asn Ala Lys Ser Gly Ala Gly Ile Arg Asn Ser Leu His Leu
             45                  50                  55 ctg gga tta gcc ggt gat ctt atc ctc tac aag gat ggt aaa tac atg          246
Leu Gly Leu Ala Gly Asp Leu Ile Leu Tyr Lys Asp Gly Lys Tyr Met
         60                  65                  70 gat aag agc gag gat tat aag ttc ctg gga gat tac tgg aag agt ctc          294
Asp Lys Ser Glu Asp Tyr Lys Phe Leu Gly Asp Tyr Trp Lys Ser Leu
 75                  80                  85 cat cct ctt tgt cgg tgg ggc gga gat ttt aaa agc cgt cct gat ggt          342
His Pro Leu Cys Arg Trp Gly Gly Asp Phe Lys Ser Arg Pro Asp Gly
 90                  95                 100                 105 aat cat ttc tcc ttg gaa cac gaa gga gtg caa cgt aaa aaa acc cgt          390
Asn His Phe Ser Leu Glu His Glu Gly Val Gln Arg Lys Lys Thr Arg
                 110                 115                 120 aaa cgt ctg aaa aaa atc ggt aaa gtt ctg aaa tgg atc ggc ggt ggc          438
Lys Arg Leu Lys Lys Ile Gly Lys Val Leu Lys Trp Ile Gly Gly Gly
             125                 130                 135 tct gga ggt ggt ggg tcc ggc ggt ggc tct cca cca acc cgc aaa cgc          486
Ser Gly Gly Gly Gly Ser Gly Gly Gly Ser Pro Pro Thr Arg Lys Arg
         140                 145                 150 ctg aaa aaa att ggc aaa gtg ctg aaa tgg att taataaaagc ttggctgttt        539
Leu Lys Lys Ile Gly Lys Val Leu Lys Trp Ile
 155                 160 tggc                                                                     543
```

<210> SEQ ID NO 20
<211> LENGTH: 164
<212> TYPE: PRT
<213> ORGANISM: Artificial Sequence
<220> FEATURE:
<223> OTHER INFORMATION: Synthetic Construct

<400> SEQUENCE: 20

```
Met Lys Leu Ser Glu Lys Arg Ala Leu Phe Thr Gln Leu Leu Ala Gln
 1               5                  10                  15

Leu Ile Leu Trp Ala Gly Thr Gln Asp Arg Val Ser Val Ala Leu Asp
             20                  25                  30

Gln Val Lys Arg Thr Gln Ala Glu Ala Asp Ala Asn Ala Lys Ser Gly
         35                  40                  45

Ala Gly Ile Arg Asn Ser Leu His Leu Leu Gly Leu Ala Gly Asp Leu
     50                  55                  60

Ile Leu Tyr Lys Asp Gly Lys Tyr Met Asp Lys Ser Glu Asp Tyr Lys
 65                  70                  75                  80

Phe Leu Gly Asp Tyr Trp Lys Ser Leu His Pro Leu Cys Arg Trp Gly
                 85                  90                  95

Gly Asp Phe Lys Ser Arg Pro Asp Gly Asn His Phe Ser Leu Glu His
            100                 105                 110
```

Glu Gly Val Gln Arg Lys Lys Thr Arg Lys Arg Leu Lys Lys Ile Gly
            115                 120                 125

Lys Val Leu Lys Trp Ile Gly Gly Ser Gly Gly Gly Ser Gly
        130                 135                 140

Gly Gly Ser Pro Pro Thr Arg Lys Arg Leu Lys Lys Ile Gly Lys Val
145                 150                 155                 160

Leu Lys Trp Ile

<210> SEQ ID NO 21
<211> LENGTH: 852
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<223> OTHER INFORMATION: GN316 lysin

<400> SEQUENCE: 21
gaattcacca tgggatccca tcatcaccac catcatggtg ccatttttaaa gattggcagc      60 aaaggtctgg aagttaagaa tcttcagacc agtctcaaca aaatcgggtt caatctggtt     120
gccgatggca tatttggtaa agcgactgac aacgccgtca gggcagttca ggcaggtgcc     180
ggactggtcg ttgatggtat tgctggcccc aagaccatgt atgcgattcg caacgcaggg     240
gagtctcatc aggatcatct gactgaggct gacttgattg acgctgctcg tgaattgtct     300
gttgaccttg ctagcatcaa ggcagtcaac caagtagaat cgcgcggtac tggcttcacc     360
aagtctggta agatcaagac attgtttgaa cgccacatca tgtacaaaaa gctgaatgcc     420
aagttcggtc aggcaaaagc caatgctctg gcccagcttt acccgacgtt ggttaacgcc     480
aaagccgggg atacacagg tggggacgcg gagttggaac gactccatgg tgcaatagcg     540
atcgataaag attgcgccta cgagagcgct tcctacgggt tattccagat catgggcttc     600
aactgcgtta tttgtggata tgacaatgcc gaggagatgt tcaacgactt tctcactggt     660
gaacgtgctc agctcatggc atttgtcaag ttcatcaagg ctgacgccaa tctgtggaaa     720
gcattgaagg acaagaattg gcctgagttt gctcggcgtt acaatggccc ggcgtatgca     780
cagaaccagt acgacaccaa gctggctgca gcatacaaat cattcagtta gtaaaagctt     840
ggctgttttg gc                                                          852

<210> SEQ ID NO 22
<211> LENGTH: 264
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(264)
<223> OTHER INFORMATION: GN316 lysin

<400> SEQUENCE: 22

Met Ala Ile Leu Lys Ile Gly Ser Lys Gly Leu Glu Val Lys Asn Leu
1               5                   10                  15

Gln Thr Ser Leu Asn Lys Ile Gly Phe Asn Leu Val Ala Asp Gly Ile
            20                  25                  30

Phe Gly Lys Ala Thr Asp Asn Ala Val Arg Ala Val Gln Ala Gly Ala
        35                  40                  45

Gly Leu Val Val Asp Gly Ile Ala Gly Pro Lys Thr Met Tyr Ala Ile
 50                  55                  60

Arg Asn Ala Gly Glu Ser His Gln Asp His Leu Thr Glu Ala Asp Leu
 65                  70                  75                  80

Ile Asp Ala Ala Arg Glu Leu Ser Val Asp Leu Ala Ser Ile Lys Ala
                 85                  90                  95

Val Asn Gln Val Glu Ser Arg Gly Thr Gly Phe Thr Lys Ser Gly Lys
            100                 105                 110

Ile Lys Thr Leu Phe Glu Arg His Ile Met Tyr Lys Lys Leu Asn Ala
        115                 120                 125

Lys Phe Gly Gln Ala Lys Ala Asn Ala Leu Ala Gln Leu Tyr Pro Thr
130                 135                 140

Leu Val Asn Ala Lys Ala Gly Gly Tyr Thr Gly Gly Asp Ala Glu Leu
145                 150                 155                 160

Glu Arg Leu His Gly Ala Ile Ala Ile Asp Lys Asp Cys Ala Tyr Glu
                165                 170                 175

Ser Ala Ser Tyr Gly Leu Phe Gln Ile Met Gly Phe Asn Cys Val Ile
            180                 185                 190

Cys Gly Tyr Asp Asn Ala Glu Glu Met Phe Asn Asp Phe Leu Thr Gly
        195                 200                 205

Glu Arg Ala Gln Leu Met Ala Phe Val Lys Phe Ile Lys Ala Asp Ala
210                 215                 220

Asn Leu Trp Lys Ala Leu Lys Asp Lys Asn Trp Ala Glu Phe Ala Arg
225                 230                 235                 240

Arg Tyr Asn Gly Pro Ala Tyr Ala Gln Asn Gln Tyr Asp Thr Lys Leu
                245                 250                 255

Ala Ala Ala Tyr Lys Ser Phe Ser
            260

<210> SEQ ID NO 23
<211> LENGTH: 879
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(879)
<223> OTHER INFORMATION: modified GN316 lysin

<400> SEQUENCE: 23
gaattcacca tgggatccca tcatcaccac catcatggtg ccggatccca tcatcaccac      60
catcatggta ttttaaagat tggcagcaaa ggtctggaag ttaagaatct tcagaccagt     120
ctcaacaaaa tcgggttcaa tctggttgcc gatggcatat tggtaaagc gactgacaac      180 gccgtcaggg cagttcaggc aggtgccgga ctggtcgttg atggtattgc tggccccaag     240
accatgtatg cgattcgcaa cgcaggggag tctcatcagg atcatctgac tgaggctgac     300
ttgattgacg ctgctcgtga attgtctgtt gaccttgcta gcatcaaggc agtcaaccaa     360
gtagaatcgc gcggtactgg cttcaccaag tctggtaaga tcaagacatt gtttgaacgc     420
cacatcatgt acaaaaagct gaatgccaag ttcggtcagg caaaagccaa tgctctggcc     480
cagctttacc cgacgttggt taacgccaaa gccgggggat acacaggtgg ggacgcggag     540
ttggaacgac tccatggtgc aatagcgatc gataaagatt gcgcctacga gagcgcttcc     600
tacgggttat tccagatcat ggggttcaac tgcgttattt gtggatatga caatgccgag     660

```
gagatgttca acgactttct cactggtgaa cgtgctcagc tcatggcatt tgtcaagttc      720
atcaaggctg acgccaatct gtggaaagca ttgaaggaca agaattgggc tgagtttgct      780
cggcgttaca atggcccggc gtatgcacag aaccagtacg acaccaagct ggctgcagca      840
tacaaatcat tcagttagta aaagcttggc tgttttggc                              879
```

<210> SEQ ID NO 24
<211> LENGTH: 273
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(273)
<223> OTHER INFORMATION: modified GN316 lysin
<400> SEQUENCE: 24

```
Met Gly Ser His His His His His Gly Ala Ile Leu Lys Ile Gly
1               5                   10                  15

Ser Lys Gly Leu Glu Val Lys Asn Leu Gln Thr Ser Leu Asn Lys Ile
            20                  25                  30

Gly Phe Asn Leu Val Ala Asp Gly Ile Phe Gly Lys Ala Thr Asp Asn
        35                  40                  45

Ala Val Arg Ala Val Gln Ala Gly Ala Gly Leu Val Val Asp Gly Ile
    50                  55                  60

Ala Gly Pro Lys Thr Met Tyr Ala Ile Arg Asn Ala Gly Glu Ser His
65                  70                  75                  80

Gln Asp His Leu Thr Glu Ala Asp Leu Ile Asp Ala Ala Arg Glu Leu
                85                  90                  95

Ser Val Asp Leu Ala Ser Ile Lys Ala Val Asn Gln Val Glu Ser Arg
            100                 105                 110

Gly Thr Gly Phe Thr Lys Ser Gly Lys Ile Lys Thr Leu Phe Glu Arg
        115                 120                 125

His Ile Met Tyr Lys Lys Leu Asn Ala Lys Phe Gly Gln Ala Lys Ala
    130                 135                 140

Asn Ala Leu Ala Gln Leu Tyr Pro Thr Leu Val Asn Ala Lys Ala Gly
145                 150                 155                 160

Gly Tyr Thr Gly Gly Asp Ala Glu Leu Glu Arg Leu His Gly Ala Ile
                165                 170                 175

Ala Ile Asp Lys Asp Cys Ala Tyr Glu Ser Ala Ser Tyr Gly Leu Phe
            180                 185                 190

Gln Ile Met Gly Phe Asn Cys Val Ile Cys Gly Tyr Asp Asn Ala Glu
        195                 200                 205

Glu Met Phe Asn Asp Phe Leu Thr Gly Glu Arg Ala Gln Leu Met Ala
    210                 215                 220

Phe Val Lys Phe Ile Lys Ala Asp Ala Asn Leu Trp Lys Ala Leu Lys
225                 230                 235                 240

Asp Lys Asn Trp Ala Glu Phe Ala Arg Arg Tyr Asn Gly Pro Ala Tyr
                245                 250                 255

Ala Gln Asn Gln Tyr Asp Thr Lys Leu Ala Ala Ala Tyr Lys Ser Phe
            260                 265                 270

Ser
```

<210> SEQ ID NO 25
<211> LENGTH: 612

```
<212> TYPE: DNA
<213> ORGANISM: Pseudomonas phage KPP10
<220> FEATURE:
<221> NAME/KEY: misc_feature
<222> LOCATION: (28)..(588)
<223> OTHER INFORMATION: GN329
<220> FEATURE:
<221> NAME/KEY: CDS
<222> LOCATION: (28)..(588)

<400> SEQUENCE: 25
gtttaacttt aagaaggaga attcacc atg atc acc gac aga gag tat cag caa    54
                               Met Ile Thr Asp Arg Glu Tyr Gln Gln
                                1               5 gct gct gag atg ttg gga gta gat gtc cca gcg atc aag gca gtg acc    102
Ala Ala Glu Met Leu Gly Val Asp Val Pro Ala Ile Lys Ala Val Thr
 10              15                  20                  25 aag gtg gag gcc ccg gta ggg ggc ttc cag cct aca gga gag cca acg    150
Lys Val Glu Ala Pro Val Gly Gly Phe Gln Pro Thr Gly Glu Pro Thr
                 30                  35                  40 atc ctc tac gag cgt cac cag atg tac cga cag ctc cag gcc aaa ggg    198
Ile Leu Tyr Glu Arg His Gln Met Tyr Arg Gln Leu Gln Ala Lys Gly
         45                  50                  55 ctc cca acg gaa ggt cat ccc cca gac ctg gta aat aag gta gct ggt    246
Leu Pro Thr Glu Gly His Pro Pro Asp Leu Val Asn Lys Val Ala Gly
 60                  65                  70 ggg tat gga aaa tac agc gag caa cac gct aaa ctg gcc cgt gcc gta    294
Gly Tyr Gly Lys Tyr Ser Glu Gln His Ala Lys Leu Ala Arg Ala Val
     75                  80                  85 aag atc gac agg gac agc gcc ctg gag tcc tgc tcc tgg ggg atg ttc    342
Lys Ile Asp Arg Asp Ser Ala Leu Glu Ser Cys Ser Trp Gly Met Phe
 90                  95                 100                 105 cag atc atg ggc tac cac tgg aag ctg atg ggg tac cct acc ctt caa    390
Gln Ile Met Gly Tyr His Trp Lys Leu Met Gly Tyr Pro Thr Leu Gln
                110                 115                 120 gct ttc gta aac gcc atg tac gcc agc gaa gga gcc cag atg gac gcc    438
Ala Phe Val Asn Ala Met Tyr Ala Ser Glu Gly Ala Gln Met Asp Ala
        125                 130                 135 ttc tgc cgg ttc atc aag gca caa ccc acc acg cat gct gcc ttg aaa    486
Phe Cys Arg Phe Ile Lys Ala Gln Pro Thr Thr His Ala Ala Leu Lys
            140                 145                 150 gcc cat gat tgg gcc aag ttt gcc aga ctg tac aac ggt cca ggc tac    534
Ala His Asp Trp Ala Lys Phe Ala Arg Leu Tyr Asn Gly Pro Gly Tyr
155                 160                 165 gcc aag aac aag tat gac gtg aaa ttg gag aaa gca tat gct gaa gct    582
Ala Lys Asn Lys Tyr Asp Val Lys Leu Glu Lys Ala Tyr Ala Glu Ala
170                 175                 180                 185 agt ggc tgataaaagc ttggctgttt tggc                                  612
Ser Gly

<210> SEQ ID NO 26
<211> LENGTH: 187
<212> TYPE: PRT
<213> ORGANISM: Pseudomonas phage KPP10

<400> SEQUENCE: 26

Met Ile Thr Asp Arg Glu Tyr Gln Gln Ala Ala Glu Met Leu Gly Val
  1               5                  10                  15

Asp Val Pro Ala Ile Lys Ala Val Thr Lys Val Glu Ala Pro Val Gly
                 20                  25                  30

Gly Phe Gln Pro Thr Gly Glu Pro Thr Ile Leu Tyr Glu Arg His Gln
             35                  40                  45
```

```
Met Tyr Arg Gln Leu Gln Ala Lys Gly Leu Pro Thr Glu Gly His Pro
    50                  55                  60

Pro Asp Leu Val Asn Lys Val Ala Gly Tyr Gly Lys Tyr Ser Glu
65                  70                  75                  80

Gln His Ala Lys Leu Ala Arg Ala Val Lys Ile Asp Arg Asp Ser Ala
                85                  90                  95

Leu Glu Ser Cys Ser Trp Gly Met Phe Gln Ile Met Gly Tyr His Trp
            100                 105                 110

Lys Leu Met Gly Tyr Pro Thr Leu Gln Ala Phe Val Asn Ala Met Tyr
            115                 120                 125

Ala Ser Glu Gly Ala Gln Met Asp Ala Phe Cys Arg Phe Ile Lys Ala
        130                 135                 140

Gln Pro Thr Thr His Ala Ala Leu Lys Ala His Asp Trp Ala Lys Phe
145                 150                 155                 160

Ala Arg Leu Tyr Asn Gly Pro Gly Tyr Ala Lys Asn Lys Tyr Asp Val
                165                 170                 175

Lys Leu Glu Lys Ala Tyr Ala Glu Ala Ser Gly
            180                 185

<210> SEQ ID NO 27
<211> LENGTH: 609
<212> TYPE: DNA
<213> ORGANISM: Delftia sp.
<220> FEATURE:
<221> NAME/KEY: CDS
<222> LOCATION: (28)..(585)
<220> FEATURE:
<221> NAME/KEY: misc_feature
<222> LOCATION: (28)..(585)
<223> OTHER INFORMATION: GN333 lysin

<400> SEQUENCE: 27
gtttaacttt aagaaggaga attcacc atg gct cta act gag caa gac ttc caa      54
                            Met Ala Leu Thr Glu Gln Asp Phe Gln
                            1               5 tcg gct gcc gat gat ctc gga gtc gat gtt gcc agt gta aag gcc gtc     102
Ser Ala Ala Asp Asp Leu Gly Val Asp Val Ala Ser Val Lys Ala Val
10              15                  20                  25 act aaa gta gag agt cgt ggg agc ggc ttt cta ctt tct ggc gtc cct     150
Thr Lys Val Glu Ser Arg Gly Ser Gly Phe Leu Leu Ser Gly Val Pro
                30                  35                  40 aag att cta ttc gaa agg cac tgg atg ttc aag ctt ctc aaa agg aag     198
Lys Ile Leu Phe Glu Arg His Trp Met Phe Lys Leu Leu Lys Arg Lys
            45                  50                  55 cta ggt cgt gac cct gaa ata aac gac gtt tgc aac cct aaa gct gga     246
Leu Gly Arg Asp Pro Glu Ile Asn Asp Val Cys Asn Pro Lys Ala Gly
        60                  65                  70 gga tac ctc ggc gga caa gcg gag cac gaa cgt cta gat aaa gca gtc     294
Gly Tyr Leu Gly Gly Gln Ala Glu His Glu Arg Leu Asp Lys Ala Val
75                  80                  85 aag atg gat aga gac tgc gca ctt caa agt gcc tct tgg ggc cta ttc     342
Lys Met Asp Arg Asp Cys Ala Leu Gln Ser Ala Ser Trp Gly Leu Phe
90                  95                  100                 105 cag att atg gga ttc cat tgg gag gca cta ggt tat gcg agt gtt cag     390
Gln Ile Met Gly Phe His Trp Glu Ala Leu Gly Tyr Ala Ser Val Gln
                110                 115                 120 gca ttt gtc aat gcc cag tac gct agc gag gga tcg caa cta aac act     438
Ala Phe Val Asn Ala Gln Tyr Ala Ser Glu Gly Ser Gln Leu Asn Thr
            125                 130                 135
```

```
ttt gtg cgc ttc atc aag acc aac ccg gca att cac aaa gct tta aag    486
Phe Val Arg Phe Ile Lys Thr Asn Pro Ala Ile His Lys Ala Leu Lys
    140                 145                 150 tct aag gac tgg gca gaa ttc gca aga agg tat aac ggg ccg gat tac    534
Ser Lys Asp Trp Ala Glu Phe Ala Arg Arg Tyr Asn Gly Pro Asp Tyr
155                 160                 165 aag aaa aac aac tac gat gtt aag cta gca gaa gcc tat caa tcc ttc    582
Lys Lys Asn Asn Tyr Asp Val Lys Leu Ala Glu Ala Tyr Gln Ser Phe
170                 175                 180                 185 aag taataaaagc ttggctgttt tggc                                      609
Lys
```

<210> SEQ ID NO 28
<211> LENGTH: 186
<212> TYPE: PRT
<213> ORGANISM: Delftia sp.

<400> SEQUENCE: 28

```
Met Ala Leu Thr Glu Gln Asp Phe Gln Ser Ala Ala Asp Asp Leu Gly
1               5                   10                  15

Val Asp Val Ala Ser Val Lys Ala Val Thr Lys Val Glu Ser Arg Gly
            20                  25                  30

Ser Gly Phe Leu Leu Ser Gly Val Pro Lys Ile Leu Phe Glu Arg His
        35                  40                  45

Trp Met Phe Lys Leu Leu Lys Arg Lys Leu Gly Arg Asp Pro Glu Ile
    50                  55                  60

Asn Asp Val Cys Asn Pro Lys Ala Gly Gly Tyr Leu Gly Gly Gln Ala
65                  70                  75                  80

Glu His Glu Arg Leu Asp Lys Ala Val Lys Met Asp Arg Asp Cys Ala
                85                  90                  95

Leu Gln Ser Ala Ser Trp Gly Leu Phe Gln Ile Met Gly Phe His Trp
            100                 105                 110

Glu Ala Leu Gly Tyr Ala Ser Val Gln Ala Phe Val Asn Ala Gln Tyr
        115                 120                 125

Ala Ser Glu Gly Ser Gln Leu Asn Thr Phe Val Arg Phe Ile Lys Thr
    130                 135                 140

Asn Pro Ala Ile His Lys Ala Leu Lys Ser Lys Asp Trp Ala Glu Phe
145                 150                 155                 160

Ala Arg Arg Tyr Asn Gly Pro Asp Tyr Lys Asn Asn Tyr Asp Val
                165                 170                 175

Lys Leu Ala Glu Ala Tyr Gln Ser Phe Lys
            180                 185
```

<210> SEQ ID NO 29
<211> LENGTH: 984
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: misc_feature
<222> LOCATION: (28)..(957)
<223> OTHER INFORMATION: GN349 lysin
<220> FEATURE:
<221> NAME/KEY: CDS
<222> LOCATION: (28)..(957)

<400> SEQUENCE: 29

```
gtttaacttt aagaaggaga attcacc atg gcc att tta aag att ggc agc aaa    54
                                Met Ala Ile Leu Lys Ile Gly Ser Lys
```

```
ggt ctg gaa gtt aag aat ctt cag acc agt ctc aac aaa atc ggg ttc    102
Gly Leu Glu Val Lys Asn Leu Gln Thr Ser Leu Asn Lys Ile Gly Phe
 10              15                  20                  25 aat ctg gtt gcc gat ggc ata ttt ggt aaa gcg act gac aac gcc gtc    150
Asn Leu Val Ala Asp Gly Ile Phe Gly Lys Ala Thr Asp Asn Ala Val
                 30                  35                  40 agg gca gtt cag gca ggt gcc gga ctg gtc gtt gat ggt att gct ggc    198
Arg Ala Val Gln Ala Gly Ala Gly Leu Val Val Asp Gly Ile Ala Gly
             45                  50                  55 ccc aag acc atg tat gcg att cgc aac gca ggg gag tct cat cag gat    246
Pro Lys Thr Met Tyr Ala Ile Arg Asn Ala Gly Glu Ser His Gln Asp
         60                  65                  70 cat ctg act gag gct gac ttg att gac gct gct cgt gaa ttg tct gtt    294
His Leu Thr Glu Ala Asp Leu Ile Asp Ala Ala Arg Glu Leu Ser Val
 75                  80                  85 gac ctt gct agc atc aag gca gtc aac caa gta gaa tcg cgc ggt act    342
Asp Leu Ala Ser Ile Lys Ala Val Asn Gln Val Glu Ser Arg Gly Thr
 90                  95                 100                 105 ggc ttc acc aag tct ggt aag atc aag aca ttg ttt gaa cgc cac atc    390
Gly Phe Thr Lys Ser Gly Lys Ile Lys Thr Leu Phe Glu Arg His Ile
                110                 115                 120 atg tac aaa aag ctg aat gcc aag ttc ggt cag gca aaa gcc aat gct    438
Met Tyr Lys Lys Leu Asn Ala Lys Phe Gly Gln Ala Lys Ala Asn Ala
            125                 130                 135 ctg gcc cag ctt tac ccg acg ttg gtt aac gcc aaa gcc ggg gga tac    486
Leu Ala Gln Leu Tyr Pro Thr Leu Val Asn Ala Lys Ala Gly Gly Tyr
        140                 145                 150 aca ggt ggg gac gcg gag ttg gaa cga ctc cat ggt gca ata gcg atc    534
Thr Gly Gly Asp Ala Glu Leu Glu Arg Leu His Gly Ala Ile Ala Ile
        155                 160                 165 gat aaa gat tgc gcc tac gag agc gct tcc tac ggg tta ttc cag atc    582
Asp Lys Asp Cys Ala Tyr Glu Ser Ala Ser Tyr Gly Leu Phe Gln Ile
170                 175                 180                 185 atg ggg ttc aac tgc gtt att tgt gga tat gac aat gcc gag gag atg    630
Met Gly Phe Asn Cys Val Ile Cys Gly Tyr Asp Asn Ala Glu Glu Met
                190                 195                 200 ttc aac gac ttt ctc act ggt gaa cgt gct cag ctc atg gca ttt gtc    678
Phe Asn Asp Phe Leu Thr Gly Glu Arg Ala Gln Leu Met Ala Phe Val
            205                 210                 215 aag ttc atc aag gct gac gcc aat ctg tgg aaa gca ttg aag gac aag    726
Lys Phe Ile Lys Ala Asp Ala Asn Leu Trp Lys Ala Leu Lys Asp Lys
        220                 225                 230 aat tgg gct gag ttt gct cgg cgt tac aat ggc ccg gcg tat gca cag    774
Asn Trp Ala Glu Phe Ala Arg Arg Tyr Asn Gly Pro Ala Tyr Ala Gln
235                 240                 245 aac cag tac gac acc aag ctg gct gca gca tac aaa tca ttc agt acc    822
Asn Gln Tyr Asp Thr Lys Leu Ala Ala Ala Tyr Lys Ser Phe Ser Thr
250                 255                 260                 265 gcg ggc ggc acc gcg ggc ggc gca cga aga tac aga ctt tcg cga cgc    870
Ala Gly Gly Thr Ala Gly Gly Ala Arg Arg Tyr Arg Leu Ser Arg Arg
                270                 275                 280 aga agt cga cga ctt ttt tca aga act gca tta aga atg cat cga aga    918
Arg Ser Arg Arg Leu Phe Ser Arg Thr Ala Leu Arg Met His Arg Arg
            285                 290                 295 aat aga ctt cga aga att atg cgt ggc ggc att agg ttt tagtaataaa    967
Asn Arg Leu Arg Arg Ile Met Arg Gly Gly Ile Arg Phe
        300                 305                 310 agcttggctg ttttggc                                                  984
```

<210> SEQ ID NO 30
<211> LENGTH: 310
<212> TYPE: PRT
<213> ORGANISM: Artificial Sequence
<220> FEATURE:
<223> OTHER INFORMATION: Synthetic Construct

<400> SEQUENCE: 30

```
Met Ala Ile Leu Lys Ile Gly Ser Lys Gly Leu Glu Val Lys Asn Leu
1               5                   10                  15

Gln Thr Ser Leu Asn Lys Ile Gly Phe Asn Leu Val Ala Asp Gly Ile
            20                  25                  30

Phe Gly Lys Ala Thr Asp Asn Ala Val Arg Ala Val Gln Ala Gly Ala
        35                  40                  45

Gly Leu Val Val Asp Gly Ile Ala Gly Pro Lys Thr Met Tyr Ala Ile
    50                  55                  60

Arg Asn Ala Gly Glu Ser His Gln Asp His Leu Thr Glu Ala Asp Leu
65                  70                  75                  80

Ile Asp Ala Ala Arg Glu Leu Ser Val Asp Leu Ala Ser Ile Lys Ala
                85                  90                  95

Val Asn Gln Val Glu Ser Arg Gly Thr Gly Phe Thr Lys Ser Gly Lys
            100                 105                 110

Ile Lys Thr Leu Phe Glu Arg His Ile Met Tyr Lys Lys Leu Asn Ala
        115                 120                 125

Lys Phe Gly Gln Ala Lys Ala Asn Ala Leu Ala Gln Leu Tyr Pro Thr
    130                 135                 140

Leu Val Asn Ala Lys Ala Gly Gly Tyr Thr Gly Gly Asp Ala Glu Leu
145                 150                 155                 160

Glu Arg Leu His Gly Ala Ile Ala Ile Asp Lys Asp Cys Ala Tyr Glu
                165                 170                 175

Ser Ala Ser Tyr Gly Leu Phe Gln Ile Met Gly Phe Asn Cys Val Ile
            180                 185                 190

Cys Gly Tyr Asp Asn Ala Glu Glu Met Phe Asn Asp Phe Leu Thr Gly
        195                 200                 205

Glu Arg Ala Gln Leu Met Ala Phe Val Lys Phe Ile Lys Ala Asp Ala
    210                 215                 220

Asn Leu Trp Lys Ala Leu Lys Asp Lys Asn Trp Ala Glu Phe Ala Arg
225                 230                 235                 240

Arg Tyr Asn Gly Pro Ala Tyr Ala Gln Asn Gln Tyr Asp Thr Lys Leu
                245                 250                 255

Ala Ala Ala Tyr Lys Ser Phe Ser Thr Ala Gly Gly Thr Ala Gly Gly
            260                 265                 270

Ala Arg Arg Tyr Arg Leu Ser Arg Arg Ser Arg Leu Phe Ser
        275                 280                 285

Arg Thr Ala Leu Arg Met His Arg Arg Asn Arg Leu Arg Arg Ile Met
    290                 295                 300

Arg Gly Gly Ile Arg Phe
305                 310
```

<210> SEQ ID NO 31
<211> LENGTH: 984
<212> TYPE: DNA
<213> ORGANISM: Artificial Sequence
<220> FEATURE:
<223> OTHER INFORMATION: Description of Artificial Sequence: Synthetic polynucleotide

```
<220> FEATURE:
<221> NAME/KEY: misc_feature
<222> LOCATION: (28)..(957)
<223> OTHER INFORMATION: GN351 lysin
<220> FEATURE:
<221> NAME/KEY: CDS
<222> LOCATION: (28)..(957)

<400> SEQUENCE: 31
gtttaacttt aagaaggaga attcacc atg gcc att tta aag att ggc agc aaa      54
                           Met Ala Ile Leu Lys Ile Gly Ser Lys
                           1               5 ggt ctg gaa gtt aag aat ctt cag acc agt ctc aac aaa atc ggg ttc      102
Gly Leu Glu Val Lys Asn Leu Gln Thr Ser Leu Asn Lys Ile Gly Phe
 10              15                  20                  25 aat ctg gtt gcc gat ggc ata ttt ggt aaa gcg act gac aac gcc gtc      150
Asn Leu Val Ala Asp Gly Ile Phe Gly Lys Ala Thr Asp Asn Ala Val
             30                  35                  40 agg gca gtt cag gca ggt gcc gga ctg gtc gtt gat ggt att gct ggc      198
Arg Ala Val Gln Ala Gly Ala Gly Leu Val Val Asp Gly Ile Ala Gly
         45                  50                  55 ccc aag acc atg tat gcg att cgc aac gca ggg gag tct cat cag gat      246
Pro Lys Thr Met Tyr Ala Ile Arg Asn Ala Gly Glu Ser His Gln Asp
     60                  65                  70 cat ctg act gag gct gac ttg att gac gct gct cgt gaa ttg tct gtt      294
His Leu Thr Glu Ala Asp Leu Ile Asp Ala Ala Arg Glu Leu Ser Val
 75                  80                  85 gac ctt gct agc atc aag gca gtc aac caa gta gaa tcg cgc ggt act      342
Asp Leu Ala Ser Ile Lys Ala Val Asn Gln Val Glu Ser Arg Gly Thr
 90                  95                 100                 105 ggc ttc acc aag tct ggt aag atc aag aca ttg ttt gaa cgc cac atc      390
Gly Phe Thr Lys Ser Gly Lys Ile Lys Thr Leu Phe Glu Arg His Ile
             110                 115                 120 atg tac aaa aag ctg aat gcc aag ttc ggt cag gca aaa gcc aat gct      438
Met Tyr Lys Lys Leu Asn Ala Lys Phe Gly Gln Ala Lys Ala Asn Ala
         125                 130                 135 ctg gcc cag ctt tac ccg acg ttg gtt aac gcc aaa gcc ggg gga tac      486
Leu Ala Gln Leu Tyr Pro Thr Leu Val Asn Ala Lys Ala Gly Gly Tyr
     140                 145                 150 aca ggt ggg gac gcg gag ttg gaa cga ctc cat ggt gca ata gcg atc      534
Thr Gly Gly Asp Ala Glu Leu Glu Arg Leu His Gly Ala Ile Ala Ile
 155                 160                 165 gat aaa gat tgc gcc tac gag agc gct tcc tac ggg tta ttc cag atc      582
Asp Lys Asp Cys Ala Tyr Glu Ser Ala Ser Tyr Gly Leu Phe Gln Ile
170                 175                 180                 185 atg ggg ttc aac tgc gtt att tgt gga tat gac aat gcc gag gag atg      630
Met Gly Phe Asn Cys Val Ile Cys Gly Tyr Asp Asn Ala Glu Glu Met
             190                 195                 200 ttc aac gac ttt ctc act ggt gaa cgt gct cag ctc atg gca ttt gtc      678
Phe Asn Asp Phe Leu Thr Gly Glu Arg Ala Gln Leu Met Ala Phe Val
         205                 210                 215 aag ttc atc aag gct gac gcc aat ctg tgg aaa gca ttg aag gac aag      726
Lys Phe Ile Lys Ala Asp Ala Asn Leu Trp Lys Ala Leu Lys Asp Lys
     220                 225                 230 aat tgg gct gag ttt gct cgg cgt tac aat ggc ccg gcg tat gca cag      774
Asn Trp Ala Glu Phe Ala Arg Arg Tyr Asn Gly Pro Ala Tyr Ala Gln
 235                 240                 245 aac cag tac gac acc aag ctg gct gca gca tac aaa tca ttc agt acc      822
Asn Gln Tyr Asp Thr Lys Leu Ala Ala Ala Tyr Lys Ser Phe Ser Thr
250                 255                 260                 265 gcg ggc ggc acc gcg ggc ggc gct cgt tcc cgt aga cgt atg tct aag      870
Ala Gly Gly Thr Ala Gly Gly Ala Arg Ser Arg Arg Arg Met Ser Lys
```

```
Ala Gly Gly Thr Ala Gly Gly Ala Arg Ser Arg Arg Met Ser Lys
                270                 275                 280 cgt tct tcc cgc cgt tcg ttc cgc aag tat gcg aag tcg cat aag aag       918
Arg Ser Ser Arg Arg Ser Phe Arg Lys Tyr Ala Lys Ser His Lys Lys
            285                 290                 295 aac ttt aaa gcc cgc tca atg cgt ggc ggt atc cgt tta tgataataaa        967
Asn Phe Lys Ala Arg Ser Met Arg Gly Gly Ile Arg Leu
        300                 305                 310 agcttggctg ttttggc                                                    984

<210> SEQ ID NO 32
<211> LENGTH: 310
<212> TYPE: PRT
<213> ORGANISM: Artificial Sequence
<220> FEATURE:
<223> OTHER INFORMATION: Synthetic Construct

<400> SEQUENCE: 32

Met Ala Ile Leu Lys Ile Gly Ser Lys Gly Leu Glu Val Lys Asn Leu
1               5                   10                  15

Gln Thr Ser Leu Asn Lys Ile Gly Phe Asn Leu Val Ala Asp Gly Ile
            20                  25                  30

Phe Gly Lys Ala Thr Asp Asn Ala Val Arg Ala Val Gln Ala Gly Ala
        35                  40                  45

Gly Leu Val Val Asp Gly Ile Ala Gly Pro Lys Thr Met Tyr Ala Ile
    50                  55                  60

Arg Asn Ala Gly Glu Ser His Gln Asp His Leu Thr Glu Ala Asp Leu
65                  70                  75                  80

Ile Asp Ala Ala Arg Glu Leu Ser Val Asp Leu Ala Ser Ile Lys Ala
                85                  90                  95

Val Asn Gln Val Glu Ser Arg Gly Thr Gly Phe Thr Lys Ser Gly Lys
            100                 105                 110

Ile Lys Thr Leu Phe Glu Arg His Ile Met Tyr Lys Lys Leu Asn Ala
        115                 120                 125

Lys Phe Gly Gln Ala Lys Ala Asn Ala Leu Ala Gln Leu Tyr Pro Thr
    130                 135                 140

Leu Val Asn Ala Lys Ala Gly Gly Tyr Thr Gly Gly Asp Ala Glu Leu
145                 150                 155                 160

Glu Arg Leu His Gly Ala Ile Ala Ile Asp Lys Asp Cys Ala Tyr Glu
                165                 170                 175

Ser Ala Ser Tyr Gly Leu Phe Gln Ile Met Gly Phe Asn Cys Val Ile
            180                 185                 190

Cys Gly Tyr Asp Asn Ala Glu Glu Met Phe Asn Asp Phe Leu Thr Gly
        195                 200                 205

Glu Arg Ala Gln Leu Met Ala Phe Val Lys Phe Ile Lys Ala Asp Ala
    210                 215                 220

Asn Leu Trp Lys Ala Leu Lys Asp Lys Asn Trp Ala Glu Phe Ala Arg
225                 230                 235                 240

Arg Tyr Asn Gly Pro Ala Tyr Ala Gln Asn Gln Tyr Asp Thr Lys Leu
                245                 250                 255

Ala Ala Ala Tyr Lys Ser Phe Ser Thr Ala Gly Thr Ala Gly Gly
            260                 265                 270

Ala Arg Ser Arg Arg Met Ser Lys Arg Ser Ser Arg Arg Ser Phe
        275                 280                 285

Arg Lys Tyr Ala Lys Ser His Lys Lys Asn Phe Lys Ala Arg Ser Met
    290                 295                 300
```

```
<210> SEQ ID NO 33
<211> LENGTH: 981
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<223> OTHER INFORMATION: GN352 lysin28
<220> FEATURE:
<221> NAME/KEY: CDS
<222> LOCATION: (28)..(954)

<400> SEQUENCE: 33
gtttaacttt aagaaggaga attcacc atg gcc att tta aag att ggc agc aaa         54
                               Met Ala Ile Leu Lys Ile Gly Ser Lys
                                 1               5 ggt ctg gaa gtt aag aat ctt cag acc agt ctc aac aaa atc ggg ttc         102
Gly Leu Glu Val Lys Asn Leu Gln Thr Ser Leu Asn Lys Ile Gly Phe
 10              15                  20                  25 aat ctg gtt gcc gat ggc ata ttt ggt aaa gcg act gac aac gcc gtc         150
Asn Leu Val Ala Asp Gly Ile Phe Gly Lys Ala Thr Asp Asn Ala Val
                 30                  35                  40 agg gca gtt cag gca ggt gcc gga ctg gtc gtt gat ggt att gct ggc         198
Arg Ala Val Gln Ala Gly Ala Gly Leu Val Val Asp Gly Ile Ala Gly
             45                  50                  55 ccc aag acc atg tat gcg att cgc aac gca ggg gag tct cat cag gat         246
Pro Lys Thr Met Tyr Ala Ile Arg Asn Ala Gly Glu Ser His Gln Asp
         60                  65                  70 cat ctg act gag gct gac ttg att gac gct gct cgt gaa ttg tct gtt         294
His Leu Thr Glu Ala Asp Leu Ile Asp Ala Ala Arg Glu Leu Ser Val
     75                  80                  85 gac ctt gct agc atc aag gca gtc aac caa gta gaa tcg cgc ggt act         342
Asp Leu Ala Ser Ile Lys Ala Val Asn Gln Val Glu Ser Arg Gly Thr
 90                  95                 100                 105 ggc ttc acc aag tct ggt aag atc aag aca ttg ttt gaa cgc cac atc         390
Gly Phe Thr Lys Ser Gly Lys Ile Lys Thr Leu Phe Glu Arg His Ile
                110                 115                 120 atg tac aaa aag ctg aat gcc aag ttc ggt cag gca aaa gcc aat gct         438
Met Tyr Lys Lys Leu Asn Ala Lys Phe Gly Gln Ala Lys Ala Asn Ala
            125                 130                 135 ctg gcc cag ctt tac ccg acg ttg gtt aac gcc aaa gcc ggg gga tac         486
Leu Ala Gln Leu Tyr Pro Thr Leu Val Asn Ala Lys Ala Gly Gly Tyr
        140                 145                 150 aca ggt ggg gac gcg gag ttg gaa cga ctc cat ggt gca ata gcg atc         534
Thr Gly Gly Asp Ala Glu Leu Glu Arg Leu His Gly Ala Ile Ala Ile
    155                 160                 165 gat aaa gat tgc gcc tac gag agc gct tcc tac ggg tta ttc cag atc         582
Asp Lys Asp Cys Ala Tyr Glu Ser Ala Ser Tyr Gly Leu Phe Gln Ile
170                 175                 180                 185 atg ggg ttc aac tgc gtt att tgt gga tat gac aat gcc gag gag atg         630
Met Gly Phe Asn Cys Val Ile Cys Gly Tyr Asp Asn Ala Glu Glu Met
                190                 195                 200 ttc aac gac ttt ctc act ggt gaa cgt gct cag ctc atg gca ttt gtc         678
Phe Asn Asp Phe Leu Thr Gly Glu Arg Ala Gln Leu Met Ala Phe Val
            205                 210                 215 aag ttc atc aag gct gac gcc aat ctg tgg aaa gca ttg aag gac aag         726
Lys Phe Ile Lys Ala Asp Ala Asn Leu Trp Lys Ala Leu Lys Asp Lys
        220                 225                 230
```

```
                   220                 225                 230
aat tgg gct gag ttt gct cgg cgt tac aat ggc ccg gcg tat gca cag      774
Asn Trp Ala Glu Phe Ala Arg Arg Tyr Asn Gly Pro Ala Tyr Ala Gln
    235                 240                 245 aac cag tac gac acc aag ctg gct gca gca tac aaa tca ttc agt acc      822
Asn Gln Tyr Asp Thr Lys Leu Ala Ala Ala Tyr Lys Ser Phe Ser Thr
250                 255                 260                 265 gcg ggc ggc acc gcg ggc ggc aaa cgt aga aaa atg aca aga aaa ggt      870
Ala Gly Gly Thr Ala Gly Gly Lys Arg Arg Lys Met Thr Arg Lys Gly
                270                 275                 280 tct aag cgt ctt ttt act gca act gct gat aaa act aaa tct atc aat      918
Ser Lys Arg Leu Phe Thr Ala Thr Ala Asp Lys Thr Lys Ser Ile Asn
            285                 290                 295 act gcc ccg ccg cca atg cgt ggc ggt atc cgg ttg tagtaataaa          964
Thr Ala Pro Pro Pro Met Arg Gly Gly Ile Arg Leu
        300                 305 agcttggctg ttttggc                                                   981
```

<210> SEQ ID NO 34
<211> LENGTH: 309
<212> TYPE: PRT
<213> ORGANISM: Artificial Sequence
<220> FEATURE:
<223> OTHER INFORMATION: Synthetic Construct

<400> SEQUENCE: 34

```
Met Ala Ile Leu Lys Ile Gly Ser Lys Gly Leu Glu Val Lys Asn Leu
1               5                   10                  15

Gln Thr Ser Leu Asn Lys Ile Gly Phe Asn Leu Val Ala Asp Gly Ile
            20                  25                  30

Phe Gly Lys Ala Thr Asp Asn Ala Val Arg Ala Val Gln Ala Gly Ala
        35                  40                  45

Gly Leu Val Val Asp Gly Ile Ala Gly Pro Lys Thr Met Tyr Ala Ile
    50                  55                  60

Arg Asn Ala Gly Glu Ser His Gln Asp His Leu Thr Glu Ala Asp Leu
65                  70                  75                  80

Ile Asp Ala Ala Arg Glu Leu Ser Val Asp Leu Ala Ser Ile Lys Ala
                85                  90                  95

Val Asn Gln Val Glu Ser Arg Gly Thr Gly Phe Thr Lys Ser Gly Lys
            100                 105                 110

Ile Lys Thr Leu Phe Glu Arg His Ile Met Tyr Lys Lys Leu Asn Ala
        115                 120                 125

Lys Phe Gly Gln Ala Lys Ala Asn Ala Leu Ala Gln Leu Tyr Pro Thr
    130                 135                 140

Leu Val Asn Ala Lys Ala Gly Gly Tyr Thr Gly Gly Asp Ala Glu Leu
145                 150                 155                 160

Glu Arg Leu His Gly Ala Ile Ala Ile Asp Lys Asp Cys Ala Tyr Glu
                165                 170                 175

Ser Ala Ser Tyr Gly Leu Phe Gln Ile Met Gly Phe Asn Cys Val Ile
            180                 185                 190

Cys Gly Tyr Asp Asn Ala Glu Glu Met Phe Asn Asp Phe Leu Thr Gly
        195                 200                 205

Glu Arg Ala Gln Leu Met Ala Phe Val Lys Phe Ile Lys Ala Asp Ala
    210                 215                 220

Asn Leu Trp Lys Ala Leu Lys Asp Lys Asn Trp Ala Glu Phe Ala Arg
225                 230                 235                 240
```

```
Arg Tyr Asn Gly Pro Ala Tyr Ala Gln Asn Gln Tyr Asp Thr Lys Leu
                245                 250                 255

Ala Ala Ala Tyr Lys Ser Phe Ser Thr Ala Gly Gly Thr Ala Gly Gly
            260                 265                 270

Lys Arg Arg Lys Met Thr Arg Lys Gly Ser Lys Arg Leu Phe Thr Ala
        275                 280                 285

Thr Ala Asp Lys Thr Lys Ser Ile Asn Thr Ala Pro Pro Met Arg
290                 295                 300

Gly Gly Ile Arg Leu
305

<210> SEQ ID NO 35
<211> LENGTH: 978
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (28)..(951)
<223> OTHER INFORMATION: GN353 lysin
<220> FEATURE:
<221> NAME/KEY: CDS
<222> LOCATION: (28)..(951)

<400> SEQUENCE: 35
gtttaacttt aagaaggaga attcacc atg gcc att tta aag att ggc agc aaa       54
                            Met Ala Ile Leu Lys Ile Gly Ser Lys
                              1               5 ggt ctg gaa gtt aag aat ctt cag acc agt ctc aac aaa atc ggg ttc      102
Gly Leu Glu Val Lys Asn Leu Gln Thr Ser Leu Asn Lys Ile Gly Phe
 10              15                  20                  25 aat ctg gtt gcc gat ggc ata ttt ggt aaa gcg act gac aac gcc gtc      150
Asn Leu Val Ala Asp Gly Ile Phe Gly Lys Ala Thr Asp Asn Ala Val
                 30                  35                  40 agg gca gtt cag gca ggt gcc gga ctg gtc gtt gat ggt att gct ggc      198
Arg Ala Val Gln Ala Gly Ala Gly Leu Val Val Asp Gly Ile Ala Gly
             45                  50                  55 ccc aag acc atg tat gcg att cgc aac gca ggg gag tct cat cag gat      246
Pro Lys Thr Met Tyr Ala Ile Arg Asn Ala Gly Glu Ser His Gln Asp
         60                  65                  70 cat ctg act gag gct gac ttg att gac gct gct cgt gaa ttg tct gtt      294
His Leu Thr Glu Ala Asp Leu Ile Asp Ala Ala Arg Glu Leu Ser Val
     75                  80                  85 gac ctt gct agc atc aag gca gtc aac caa gta gaa tcg cgc ggt act      342
Asp Leu Ala Ser Ile Lys Ala Val Asn Gln Val Glu Ser Arg Gly Thr
 90                  95                 100                 105 ggc ttc acc aag tct ggt aag atc aag aca ttg ttt gaa cgc cac atc      390
Gly Phe Thr Lys Ser Gly Lys Ile Lys Thr Leu Phe Glu Arg His Ile
                110                 115                 120 atg tac aaa aag ctg aat gcc aag ttc ggt cag gca aaa gcc aat gct      438
Met Tyr Lys Lys Leu Asn Ala Lys Phe Gly Gln Ala Lys Ala Asn Ala
            125                 130                 135 ctg gcc cag ctt tac ccg acg ttg gtt aac gcc aaa gcc ggg gga tac      486
Leu Ala Gln Leu Tyr Pro Thr Leu Val Asn Ala Lys Ala Gly Gly Tyr
        140                 145                 150 aca ggt ggg gac gcg gag ttg gaa cga ctc cat ggt gca ata gcg atc      534
Thr Gly Gly Asp Ala Glu Leu Glu Arg Leu His Gly Ala Ile Ala Ile
    155                 160                 165 gat aaa gat tgc gcc tac gag agc gct tcc tac ggg tta ttc cag atc      582
Asp Lys Asp Cys Ala Tyr Glu Ser Ala Ser Tyr Gly Leu Phe Gln Ile
```

```
atg ggg ttc aac tgc gtt att tgt gga tat gac aat gcc gag gag atg         630
Met Gly Phe Asn Cys Val Ile Cys Gly Tyr Asp Asn Ala Glu Glu Met
            190                 195                 200 ttc aac gac ttt ctc act ggt gaa cgt gct cag ctc atg gca ttt gtc         678
Phe Asn Asp Phe Leu Thr Gly Glu Arg Ala Gln Leu Met Ala Phe Val
            205                 210                 215 aag ttc atc aag gct gac gcc aat ctg tgg aaa gca ttg aag gac aag         726
Lys Phe Ile Lys Ala Asp Ala Asn Leu Trp Lys Ala Leu Lys Asp Lys
            220                 225                 230 aat tgg gct gag ttt gct cgg cgt tac aat ggc ccg gcg tat gca cag         774
Asn Trp Ala Glu Phe Ala Arg Arg Tyr Asn Gly Pro Ala Tyr Ala Gln
        235                 240                 245 aac cag tac gac acc aag ctg gct gca gca tac aaa tca ttc agt acc         822
Asn Gln Tyr Asp Thr Lys Leu Ala Ala Ala Tyr Lys Ser Phe Ser Thr
250                 255                 260                 265 gcg ggc ggc acc gcg ggc ggc aga aag cga atg tct aag cgt gtt gac         870
Ala Gly Gly Thr Ala Gly Gly Arg Lys Arg Met Ser Lys Arg Val Asp
            270                 275                 280 aag aag gtg ttc cgt cgt act gcc gca tct gcc aag aag att aac att         918
Lys Lys Val Phe Arg Arg Thr Ala Ala Ser Ala Lys Lys Ile Asn Ile
            285                 290                 295 gac ccc aag att tac cgt gga ggt att cgc cta tgataataaa agcttggctg      971
Asp Pro Lys Ile Tyr Arg Gly Gly Ile Arg Leu
            300                 305 tttggc                                                                  978
```

<210> SEQ ID NO 36
<211> LENGTH: 308
<212> TYPE: PRT
<213> ORGANISM: Artificial Sequence
<220> FEATURE:
<223> OTHER INFORMATION: Synthetic Construct

<400> SEQUENCE: 36

```
Met Ala Ile Leu Lys Ile Gly Ser Lys Gly Leu Glu Val Lys Asn Leu
1               5                   10                  15

Gln Thr Ser Leu Asn Lys Ile Gly Phe Asn Leu Val Ala Asp Gly Ile
            20                  25                  30

Phe Gly Lys Ala Thr Asp Asn Ala Val Arg Ala Val Gln Ala Gly Ala
        35                  40                  45

Gly Leu Val Val Asp Gly Ile Ala Gly Pro Lys Thr Met Tyr Ala Ile
    50                  55                  60

Arg Asn Ala Gly Glu Ser His Gln Asp His Leu Thr Glu Ala Asp Leu
65                  70                  75                  80

Ile Asp Ala Ala Arg Glu Leu Ser Val Asp Leu Ala Ser Ile Lys Ala
                85                  90                  95

Val Asn Gln Val Glu Ser Arg Gly Thr Gly Phe Thr Lys Ser Gly Lys
            100                 105                 110

Ile Lys Thr Leu Phe Glu Arg His Ile Met Tyr Lys Lys Leu Asn Ala
        115                 120                 125

Lys Phe Gly Gln Ala Lys Ala Asn Ala Leu Ala Gln Leu Tyr Pro Thr
    130                 135                 140

Leu Val Asn Ala Lys Ala Gly Gly Tyr Thr Gly Gly Asp Ala Glu Leu
145                 150                 155                 160

Glu Arg Leu His Gly Ala Ile Ala Ile Asp Lys Asp Cys Ala Tyr Glu
                165                 170                 175
```

```
Ser Ala Ser Tyr Gly Leu Phe Gln Ile Met Gly Phe Asn Cys Val Ile
            180                 185                 190

Cys Gly Tyr Asp Asn Ala Glu Glu Met Phe Asn Asp Phe Leu Thr Gly
        195                 200                 205

Glu Arg Ala Gln Leu Met Ala Phe Val Lys Phe Ile Lys Ala Asp Ala
    210                 215                 220

Asn Leu Trp Lys Ala Leu Lys Asp Lys Asn Trp Ala Glu Phe Ala Arg
225                 230                 235                 240

Arg Tyr Asn Gly Pro Ala Tyr Ala Gln Asn Gln Tyr Asp Thr Lys Leu
                245                 250                 255

Ala Ala Ala Tyr Lys Ser Phe Ser Thr Ala Gly Gly Thr Ala Gly Gly
            260                 265                 270

Arg Lys Arg Met Ser Lys Arg Val Asp Lys Lys Val Phe Arg Arg Thr
        275                 280                 285

Ala Ala Ser Ala Lys Lys Ile Asn Ile Asp Pro Lys Ile Tyr Arg Gly
    290                 295                 300

Gly Ile Arg Leu
305

<210> SEQ ID NO 37
<211> LENGTH: 903
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (28)..(879)
<220> FEATURE:
<221> NAME/KEY: misc_feature
<222> LOCATION: (28)..(879)
<223> OTHER INFORMATION: GN357 lysin
<220> FEATURE:
<221> NAME/KEY: CDS
<222> LOCATION: (28)..(879)

<400> SEQUENCE: 37
gtttaacttt aagaaggaga attcacc atg gcc att tta aag att ggc agc aaa       54
                                Met Ala Ile Leu Lys Ile Gly Ser Lys
                                  1               5 ggt ctg gaa gtt aag aat ctt cag acc agt ctc aac aaa atc ggg ttc      102
Gly Leu Glu Val Lys Asn Leu Gln Thr Ser Leu Asn Lys Ile Gly Phe
 10              15                  20                  25 aat ctg gtt gcc gat ggc ata ttt ggt aaa gcg act gac aac gcc gtc      150
Asn Leu Val Ala Asp Gly Ile Phe Gly Lys Ala Thr Asp Asn Ala Val
                 30                  35                  40 agg gca gtt cag gca ggt gcc gga ctg gtc gtt gat ggt att gct ggc      198
Arg Ala Val Gln Ala Gly Ala Gly Leu Val Val Asp Gly Ile Ala Gly
             45                  50                  55 ccc aag acc atg tat gcg att cgc aac gca ggg gag tct cat cag gat      246
Pro Lys Thr Met Tyr Ala Ile Arg Asn Ala Gly Glu Ser His Gln Asp
         60                  65                  70 cat ctg act gag gct gac ttg att gac gct gct cgt gaa ttg tct gtt      294
His Leu Thr Glu Ala Asp Leu Ile Asp Ala Ala Arg Glu Leu Ser Val
     75                  80                  85 gac ctt gct agc atc aag gca gtc aac caa gta gaa tcg cgc ggt act      342
Asp Leu Ala Ser Ile Lys Ala Val Asn Gln Val Glu Ser Arg Gly Thr
 90                  95                 100                 105 ggc ttc acc aag tct ggt aag atc aag aca ttg ttt gaa cgc cac atc      390
Gly Phe Thr Lys Ser Gly Lys Ile Lys Thr Leu Phe Glu Arg His Ile
                110                 115                 120
```

```
atg tac aaa aag ctg aat gcc aag ttc ggt cag gca aaa gcc aat gct    438
Met Tyr Lys Lys Leu Asn Ala Lys Phe Gly Gln Ala Lys Ala Asn Ala
            125                 130                 135 ctg gcc cag ctt tac ccg acg ttg gtt aac gcc aaa gcc ggg gga tac    486
Leu Ala Gln Leu Tyr Pro Thr Leu Val Asn Ala Lys Ala Gly Gly Tyr
        140                 145                 150 aca ggt ggg gac gcg gag ttg gaa cga ctc cat ggt gca ata gcg atc    534
Thr Gly Gly Asp Ala Glu Leu Glu Arg Leu His Gly Ala Ile Ala Ile
    155                 160                 165 gat aaa gat tgc gcc tac gag agc gct tcc tac ggg tta ttc cag atc    582
Asp Lys Asp Cys Ala Tyr Glu Ser Ala Ser Tyr Gly Leu Phe Gln Ile
170                 175                 180                 185 atg ggg ttc aac tgc gtt att tgt gga tat gac aat gcc gag gag atg    630
Met Gly Phe Asn Cys Val Ile Cys Gly Tyr Asp Asn Ala Glu Glu Met
                190                 195                 200 ttc aac gac ttt ctc act ggt gaa cgt gct cag ctc atg gca ttt gtc    678
Phe Asn Asp Phe Leu Thr Gly Glu Arg Ala Gln Leu Met Ala Phe Val
            205                 210                 215 aag ttc atc aag gct gac gcc aat ctg tgg aaa gca ttg aag gac aag    726
Lys Phe Ile Lys Ala Asp Ala Asn Leu Trp Lys Ala Leu Lys Asp Lys
        220                 225                 230 aat tgg gct gag ttt gct cgg cgt tac aat ggc ccg gcg tat gca cag    774
Asn Trp Ala Glu Phe Ala Arg Arg Tyr Asn Gly Pro Ala Tyr Ala Gln
    235                 240                 245 aac cag tac gac acc aag ctg gct gca gca tac aaa tca ttc agt acc    822
Asn Gln Tyr Asp Thr Lys Leu Ala Ala Ala Tyr Lys Ser Phe Ser Thr
250                 255                 260                 265 gcg ggc ggc acc gcg ggc ggc cgc cgc ctg att cgc ctg tgg ctg cgc    870
Ala Gly Gly Thr Ala Gly Gly Arg Arg Leu Ile Arg Leu Trp Leu Arg
                270                 275                 280 ctg ctg cgc taataaaagc ttggctgttt tggc                             903
Leu Leu Arg <210> SEQ ID NO 38
<211> LENGTH: 284
<212> TYPE: PRT
<213> ORGANISM: Artificial Sequence
<220> FEATURE:
<223> OTHER INFORMATION: Synthetic Construct

<400> SEQUENCE: 38

Met Ala Ile Leu Lys Ile Gly Ser Lys Gly Leu Glu Val Lys Asn Leu
1               5                   10                  15

Gln Thr Ser Leu Asn Lys Ile Gly Phe Asn Leu Val Ala Asp Gly Ile
            20                  25                  30

Phe Gly Lys Ala Thr Asp Asn Ala Val Arg Ala Val Gln Ala Gly Ala
        35                  40                  45

Gly Leu Val Val Asp Gly Ile Ala Gly Pro Lys Thr Met Tyr Ala Ile
    50                  55                  60

Arg Asn Ala Gly Glu Ser His Gln Asp His Leu Thr Glu Ala Asp Leu
65                  70                  75                  80

Ile Asp Ala Ala Arg Glu Leu Ser Val Asp Leu Ala Ser Ile Lys Ala
                85                  90                  95

Val Asn Gln Val Glu Ser Arg Gly Thr Gly Phe Thr Lys Ser Gly Lys
            100                 105                 110

Ile Lys Thr Leu Phe Glu Arg His Ile Met Tyr Lys Lys Leu Asn Ala
        115                 120                 125

Lys Phe Gly Gln Ala Lys Ala Asn Ala Leu Ala Gln Leu Tyr Pro Thr
```

```
                130                 135                 140
Leu Val Asn Ala Lys Ala Gly Gly Tyr Thr Gly Gly Asp Ala Glu Leu
145                 150                 155                 160

Glu Arg Leu His Gly Ala Ile Ala Ile Asp Lys Asp Cys Ala Tyr Glu
                165                 170                 175

Ser Ala Ser Tyr Gly Leu Phe Gln Ile Met Gly Phe Asn Cys Val Ile
            180                 185                 190

Cys Gly Tyr Asp Asn Ala Glu Glu Met Phe Asn Asp Phe Leu Thr Gly
        195                 200                 205

Glu Arg Ala Gln Leu Met Ala Phe Val Lys Phe Ile Lys Ala Asp Ala
    210                 215                 220

Asn Leu Trp Lys Ala Leu Lys Asp Lys Asn Trp Ala Glu Phe Ala Arg
225                 230                 235                 240

Arg Tyr Asn Gly Pro Ala Tyr Ala Gln Asn Gln Tyr Asp Thr Lys Leu
                245                 250                 255

Ala Ala Ala Tyr Lys Ser Phe Ser Thr Ala Gly Gly Thr Ala Gly Gly
            260                 265                 270

Arg Arg Leu Ile Arg Leu Trp Leu Arg Leu Leu Arg
        275                 280

<210> SEQ ID NO 39
<211> LENGTH: 912
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (28)..(888)
<223> OTHER INFORMATION: GN359 lysin
<220> FEATURE:
<221> NAME/KEY: CDS
<222> LOCATION: (28)..(888)

<400> SEQUENCE: 39
gtttaacttt aagaaggaga attcacc atg gcc att tta aag att ggc agc aaa      54
                                Met Ala Ile Leu Lys Ile Gly Ser Lys
                                 1               5 ggt ctg gaa gtt aag aat ctt cag acc agt ctc aac aaa atc ggg ttc     102
Gly Leu Glu Val Lys Asn Leu Gln Thr Ser Leu Asn Lys Ile Gly Phe
 10              15                  20                  25 aat ctg gtt gcc gat ggc ata ttt ggt aaa gcg act gac aac gcc gtc     150
Asn Leu Val Ala Asp Gly Ile Phe Gly Lys Ala Thr Asp Asn Ala Val
                 30                  35                  40 agg gca gtt cag gca ggt gcc gga ctg gtc gtt gat ggt att gct ggc     198
Arg Ala Val Gln Ala Gly Ala Gly Leu Val Val Asp Gly Ile Ala Gly
             45                  50                  55 ccc aag acc atg tat gcg att cgc aac gca ggg gag tct cat cag gat     246
Pro Lys Thr Met Tyr Ala Ile Arg Asn Ala Gly Glu Ser His Gln Asp
         60                  65                  70 cat ctg act gag gct gac ttg att gac gct gct cgt gaa ttg tct gtt     294
His Leu Thr Glu Ala Asp Leu Ile Asp Ala Ala Arg Glu Leu Ser Val
     75                  80                  85 gac ctt gct agc atc aag gca gtc aac caa gta gaa tcg cgc ggt act     342
Asp Leu Ala Ser Ile Lys Ala Val Asn Gln Val Glu Ser Arg Gly Thr
 90                  95                 100                 105 ggc ttc acc aag tct ggt aag atc aag aca ttg ttt gaa cgc cac atc     390
Gly Phe Thr Lys Ser Gly Lys Ile Lys Thr Leu Phe Glu Arg His Ile
                110                 115                 120
```

```
atg tac aaa aag ctg aat gcc aag ttc ggt cag gca aaa gcc aat gct       438
Met Tyr Lys Lys Leu Asn Ala Lys Phe Gly Gln Ala Lys Ala Asn Ala
            125                 130                 135 ctg gcc cag ctt tac ccg acg ttg gtt aac gcc aaa gcc ggg gga tac       486
Leu Ala Gln Leu Tyr Pro Thr Leu Val Asn Ala Lys Ala Gly Gly Tyr
        140                 145                 150 aca ggt ggg gac gcg gag ttg gaa cga ctc cat ggt gca ata gcg atc       534
Thr Gly Gly Asp Ala Glu Leu Glu Arg Leu His Gly Ala Ile Ala Ile
    155                 160                 165 gat aaa gat tgc gcc tac gag agc gct tcc tac ggg tta ttc cag atc       582
Asp Lys Asp Cys Ala Tyr Glu Ser Ala Ser Tyr Gly Leu Phe Gln Ile
170                 175                 180                 185 atg ggg ttc aac tgc gtt att tgt gga tat gac aat gcc gag gag atg       630
Met Gly Phe Asn Cys Val Ile Cys Gly Tyr Asp Asn Ala Glu Glu Met
            190                 195                 200 ttc aac gac ttt ctc act ggt gaa cgt gct cag ctc atg gca ttt gtc       678
Phe Asn Asp Phe Leu Thr Gly Glu Arg Ala Gln Leu Met Ala Phe Val
        205                 210                 215 aag ttc atc aag gct gac gcc aat ctg tgg aaa gca ttg aag gac aag       726
Lys Phe Ile Lys Ala Asp Ala Asn Leu Trp Lys Ala Leu Lys Asp Lys
    220                 225                 230 aat tgg gct gag ttt gct cgg cgt tac aat ggc ccg gcg tat gca cag       774
Asn Trp Ala Glu Phe Ala Arg Arg Tyr Asn Gly Pro Ala Tyr Ala Gln
235                 240                 245 aac cag tac gac acc aag ctg gct gca gca tac aaa tca ttc agt acc       822
Asn Gln Tyr Asp Thr Lys Leu Ala Ala Ala Tyr Lys Ser Phe Ser Thr
            250                 255                 260                 265 gcg ggc ggc acc gcg ggc ggc acc cgc aaa cgc ctg aaa aaa att ggc       870
Ala Gly Gly Thr Ala Gly Gly Thr Arg Lys Arg Leu Lys Lys Ile Gly
        270                 275                 280 aaa gtg ctg aaa tgg att taataaaagc ttggctgttt tggc                    912
Lys Val Leu Lys Trp Ile
            285
```

<210> SEQ ID NO 40
<211> LENGTH: 287
<212> TYPE: PRT
<213> ORGANISM: Artificial Sequence
<220> FEATURE:
<223> OTHER INFORMATION: Synthetic Construct

<400> SEQUENCE: 40

Met Ala Ile Leu Lys Ile Gly Ser Lys Gly Leu Glu Val Lys Asn Leu
1               5                   10                  15

Gln Thr Ser Leu Asn Lys Ile Gly Phe Asn Leu Val Ala Asp Gly Ile
            20                  25                  30

Phe Gly Lys Ala Thr Asp Asn Ala Val Arg Ala Val Gln Ala Gly Ala
        35                  40                  45

Gly Leu Val Val Asp Gly Ile Ala Gly Pro Lys Thr Met Tyr Ala Ile
    50                  55                  60

Arg Asn Ala Gly Glu Ser His Gln Asp His Leu Thr Glu Ala Asp Leu
65                  70                  75                  80

Ile Asp Ala Ala Arg Glu Leu Ser Val Asp Leu Ala Ser Ile Lys Ala
                85                  90                  95

Val Asn Gln Val Glu Ser Arg Gly Thr Gly Phe Thr Lys Ser Gly Lys
            100                 105                 110

Ile Lys Thr Leu Phe Glu Arg His Ile Met Tyr Lys Lys Leu Asn Ala
        115                 120                 125

Lys Phe Gly Gln Ala Lys Ala Asn Ala Leu Ala Gln Leu Tyr Pro Thr

```
                130             135             140
Leu Val Asn Ala Lys Ala Gly Gly Tyr Thr Gly Gly Asp Ala Glu Leu
145                 150                 155                 160

Glu Arg Leu His Gly Ala Ile Ala Ile Asp Lys Asp Cys Ala Tyr Glu
                165                 170                 175

Ser Ala Ser Tyr Gly Leu Phe Gln Ile Met Gly Phe Asn Cys Val Ile
            180                 185                 190

Cys Gly Tyr Asp Asn Ala Glu Glu Met Phe Asn Asp Phe Leu Thr Gly
        195                 200                 205

Glu Arg Ala Gln Leu Met Ala Phe Val Lys Phe Ile Lys Ala Asp Ala
    210                 215                 220

Asn Leu Trp Lys Ala Leu Lys Asp Lys Asn Trp Ala Glu Phe Ala Arg
225                 230                 235                 240

Arg Tyr Asn Gly Pro Ala Tyr Ala Gln Asn Gln Tyr Asp Thr Lys Leu
                245                 250                 255

Ala Ala Ala Tyr Lys Ser Phe Ser Thr Ala Gly Gly Thr Ala Gly Gly
            260                 265                 270

Thr Arg Lys Arg Leu Lys Lys Ile Gly Lys Val Leu Lys Trp Ile
        275                 280                 285

<210> SEQ ID NO 41
<211> LENGTH: 897
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (28)..(873)
<223> OTHER INFORMATION: GN369 lysin
<220> FEATURE:
<221> NAME/KEY: CDS
<222> LOCATION: (28)..(873)

<400> SEQUENCE: 41
gtttaacttt aagaaggaga attcacc atg gcc att tta aag att ggc agc aaa      54
                           Met Ala Ile Leu Lys Ile Gly Ser Lys
                             1               5 ggt ctg gaa gtt aag aat ctt cag acc agt ctc aac aaa atc ggg ttc     102
Gly Leu Glu Val Lys Asn Leu Gln Thr Ser Leu Asn Lys Ile Gly Phe
 10              15                  20                  25 aat ctg gtt gcc gat ggc ata ttt ggt aaa gcg act gac aac gcc gtc     150
Asn Leu Val Ala Asp Gly Ile Phe Gly Lys Ala Thr Asp Asn Ala Val
                 30                  35                  40 agg gca gtt cag gca ggt gcc gga ctg gtc gtt gat ggt att gct ggc     198
Arg Ala Val Gln Ala Gly Ala Gly Leu Val Val Asp Gly Ile Ala Gly
             45                  50                  55 ccc aag acc atg tat gcg att cgc aac gca ggg gag tct cat cag gat     246
Pro Lys Thr Met Tyr Ala Ile Arg Asn Ala Gly Glu Ser His Gln Asp
         60                  65                  70 cat ctg act gag gct gac ttg att gac gct gct cgt gaa ttg tct gtt     294
His Leu Thr Glu Ala Asp Leu Ile Asp Ala Ala Arg Glu Leu Ser Val
     75                  80                  85 gac ctt gct agc atc aag gca gtc aac caa gta gaa tcg cgc ggt act     342
Asp Leu Ala Ser Ile Lys Ala Val Asn Gln Val Glu Ser Arg Gly Thr
 90                  95                 100                 105 ggc ttc acc aag tct ggt aag atc aag aca ttg ttt gaa cgc cac atc     390
Gly Phe Thr Lys Ser Gly Lys Ile Lys Thr Leu Phe Glu Arg His Ile
                110                 115                 120
```

```
                                              -continued atg tac aaa aag ctg aat gcc aag ttc ggt cag gca aaa gcc aat gct    438
Met Tyr Lys Lys Leu Asn Ala Lys Phe Gly Gln Ala Lys Ala Asn Ala
        125                 130                 135 ctg gcc cag ctt tac ccg acg ttg gtt aac gcc aaa gcc ggg gga tac    486
Leu Ala Gln Leu Tyr Pro Thr Leu Val Asn Ala Lys Ala Gly Gly Tyr
140                 145                 150 aca ggt ggg gac gcg gag ttg gaa cga ctc cat ggt gca ata gcg atc    534
Thr Gly Gly Asp Ala Glu Leu Glu Arg Leu His Gly Ala Ile Ala Ile
        155                 160                 165 gat aaa gat tgc gcc tac gag agc gct tcc tac ggg tta ttc cag atc    582
Asp Lys Asp Cys Ala Tyr Glu Ser Ala Ser Tyr Gly Leu Phe Gln Ile
170                 175                 180                 185 atg ggg ttc aac tgc gtt att tgt gga tat gac aat gcc gag gag atg    630
Met Gly Phe Asn Cys Val Ile Cys Gly Tyr Asp Asn Ala Glu Glu Met
            190                 195                 200 ttc aac gac ttt ctc act ggt gaa cgt gct cag ctc atg gca ttt gtc    678
Phe Asn Asp Phe Leu Thr Gly Glu Arg Ala Gln Leu Met Ala Phe Val
                205                 210                 215 aag ttc atc aag gct gac gcc aat ctg tgg aaa gca ttg aag gac aag    726
Lys Phe Ile Lys Ala Asp Ala Asn Leu Trp Lys Ala Leu Lys Asp Lys
            220                 225                 230 aat tgg gct gag ttt gct cgg cgt tac aat ggc ccg gcg tat gca cag    774
Asn Trp Ala Glu Phe Ala Arg Arg Tyr Asn Gly Pro Ala Tyr Ala Gln
235                 240                 245 aac cag tac gac acc aag ctg gct gca gca tac aaa tca ttc agt cgt    822
Asn Gln Tyr Asp Thr Lys Leu Ala Ala Ala Tyr Lys Ser Phe Ser Arg
250                 255                 260                 265 aaa aaa acc cgt aaa cgt ctg aaa aaa atc ggt aaa gtt ctg aaa tgg    870
Lys Lys Thr Arg Lys Arg Leu Lys Lys Ile Gly Lys Val Leu Lys Trp
            270                 275                 280 atc tagtaaaagc ttggctgttt tggc                                     897
Ile

<210> SEQ ID NO 42
<211> LENGTH: 282
<212> TYPE: PRT
<213> ORGANISM: Artificial Sequence
<220> FEATURE:
<223> OTHER INFORMATION: Synthetic Construct

<400> SEQUENCE: 42

Met Ala Ile Leu Lys Ile Gly Ser Lys Gly Leu Glu Val Lys Asn Leu
1               5                   10                  15

Gln Thr Ser Leu Asn Lys Ile Gly Phe Asn Leu Val Ala Asp Gly Ile
            20                  25                  30

Phe Gly Lys Ala Thr Asp Asn Ala Val Arg Ala Val Gln Ala Gly Ala
        35                  40                  45

Gly Leu Val Val Asp Gly Ile Ala Gly Pro Lys Thr Met Tyr Ala Ile
    50                  55                  60

Arg Asn Ala Gly Glu Ser His Gln Asp His Leu Thr Glu Ala Asp Leu
65                  70                  75                  80

Ile Asp Ala Ala Arg Glu Leu Ser Val Asp Leu Ala Ser Ile Lys Ala
                85                  90                  95

Val Asn Gln Val Glu Ser Arg Gly Thr Gly Phe Thr Lys Ser Gly Lys
            100                 105                 110

Ile Lys Thr Leu Phe Glu Arg His Ile Met Tyr Lys Lys Leu Asn Ala
        115                 120                 125

Lys Phe Gly Gln Ala Lys Ala Asn Ala Leu Ala Gln Leu Tyr Pro Thr
    130                 135                 140
```

```
Leu Val Asn Ala Lys Ala Gly Gly Tyr Thr Gly Gly Asp Ala Glu Leu
145                 150                 155                 160

Glu Arg Leu His Gly Ala Ile Ala Ile Asp Lys Asp Cys Ala Tyr Glu
            165                 170                 175

Ser Ala Ser Tyr Gly Leu Phe Gln Ile Met Gly Phe Asn Cys Val Ile
        180                 185                 190

Cys Gly Tyr Asp Asn Ala Glu Glu Met Phe Asn Asp Phe Leu Thr Gly
    195                 200                 205

Glu Arg Ala Gln Leu Met Ala Phe Val Lys Phe Ile Lys Ala Asp Ala
210                 215                 220

Asn Leu Trp Lys Ala Leu Lys Asp Lys Asn Trp Ala Glu Phe Ala Arg
225                 230                 235                 240

Arg Tyr Asn Gly Pro Ala Tyr Ala Gln Asn Gln Tyr Asp Thr Lys Leu
                245                 250                 255

Ala Ala Ala Tyr Lys Ser Phe Ser Arg Lys Thr Arg Lys Arg Leu
            260                 265                 270

Lys Lys Ile Gly Lys Val Leu Lys Trp Ile
275                 280

<210> SEQ ID NO 43
<211> LENGTH: 558
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (28)..(534)
<223> OTHER INFORMATION: GN370 lysin
<220> FEATURE:
<221> NAME/KEY: CDS
<222> LOCATION: (28)..(534)

<400> SEQUENCE: 43
gtttaacttt aagaaggaga attcacc atg atc gac cgt ttc att cgt ctg aat        54
                            Met Ile Asp Arg Phe Ile Arg Leu Asn
                            1               5 ccg acc cat ggt ccg cgt cgt ccg cgt cgt ccg ggt cgt cgt gct ccg       102
Pro Thr His Gly Pro Arg Arg Pro Arg Arg Pro Gly Arg Arg Ala Pro
10                  15                  20                  25 gtt cgt aca tcc caa cga ggc atc gac ctc atc aaa tcc ttc gag ggc       150
Val Arg Thr Ser Gln Arg Gly Ile Asp Leu Ile Lys Ser Phe Glu Gly
                30                  35                  40 ctg cgc ctg tcc gct tac cag gac tcg gtg ggt gtc tgg acc ata ggt       198
Leu Arg Leu Ser Ala Tyr Gln Asp Ser Val Gly Val Trp Thr Ile Gly
            45                  50                  55 tac ggc acc act cgg ggc gtc acc cgc tac atg acg atc acc gtc gag       246
Tyr Gly Thr Thr Arg Gly Val Thr Arg Tyr Met Thr Ile Thr Val Glu
        60                  65                  70 cag gcc gag cgg atg ctg tcg aac gac att cag cgc ttc gag cca gag       294
Gln Ala Glu Arg Met Leu Ser Asn Asp Ile Gln Arg Phe Glu Pro Glu
75                  80                  85 cta gac agg ctg gcg aag gtg cca ctg aac cag aac cag tgg gat gcc       342
Leu Asp Arg Leu Ala Lys Val Pro Leu Asn Gln Asn Gln Trp Asp Ala
90                  95                  100                 105 ctg atg agc ttc gtg tac aac ctg ggc gcg gcc aat ctg gcg tcg tcc       390
Leu Met Ser Phe Val Tyr Asn Leu Gly Ala Ala Asn Leu Ala Ser Ser
                110                 115                 120 acg ctg ctc gac ctg ctg aac aag ggt gac tac cag gga gca gcg gac       438
Thr Leu Leu Asp Leu Leu Asn Lys Gly Asp Tyr Gln Gly Ala Ala Asp
```

```
Thr Leu Leu Asp Leu Leu Asn Lys Gly Asp Tyr Gln Gly Ala Ala Asp
            125                 130                 135 cag ttc ccg cat tgg gtg aat gcg ggc ggt aag cgc ttg gat ggt ctg     486
Gln Phe Pro His Trp Val Asn Ala Gly Gly Lys Arg Leu Asp Gly Leu
        140                 145                 150 gtt aag cgt cga gca gcc gag cgt gcg ctg ttc ctg gag cca cta tcg     534
Val Lys Arg Arg Ala Ala Glu Arg Ala Leu Phe Leu Glu Pro Leu Ser
    155                 160                 165 tgataaaagc ttggctgttt tggc                                          558

<210> SEQ ID NO 44
<211> LENGTH: 169
<212> TYPE: PRT
<213> ORGANISM: Artificial Sequence
<220> FEATURE:
<223> OTHER INFORMATION: Synthetic Construct

<400> SEQUENCE: 44

Met Ile Asp Arg Phe Ile Arg Leu Asn Pro Thr His Gly Pro Arg Arg
1               5                   10                  15

Pro Arg Arg Pro Gly Arg Arg Ala Pro Val Arg Thr Ser Gln Arg Gly
            20                  25                  30

Ile Asp Leu Ile Lys Ser Phe Glu Gly Leu Arg Leu Ser Ala Tyr Gln
        35                  40                  45

Asp Ser Val Gly Val Trp Thr Ile Gly Tyr Gly Thr Thr Arg Gly Val
    50                  55                  60

Thr Arg Tyr Met Thr Ile Thr Val Glu Gln Ala Glu Arg Met Leu Ser
65                  70                  75                  80

Asn Asp Ile Gln Arg Phe Glu Pro Glu Leu Asp Arg Leu Ala Lys Val
                85                  90                  95

Pro Leu Asn Gln Asn Gln Trp Asp Ala Leu Met Ser Phe Val Tyr Asn
            100                 105                 110

Leu Gly Ala Ala Asn Leu Ala Ser Ser Thr Leu Leu Asp Leu Leu Asn
        115                 120                 125

Lys Gly Asp Tyr Gln Gly Ala Ala Asp Gln Phe Pro His Trp Val Asn
    130                 135                 140

Ala Gly Gly Lys Arg Leu Asp Gly Leu Val Lys Arg Arg Ala Ala Glu
145                 150                 155                 160

Arg Ala Leu Phe Leu Glu Pro Leu Ser
                165

<210> SEQ ID NO 45
<211> LENGTH: 516
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (28)..(492)
<223> OTHER INFORMATION: GN371lysin
<220> FEATURE:
<221> NAME/KEY: CDS
<222> LOCATION: (28)..(492)

<400> SEQUENCE: 45
gtttaacttt aagaaggaga attcacc atg atc gac cgt ttc att cgt ctg aat    54
                                Met Ile Asp Arg Phe Ile Arg Leu Asn
                                1               5 ccg acc cat cgt aca tcc caa cga ggc atc gac ctc atc aaa tcc ttc     102
```

```
Pro Thr His Arg Thr Ser Gln Arg Gly Ile Asp Leu Ile Lys Ser Phe
 10              15                  20                  25 gag ggc ctg cgc ctg tcc gct tac cag gac tcg gtg ggt gtc tgg acc     150
Glu Gly Leu Arg Leu Ser Ala Tyr Gln Asp Ser Val Gly Val Trp Thr
                 30                  35                  40 ata ggt tac ggc acc act cgg ggc gtc acc cgc tac atg acg atc acc     198
Ile Gly Tyr Gly Thr Thr Arg Gly Val Thr Arg Tyr Met Thr Ile Thr
             45                  50                  55 gtc gag cag gcc gag cgg atg ctg tcg aac gac att cag cgc ttc gag     246
Val Glu Gln Ala Glu Arg Met Leu Ser Asn Asp Ile Gln Arg Phe Glu
         60                  65                  70 cca gag cta gac agg ctg gcg aag gtg cca ctg aac cag aac cag tgg     294
Pro Glu Leu Asp Arg Leu Ala Lys Val Pro Leu Asn Gln Asn Gln Trp
     75                  80                  85 gat gcc ctg atg agc ttc gtg tac aac ctg ggc gcg gcc aat ctg gcg     342
Asp Ala Leu Met Ser Phe Val Tyr Asn Leu Gly Ala Ala Asn Leu Ala
 90                  95                 100                 105 tcg tcc acg ctg ctc gac ctg ctg aac aag ggt gac tac cag gga gca     390
Ser Ser Thr Leu Leu Asp Leu Leu Asn Lys Gly Asp Tyr Gln Gly Ala
                110                 115                 120 gcg gac cag ttc ccg cat tgg gtg aat gcg ggc ggt aag cgc ttg gat     438
Ala Asp Gln Phe Pro His Trp Val Asn Ala Gly Gly Lys Arg Leu Asp
            125                 130                 135 ggt ctg gtt aag cgt cga gca gcc gag cgt gcg ctg ttc ctg gag cca     486
Gly Leu Val Lys Arg Arg Ala Ala Glu Arg Ala Leu Phe Leu Glu Pro
        140                 145                 150 cta tcg tgataaaagc ttggctgttt tggc                                  516
Leu Ser
    155
```

<210> SEQ ID NO 46
<211> LENGTH: 155
<212> TYPE: PRT
<213> ORGANISM: Artificial Sequence
<220> FEATURE:
<223> OTHER INFORMATION: Synthetic Construct

<400> SEQUENCE: 46

```
Met Ile Asp Arg Phe Ile Arg Leu Asn Pro Thr His Arg Thr Ser Gln
 1               5                  10                  15

Arg Gly Ile Asp Leu Ile Lys Ser Phe Glu Gly Leu Arg Leu Ser Ala
             20                  25                  30

Tyr Gln Asp Ser Val Gly Val Trp Thr Ile Gly Tyr Gly Thr Thr Arg
         35                  40                  45

Gly Val Thr Arg Tyr Met Thr Ile Thr Val Glu Gln Ala Glu Arg Met
     50                  55                  60

Leu Ser Asn Asp Ile Gln Arg Phe Glu Pro Glu Leu Asp Arg Leu Ala
 65                  70                  75                  80

Lys Val Pro Leu Asn Gln Asn Gln Trp Asp Ala Leu Met Ser Phe Val
                 85                  90                  95

Tyr Asn Leu Gly Ala Ala Asn Leu Ala Ser Ser Thr Leu Leu Asp Leu
            100                 105                 110

Leu Asn Lys Gly Asp Tyr Gln Gly Ala Ala Asp Gln Phe Pro His Trp
        115                 120                 125

Val Asn Ala Gly Gly Lys Arg Leu Asp Gly Leu Val Lys Arg Arg Ala
    130                 135                 140

Ala Glu Arg Ala Leu Phe Leu Glu Pro Leu Ser
145                 150                 155
```

```
<210> SEQ ID NO 47
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (28)..(819)
<223> OTHER INFORMATION: GN394 lysin
<220> FEATURE:
<221> NAME/KEY: CDS
<222> LOCATION: (28)..(819)

<400> SEQUENCE: 47
gtttaacttt aagaaggaga attcacc atg gcc att tta aag att ggc agc aaa      54
                               Met Ala Ile Leu Lys Ile Gly Ser Lys
                               1               5 ggt ctg gaa gtt aag aat ctt cag acc agt ctc aac aaa atc ggg ttc      102
Gly Leu Glu Val Lys Asn Leu Gln Thr Ser Leu Asn Lys Ile Gly Phe
10              15                  20                  25 aat ctg gtt gcc gat ggc ata ttt ggt aaa gcg act gac aac gcc gtc      150
Asn Leu Val Ala Asp Gly Ile Phe Gly Lys Ala Thr Asp Asn Ala Val
                30                  35                  40 agg gca gtt cag gca ggt gcc gga ctg gtc gtt gat ggt att gct ggc      198
Arg Ala Val Gln Ala Gly Ala Gly Leu Val Val Asp Gly Ile Ala Gly
            45                  50                  55 ccc aag acc atg tat gcg att cgc aac gca ggg gag tct cat cag gat      246
Pro Lys Thr Met Tyr Ala Ile Arg Asn Ala Gly Glu Ser His Gln Asp
        60                  65                  70 cat ctg act gag gct gac ttg att gac gct gct cgt gaa ttg tct gtt      294
His Leu Thr Glu Ala Asp Leu Ile Asp Ala Ala Arg Glu Leu Ser Val
75                  80                  85 gac ctt gct agc atc aag gca gtc aac caa gta gaa tcg cgc ggt act      342
Asp Leu Ala Ser Ile Lys Ala Val Asn Gln Val Glu Ser Arg Gly Thr
90                  95                  100                 105 ggc ttc acc aag tct ggt aag atc aag aca ttg ttt gaa cgc cac atc      390
Gly Phe Thr Lys Ser Gly Lys Ile Lys Thr Leu Phe Glu Arg His Ile
                110                 115                 120 atg tac aaa aag ctg aat gcc aag ttc ggt cag gca aaa gcc aat gct      438
Met Tyr Lys Lys Leu Asn Ala Lys Phe Gly Gln Ala Lys Ala Asn Ala
            125                 130                 135 ctg gcc cag ctt tac ccg acg ttg gtt aac gcc aaa gcc ggg gga tac      486
Leu Ala Gln Leu Tyr Pro Thr Leu Val Asn Ala Lys Ala Gly Gly Tyr
        140                 145                 150 aca ggt ggg gac gcg gag ttg gaa cga ctc cat ggt gca ata gcg atc      534
Thr Gly Gly Asp Ala Glu Leu Glu Arg Leu His Gly Ala Ile Ala Ile
155                 160                 165 gat aaa gat tgc gcc tac gag agc gct tcc tac ggg tta ttc cag atc      582
Asp Lys Asp Cys Ala Tyr Glu Ser Ala Ser Tyr Gly Leu Phe Gln Ile
170                 175                 180                 185 atg ggg ttc aac tgc gtt att tgt gga tat gac aat gcc gag gag atg      630
Met Gly Phe Asn Cys Val Ile Cys Gly Tyr Asp Asn Ala Glu Glu Met
                190                 195                 200 ttc aac gac ttt ctc act ggt gaa cgt gct cag ctc atg gca ttt gtc      678
Phe Asn Asp Phe Leu Thr Gly Glu Arg Ala Gln Leu Met Ala Phe Val
            205                 210                 215 gac ttc atc aag gct gac gcc aat ctg tgg aaa gca ttg aag gac aag      726
Asp Phe Ile Lys Ala Asp Ala Asn Leu Trp Lys Ala Leu Lys Asp Lys
        220                 225                 230 aat tgg gct gag ttt gct cgg cgt tac aat ggc ccg gcg tat gca cag      774
Asn Trp Ala Glu Phe Ala Arg Arg Tyr Asn Gly Pro Ala Tyr Ala Gln
```

```
Asn Trp Ala Glu Phe Ala Arg Arg Tyr Asn Gly Pro Ala Tyr Ala Gln
        235                 240                 245 aac cag tac gac acc aag ctg gct gca gca tac aaa tca ttc agt         819
Asn Gln Tyr Asp Thr Lys Leu Ala Ala Ala Tyr Lys Ser Phe Ser
250                 255                 260 tagtaataaa agcttggctg ttttggc                                       846

<210> SEQ ID NO 48
<211> LENGTH: 264
<212> TYPE: PRT
<213> ORGANISM: Artificial Sequence
<220> FEATURE:
<223> OTHER INFORMATION: Synthetic Construct

<400> SEQUENCE: 48

Met Ala Ile Leu Lys Ile Gly Ser Lys Gly Leu Glu Val Lys Asn Leu
1               5                   10                  15

Gln Thr Ser Leu Asn Lys Ile Gly Phe Asn Leu Val Ala Asp Gly Ile
            20                  25                  30

Phe Gly Lys Ala Thr Asp Asn Ala Val Arg Ala Val Gln Ala Gly Ala
        35                  40                  45

Gly Leu Val Val Asp Gly Ile Ala Gly Pro Lys Thr Met Tyr Ala Ile
    50                  55                  60

Arg Asn Ala Gly Glu Ser His Gln Asp His Leu Thr Glu Ala Asp Leu
65                  70                  75                  80

Ile Asp Ala Ala Arg Glu Leu Ser Val Asp Leu Ala Ser Ile Lys Ala
                85                  90                  95

Val Asn Gln Val Glu Ser Arg Gly Thr Gly Phe Thr Lys Ser Gly Lys
            100                 105                 110

Ile Lys Thr Leu Phe Glu Arg His Ile Met Tyr Lys Lys Leu Asn Ala
        115                 120                 125

Lys Phe Gly Gln Ala Lys Ala Asn Ala Leu Ala Gln Leu Tyr Pro Thr
    130                 135                 140

Leu Val Asn Ala Lys Ala Gly Gly Tyr Thr Gly Gly Asp Ala Glu Leu
145                 150                 155                 160

Glu Arg Leu His Gly Ala Ile Ala Ile Asp Lys Asp Cys Ala Tyr Glu
                165                 170                 175

Ser Ala Ser Tyr Gly Leu Phe Gln Ile Met Gly Phe Asn Cys Val Ile
            180                 185                 190

Cys Gly Tyr Asp Asn Ala Glu Glu Met Phe Asn Asp Phe Leu Thr Gly
        195                 200                 205

Glu Arg Ala Gln Leu Met Ala Phe Val Asp Phe Ile Lys Ala Asp Ala
    210                 215                 220

Asn Leu Trp Lys Ala Leu Lys Asp Lys Asn Trp Ala Glu Phe Ala Arg
225                 230                 235                 240

Arg Tyr Asn Gly Pro Ala Tyr Ala Gln Asn Gln Tyr Asp Thr Lys Leu
                245                 250                 255

Ala Ala Ala Tyr Lys Ser Phe Ser
            260

<210> SEQ ID NO 49
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

```
<221> NAME/KEY: misc_feature
<222> LOCATION: (28)..(819)
<223> OTHER INFORMATION: GN396 lysin
<220> FEATURE:
<221> NAME/KEY: CDS
<222> LOCATION: (28)..(819)

<400> SEQUENCE: 49
```

| | | | | | | | | | | | |
|---|---|---|---|---|---|---|---|---|---|---|---|
| gtttaacttt aagaaggaga attcacc | atg | gcc | att | tta | aag | att | ggc | agc | aaa | | 54 |
| | Met | Ala | Ile | Leu | Lys | Ile | Gly | Ser | Lys | | |
| | 1 | | | | 5 | | | | | | |

```
ggt ctg gaa gtt aag aat ctt cag acc agt ctc aac aaa atc ggg ttc      102
Gly Leu Glu Val Lys Asn Leu Gln Thr Ser Leu Asn Lys Ile Gly Phe
 10          15                  20                  25 aat ctg gtt gcc gat ggc ata ttt ggt aaa gcg act gac aac gcc gtc      150
Asn Leu Val Ala Asp Gly Ile Phe Gly Lys Ala Thr Asp Asn Ala Val
                 30                  35                  40 agg gca gtt cag gca ggt gcc gga ctg gtc gtt gat ggt att gct ggc      198
Arg Ala Val Gln Ala Gly Ala Gly Leu Val Val Asp Gly Ile Ala Gly
             45                  50                  55 ccc aag acc atg tat gcg att cgc aac gca ggg gag tct cat cag gat      246
Pro Lys Thr Met Tyr Ala Ile Arg Asn Ala Gly Glu Ser His Gln Asp
         60                  65                  70 cat ctg act gag gct gac ttg att gac gct gct cgt gaa ttg tct gtt      294
His Leu Thr Glu Ala Asp Leu Ile Asp Ala Ala Arg Glu Leu Ser Val
 75                  80                  85 gac ctt gct agc atc aag gca gtc aac caa gta gaa tcg cgc ggt act      342
Asp Leu Ala Ser Ile Lys Ala Val Asn Gln Val Glu Ser Arg Gly Thr
 90                  95                 100                 105 ggc ttc acc aag tct ggt aag atc aag aca ttg ttt gaa cgc cac atc      390
Gly Phe Thr Lys Ser Gly Lys Ile Lys Thr Leu Phe Glu Arg His Ile
                110                 115                 120 atg tac aaa aag ctg aat gcc aag ttc ggt cag gca aaa gcc aat gct      438
Met Tyr Lys Lys Leu Asn Ala Lys Phe Gly Gln Ala Lys Ala Asn Ala
            125                 130                 135 ctg gcc cag ctt tac ccg acg ttg gtt aac gcc aaa gcc ggg gga tac      486
Leu Ala Gln Leu Tyr Pro Thr Leu Val Asn Ala Lys Ala Gly Gly Tyr
        140                 145                 150 aca ggt ggg gac gcg gag ttg gaa cga ctc cat ggt gca ata gcg atc      534
Thr Gly Gly Asp Ala Glu Leu Glu Arg Leu His Gly Ala Ile Ala Ile
155                 160                 165 gat aaa gat tgc gcc tac gag agc gct tcc tac ggg tta ttc cag atc      582
Asp Lys Asp Cys Ala Tyr Glu Ser Ala Ser Tyr Gly Leu Phe Gln Ile
170                 175                 180                 185 atg ggg ttc aac tgc gtt att tgt gga tat gac aat gcc gag gag atg      630
Met Gly Phe Asn Cys Val Ile Cys Gly Tyr Asp Asn Ala Glu Glu Met
                190                 195                 200 ttc aac gac ttt ctc act ggt gaa cgt gct cag ctc atg gca ttt gtc      678
Phe Asn Asp Phe Leu Thr Gly Glu Arg Ala Gln Leu Met Ala Phe Val
            205                 210                 215 aag ttc atc aag gct gac gcc aat ctg tgg gac gca ttg aag gac aag      726
Lys Phe Ile Lys Ala Asp Ala Asn Leu Trp Asp Ala Leu Lys Asp Lys
        220                 225                 230 aat tgg gct gag ttt gct cgg cgt tac aat ggc ccg gcg tat gca cag      774
Asn Trp Ala Glu Phe Ala Arg Arg Tyr Asn Gly Pro Ala Tyr Ala Gln
235                 240                 245 aac cag tac gac acc aag ctg gct gca gca tac aaa tca ttc agt          819
Asn Gln Tyr Asp Thr Lys Leu Ala Ala Ala Tyr Lys Ser Phe Ser
250                 255                 260 tagtaataaa agcttggctg ttttggc                                        846
```

-continued

<210> SEQ ID NO 50
<211> LENGTH: 264
<212> TYPE: PRT
<213> ORGANISM: Artificial Sequence
<220> FEATURE:
<223> OTHER INFORMATION: Synthetic Construct

<400> SEQUENCE: 50

```
Met Ala Ile Leu Lys Ile Gly Ser Lys Gly Leu Glu Val Lys Asn Leu
1               5                   10                  15

Gln Thr Ser Leu Asn Lys Ile Gly Phe Asn Leu Val Ala Asp Gly Ile
            20                  25                  30

Phe Gly Lys Ala Thr Asp Asn Ala Val Arg Ala Val Gln Ala Gly Ala
        35                  40                  45

Gly Leu Val Val Asp Gly Ile Ala Gly Pro Lys Thr Met Tyr Ala Ile
    50                  55                  60

Arg Asn Ala Gly Glu Ser His Gln Asp His Leu Thr Glu Ala Asp Leu
65                  70                  75                  80

Ile Asp Ala Ala Arg Glu Leu Ser Val Asp Leu Ala Ser Ile Lys Ala
                85                  90                  95

Val Asn Gln Val Glu Ser Arg Gly Thr Gly Phe Thr Lys Ser Gly Lys
            100                 105                 110

Ile Lys Thr Leu Phe Glu Arg His Ile Met Tyr Lys Lys Leu Asn Ala
        115                 120                 125

Lys Phe Gly Gln Ala Lys Ala Asn Ala Leu Ala Gln Leu Tyr Pro Thr
    130                 135                 140

Leu Val Asn Ala Lys Ala Gly Gly Tyr Thr Gly Gly Asp Ala Glu Leu
145                 150                 155                 160

Glu Arg Leu His Gly Ala Ile Ala Ile Asp Lys Asp Cys Ala Tyr Glu
                165                 170                 175

Ser Ala Ser Tyr Gly Leu Phe Gln Ile Met Gly Phe Asn Cys Val Ile
            180                 185                 190

Cys Gly Tyr Asp Asn Ala Glu Glu Met Phe Asn Asp Phe Leu Thr Gly
        195                 200                 205

Glu Arg Ala Gln Leu Met Ala Phe Val Lys Phe Ile Lys Ala Asp Ala
    210                 215                 220

Asn Leu Trp Asp Ala Leu Lys Asp Lys Asn Trp Ala Glu Phe Ala Arg
225                 230                 235                 240

Arg Tyr Asn Gly Pro Ala Tyr Ala Gln Asn Gln Tyr Asp Thr Lys Leu
                245                 250                 255

Ala Ala Ala Tyr Lys Ser Phe Ser
            260
```

<210> SEQ ID NO 51
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (28)..(819)
<223> OTHER INFORMATION: GN408 lysin
<220> FEATURE:
<221> NAME/KEY: CDS
<222> LOCATION: (28)..(819)

<400> SEQUENCE: 51

```
gtttaacttt aagaaggaga attcacc atg gcc att tta aag att ggc agc aaa      54
                                Met Ala Ile Leu Lys Ile Gly Ser Lys
                                1               5 ggt ctg gaa gtt aag aat ctt cag acc agt ctc aac aaa atc ggg ttc       102
Gly Leu Glu Val Lys Asn Leu Gln Thr Ser Leu Asn Lys Ile Gly Phe
10              15                  20                  25 aat ctg gtt gcc gat ggc ata ttt ggt aaa gcg act gac aac gcc gtc       150
Asn Leu Val Ala Asp Gly Ile Phe Gly Lys Ala Thr Asp Asn Ala Val
                30                  35                  40 agg gca gtt cag gca ggt gcc gga ctg gtc gtt gat ggt att gct ggc       198
Arg Ala Val Gln Ala Gly Ala Gly Leu Val Val Asp Gly Ile Ala Gly
            45                  50                  55 ccc aag acc atg tat gcg att cgc aac gca ggg gag tct cat cag gat       246
Pro Lys Thr Met Tyr Ala Ile Arg Asn Ala Gly Glu Ser His Gln Asp
        60                  65                  70 cat ctg act gag gct gac ttg att gac gct gct cat gaa ttg tct gtt       294
His Leu Thr Glu Ala Asp Leu Ile Asp Ala Ala His Glu Leu Ser Val
    75                  80                  85 gac ctt gct agc atc aag gca gtc aac caa gta gaa tcg cgc ggt act       342
Asp Leu Ala Ser Ile Lys Ala Val Asn Gln Val Glu Ser Arg Gly Thr
90                  95                 100                 105 ggc ttc acc aag tct ggt aag atc aag aca ttg ttt gaa cgc cac atc       390
Gly Phe Thr Lys Ser Gly Lys Ile Lys Thr Leu Phe Glu Arg His Ile
                110                 115                 120 atg tac aaa aag ctg aat gcc aag ttc ggt cag gca aaa gcc aat gct       438
Met Tyr Lys Lys Leu Asn Ala Lys Phe Gly Gln Ala Lys Ala Asn Ala
            125                 130                 135 ctg gcc cag ctt tac ccg acg ttg gtt aac gcc aaa gcc ggg gga tac       486
Leu Ala Gln Leu Tyr Pro Thr Leu Val Asn Ala Lys Ala Gly Gly Tyr
        140                 145                 150 aca ggt ggg gac gcg gag ttg gaa cga ctc cat ggt gca ata gcg atc       534
Thr Gly Gly Asp Ala Glu Leu Glu Arg Leu His Gly Ala Ile Ala Ile
    155                 160                 165 gat aaa gat tgc gcc tac gag agc gct tcc tac ggg tta ttc cag atc       582
Asp Lys Asp Cys Ala Tyr Glu Ser Ala Ser Tyr Gly Leu Phe Gln Ile
170                 175                 180                 185 atg ggg ttc aac tgc gtt att tgt gga tat gac aat gcc gag gag atg       630
Met Gly Phe Asn Cys Val Ile Cys Gly Tyr Asp Asn Ala Glu Glu Met
                190                 195                 200 ttc aac gac ttt ctc act ggt gaa cgt gct cag ctc atg gca ttt gtc       678
Phe Asn Asp Phe Leu Thr Gly Glu Arg Ala Gln Leu Met Ala Phe Val
            205                 210                 215 aag ttc atc aag gct gac gcc aat ctg tgg aaa gca ttg aag gac aag       726
Lys Phe Ile Lys Ala Asp Ala Asn Leu Trp Lys Ala Leu Lys Asp Lys
        220                 225                 230 aat tgg gct gag ttt gct cgg cgt tac aat ggc ccg gcg tat gca cag       774
Asn Trp Ala Glu Phe Ala Arg Arg Tyr Asn Gly Pro Ala Tyr Ala Gln
    235                 240                 245 aac cag tac gac acc aag ctg gct gca gca tac aaa tca ttc agt           819
Asn Gln Tyr Asp Thr Lys Leu Ala Ala Ala Tyr Lys Ser Phe Ser
250                 255                 260 tagtaataaa agcttggctg ttttggc                                         846
```

<210> SEQ ID NO 52
<211> LENGTH: 264
<212> TYPE: PRT
<213> ORGANISM: Artificial Sequence
<220> FEATURE:
<223> OTHER INFORMATION: Synthetic Construct

<400> SEQUENCE: 52

Met Ala Ile Leu Lys Ile Gly Ser Lys Gly Leu Glu Val Lys Asn Leu
1               5                   10                  15

Gln Thr Ser Leu Asn Lys Ile Gly Phe Asn Leu Val Ala Asp Gly Ile
            20                  25                  30

Phe Gly Lys Ala Thr Asp Asn Ala Val Arg Ala Val Gln Ala Gly Ala
        35                  40                  45

Gly Leu Val Val Asp Gly Ile Ala Gly Pro Lys Thr Met Tyr Ala Ile
    50                  55                  60

Arg Asn Ala Gly Glu Ser His Gln Asp His Leu Thr Glu Ala Asp Leu
65                  70                  75                  80

Ile Asp Ala Ala His Glu Leu Ser Val Asp Leu Ala Ser Ile Lys Ala
                85                  90                  95

Val Asn Gln Val Glu Ser Arg Gly Thr Gly Phe Thr Lys Ser Gly Lys
            100                 105                 110

Ile Lys Thr Leu Phe Glu Arg His Ile Met Tyr Lys Lys Leu Asn Ala
        115                 120                 125

Lys Phe Gly Gln Ala Lys Ala Asn Ala Leu Ala Gln Leu Tyr Pro Thr
130                 135                 140

Leu Val Asn Ala Lys Ala Gly Gly Tyr Thr Gly Gly Asp Ala Glu Leu
145                 150                 155                 160

Glu Arg Leu His Gly Ala Ile Ala Ile Asp Lys Asp Cys Ala Tyr Glu
                165                 170                 175

Ser Ala Ser Tyr Gly Leu Phe Gln Ile Met Gly Phe Asn Cys Val Ile
            180                 185                 190

Cys Gly Tyr Asp Asn Ala Glu Glu Met Phe Asn Asp Phe Leu Thr Gly
        195                 200                 205

Glu Arg Ala Gln Leu Met Ala Phe Val Lys Phe Ile Lys Ala Asp Ala
210                 215                 220

Asn Leu Trp Lys Ala Leu Lys Asp Lys Asn Trp Ala Glu Phe Ala Arg
225                 230                 235                 240

Arg Tyr Asn Gly Pro Ala Tyr Ala Gln Asn Gln Tyr Asp Thr Lys Leu
                245                 250                 255

Ala Ala Ala Tyr Lys Ser Phe Ser
            260

<210> SEQ ID NO 53
<211> LENGTH: 846
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (28)..(819)
<223> OTHER INFORMATION: GN418 lysin
<220> FEATURE:
<221> NAME/KEY: CDS
<222> LOCATION: (28)..(819)

<400> SEQUENCE: 53
gtttaacttt aagaaggaga attcacc atg gcc att tta aag att ggc agc aaa      54
                           Met Ala Ile Leu Lys Ile Gly Ser Lys
                           1               5 ggt ctg gaa gtt aag aat ctt cag acc agt ctc aac gac atc ggg ttc     102
Gly Leu Glu Val Lys Asn Leu Gln Thr Ser Leu Asn Asp Ile Gly Phe
10                  15                  20                  25 aat ctg gtt gcc gat ggc ata ttt ggt aaa gcg act gac aac gcc gtc     150

|  |  |  |  |  |  |  |  |  |  |  |  |  |  |
|---|---|---|---|---|---|---|---|---|---|---|---|---|---|
| Asn | Leu | Val | Ala | Asp | Gly | Ile | Phe | Gly | Lys | Ala | Thr | Asp | Asn | Ala | Val |
|  |  |  | 30 |  |  |  | 35 |  |  |  | 40 |

```
agg gca gtt cag gca ggt gcc gga ctg gtc gtt gat ggt att gct ggc     198
Arg Ala Val Gln Ala Gly Ala Gly Leu Val Val Asp Gly Ile Ala Gly
             45                  50                  55 ccc aag acc atg tat gcg att cgc aac gca ggg gag tct cat cag gat     246
Pro Lys Thr Met Tyr Ala Ile Arg Asn Ala Gly Glu Ser His Gln Asp
     60                  65                  70 cat ctg act gag gct gac ttg att gac gct gct cgt gaa ttg tct gtt     294
His Leu Thr Glu Ala Asp Leu Ile Asp Ala Ala Arg Glu Leu Ser Val
 75                  80                  85 gac ctt gct agc atc aag gca gtc aac caa gta gaa tcg cgc ggt act     342
Asp Leu Ala Ser Ile Lys Ala Val Asn Gln Val Glu Ser Arg Gly Thr
 90                  95                 100                 105 ggc ttc acc aag tct ggt aag atc aag aca ttg ttt gaa cgc cac atc     390
Gly Phe Thr Lys Ser Gly Lys Ile Lys Thr Leu Phe Glu Arg His Ile
             110                 115                 120 atg tac aaa aag ctg aat gcc aag ttc ggt cag gca aaa gcc aat gct     438
Met Tyr Lys Lys Leu Asn Ala Lys Phe Gly Gln Ala Lys Ala Asn Ala
             125                 130                 135 ctg gcc cag ctt tac ccg acg ttg gtt aac gcc aaa gcc ggg gga tac     486
Leu Ala Gln Leu Tyr Pro Thr Leu Val Asn Ala Lys Ala Gly Gly Tyr
             140                 145                 150 aca ggt ggg gac gcg gag ttg gaa cga ctc cat ggt gca ata gcg atc     534
Thr Gly Gly Asp Ala Glu Leu Glu Arg Leu His Gly Ala Ile Ala Ile
 155                 160                 165 gat aaa gat tgc gcc tac gag agc gct tcc tac ggg tta ttc cag atc     582
Asp Lys Asp Cys Ala Tyr Glu Ser Ala Ser Tyr Gly Leu Phe Gln Ile
170                 175                 180                 185 atg ggg ttc aac tgc gtt att tgt gga tat gac aat gcc gag gag atg     630
Met Gly Phe Asn Cys Val Ile Cys Gly Tyr Asp Asn Ala Glu Glu Met
             190                 195                 200 ttc aac gac ttt ctc act ggt gaa cgt gct cag ctc atg gca ttt gtc     678
Phe Asn Asp Phe Leu Thr Gly Glu Arg Ala Gln Leu Met Ala Phe Val
             205                 210                 215 aag ttc atc aag gct gac gcc aat ctg tgg aaa gca ttg aag gac aag     726
Lys Phe Ile Lys Ala Asp Ala Asn Leu Trp Lys Ala Leu Lys Asp Lys
             220                 225                 230 aat tgg gct gag ttt gct cgg cgt tac aat ggc ccg gcg tat gca cag     774
Asn Trp Ala Glu Phe Ala Arg Arg Tyr Asn Gly Pro Ala Tyr Ala Gln
             235                 240                 245 aac cag tac gac acc aag ctg gct gca gca tac aaa tca ttc agt         819
Asn Gln Tyr Asp Thr Lys Leu Ala Ala Ala Tyr Lys Ser Phe Ser
250                 255                 260 tagtaataaa agcttggctg ttttggc                                       846
```

<210> SEQ ID NO 54
<211> LENGTH: 264
<212> TYPE: PRT
<213> ORGANISM: Artificial Sequence
<220> FEATURE:
<223> OTHER INFORMATION: Synthetic Construct

<400> SEQUENCE: 54

|  |  |  |  |  |  |  |  |  |  |  |  |  |  |  |
|---|---|---|---|---|---|---|---|---|---|---|---|---|---|---|
| Met | Ala | Ile | Leu | Lys | Ile | Gly | Ser | Lys | Gly | Leu | Glu | Val | Lys | Asn | Leu |
| 1 |  |  |  | 5 |  |  |  |  | 10 |  |  |  |  | 15 |

|  |  |  |  |  |  |  |  |  |  |  |  |  |  |  |
|---|---|---|---|---|---|---|---|---|---|---|---|---|---|---|
| Gln | Thr | Ser | Leu | Asn | Asp | Ile | Gly | Phe | Asn | Leu | Val | Ala | Asp | Gly | Ile |
|  |  |  | 20 |  |  |  |  | 25 |  |  |  |  | 30 |

|  |  |  |  |  |  |  |  |  |  |  |  |  |  |
|---|---|---|---|---|---|---|---|---|---|---|---|---|---|
| Phe | Gly | Lys | Ala | Thr | Asp | Asn | Ala | Val | Arg | Ala | Val | Gln | Ala | Gly | Ala |
|  |  |  | 35 |  |  |  |  | 40 |  |  |  |  | 45 |

```
Gly Leu Val Val Asp Gly Ile Ala Gly Pro Lys Thr Met Tyr Ala Ile
     50                  55                  60

Arg Asn Ala Gly Glu Ser His Gln Asp His Leu Thr Glu Ala Asp Leu
 65                  70                  75                  80

Ile Asp Ala Ala Arg Glu Leu Ser Val Asp Leu Ala Ser Ile Lys Ala
                 85                  90                  95

Val Asn Gln Val Glu Ser Arg Gly Thr Gly Phe Thr Lys Ser Gly Lys
            100                 105                 110

Ile Lys Thr Leu Phe Glu Arg His Ile Met Tyr Lys Lys Leu Asn Ala
        115                 120                 125

Lys Phe Gly Gln Ala Lys Ala Asn Ala Leu Ala Gln Leu Tyr Pro Thr
130                 135                 140

Leu Val Asn Ala Lys Ala Gly Gly Tyr Thr Gly Gly Asp Ala Glu Leu
145                 150                 155                 160

Glu Arg Leu His Gly Ala Ile Ala Ile Asp Lys Asp Cys Ala Tyr Glu
                165                 170                 175

Ser Ala Ser Tyr Gly Leu Phe Gln Ile Met Gly Phe Asn Cys Val Ile
            180                 185                 190

Cys Gly Tyr Asp Asn Ala Glu Glu Met Phe Asn Asp Phe Leu Thr Gly
        195                 200                 205

Glu Arg Ala Gln Leu Met Ala Phe Val Lys Phe Ile Lys Ala Asp Ala
210                 215                 220

Asn Leu Trp Lys Ala Leu Lys Asp Lys Asn Trp Ala Glu Phe Ala Arg
225                 230                 235                 240

Arg Tyr Asn Gly Pro Ala Tyr Ala Gln Asn Gln Tyr Asp Thr Lys Leu
                245                 250                 255

Ala Ala Ala Tyr Lys Ser Phe Ser
            260

<210> SEQ ID NO 55
<211> LENGTH: 858
<212> TYPE: DNA
<213> ORGANISM: Burkholderia pseudomultivorans
<220> FEATURE:
<221> NAME/KEY: misc_feature
<222> LOCATION: (28)..(834)
<223> OTHER INFORMATION: GN424 lysin
<220> FEATURE:
<221> NAME/KEY: CDS
<222> LOCATION: (28)..(834)

<400> SEQUENCE: 55
gtttaacttt aagaaggaga attcacc atg aat acc ctt cgt ttc aac agt cgc       54
                              Met Asn Thr Leu Arg Phe Asn Ser Arg
                                1               5 ggc gcc gaa gtc ggc gtg ctg cag caa cgg ctc gtg cgc gcc ggc tat      102
Gly Ala Glu Val Gly Val Leu Gln Gln Arg Leu Val Arg Ala Gly Tyr
 10                  15                  20                  25 ccg atc gac gtc acg cat ctc tac gac gaa gcg acg gag cag gcc gtg      150
Pro Ile Asp Val Thr His Leu Tyr Asp Glu Ala Thr Glu Gln Ala Val
                 30                  35                  40 aag gcg ttg cag gca gcg gcc gga atc gtc gtc gac gga atc gcc ggc      198
Lys Ala Leu Gln Ala Ala Ala Gly Ile Val Val Asp Gly Ile Ala Gly
             45                  50                  55 ccg aac acc tat gcc gtg ttg tcg gcc ggc cag cgc gac cgc aag cac      246
Pro Asn Thr Tyr Ala Val Leu Ser Ala Gly Gln Arg Asp Arg Lys His
         60                  65                  70 ttg acc gaa gcg gac atc gcc cgc gcc gca gac aag ctc ggt gtc tcg      294
```

-continued

```
Leu Thr Glu Ala Asp Ile Ala Arg Ala Ala Asp Lys Leu Gly Val Ser
    75                  80                  85 ccg gca tgc gtc cgc gcc gtc aac gaa gtc gag tca cgc ggc tcg ggc      342
Pro Ala Cys Val Arg Ala Val Asn Glu Val Glu Ser Arg Gly Ser Gly
90                  95                  100                 105 ttt ctg gcg gac ggc cgg ccc gtg att ctc ttc gag cgg cac gtg atg      390
Phe Leu Ala Asp Gly Arg Pro Val Ile Leu Phe Glu Arg His Val Met
                110                 115                 120 tac aac cgc ctc gtc gcg gcg aag cgt gcc gtc gac gca gcg agc gca      438
Tyr Asn Arg Leu Val Ala Ala Lys Arg Ala Val Asp Ala Ala Ser Ala
            125                 130                 135 gcg cag cgc ttt ccg aac gtc gtc agc gcg aag ccg ggc gga tac cag      486
Ala Gln Arg Phe Pro Asn Val Val Ser Ala Lys Pro Gly Gly Tyr Gln
        140                 145                 150 ggc ggc gca gcc gaa tat gtg cga ctc gac acc gcc gcg cgc atc gat      534
Gly Gly Ala Ala Glu Tyr Val Arg Leu Asp Thr Ala Ala Arg Ile Asp
    155                 160                 165 gcg gca atc gcg tac gaa tcg gcg agc tgg ggc gca ttt cag gtg atg      582
Ala Ala Ile Ala Tyr Glu Ser Ala Ser Trp Gly Ala Phe Gln Val Met
170                 175                 180                 185 ggc tat cac tgg gaa cgc ctg ggc tac tcg agc atc gac gag ttc gtt      630
Gly Tyr His Trp Glu Arg Leu Gly Tyr Ser Ser Ile Asp Glu Phe Val
                190                 195                 200 gcc cgg atg gag acg agc gaa ggc gaa cag ctc gac gcg ttt gtg cgg      678
Ala Arg Met Glu Thr Ser Glu Gly Glu Gln Leu Asp Ala Phe Val Arg
            205                 210                 215 ttc gtc gcc gcc gac tcg tcg ctg cgc acg gcg ctg aaa aac cgg aag      726
Phe Val Ala Ala Asp Ser Ser Leu Arg Thr Ala Leu Lys Asn Arg Lys
        220                 225                 230 tgg gct gca ttc gcg aag ggc tac aac ggc ccg gac tat gcg cgc aac      774
Trp Ala Ala Phe Ala Lys Gly Tyr Asn Gly Pro Asp Tyr Ala Arg Asn
    235                 240                 245 ctc tac gac gcg aag ctc gcc cag gcg tac gaa cgg tat gcc ggc acg      822
Leu Tyr Asp Ala Lys Leu Ala Gln Ala Tyr Glu Arg Tyr Ala Gly Thr
250                 255                 260                 265 aag gcg gcc gcg tgataaaagc ttggctgttt tggc                           858
Lys Ala Ala Ala <210> SEQ ID NO 56
<211> LENGTH: 269
<212> TYPE: PRT
<213> ORGANISM: Burkholderia pseudomultivorans

<400> SEQUENCE: 56

Met Asn Thr Leu Arg Phe Asn Ser Arg Gly Ala Glu Val Gly Val Leu
1               5                   10                  15

Gln Gln Arg Leu Val Arg Ala Gly Tyr Pro Ile Asp Val Thr His Leu
            20                  25                  30

Tyr Asp Glu Ala Thr Glu Gln Ala Val Lys Ala Leu Gln Ala Ala Ala
        35                  40                  45

Gly Ile Val Val Asp Gly Ile Ala Gly Pro Asn Thr Tyr Ala Val Leu
    50                  55                  60

Ser Ala Gly Gln Arg Asp Arg Lys His Leu Thr Glu Ala Asp Ile Ala
65                  70                  75                  80

Arg Ala Ala Asp Lys Leu Gly Val Ser Pro Ala Cys Val Arg Ala Val
                85                  90                  95

Asn Glu Val Glu Ser Arg Gly Ser Gly Phe Leu Ala Asp Gly Arg Pro
            100                 105                 110
```

| | | | | | | | | | | | |
|---|---|---|---|---|---|---|---|---|---|---|---|
|Val|Ile|Leu|Phe|Glu|Arg|His|Val|Met|Tyr|Asn|Arg|Leu|Val|Ala|Ala|
| | |115| | | |120| | | |125| | | | | |

Lys Arg Ala Val Asp Ala Ala Ser Ala Ala Gln Arg Phe Pro Asn Val
130 135 140

Val Ser Ala Lys Pro Gly Gly Tyr Gln Gly Gly Ala Ala Glu Tyr Val
145 150 155 160

Arg Leu Asp Thr Ala Ala Arg Ile Asp Ala Ala Ile Ala Tyr Glu Ser
165 170 175

Ala Ser Trp Gly Ala Phe Gln Val Met Gly Tyr His Trp Glu Arg Leu
180 185 190

Gly Tyr Ser Ser Ile Asp Glu Phe Val Ala Arg Met Glu Thr Ser Glu
195 200 205

Gly Glu Gln Leu Asp Ala Phe Val Arg Phe Val Ala Ala Asp Ser Ser
210 215 220

Leu Arg Thr Ala Leu Lys Asn Arg Lys Trp Ala Ala Phe Ala Lys Gly
225 230 235 240

Tyr Asn Gly Pro Asp Tyr Ala Arg Asn Leu Tyr Asp Ala Lys Leu Ala
245 250 255

Gln Ala Tyr Glu Arg Tyr Ala Gly Thr Lys Ala Ala Ala
260 265

<210> SEQ ID NO 57
<211> LENGTH: 864
<212> TYPE: DNA
<213> ORGANISM: Pseudomonas flexibilis
<220> FEATURE:
<221> NAME/KEY: misc_feature
<222> LOCATION: (28)..(840)
<223> OTHER INFORMATION: GN425 lysin
<220> FEATURE:
<221> NAME/KEY: CDS
<222> LOCATION: (28)..(840)

<400> SEQUENCE: 57

```
gtttaacttt aagaaggaga attcacc atg acc ctg cgc ctc gat gac gtc ggc       54
                                Met Thr Leu Arg Leu Asp Asp Val Gly
                                 1               5 ctc gac gtg ctc cat ctg cag aag cgc ctc aac gag ctg ggc gcg aat       102
Leu Asp Val Leu His Leu Gln Lys Arg Leu Asn Glu Leu Gly Ala Asn
 10              15                  20                  25 ccg cgg ctg ctg ccc gat ggc cag ttc ggc gag gtc acc gag cgc gcc       150
Pro Arg Leu Leu Pro Asp Gly Gln Phe Gly Glu Val Thr Glu Arg Ala
                 30                  35                  40 gtg cgg gcc ttc cag caa cgt gcc ggc ctg gtg gtc gat ggc gtg gcc       198
Val Arg Ala Phe Gln Gln Arg Ala Gly Leu Val Val Asp Gly Val Ala
             45                  50                  55 gga ccc aag acg atg gcc gcc ctg tcc ggc cat tcc acc agc cgc ctg       246
Gly Pro Lys Thr Met Ala Ala Leu Ser Gly His Ser Thr Ser Arg Leu
         60                  65                  70 ctc ggc cag cgc gac ctg caa cgc gcc gcc gac cgc ttg ggc gtg ccg       294
Leu Gly Gln Arg Asp Leu Gln Arg Ala Ala Asp Arg Leu Gly Val Pro
     75                  80                  85 ctg gcc agc gtc atg gcc ctc aat gcc gtg gaa agt cgc ggc gag ggc       342
Leu Ala Ser Val Met Ala Leu Asn Ala Val Glu Ser Arg Gly Glu Gly
 90                  95                 100                 105 ttc gcc gcc aat ggc cgg ccg gtg atc ctg ttc gag cgg cac gtg atg       390
Phe Ala Ala Asn Gly Arg Pro Val Ile Leu Phe Glu Arg His Val Met
                110                 115                 120 cac gaa cgc ttg cag gtc aac ggc ctg agc gaa gcc gag gcg gac gcc       438
His Glu Arg Leu Gln Val Asn Gly Leu Ser Glu Ala Glu Ala Asp Ala
```

```
                                 125                 130                 135
ctg gcg gca cgc cac ccc ggc ctg gtg agt cgc cgg cca ggc ggc tac     486
Leu Ala Ala Arg His Pro Gly Leu Val Ser Arg Arg Pro Gly Gly Tyr
            140                 145                 150 gtc ggc gac acc gcc gag cat cag cgc ctg gcc aat gcc cgc ctg ttg     534
Val Gly Asp Thr Ala Glu His Gln Arg Leu Ala Asn Ala Arg Leu Leu
        155                 160                 165 cat gac acc gct gcc ctg gaa tcc gcc agt tgg gga ctg ttc cag gtg     582
His Asp Thr Ala Ala Leu Glu Ser Ala Ser Trp Gly Leu Phe Gln Val
170                 175                 180                 185 atg ggc tac cac tgg cag gcc ctg ggc tac gac acc cag gac ttc         630
Met Gly Tyr His Trp Gln Ala Leu Gly Tyr Asp Thr Thr Gln Asp Phe
                190                 195                 200 acc gag cgc atg gcc cgc cac gaa gcc gag cac ctg gaa gcg ttc gtg     678
Thr Glu Arg Met Ala Arg His Glu Ala Glu His Leu Glu Ala Phe Val
            205                 210                 215 cgc ttc atc gaa gcc gat ccg gca ctg cac aag gca ctc aag ggc cgt     726
Arg Phe Ile Glu Ala Asp Pro Ala Leu His Lys Ala Leu Lys Gly Arg
        220                 225                 230 aag tgg gcc gag ttc gcc cgc cgc tac aac ggc ccg gcc tac gcc cgc     774
Lys Trp Ala Glu Phe Ala Arg Arg Tyr Asn Gly Pro Ala Tyr Ala Arg
235                 240                 245 aat ttg tac gac gtg aag ctg gct cgg gca ttc gag caa ttc agc gac     822
Asn Leu Tyr Asp Val Lys Leu Ala Arg Ala Phe Glu Gln Phe Ser Asp
250                 255                 260                 265 gca ctg cag gcc gcc gca tgataaaagc ttggctgttt tggc                  864
Ala Leu Gln Ala Ala Ala
                270

<210> SEQ ID NO 58
<211> LENGTH: 271
<212> TYPE: PRT
<213> ORGANISM: Pseudomonas flexibilis

<400> SEQUENCE: 58

Met Thr Leu Arg Leu Asp Asp Val Gly Leu Asp Val Leu His Leu Gln
1               5                   10                  15

Lys Arg Leu Asn Glu Leu Gly Ala Asn Pro Arg Leu Leu Pro Asp Gly
            20                  25                  30

Gln Phe Gly Glu Val Thr Glu Arg Ala Val Arg Ala Phe Gln Gln Arg
        35                  40                  45

Ala Gly Leu Val Val Asp Gly Val Ala Gly Pro Lys Thr Met Ala Ala
    50                  55                  60

Leu Ser Gly His Ser Thr Ser Arg Leu Leu Gly Gln Arg Asp Leu Gln
65                  70                  75                  80

Arg Ala Ala Asp Arg Leu Gly Val Pro Leu Ala Ser Val Met Ala Leu
                85                  90                  95

Asn Ala Val Glu Ser Arg Gly Glu Gly Phe Ala Ala Asn Gly Arg Pro
            100                 105                 110

Val Ile Leu Phe Glu Arg His Val Met His Glu Arg Leu Gln Val Asn
        115                 120                 125

Gly Leu Ser Glu Ala Glu Ala Asp Ala Leu Ala Ala Arg His Pro Gly
    130                 135                 140

Leu Val Ser Arg Arg Pro Gly Gly Tyr Val Gly Asp Thr Ala Glu His
145                 150                 155                 160

Gln Arg Leu Ala Asn Ala Arg Leu Leu His Asp Thr Ala Ala Leu Glu
                165                 170                 175
```

```
Ser Ala Ser Trp Gly Leu Phe Gln Val Met Gly Tyr His Trp Gln Ala
            180                 185                 190

Leu Gly Tyr Asp Thr Thr Gln Asp Phe Thr Glu Arg Met Ala Arg His
        195                 200                 205

Glu Ala Glu His Leu Glu Ala Phe Val Arg Phe Ile Glu Ala Asp Pro
    210                 215                 220

Ala Leu His Lys Ala Leu Lys Gly Arg Lys Trp Ala Glu Phe Ala Arg
225                 230                 235                 240

Arg Tyr Asn Gly Pro Ala Tyr Ala Arg Asn Leu Tyr Asp Val Lys Leu
                245                 250                 255

Ala Arg Ala Phe Glu Gln Phe Ser Asp Ala Leu Gln Ala Ala Ala
            260                 265                 270

<210> SEQ ID NO 59
<211> LENGTH: 843
<212> TYPE: DNA
<213> ORGANISM: Escherichia virus
<220> FEATURE:
<221> NAME/KEY: misc_feature
<222> LOCATION: (28)..(819)
<223> OTHER INFORMATION: GN428 lysin
<220> FEATURE:
<221> NAME/KEY: CDS
<222> LOCATION: (28)..(819)

<400> SEQUENCE: 59
gtttaacttt aagaaggaga attcacc atg gcc att cta aaa ctt ggc aac cga      54
                                Met Ala Ile Leu Lys Leu Gly Asn Arg
                                  1               5 ggt tct gaa gtc aaa gca ctt caa caa agc ctc aac aaa atc ggt ttc       102
Gly Ser Glu Val Lys Ala Leu Gln Gln Ser Leu Asn Lys Ile Gly Phe
 10              15                  20                  25 tct ctt aca gcc gat ggc ata ttt ggt aag gca aca gag aat gcc gtc       150
Ser Leu Thr Ala Asp Gly Ile Phe Gly Lys Ala Thr Glu Asn Ala Val
             30                  35                  40 aaa tcc gtt cag gca ggt gct gga ttg gtt att gat ggt att gct ggg       198
Lys Ser Val Gln Ala Gly Ala Gly Leu Val Ile Asp Gly Ile Ala Gly
         45                  50                  55 cca aag acc ttc tat gct atc cgc aac gct gga gac gct cac cag gaa       246
Pro Lys Thr Phe Tyr Ala Ile Arg Asn Ala Gly Asp Ala His Gln Glu
     60                  65                  70 cat ctg acc gaa gcg gac ttg gtt gac gca gca cgt gaa ctt ggt gtt       294
His Leu Thr Glu Ala Asp Leu Val Asp Ala Ala Arg Glu Leu Gly Val
 75                  80                  85 gag ctg gcc agt atg aaa gcg gtg aac cag gta gaa tcc cgt ggt acg       342
Glu Leu Ala Ser Met Lys Ala Val Asn Gln Val Glu Ser Arg Gly Thr
 90                  95                 100                 105 ggt ttt acc aaa act ggc aag atc aaa act ctg ttt gag cgc cac atc       390
Gly Phe Thr Lys Thr Gly Lys Ile Lys Thr Leu Phe Glu Arg His Ile
             110                 115                 120 atg tac aaa aag gtg acg gcc aaa ttc ggg caa gca aga gcc aat gct       438
Met Tyr Lys Lys Val Thr Ala Lys Phe Gly Gln Ala Arg Ala Asn Ala
         125                 130                 135 ctg tac caa ctc tac cca aca ttg gtt aac ccc aat tct ggc ggg tat       486
Leu Tyr Gln Leu Tyr Pro Thr Leu Val Asn Pro Asn Ser Gly Gly Tyr
     140                 145                 150 atc ggc gga gac gcg gag ttg gaa cgc ctt cag ggt gca atc gcc ctt       534
Ile Gly Gly Asp Ala Glu Leu Glu Arg Leu Gln Gly Ala Ile Ala Leu
 155                 160                 165 gac gag gac tgc gct tac gag agt gct tcc tac ggc cta ttc cag atc       582
Asp Glu Asp Cys Ala Tyr Glu Ser Ala Ser Tyr Gly Leu Phe Gln Ile
```

```
                170                 175                 180                 185
atg ggg ttc aac tgc caa atc tgt ggc tat tca aat gcc aaa gag atg        630
Met Gly Phe Asn Cys Gln Ile Cys Gly Tyr Ser Asn Ala Lys Glu Met
                190                 195                 200 ttc act gat ttc ctg act ggt gaa cgc gct cat ctt ctg gca ttt gtc        678
Phe Thr Asp Phe Leu Thr Gly Glu Arg Ala His Leu Leu Ala Phe Val
            205                 210                 215 aag ttc atc aag gct gat gcc aat atg tgg aaa gcc ctg aag aac aag        726
Lys Phe Ile Lys Ala Asp Ala Asn Met Trp Lys Ala Leu Lys Asn Lys
        220                 225                 230 aat tgg gcc gag ttt gct cgt cgg tac aat ggt ccg gca tat gcg aaa        774
Asn Trp Ala Glu Phe Ala Arg Arg Tyr Asn Gly Pro Ala Tyr Ala Lys
    235                 240                 245 aac cag tat gat act aaa ctg gcg gca gca tac aag agt ttc tgt            819
Asn Gln Tyr Asp Thr Lys Leu Ala Ala Ala Tyr Lys Ser Phe Cys
250                 255                 260 taataaaagc ttggctgttt tggc                                             843

<210> SEQ ID NO 60
<211> LENGTH: 264
<212> TYPE: PRT
<213> ORGANISM: Escherichia virus

<400> SEQUENCE: 60

Met Ala Ile Leu Lys Leu Gly Asn Arg Gly Ser Glu Val Lys Ala Leu
1               5                   10                  15

Gln Gln Ser Leu Asn Lys Ile Gly Phe Ser Leu Thr Ala Asp Gly Ile
            20                  25                  30

Phe Gly Lys Ala Thr Glu Asn Ala Val Lys Ser Val Gln Ala Gly Ala
        35                  40                  45

Gly Leu Val Ile Asp Gly Ile Ala Gly Pro Lys Thr Phe Tyr Ala Ile
    50                  55                  60

Arg Asn Ala Gly Asp Ala His Gln Glu His Leu Thr Glu Ala Asp Leu
65                  70                  75                  80

Val Asp Ala Ala Arg Glu Leu Gly Val Glu Leu Ala Ser Met Lys Ala
                85                  90                  95

Val Asn Gln Val Glu Ser Arg Gly Thr Gly Phe Thr Lys Thr Gly Lys
            100                 105                 110

Ile Lys Thr Leu Phe Glu Arg His Ile Met Tyr Lys Lys Val Thr Ala
        115                 120                 125

Lys Phe Gly Gln Ala Arg Ala Asn Ala Leu Tyr Gln Leu Tyr Pro Thr
    130                 135                 140

Leu Val Asn Pro Asn Ser Gly Gly Tyr Ile Gly Gly Asp Ala Glu Leu
145                 150                 155                 160

Glu Arg Leu Gln Gly Ala Ile Ala Leu Asp Glu Asp Cys Ala Tyr Glu
                165                 170                 175

Ser Ala Ser Tyr Gly Leu Phe Gln Ile Met Gly Phe Asn Cys Gln Ile
            180                 185                 190

Cys Gly Tyr Ser Asn Ala Lys Glu Met Phe Thr Asp Phe Leu Thr Gly
        195                 200                 205

Glu Arg Ala His Leu Leu Ala Phe Val Lys Phe Ile Lys Ala Asp Ala
    210                 215                 220

Asn Met Trp Lys Ala Leu Lys Asn Lys Asn Trp Ala Glu Phe Ala Arg
225                 230                 235                 240

Arg Tyr Asn Gly Pro Ala Tyr Ala Lys Asn Gln Tyr Asp Thr Lys Leu
                245                 250                 255
```

<210> SEQ ID NO 61
<211> LENGTH: 660
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: misc_feature
<222> LOCATION: (13)..(639)
<223> OTHER INFORMATION: GN93 lysin
<220> FEATURE:
<221> NAME/KEY: CDS
<222> LOCATION: (13)..(639)

<400> SEQUENCE: 61

```
ggagaattca cc atg aaa ttc ttt aag ttc ttt aag ttt ttt aaa gcc ggc      51
              Met Lys Phe Phe Lys Phe Phe Lys Phe Phe Lys Ala Gly
                1               5                  10 gca gga gct ggt gca gga gct ggt gca gga gct ggt gca gga gct agc       99
Ala Gly Ala Gly Ala Gly Ala Gly Ala Gly Ala Gly Ala Gly Ala Ser
         15                  20                  25 aat aac gaa ctt cct tgg gta gcc gaa gcc cga aag tat atc ggc ctt      147
Asn Asn Glu Leu Pro Trp Val Ala Glu Ala Arg Lys Tyr Ile Gly Leu
 30                  35                  40                  45 cgc gaa gac act tcg aag act tcg cat aac ccg aaa ctt ctt gcc atg      195
Arg Glu Asp Thr Ser Lys Thr Ser His Asn Pro Lys Leu Leu Ala Met
                 50                  55                  60 ctt gac cgc atg ggc gaa ttt tcc aac gaa tcc cgc gct tgg tgg cac      243
Leu Asp Arg Met Gly Glu Phe Ser Asn Glu Ser Arg Ala Trp Trp His
             65                  70                  75 gac gac gaa acg cct tgg tgc gga ctg ttc gtc ggc tat tgc ttg ggc      291
Asp Asp Glu Thr Pro Trp Cys Gly Leu Phe Val Gly Tyr Cys Leu Gly
         80                  85                  90 gtt gcc ggg cgc tac gtc gtc cgc gaa tgg tac agg gcg cgg gca tgg      339
Val Ala Gly Arg Tyr Val Val Arg Glu Trp Tyr Arg Ala Arg Ala Trp
     95                 100                 105 gaa gcc ccg cag ctt acg aag ctt gac cgg ccc gca tac ggc gcg ctt      387
Glu Ala Pro Gln Leu Thr Lys Leu Asp Arg Pro Ala Tyr Gly Ala Leu
110                 115                 120                 125 gtg acc ttc acg cga agc ggc ggc ggc cac gtc ggt ttt att gtg ggc      435
Val Thr Phe Thr Arg Ser Gly Gly Gly His Val Gly Phe Ile Val Gly
                130                 135                 140 aag gat gcg cgc gga aat ctt atg gtt ctt ggc ggt aat cag tcg aac      483
Lys Asp Ala Arg Gly Asn Leu Met Val Leu Gly Gly Asn Gln Ser Asn
            145                 150                 155 gcc gta agt atc gca ccg ttc gca gta tcc cgc gta acc ggc tat ttc      531
Ala Val Ser Ile Ala Pro Phe Ala Val Ser Arg Val Thr Gly Tyr Phe
        160                 165                 170 tgg ccg tcg ttc tgg cga aac aag acc gca gtt aaa agc gtt ccg ttt      579
Trp Pro Ser Phe Trp Arg Asn Lys Thr Ala Val Lys Ser Val Pro Phe
    175                 180                 185 gaa gaa cgt tat tcg ctg ccg ctg ttg aag tcg aac ggc gaa ctt tcg      627
Glu Glu Arg Tyr Ser Leu Pro Leu Leu Lys Ser Asn Gly Glu Leu Ser
190                 195                 200                 205 acg aat gaa gcg taataagctt ggctgttttg g                              660
Thr Asn Glu Ala
```

<210> SEQ ID NO 62

-continued

```
<211> LENGTH: 209
<212> TYPE: PRT
<213> ORGANISM: Artificial Sequence
<220> FEATURE:
<223> OTHER INFORMATION: Synthetic Construct

<400> SEQUENCE: 62

Met Lys Phe Phe Lys Phe Phe Lys Phe Phe Lys Ala Gly Ala Gly Ala
1               5                   10                  15

Gly Ala Gly Ala Gly Ala Gly Ala Gly Ala Ser Asn Asn Glu
            20                  25                  30

Leu Pro Trp Val Ala Glu Ala Arg Lys Tyr Ile Gly Leu Arg Glu Asp
        35                  40                  45

Thr Ser Lys Thr Ser His Asn Pro Lys Leu Leu Ala Met Leu Asp Arg
    50                  55                  60

Met Gly Glu Phe Ser Asn Glu Ser Arg Ala Trp Trp His Asp Asp Glu
65                  70                  75                  80

Thr Pro Trp Cys Gly Leu Phe Val Gly Tyr Cys Leu Gly Val Ala Gly
                85                  90                  95

Arg Tyr Val Val Arg Glu Trp Tyr Arg Ala Arg Ala Trp Glu Ala Pro
            100                 105                 110

Gln Leu Thr Lys Leu Asp Arg Pro Ala Tyr Gly Ala Leu Val Thr Phe
        115                 120                 125

Thr Arg Ser Gly Gly Gly His Val Gly Phe Ile Val Gly Lys Asp Ala
    130                 135                 140

Arg Gly Asn Leu Met Val Leu Gly Gly Asn Gln Ser Asn Ala Val Ser
145                 150                 155                 160

Ile Ala Pro Phe Ala Val Ser Arg Val Thr Gly Tyr Phe Trp Pro Ser
                165                 170                 175

Phe Trp Arg Asn Lys Thr Ala Val Lys Ser Val Pro Phe Glu Glu Arg
            180                 185                 190

Tyr Ser Leu Pro Leu Leu Lys Ser Asn Gly Glu Leu Ser Thr Asn Glu
        195                 200                 205

Ala

<210> SEQ ID NO 63
<211> LENGTH: 843
<212> TYPE: DNA
<213> ORGANISM: Dickeya phage phiD3
<220> FEATURE:
<221> NAME/KEY: misc_feature
<222> LOCATION: (28)..(819)
<223> OTHER INFORMATION: GN431 lysin
<220> FEATURE:
<221> NAME/KEY: CDS
<222> LOCATION: (28)..(819)

<400> SEQUENCE: 63
gtttaacttt aagaaggaga attcacc atg gcc att cta aaa ctt ggc aac cgt    54
                           Met Ala Ile Leu Lys Leu Gly Asn Arg
                           1               5 ggc act gaa gtg aag gca ctt cag gat agc ctc aac aaa atc ggc ttc    102
Gly Thr Glu Val Lys Ala Leu Gln Asp Ser Leu Asn Lys Ile Gly Phe
10              15                  20                  25 acc ctc gtc gct gac ggc atc ttt ggt aag gca aca gag aac gct gtc    150
Thr Leu Val Ala Asp Gly Ile Phe Gly Lys Ala Thr Glu Asn Ala Val
                30                  35                  40 aag acc gtt cag gcg ggt gcg ggg ctt gtc att gat ggt atc gtg ggt    198
Lys Thr Val Gln Ala Gly Ala Gly Leu Val Ile Asp Gly Ile Val Gly
            45                  50                  55
```

-continued

```
cca aag acc tcc tat gct att cgc aac gcc ggg gaa gcg cat cag gat    246
Pro Lys Thr Ser Tyr Ala Ile Arg Asn Ala Gly Glu Ala His Gln Asp
         60                  65                  70 cac ctg act gag gct gac ctt atc gag gcg gcc aat cag ctg ggc gtc    294
His Leu Thr Glu Ala Asp Leu Ile Glu Ala Ala Asn Gln Leu Gly Val
     75                  80                  85 gac ctc gct tct gtg aag gca gtc aac cag gtt gaa tcc cgt ggc aca    342
Asp Leu Ala Ser Val Lys Ala Val Asn Gln Val Glu Ser Arg Gly Thr
 90                  95                 100                 105 ggc ttc acc aag tca ggc aag atc aag aca ttg ttc gag cgt cac atc    390
Gly Phe Thr Lys Ser Gly Lys Ile Lys Thr Leu Phe Glu Arg His Ile
                 110                 115                 120 atg tat aag aaa ctg atg gca aag ttc gga cag gct cga gcg aat gcc    438
Met Tyr Lys Lys Leu Met Ala Lys Phe Gly Gln Ala Arg Ala Asn Ala
             125                 130                 135 atg ggt cag atg tat ccg act ctg gtc agc ccg gtt gca ggc ggg tac    486
Met Gly Gln Met Tyr Pro Thr Leu Val Ser Pro Val Ala Gly Gly Tyr
         140                 145                 150 acg gga ggt gac gca gaa ttg gat cga ctc cac gca gcg atc aac atc    534
Thr Gly Gly Asp Ala Glu Leu Asp Arg Leu His Ala Ala Ile Asn Ile
     155                 160                 165 gac gag gat tgt gcg tac gag agc gct tca tac ggc ctc ttc cag atc    582
Asp Glu Asp Cys Ala Tyr Glu Ser Ala Ser Tyr Gly Leu Phe Gln Ile
170                 175                 180                 185 atg ggc ttc aac tgc cag gtc tgc ggg tat gcc aac gcc aag gag atg    630
Met Gly Phe Asn Cys Gln Val Cys Gly Tyr Ala Asn Ala Lys Glu Met
                 190                 195                 200 ttc aat gac ttc ctg acg gga gaa cgt gct cac ctg atg gca ttc gtg    678
Phe Asn Asp Phe Leu Thr Gly Glu Arg Ala His Leu Met Ala Phe Val
             205                 210                 215 aag ttc atc aag gct gat gcc aag ctc tgg cag gct ctg aag gac aag    726
Lys Phe Ile Lys Ala Asp Ala Lys Leu Trp Gln Ala Leu Lys Asp Lys
         220                 225                 230 aat tgg gct gag ttc gcg cgg cgc tat aat ggt ccg gcg tat acc aag    774
Asn Trp Ala Glu Phe Ala Arg Arg Tyr Asn Gly Pro Ala Tyr Thr Lys
235                 240                 245 aac cag tac gac acg aag ctc gca gca gca tac aac agc ttc aat        819
Asn Gln Tyr Asp Thr Lys Leu Ala Ala Ala Tyr Asn Ser Phe Asn
250                 255                 260 taataaaagc ttggctgttt tggc                                         843
```

<210> SEQ ID NO 64
<211> LENGTH: 264
<212> TYPE: PRT
<213> ORGANISM: Dickeya phage phiD3

<400> SEQUENCE: 64

```
Met Ala Ile Leu Lys Leu Gly Asn Arg Gly Thr Glu Val Lys Ala Leu
1               5                   10                  15

Gln Asp Ser Leu Asn Lys Ile Gly Phe Thr Leu Val Ala Asp Gly Ile
            20                  25                  30

Phe Gly Lys Ala Thr Glu Asn Ala Val Lys Thr Val Gln Ala Gly Ala
        35                  40                  45

Gly Leu Val Ile Asp Gly Ile Val Gly Pro Lys Thr Ser Tyr Ala Ile
    50                  55                  60

Arg Asn Ala Gly Glu Ala His Gln Asp His Leu Thr Glu Ala Asp Leu
65                  70                  75                  80

Ile Glu Ala Ala Asn Gln Leu Gly Val Asp Leu Ala Ser Val Lys Ala
```

```
                85                  90                  95
Val Asn Gln Val Glu Ser Arg Gly Thr Gly Phe Thr Lys Ser Gly Lys
            100                 105                 110

Ile Lys Thr Leu Phe Glu Arg His Ile Met Tyr Lys Lys Leu Met Ala
        115                 120                 125

Lys Phe Gly Gln Ala Arg Ala Asn Ala Met Gly Gln Met Tyr Pro Thr
    130                 135                 140

Leu Val Ser Pro Val Ala Gly Gly Tyr Thr Gly Gly Asp Ala Glu Leu
145                 150                 155                 160

Asp Arg Leu His Ala Ala Ile Asn Ile Asp Glu Asp Cys Ala Tyr Glu
                165                 170                 175

Ser Ala Ser Tyr Gly Leu Phe Gln Ile Met Gly Phe Asn Cys Gln Val
            180                 185                 190

Cys Gly Tyr Ala Asn Ala Lys Glu Met Phe Asn Asp Phe Leu Thr Gly
        195                 200                 205

Glu Arg Ala His Leu Met Ala Phe Val Lys Phe Ile Lys Ala Asp Ala
    210                 215                 220

Lys Leu Trp Gln Ala Leu Lys Asp Lys Asn Trp Ala Glu Phe Ala Arg
225                 230                 235                 240

Arg Tyr Asn Gly Pro Ala Tyr Thr Lys Asn Gln Tyr Asp Thr Lys Leu
                245                 250                 255

Ala Ala Ala Tyr Asn Ser Phe Asn
            260

<210> SEQ ID NO 65
<211> LENGTH: 510
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (10)..(510)
<223> OTHER INFORMATION: GN486 lysin
<220> FEATURE:
<221> NAME/KEY: CDS
<222> LOCATION: (10)..(510)

<400> SEQUENCE: 65 gaattcacc atg gga tcc cat cat cac cac cat cat ggt ggt ccg cgt cgt      51
          Met Gly Ser His His His His His His Gly Gly Pro Arg Arg
            1               5                   10 ccg cgt cgt ccg ggt cgt cgt gct ccg gtt cgt acc tct cag cgt ggt        99
Pro Arg Arg Pro Gly Arg Arg Ala Pro Val Arg Thr Ser Gln Arg Gly
15                  20                  25                  30 atc gac ctg atc aaa tct ttc gaa ggt ctg cgt ctg tct gct tac cag       147
Ile Asp Leu Ile Lys Ser Phe Glu Gly Leu Arg Leu Ser Ala Tyr Gln
                35                  40                  45 gac tct gtt ggt gtt tgg acc atc ggt tac ggt acc acc cgt ggt gtt       195
Asp Ser Val Gly Val Trp Thr Ile Gly Tyr Gly Thr Thr Arg Gly Val
            50                  55                  60 acc cgt tac atg acc atc acc gtt gaa cag gct gaa cgt atg ctg tct       243
Thr Arg Tyr Met Thr Ile Thr Val Glu Gln Ala Glu Arg Met Leu Ser
        65                  70                  75 aac gac atc cag cgt ttc gaa ccg gaa ctg gac cgt ctg gct aaa gtt       291
Asn Asp Ile Gln Arg Phe Glu Pro Glu Leu Asp Arg Leu Ala Lys Val
    80                  85                  90 ccg ctg aac cag aac cag tgg gac gct ctg atg tct ttc gtt tac aac       339
Pro Leu Asn Gln Asn Gln Trp Asp Ala Leu Met Ser Phe Val Tyr Asn
```

```
                    95                  100                 105                 110
ctg  ggt  gct  gct  aac  ctg  gct  tct  tct  acc  ctg  ctg  aaa  ctg  ctg  aac        387
Leu  Gly  Ala  Ala  Asn  Leu  Ala  Ser  Ser  Thr  Leu  Leu  Lys  Leu  Leu  Asn
                    115                 120                 125 aaa  ggt  gac  tac  cag  ggt  gct  gct  gac  cag  ttc  ccg  cgt  tgg  gtt  aac        435
Lys  Gly  Asp  Tyr  Gln  Gly  Ala  Ala  Asp  Gln  Phe  Pro  Arg  Trp  Val  Asn
               130                 135                 140 gct  ggt  ggt  aaa  cgt  ctg  gac  ggt  ctg  gtt  aaa  cgt  cgt  gct  gct  gaa        483
Ala  Gly  Gly  Lys  Arg  Leu  Asp  Gly  Leu  Val  Lys  Arg  Arg  Ala  Ala  Glu
               145                 150                 155 cgt  gct  ctg  ttc  ctg  gaa  ccg  ctg  tct                                            510
Arg  Ala  Leu  Phe  Leu  Glu  Pro  Leu  Ser
          160                 165

<210> SEQ ID NO 66
<211> LENGTH: 167
<212> TYPE: PRT
<213> ORGANISM: Artificial Sequence
<220> FEATURE:
<223> OTHER INFORMATION: Synthetic Construct

<400> SEQUENCE: 66

Met  Gly  Ser  His  His  His  His  His  Gly  Gly  Pro  Arg  Arg  Pro  Arg
1                 5                  10                  15

Arg  Pro  Gly  Arg  Arg  Ala  Pro  Val  Arg  Thr  Ser  Gln  Arg  Gly  Ile  Asp
              20                  25                  30

Leu  Ile  Lys  Ser  Phe  Glu  Gly  Leu  Arg  Leu  Ser  Ala  Tyr  Gln  Asp  Ser
         35                  40                  45

Val  Gly  Val  Trp  Thr  Ile  Gly  Tyr  Gly  Thr  Thr  Arg  Gly  Val  Thr  Arg
 50                  55                  60

Tyr  Met  Thr  Ile  Thr  Val  Glu  Gln  Ala  Glu  Arg  Met  Leu  Ser  Asn  Asp
65                  70                  75                  80

Ile  Gln  Arg  Phe  Glu  Pro  Glu  Leu  Asp  Arg  Leu  Ala  Lys  Val  Pro  Leu
                 85                  90                  95

Asn  Gln  Asn  Gln  Trp  Asp  Ala  Leu  Met  Ser  Phe  Val  Tyr  Asn  Leu  Gly
             100                 105                 110

Ala  Ala  Asn  Leu  Ala  Ser  Ser  Thr  Leu  Leu  Lys  Leu  Leu  Asn  Lys  Gly
         115                 120                 125

Asp  Tyr  Gln  Gly  Ala  Ala  Asp  Gln  Phe  Pro  Arg  Trp  Val  Asn  Ala  Gly
    130                 135                 140

Gly  Lys  Arg  Leu  Asp  Gly  Leu  Val  Lys  Arg  Arg  Ala  Ala  Glu  Arg  Ala
145                 150                 155                 160

Leu  Phe  Leu  Glu  Pro  Leu  Ser
                165

<210> SEQ ID NO 67
<211> LENGTH: 219
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(216)
<223> OTHER INFORMATION: GN485 lysin
<220> FEATURE:
<221> NAME/KEY: CDS
<222> LOCATION: (1)..(216)

<400> SEQUENCE: 67
```

```
atg ccg ggt ctg tct ggt ttc atc cgt aac gct gac acc ccg gtt acc      48
Met Pro Gly Leu Ser Gly Phe Ile Arg Asn Ala Asp Thr Pro Val Thr
1               5                   10                  15 tct ctg ggt tct gct ggt cac gtt cac gtt ccg gaa ggt ccg ctg atc      96
Ser Leu Gly Ser Ala Gly His Val His Val Pro Glu Gly Pro Leu Ile
                20                  25                  30 cgt atc aac ccg gac tgc ctg ctg ggt acc ccg ttc aaa ttc ttc aag     144
Arg Ile Asn Pro Asp Cys Leu Leu Gly Thr Pro Phe Lys Phe Phe Lys
            35                  40                  45 ttc ttc aag ttc ttc aag ttc ttt aag ttc ttt aag ttt ttc aag ttc     192
Phe Phe Lys Phe Phe Lys Phe Phe Lys Phe Phe Lys Phe Phe Lys Phe
        50                  55                  60 ttc aag aac gaa tgc gtt ctg ctg taa                                 219
Phe Lys Asn Glu Cys Val Leu Leu
65                  70

<210> SEQ ID NO 68
<211> LENGTH: 72
<212> TYPE: PRT
<213> ORGANISM: Artificial Sequence
<220> FEATURE:
<223> OTHER INFORMATION: Synthetic Construct

<400> SEQUENCE: 68

Met Pro Gly Leu Ser Gly Phe Ile Arg Asn Ala Asp Thr Pro Val Thr
1               5                   10                  15

Ser Leu Gly Ser Ala Gly His Val His Val Pro Glu Gly Pro Leu Ile
                20                  25                  30

Arg Ile Asn Pro Asp Cys Leu Leu Gly Thr Pro Phe Lys Phe Lys
            35                  40                  45

Phe Phe Lys Phe Phe Lys Phe Phe Lys Phe Phe Lys Phe Phe Lys Phe
        50                  55                  60

Phe Lys Asn Glu Cys Val Leu Leu
65                  70

<210> SEQ ID NO 69
<211> LENGTH: 132
<212> TYPE: DNA
<213> ORGANISM: Chlamydia phage 2

<400> SEQUENCE: 69
atgaggttaa aaatggcacg aagaagatac agacttccgc gacgtagaag tcgaagactt      60
ttttcaagaa ctgcattgag gatgcatcca agaaataggc ttcgaagaat tatgcgtggc     120
ggcattaggt tc                                                        132

<210> SEQ ID NO 70
<211> LENGTH: 44
<212> TYPE: PRT
<213> ORGANISM: Chlamydia phage 2

<400> SEQUENCE: 70

Met Arg Leu Lys Met Ala Arg Arg Arg Tyr Arg Leu Pro Arg Arg Arg
1               5                   10                  15

Ser Arg Arg Leu Phe Ser Arg Thr Ala Leu Arg Met His Pro Arg Asn
                20                  25                  30

Arg Leu Arg Arg Ile Met Arg Gly Gly Ile Arg Phe
            35                  40

<210> SEQ ID NO 71
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(24)
<223> OTHER INFORMATION: linker

<400> SEQUENCE: 71
accgcgggcg gcaccgcggg cggc                                          24

<210> SEQ ID NO 72
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(8)
<223> OTHER INFORMATION: linker

<400> SEQUENCE: 72

Thr Ala Gly Gly Thr Ala Gly Gly
1               5

<210> SEQ ID NO 73
<211> LENGTH: 435
<212> TYPE: DNA
<213> ORGANISM: Pseudomonas phage PAJU2
<220> FEATURE:
<221> NAME/KEY: misc_feature
<222> LOCATION: (1)..(435)
<223> OTHER INFORMATION: GN4

<400> SEQUENCE: 73
atgcgtacat cccaacgagg catcgacctc atcaaatcct tcgagggcct gcgcctgtcc    60
gcttaccagg actcggtggg tgtctggacc ataggttacg gcaccactcg ggcgtcacc   120 cgctacatga cgatcaccgt cgagcaggcc gagcggatgc tgtcgaacga cattcagcgc   180
ttcgagccag agctagacag gctggcgaag gtgccactga accagaacca gtgggatgcc   240
ctgatgagct tcgtgtacaa cctgggcgcg gccaatctgg cgtcgtccac gctgctcaag   300
ctgctgaaca agggtgacta ccagggagca gcggaccagt tcccgcgctg ggtgaatgcg   360
ggcggtaagc gcttggatgg tctggttaag cgtcgagcag ccgagcgtgc gctgttcctg   420
gagccactat cgtga                                                    435

<210> SEQ ID NO 74
<211> LENGTH: 144
<212> TYPE: PRT
<213> ORGANISM: Pseudomonas phage PAJU2
<220> FEATURE:
<221> NAME/KEY: MISC_FEATURE
<222> LOCATION: (1)..(144)
<223> OTHER INFORMATION: GN4

<400> SEQUENCE: 74

Met Arg Thr Ser Gln Arg Gly Ile Asp Leu Ile Lys Ser Phe Glu Gly
1               5                   10                  15

Leu Arg Leu Ser Ala Tyr Gln Asp Ser Val Gly Val Trp Thr Ile Gly
            20                  25                  30

Tyr Gly Thr Thr Arg Gly Val Thr Arg Tyr Met Thr Ile Thr Val Glu
```

```
                35                  40                  45
Gln Ala Glu Arg Met Leu Ser Asn Asp Ile Gln Arg Phe Glu Pro Glu
 50                  55                  60

Leu Asp Arg Leu Ala Lys Val Pro Leu Asn Gln Asn Gln Trp Asp Ala
 65                  70                  75                  80

Leu Met Ser Phe Val Tyr Asn Leu Gly Ala Ala Asn Leu Ala Ser Ser
                 85                  90                  95

Thr Leu Leu Lys Leu Leu Asn Lys Gly Asp Tyr Gln Gly Ala Ala Asp
            100                 105                 110

Gln Phe Pro Arg Trp Val Asn Ala Gly Gly Lys Arg Leu Asp Gly Leu
        115                 120                 125

Val Lys Arg Arg Ala Ala Glu Arg Ala Leu Phe Leu Glu Pro Leu Ser
    130                 135                 140

<210> SEQ ID NO 75
<211> LENGTH: 63
<212> TYPE: DNA
<213> ORGANISM: Penaeus chinensis

<400> SEQUENCE: 75
atgagcttta acgtgacccc gaaatttaaa cgctggcagc tgtatttcg cggccgcatg      60 tgg                                                                  63

<210> SEQ ID NO 76
<211> LENGTH: 21
<212> TYPE: PRT
<213> ORGANISM: Penaeus chinensis

<400> SEQUENCE: 76

Met Ser Phe Asn Val Thr Pro Lys Phe Lys Arg Trp Gln Leu Tyr Phe
  1               5                  10                  15

Arg Gly Arg Met Trp
             20

<210> SEQ ID NO 77
<211> LENGTH: 438
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(438)
<223> OTHER INFORMATION: Modified GN4 lysin, GN146

<400> SEQUENCE: 77
atgcgtacat cccaacgagg catcgacctc atcaaatcct tcgagggcct gcgcctgtcc      60
gcttaccagg actcggtggg tgtctggacc ataggttacg gcaccactcg gggcgtcacc     120
cgctacatga cgatcaccgt cgagcaggcc gagcggatgc tgtcgaacga cattcagcgc     180
ttcgagccag agctagacag gctggcgaag gtgccactga accagaacca gtgggatgcc     240
ctgatgagct tcgtgtacaa cctgggcgcg gccaatctgg cgtcgtccac gctgctcgac     300
ctgctgaaca agggtgacta ccagggagca gcggaccagt tcccgcattg ggtgaatgcg     360
ggcggtaagc gcttggatgg tctggttaag cgtcgagcag ccgagcgtgc gctgttcctg     420
gagccactat cgtgataa                                                  438

<210> SEQ ID NO 78
```

```
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(144)
<223> OTHER INFORMATION: Modified GN4 lysin, GN146

<400> SEQUENCE: 78
```

Met Arg Thr Ser Gln Arg Gly Ile Asp Leu Ile Lys Ser Phe Glu Gly
1               5                   10                  15

Leu Arg Leu Ser Ala Tyr Gln Asp Ser Val Gly Val Trp Thr Ile Gly
            20                  25                  30

Tyr Gly Thr Thr Arg Gly Val Thr Arg Tyr Met Thr Ile Thr Val Glu
        35                  40                  45

Gln Ala Glu Arg Met Leu Ser Asn Asp Ile Gln Arg Phe Glu Pro Glu
    50                  55                  60

Leu Asp Arg Leu Ala Lys Val Pro Leu Asn Gln Asn Gln Trp Asp Ala
65                  70                  75                  80

Leu Met Ser Phe Val Tyr Asn Leu Gly Ala Ala Asn Leu Ala Ser Ser
                85                  90                  95

Thr Leu Leu Asp Leu Leu Asn Lys Gly Asp Tyr Gln Gly Ala Ala Asp
            100                 105                 110

Gln Phe Pro His Trp Val Asn Ala Gly Gly Lys Arg Leu Asp Gly Leu
        115                 120                 125

Val Lys Arg Arg Ala Ala Glu Arg Ala Leu Phe Leu Glu Pro Leu Ser
    130                 135                 140

```
<210> SEQ ID NO 79
<211> LENGTH: 57
<212> TYPE: DNA
<213> ORGANISM: Pelophylax esculentus

<400> SEQUENCE: 79 attttagca aactggcggg caaaaaatt aaaaacctgc tgattagcgg cctgaaa      57

<210> SEQ ID NO 80
<211> LENGTH: 19
<212> TYPE: PRT
<213> ORGANISM: Pelophylax esculentus

<400> SEQUENCE: 80
```

Ile Phe Ser Lys Leu Ala Gly Lys Lys Ile Lys Asn Leu Leu Ile Ser
1               5                   10                  15

Gly Leu Lys

```
<210> SEQ ID NO 81
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(36)
<223> OTHER INFORMATION: BBa_K1485002

<400> SEQUENCE: 81
ggcggtagcg gcagcggtag cggtagcggc agcccg                            36
```

<210> SEQ ID NO 82
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(12)
<223> OTHER INFORMATION: BBa_K1485002

<400> SEQUENCE: 82

Gly Gly Ser Gly Ser Gly Ser Gly Ser Gly Ser Pro
1               5                   10

<210> SEQ ID NO 83
<211> LENGTH: 381
<212> TYPE: DNA
<213> ORGANISM: Micavibrio aeruginosavorus
<220> FEATURE:
<221> NAME/KEY: misc_feature
<222> LOCATION: (1)..(381)
<223> OTHER INFORMATION: GN37

<400> SEQUENCE: 83
atgacataca ccctgagcaa agaagcctg gataacctaa aaggcgttca tcccgatctg      60
gttgccgttg tccatcgcgc catccagctt acaccggttg atttcgcggt gatcgaaggc     120
ctgcgctccg tatcccgcca aaaggaactg gtggccgccg gcgccagcaa gaccatgaac     180
agccgacacc tgacaggcca tgcggttgat ctagccgctt acgtcaatgg catccgctgg     240
gactggcccc tgtatgacgc catcgccgtg gctgtgaaag ccgcagcaaa ggaattgggt     300
gtggccatcg tgtgggcgg tgactggacc acgtttaagg atggcccgca ctttgaactg     360
gatcggagca aatacagatg a                                              381

<210> SEQ ID NO 84
<211> LENGTH: 126
<212> TYPE: PRT
<213> ORGANISM: Micavibrio aeruginosavorus

<400> SEQUENCE: 84

Met Thr Tyr Thr Leu Ser Lys Arg Ser Leu Asp Asn Leu Lys Gly Val
1               5                   10                  15

His Pro Asp Leu Val Ala Val Val His Arg Ala Ile Gln Leu Thr Pro
            20                  25                  30

Val Asp Phe Ala Val Ile Glu Gly Leu Arg Ser Val Ser Arg Gln Lys
        35                  40                  45

Glu Leu Val Ala Ala Gly Ala Ser Lys Thr Met Asn Ser Arg His Leu
    50                  55                  60

Thr Gly His Ala Val Asp Leu Ala Ala Tyr Val Asn Gly Ile Arg Trp
65                  70                  75                  80

Asp Trp Pro Leu Tyr Asp Ala Ile Ala Val Ala Val Lys Ala Ala Ala
                85                  90                  95

Lys Glu Leu Gly Val Ala Ile Val Trp Gly Gly Asp Trp Thr Thr Phe
            100                 105                 110

Lys Asp Gly Pro His Phe Glu Leu Asp Arg Ser Lys Tyr Arg
        115                 120                 125

<210> SEQ ID NO 85

```
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(39)
<223> OTHER INFORMATION: IGEM linker (BBA_K1486037)

<400> SEQUENCE: 85
ggcggtggct ctggaggtgg tgggtccggc ggtggctct                              39

<210> SEQ ID NO 86
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(13)
<223> OTHER INFORMATION: IGEM linker (BBA_K1486037)

<400> SEQUENCE: 86

Gly Gly Gly Ser Gly Gly Gly Ser Gly Gly Gly Ser
1               5                   10

<210> SEQ ID NO 87
<211> LENGTH: 36
<212> TYPE: DNA
<213> ORGANISM: Sus scrofa

<400> SEQUENCE: 87
cgcctgaaaa aaattggcaa agtgctgaaa tggatt                                36

<210> SEQ ID NO 88
<211> LENGTH: 12
<212> TYPE: PRT
<213> ORGANISM: Sus scrofa

<400> SEQUENCE: 88

Arg Leu Lys Lys Ile Gly Lys Val Leu Lys Trp Ile
1               5                   10

<210> SEQ ID NO 89
<211> LENGTH: 102
<212> TYPE: DNA
<213> ORGANISM: Unknown
<220> FEATURE:
<223> OTHER INFORMATION: Description of Unknown: Gokushovirinae sequence
<220> FEATURE:
<221> NAME/KEY: misc_feature
<222> LOCATION: (1)..(102)
<223> OTHER INFORMATION: gkh2
<220> FEATURE:
<221> NAME/KEY: misc_feature
<222> LOCATION: (1)..(102)
<223> OTHER INFORMATION: Description of Unknown: Gokushovirinae sequence

<400> SEQUENCE: 89
atgtcgaaga aggcgtcgag gaagagtttt actaagggtg ccgttaaggt tcataagaaa       60
aatgttccta ctcgtgttcc tatgcgtggc ggtattaggc tt                         102

<210> SEQ ID NO 90
<211> LENGTH: 34
```

```
<212> TYPE: PRT
<213> ORGANISM: Unknown
<220> FEATURE:
<223> OTHER INFORMATION: Description of Unknown: Gokushovirinae sequence

<400> SEQUENCE: 90

Met Ser Lys Lys Ala Ser Arg Lys Ser Phe Thr Lys Gly Ala Val Lys
1               5                   10                  15

Val His Lys Lys Asn Val Pro Thr Arg Val Pro Met Arg Gly Gly Ile
            20                  25                  30

Arg Leu

<210> SEQ ID NO 91
<211> LENGTH: 54
<212> TYPE: DNA
<213> ORGANISM: Sus scrofa

<400> SEQUENCE: 91
cgtaaaaaaa cccgtaaacg tctgaaaaaa atcggtaaag ttctgaaatg gatc      54

<210> SEQ ID NO 92
<211> LENGTH: 18
<212> TYPE: PRT
<213> ORGANISM: Sus scrofa

<400> SEQUENCE: 92

Arg Lys Lys Thr Arg Lys Arg Leu Lys Lys Ile Gly Lys Val Leu Lys
1               5                   10                  15

Trp Ile

<210> SEQ ID NO 93
<211> LENGTH: 45
<212> TYPE: DNA
<213> ORGANISM: Sus scrofa

<400> SEQUENCE: 93
acccgcaaac gcctgaaaaa aattggcaaa gtgctgaaat ggatt              45

<210> SEQ ID NO 94
<211> LENGTH: 15
<212> TYPE: PRT
<213> ORGANISM: Sus scrofa

<400> SEQUENCE: 94

Thr Arg Lys Arg Leu Lys Lys Ile Gly Lys Val Leu Lys Trp Ile
1               5                   10                  15

<210> SEQ ID NO 95
<211> LENGTH: 348
<212> TYPE: DNA
<213> ORGANISM: Pseudomonas phage PaP2

<400> SEQUENCE: 95
atgaaactca gcgaaaaacg agcactgttc acccagctgc ttgcccagtt aattctttgg      60
gcaggaactc aggatcgagt gtcagtagcc ttggatcaag tgaaaaggac acaggctgaa     120
gctgatgcca atgctaagtc tggagcaggc attaggaact ctctccatct actgggatta     180
gccggtgatc ttatcctcta caaggatggt aaatacatgg ataagagcga ggattataag     240
ttcctgggag attactggaa gagtctccat cctctttgtc ggtggggcgg agattttaaa     300
agccgtcctg atggtaatca tttctccttg gaacacgaag gagtgcaa               348
```

<210> SEQ ID NO 96
<211> LENGTH: 116
<212> TYPE: PRT
<213> ORGANISM: Pseudomonas phage PaP2

<400> SEQUENCE: 96

Met Lys Leu Ser Glu Lys Arg Ala Leu Phe Thr Gln Leu Leu Ala Gln
1               5                   10                  15

Leu Ile Leu Trp Ala Gly Thr Gln Asp Arg Val Ser Val Ala Leu Asp
            20                  25                  30

Gln Val Lys Arg Thr Gln Ala Glu Ala Asp Ala Asn Ala Lys Ser Gly
        35                  40                  45

Ala Gly Ile Arg Asn Ser Leu His Leu Leu Gly Leu Ala Gly Asp Leu
    50                  55                  60

Ile Leu Tyr Lys Asp Gly Lys Tyr Met Asp Lys Ser Glu Asp Tyr Lys
65                  70                  75                  80

Phe Leu Gly Asp Tyr Trp Lys Ser Leu His Pro Leu Cys Arg Trp Gly
                85                  90                  95

Gly Asp Phe Lys Ser Arg Pro Asp Gly Asn His Phe Ser Leu Glu His
            100                 105                 110

Glu Gly Val Gln
        115

<210> SEQ ID NO 97
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(30)
<223> OTHER INFORMATION: linker

<400> SEQUENCE: 97
ccaccaaccg cgggcggcac cgcgggcggc                                           30

<210> SEQ ID NO 98
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Pro Pro Thr Ala Gly Gly Thr Ala Gly Gly
1               5                   10

<210> SEQ ID NO 99
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(27)
<223> OTHER INFORMATION: purification tag GSHHHHHHG

<400> SEQUENCE: 99
ggatcccatc atcaccacca tcatggt                                              27

<210> SEQ ID NO 100
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Ser His His His His His His Gly
1               5

<210> SEQ ID NO 101
<211> LENGTH: 120
<212> TYPE: DNA
<213> ORGANISM: Chlamydia phage 4

<400> SEQUENCE: 101
atggcacgaa gatacagact ttcgcgacgc agaagtcgac gacttttttc aagaactgca    60
ttaagaatgc atcgaagaaa tagacttcga agaattatgc gtggcggcat taggttttag   120

<210> SEQ ID NO 102
<211> LENGTH: 39
<212> TYPE: PRT
<213> ORGANISM: Chlamydia phage 4

<400> SEQUENCE: 102

Met Ala Arg Arg Tyr Arg Leu Ser Arg Arg Ser Arg Arg Leu Phe
1               5                   10                  15

Ser Arg Thr Ala Leu Arg Met His Arg Arg Asn Arg Leu Arg Arg Ile
                20                  25                  30

Met Arg Gly Gly Ile Arg Phe
        35

<210> SEQ ID NO 103
<211> LENGTH: 126
<212> TYPE: DNA
<213> ORGANISM: Escherichia coli

<400> SEQUENCE: 103
atggctcgtt cccgtagacg tatgtctaag cgttcttccc gccgttcgtt ccgcaagtat    60
gcgaagtcgc ataagaagaa ctttaaagcc cgctcaatgc gtggcggtat ccgtttatga   120
taataa                                                              126

<210> SEQ ID NO 104
<211> LENGTH: 39
<212> TYPE: PRT
<213> ORGANISM: Escherichia coli

<400> SEQUENCE: 104

Met Ala Arg Ser Arg Arg Arg Met Ser Lys Arg Ser Ser Arg Arg Ser
1               5                   10                  15

Phe Arg Lys Tyr Ala Lys Ser His Lys Lys Asn Phe Lys Ala Arg Ser
                20                  25                  30

Met Arg Gly Gly Ile Arg Leu
        35

<210> SEQ ID NO 105
<211> LENGTH: 114
<212> TYPE: DNA

<213> ORGANISM: Chlamydia trachomatis

<400> SEQUENCE: 105
aaacgtagaa aaatgacaag aaaaggttct aagcgtcttt ttactgcaac tgctgataaa 60
actaaatcta tcaatactgc cccgccgcca atgcgtggcg gtatccggtt gtag 114

<210> SEQ ID NO 106
<211> LENGTH: 37
<212> TYPE: PRT
<213> ORGANISM: Chlamydia trachomatis

<400> SEQUENCE: 106

Lys Arg Arg Lys Met Thr Arg Lys Gly Ser Lys Arg Leu Phe Thr Ala
1 5 10 15

Thr Ala Asp Lys Thr Lys Ser Ile Asn Thr Ala Pro Pro Pro Met Arg
20 25 30

Gly Gly Ile Arg Leu
35

<210> SEQ ID NO 107
<211> LENGTH: 114
<212> TYPE: DNA
<213> ORGANISM: Oscillibacter sp. PC13

<400> SEQUENCE: 107
atgagaaagc gaatgtctaa gcgtgttgac aagaaggtgt tccgtcgtac tgccgcatct 60
gccaagaaga ttaacattga ccccaagatt taccgtggag gtattcgcct atga 114

<210> SEQ ID NO 108
<211> LENGTH: 37
<212> TYPE: PRT
<213> ORGANISM: Oscillibacter sp. PC13

<400> SEQUENCE: 108

Met Arg Lys Arg Met Ser Lys Arg Val Asp Lys Lys Val Phe Arg Arg
1 5 10 15

Thr Ala Ala Ser Ala Lys Lys Ile Asn Ile Asp Pro Lys Ile Tyr Arg
20 25 30

Gly Gly Ile Arg Leu
35

<210> SEQ ID NO 109
<211> LENGTH: 36
<212> TYPE: DNA
<213> ORGANISM: Artificial Sequence
<220> FEATURE:
<223> OTHER INFORMATION: Description of Artificial Sequence: Synthetic
oligonucleotide
<220> FEATURE:
<221> NAME/KEY: misc_feature
<222> LOCATION: (1)..(36)
<223> OTHER INFORMATION: RR12

<400> SEQUENCE: 109
cgccgcctga ttcgcctgtg gctgcgcctg ctgcgc 36

<210> SEQ ID NO 110
<211> LENGTH: 12
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 110

Arg Arg Leu Ile Arg Leu Trp Leu Arg Leu Leu Arg
1               5                   10

<210> SEQ ID NO 111
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(12)
<223> OTHER INFORMATION: structure moiety

<400> SEQUENCE: 111
atgatcgacc gt                                                         12

<210> SEQ ID NO 112
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Met Ile Asp Arg
1

<210> SEQ ID NO 113
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(12)
<223> OTHER INFORMATION: moiety (outer membrane binding peptide from
      PMID: 22628248)

<400> SEQUENCE: 113
ttcattcgtc tg                                                         12

<210> SEQ ID NO 114
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Phe Ile Arg Leu
1

<210> SEQ ID NO 115
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature

```
<222> LOCATION: (1)..(12)
<223> OTHER INFORMATION: structure moiety

<400> SEQUENCE: 115
aatccgaccc at                                                            12

<210> SEQ ID NO 116
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Asn Pro Thr His
1

<210> SEQ ID NO 117
<211> LENGTH: 477
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(477)
<223> OTHER INFORMATION: GN202 lysin

<400> SEQUENCE: 117
ggtccgcgtc gtccgcgtcg tccgggtcgt cgtgctccgg ttcgtacatc ccaacgaggc      60
atcgacctca tcaaatcctt cgagggcctg cgcctgtccg cttaccagga ctcggtgggt     120
gtctggacca taggttacgg caccactcgg ggcgtcaccc gctacatgac gatcaccgtc     180
gagcaggccg agcggatgct gtcgaacgac attcagcgct tcgagccaga gctagacagg     240
ctggcgaagg tgccactgaa ccagaaccag tgggatgccc tgatgagctt cgtgtacaac     300
ctgggcgcgg ccaatctggc gtcgtccacg ctgctcgacc tgctgaacaa gggtgactac     360
cagggagcag cggaccagtt cccgcattgg gtgaatgcgg gcggtaagcg cttggatggt     420
ctggttaagc gtcgagcagc cgagcgtgcg ctgttcctgg agccactatc gtgataa       477

<210> SEQ ID NO 118
<211> LENGTH: 158
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Met Gly Pro Arg Arg Pro Arg Pro Gly Arg Arg Ala Pro Val Arg
1               5                  10                  15

Thr Ser Gln Arg Gly Ile Asp Leu Ile Lys Ser Phe Glu Gly Leu Arg
            20                  25                  30

Leu Ser Ala Tyr Gln Asp Ser Val Gly Val Trp Thr Ile Gly Tyr Gly
        35                  40                  45

Thr Thr Arg Gly Val Thr Arg Tyr Met Thr Ile Thr Val Glu Gln Ala
    50                  55                  60

Glu Arg Met Leu Ser Asn Asp Ile Gln Arg Phe Glu Pro Glu Leu Asp
65                  70                  75                  80

Arg Leu Ala Lys Val Pro Leu Asn Gln Asn Gln Trp Asp Ala Leu Met
```

```
                        85                  90                  95
Ser Phe Val Tyr Asn Leu Gly Ala Ala Asn Leu Ala Ser Ser Thr Leu
                100                 105                 110

Leu Asp Leu Leu Asn Lys Gly Asp Tyr Gln Gly Ala Ala Asp Gln Phe
            115                 120                 125

Pro His Trp Val Asn Ala Gly Lys Arg Leu Asp Gly Leu Val Lys
        130                 135                 140

Arg Arg Ala Ala Glu Arg Ala Leu Phe Leu Glu Pro Leu Ser
145                 150                 155
```

<210> SEQ ID NO 119
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(30)
<223> OTHER INFORMATION: cationic peptide

<400> SEQUENCE: 119
aaattcttta agttctttaa gttttttaaa                                    30

<210> SEQ ID NO 120
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

```
Lys Phe Phe Lys Phe Phe Lys Phe Phe Lys
1               5                   10
```

<210> SEQ ID NO 121
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(54)
<223> OTHER INFORMATION: linker

<400> SEQUENCE: 121
gccggcgcag gagctggtgc aggagctggt gcaggagctg gtgcaggagc tagc         54

<210> SEQ ID NO 122
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 122

```
Ala Gly Ala Gly Ala Gly Ala Gly Ala Gly Ala Gly Ala Gly Ala Gly
1               5                   10                  15

Ala Ser
```

```
<210> SEQ ID NO 123
<211> LENGTH: 543
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(543)
<223> OTHER INFORMATION: GN14 lysin

<400> SEQUENCE: 123
aataacgaac ttccttgggt agccgaagcc cgaaagtata tcggccttcg cgaagacact    60
tcgaagactt cgcataaccc gaaacttctt gccatgcttg accgcatggg cgaattttcc   120
aacgaatccc gcgcttggtg gcacgacgac gaaacgcctt ggtgcggact gttcgtcggc   180
tattgcttgg gcgttgccgg gcgctacgtc gtccgcgaat ggtacagggc gcgggcatgg   240
gaagccccgc agcttacgaa gcttgaccgg cccgcatacg gcgcgcttgt gaccttcacg   300
cgaagcggcg gcggccacgt cggttttatt gtgggcaagg atgcgcgcgg aaatcttatg   360
gttcttggcg gtaatcagtc gaacgccgta agtatcgcac cgttcgcagt atcccgcgta   420
accggctatt tctggccgtc gttctggcga acaagaccg cagttaaaag cgttccgttt    480
gaagaacgtt attcgctgcc gctgttgaag tcgaacggcg aactttcgac gaatgaagcg   540
taa                                                                 543

<210> SEQ ID NO 124
<211> LENGTH: 180
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Asn Asn Glu Leu Pro Trp Val Ala Glu Ala Arg Lys Tyr Ile Gly Leu
1               5                   10                  15

Arg Glu Asp Thr Ser Lys Thr Ser His Asn Pro Lys Leu Leu Ala Met
            20                  25                  30

Leu Asp Arg Met Gly Glu Phe Ser Asn Glu Ser Arg Ala Trp Trp His
        35                  40                  45

Asp Asp Glu Thr Pro Trp Cys Gly Leu Phe Val Gly Tyr Cys Leu Gly
    50                  55                  60

Val Ala Gly Arg Tyr Val Val Arg Glu Trp Tyr Arg Ala Arg Ala Trp
65                  70                  75                  80

Glu Ala Pro Gln Leu Thr Lys Leu Asp Arg Pro Ala Tyr Gly Ala Leu
                85                  90                  95

Val Thr Phe Thr Arg Ser Gly Gly Gly His Val Gly Phe Ile Val Gly
            100                 105                 110

Lys Asp Ala Arg Gly Asn Leu Met Val Leu Gly Gly Asn Gln Ser Asn
        115                 120                 125

Ala Val Ser Ile Ala Pro Phe Ala Val Ser Arg Val Thr Gly Tyr Phe
    130                 135                 140

Trp Pro Ser Phe Trp Arg Asn Lys Thr Ala Val Lys Ser Val Pro Phe
145                 150                 155                 160

Glu Glu Arg Tyr Ser Leu Pro Leu Leu Lys Ser Asn Gly Glu Leu Ser
                165                 170                 175

Thr Asn Glu Ala
```

<210> SEQ ID NO 125
<211> LENGTH: 471
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: misc_feature
<222> LOCATION: (1)..(471)
<223> OTHER INFORMATION: GN156

<400> SEQUENCE: 125

```
ggtccgcgtc gtccgcgtcg tccgggtcgt cgtgctccgg ttcgtacctc tcagcgtggt      60
atcgacctga tcaaatcttt cgaaggtctg cgtctgtctg cttaccagga ctctgttggt     120
gtttggacca tcggttacgg taccacccgt ggtgttaccc gttacatgac catcaccgtt     180
gaacaggctg aacgtatgct gtctaacgac atccagcgtt tcgaaccgga actggaccgt     240
ctggctaaag ttccgctgaa ccagaaccag tgggacgctc tgatgtcttt cgtttacaac     300
ctgggtgctg ctaacctggc ttcttctacc ctgctgaaac tgctgaacaa aggtgactac     360
cagggtgctg ctgaccagtt cccgcgttgg gttaacgctg gtggtaaacg tctggacggt     420
ctggttaaac gtcgtgctgc tgaacgtgct ctgttcctgg aaccgctgtc t               471
```

<210> SEQ ID NO 126
<211> LENGTH: 157
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 126

```
Gly Pro Arg Arg Pro Arg Arg Pro Gly Arg Arg Ala Pro Val Arg Thr
  1               5                  10                  15
Ser Gln Arg Gly Ile Asp Leu Ile Lys Ser Phe Glu Gly Leu Arg Leu
             20                  25                  30
Ser Ala Tyr Gln Asp Ser Val Gly Val Trp Thr Ile Gly Tyr Gly Thr
         35                  40                  45
Thr Arg Gly Val Thr Arg Tyr Met Thr Ile Thr Val Glu Gln Ala Glu
     50                  55                  60
Arg Met Leu Ser Asn Asp Ile Gln Arg Phe Glu Pro Glu Leu Asp Arg
 65                  70                  75                  80
Leu Ala Lys Val Pro Leu Asn Gln Asn Gln Trp Asp Ala Leu Met Ser
                 85                  90                  95
Phe Val Tyr Asn Leu Gly Ala Ala Asn Leu Ala Ser Ser Thr Leu Leu
            100                 105                 110
Lys Leu Leu Asn Lys Gly Asp Tyr Gln Gly Ala Ala Asp Gln Phe Pro
        115                 120                 125
Arg Trp Val Asn Ala Gly Gly Lys Arg Leu Asp Gly Leu Val Lys Arg
    130                 135                 140
Arg Ala Ala Glu Arg Ala Leu Phe Leu Glu Pro Leu Ser
145                 150                 155
```

<210> SEQ ID NO 127
<211> LENGTH: 39
<212> TYPE: PRT
<213> ORGANISM: Artificial Sequence

```
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(39)
<223> OTHER INFORMATION: PGN4

<400> SEQUENCE: 127

Asn Lys Gly Asp Tyr Gln Gly Ala Ala Asp Gln Phe Pro Arg Trp Val
1               5                   10                  15

Asn Ala Gly Gly Lys Arg Leu Asp Gly Leu Val Lys Arg Arg Ala Ser
            20                  25                  30

Gln Ser Arg Glu Ser Gln Cys
        35

<210> SEQ ID NO 128
<211> LENGTH: 42
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(42)
<223> OTHER INFORMATION: FGN4-1

<400> SEQUENCE: 128

Asn Lys Gly Asp Tyr Gln Gly Ala Ala Asp Gln Phe Pro Arg Trp Val
1               5                   10                  15

Asn Ala Gly Gly Lys Arg Leu Asp Gly Leu Val Lys Arg Arg Ala Ala
            20                  25                  30

Glu Arg Ala Leu Phe Leu Glu Pro Leu Ser
        35                  40

<210> SEQ ID NO 129
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<222> LOCATION: (1)..(31)
<223> OTHER INFORMATION: FGN4-2

<400> SEQUENCE: 129

Asn Lys Gly Asp Tyr Gln Gly Ala Ala Asp Gln Phe Pro Arg Trp Val
1               5                   10                  15

Asn Ala Gly Gly Lys Arg Leu Asp Gly Leu Val Lys Arg Ala
            20                  25                  30

<210> SEQ ID NO 130
<211> LENGTH: 54
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(54)
<223> OTHER INFORMATION: RI18

<400> SEQUENCE: 130
```

```
cgtaaaaaaa cccgtaaacg tctgaaaaaa atcggtaaag ttctgaaatg gatc        54
```

<210> SEQ ID NO 131
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

```
Arg Lys Lys Thr Arg Lys Arg Leu Lys Lys Ile Gly Lys Val Leu Lys
1               5                   10                  15

Trp Ile
```

<210> SEQ ID NO 132
<211> LENGTH: 111
<212> TYPE: DNA
<213> ORGANISM: Chlamydia virus Chp1

<400> SEQUENCE: 132

```
atggttcgta gaagacgttt gagaagaaga ataagtagaa gaattttag aagaacagta     60 gctagagttg gtagaaggcg aaggtctttt cgtggtggta ttagatttta a            111
```

<210> SEQ ID NO 133
<211> LENGTH: 36
<212> TYPE: PRT
<213> ORGANISM: Chlamydia virus Chp1

<400> SEQUENCE: 133

```
Met Val Arg Arg Arg Arg Leu Arg Arg Ile Ser Arg Arg Ile Phe
1               5                   10                  15

Arg Arg Thr Val Ala Arg Val Gly Arg Arg Arg Ser Phe Arg Gly
                20                  25                  30

Gly Ile Arg Phe
            35
```

<210> SEQ ID NO 134
<211> LENGTH: 108
<212> TYPE: DNA
<213> ORGANISM: Chlamydia virus CPAR39

<400> SEQUENCE: 134

```
ttgtgcaaaa aagtgtgcaa aaatgccca aaaaagggc caaaaatgc ccccaaaatc       60 ggagcatttt acgagagaaa aacacctaga cttaaacagt ctacttga               108
```

<210> SEQ ID NO 135
<211> LENGTH: 35
<212> TYPE: PRT
<213> ORGANISM: Chlamydia virus CPAR39

<400> SEQUENCE: 135

```
Met Cys Lys Lys Val Cys Lys Lys Cys Pro Lys Lys Gly Pro Lys Asn
1               5                   10                  15

Ala Pro Lys Ile Gly Ala Phe Tyr Glu Arg Lys Thr Pro Arg Leu Lys
                20                  25                  30

Gln Ser Thr
            35
```

<210> SEQ ID NO 136
<211> LENGTH: 135

```
<212> TYPE: DNA
<213> ORGANISM: Chlamydia phage 3

<400> SEQUENCE: 136
atgaggttaa aaatggcacg aagaagatac agacttccgc gacgtagaag tcgaagactt    60
ttttcaagaa ctgcattaag gatgcatcca agaaataggc ttcgaagaat tatgcgtggc   120
ggcattaggt tctag                                                    135

<210> SEQ ID NO 137
<211> LENGTH: 44
<212> TYPE: PRT
<213> ORGANISM: Chlamydia phage 3

<400> SEQUENCE: 137

Met Arg Leu Lys Met Ala Arg Arg Tyr Arg Leu Pro Arg Arg
1               5                   10                  15

Ser Arg Arg Leu Phe Ser Arg Thr Ala Leu Arg Met His Pro Arg Asn
            20                  25                  30

Arg Leu Arg Arg Ile Met Arg Gly Gly Ile Arg Phe
        35                  40

<210> SEQ ID NO 138
<211> LENGTH: 117
<212> TYPE: DNA
<213> ORGANISM: Chlamydia trachomatis

<400> SEQUENCE: 138
atgaaacgta gaaaaatgac aagaaaaggt tctaagcgtc tttttactgc aactgctgat    60
aaaactaaat ctatcaatac tgccccgccg ccaatgcgtg gcggtatccg gttgtaa     117

<210> SEQ ID NO 139
<211> LENGTH: 38
<212> TYPE: PRT
<213> ORGANISM: Chlamydia trachomatis

<400> SEQUENCE: 139

Met Lys Arg Arg Lys Met Thr Arg Lys Gly Ser Lys Arg Leu Phe Thr
1               5                   10                  15

Ala Thr Ala Asp Lys Thr Lys Ser Ile Asn Thr Ala Pro Pro Pro Met
            20                  25                  30

Arg Gly Gly Ile Arg Leu
        35

<210> SEQ ID NO 140
<211> LENGTH: 120
<212> TYPE: DNA
<213> ORGANISM: Chlamydia trachomatis

<400> SEQUENCE: 140
atgtctaaaa agcgttctcg catgtctcgc cgccgttcta agaagttgtt ctcgaaaacg    60
gctctccgca cgaagagtgt caacacccgt ccgcctatgc gcggagggtt ccggttctga   120

<210> SEQ ID NO 141
<211> LENGTH: 39
<212> TYPE: PRT
<213> ORGANISM: Chlamydia trachomatis

<400> SEQUENCE: 141

Met Ser Lys Lys Arg Ser Arg Met Ser Arg Arg Arg Ser Lys Lys Leu
1               5                   10                  15
```

Phe Ser Lys Thr Ala Leu Arg Thr Lys Ser Val Asn Thr Arg Pro Pro
        20                  25                  30

Met Arg Gly Gly Phe Arg Phe
        35

<210> SEQ ID NO 142
<211> LENGTH: 123
<212> TYPE: DNA
<213> ORGANISM: Chlamydia trachomatis

<400> SEQUENCE: 142
atgtctcttc gtcgtcataa gctttctcgt aaggcgtcta agcgtatttt tcgtaaaggt     60
gcatcacgca cgaagacttt gaatactcgt gctacgccta tgcgcggcgg tttccgtatt    120
taa                                                                  123

<210> SEQ ID NO 143
<211> LENGTH: 40
<212> TYPE: PRT
<213> ORGANISM: Chlamydia trachomatis

<400> SEQUENCE: 143

Met Ser Leu Arg Arg His Lys Leu Ser Arg Lys Ala Ser Lys Arg Ile
1               5                   10                  15

Phe Arg Lys Gly Ala Ser Arg Thr Lys Thr Leu Asn Thr Arg Ala Thr
            20                  25                  30

Pro Met Arg Gly Gly Phe Arg Ile
        35                  40

<210> SEQ ID NO 144
<211> LENGTH: 117
<212> TYPE: DNA
<213> ORGANISM: Chlamydia trachomatis

<400> SEQUENCE: 144
gtgaaacgtc gtaaactgtc caaaaagaaa tctcgcaaga ttttcactcg cggtgctgta     60
aatgtgaaaa agcgtaacct tcgcgctcgc ccaatgcgcg gcggtttccg gatctaa       117

<210> SEQ ID NO 145
<211> LENGTH: 38
<212> TYPE: PRT
<213> ORGANISM: Chlamydia trachomatis

<400> SEQUENCE: 145

Met Lys Arg Arg Lys Leu Ser Lys Lys Ser Arg Lys Ile Phe Thr
1               5                   10                  15

Arg Gly Ala Val Asn Val Lys Lys Arg Asn Leu Arg Ala Arg Pro Met
            20                  25                  30

Arg Gly Gly Phe Arg Ile
        35

<210> SEQ ID NO 146
<211> LENGTH: 114
<212> TYPE: DNA
<213> ORGANISM: Chlamydia trachomatis

<400> SEQUENCE: 146
atggctaaaa aaatgactaa aggcaaggat cgtcaggttt ttcgtaaaac cgctgatcgt     60
actaagaaac tcaatgttag accgttgtta tatcgaggag gtatcagatt atga          114

<210> SEQ ID NO 147
<211> LENGTH: 37
<212> TYPE: PRT
<213> ORGANISM: Chlamydia trachomatis

<400> SEQUENCE: 147

Met Ala Lys Lys Met Thr Lys Gly Lys Asp Arg Gln Val Phe Arg Lys
1               5                   10                  15

Thr Ala Asp Arg Thr Lys Lys Leu Asn Val Arg Pro Leu Leu Tyr Arg
            20                  25                  30

Gly Gly Ile Arg Leu
        35

<210> SEQ ID NO 148
<211> LENGTH: 120
<212> TYPE: DNA
<213> ORGANISM: Chlamydia trachomatis

<400> SEQUENCE: 148
atggcaggaa aaaaatggt atcaaaagga aagatagac agattttccg aaaaactgct     60
gatcgcacta aaaaaatgaa tgtgcgcccg ctattatatc gtggaggtat tagattatga    120

<210> SEQ ID NO 149
<211> LENGTH: 39
<212> TYPE: PRT
<213> ORGANISM: Chlamydia trachomatis

<400> SEQUENCE: 149

Met Ala Gly Lys Lys Met Val Ser Lys Gly Lys Asp Arg Gln Ile Phe
1               5                   10                  15

Arg Lys Thr Ala Asp Arg Thr Lys Lys Met Asn Val Arg Pro Leu Leu
            20                  25                  30

Tyr Arg Gly Gly Ile Arg Leu
        35

<210> SEQ ID NO 150
<211> LENGTH: 126
<212> TYPE: DNA
<213> ORGANISM: Marine gokushovirus

<400> SEQUENCE: 150
atgagaagac caagaaaaat gaactataaa aaatcaaaaa gaatgttttc acgcacagca     60
gcgagaacac acagaaaaaa ctctctaaga ggtagccgac ctatgagagg cggaatacgt    120
ctttaa                                                               126

<210> SEQ ID NO 151
<211> LENGTH: 41
<212> TYPE: PRT
<213> ORGANISM: Marine gokushovirus

<400> SEQUENCE: 151

Met Arg Arg Pro Arg Lys Met Asn Tyr Lys Lys Ser Lys Arg Met Phe
1               5                   10                  15

Ser Arg Thr Ala Ala Arg Thr His Arg Lys Asn Ser Leu Arg Gly Ser
            20                  25                  30

Arg Pro Met Arg Gly Gly Ile Arg Leu
        35                  40

<210> SEQ ID NO 152

```
<211> LENGTH: 108
<212> TYPE: DNA
<213> ORGANISM: Unknown
<220> FEATURE:
<223> OTHER INFORMATION: Description of Unknown: Bacteria; environmental
      sample sequence

<400> SEQUENCE: 152
atgaaaatgc gtaagcggac ggacaagcga gtgtttaccc gcaccgctgc taagtccaag    60
aaagtgaaca ttgccccgaa aatttttaga ggaggtatcc gtctgtga               108

<210> SEQ ID NO 153
<211> LENGTH: 35
<212> TYPE: PRT
<213> ORGANISM: Unknown
<220> FEATURE:
<223> OTHER INFORMATION: Description of Unknown: Bacteria; environmental
      sample sequence

<400> SEQUENCE: 153

Met Lys Met Arg Lys Arg Thr Asp Lys Arg Val Phe Thr Arg Thr Ala
1               5                   10                  15

Ala Lys Ser Lys Lys Val Asn Ile Ala Pro Lys Ile Phe Arg Gly Gly
            20                  25                  30

Ile Arg Leu
        35

<210> SEQ ID NO 154
<211> LENGTH: 120
<212> TYPE: DNA
<213> ORGANISM: Escherichia sp.

<400> SEQUENCE: 154
atggctcgtt ctcgccgtcg tatgtccaag cgttcttccc gtcgttcgtt ccgtaagtac    60
gcaaagacgc ataaacgtaa ctttaaagcc cgctctatgc gtggtggaat cgtctttga   120

<210> SEQ ID NO 155
<211> LENGTH: 39
<212> TYPE: PRT
<213> ORGANISM: Escherichia sp.

<400> SEQUENCE: 155

Met Ala Arg Ser Arg Arg Arg Met Ser Lys Arg Ser Ser Arg Arg Ser
1               5                   10                  15

Phe Arg Lys Tyr Ala Lys Thr His Lys Arg Asn Phe Lys Ala Arg Ser
            20                  25                  30

Met Arg Gly Gly Ile Arg Leu
        35

<210> SEQ ID NO 156
<211> LENGTH: 144
<212> TYPE: DNA
<213> ORGANISM: Cognatishimia maritima

<400> SEQUENCE: 156
atggaaagcc cgaacagccg cagccagctg ggcattaccc tgtatctgct gagcaccatt    60
tttccggatg cgtgctttcg ctatcgccgc gaactgccgt atccgctggt gatttgggg c  120 gtggcgaccc tgtgcctgca gtaa                                         144

<210> SEQ ID NO 157
<211> LENGTH: 47
```

<212> TYPE: PRT
<213> ORGANISM: Cognatishimia maritima

<400> SEQUENCE: 157

Met Glu Ser Pro Asn Ser Arg Ser Gln Leu Gly Ile Thr Leu Tyr Leu
1               5                   10                  15

Leu Ser Thr Ile Phe Pro Asp Ala Cys Phe Arg Tyr Arg Arg Glu Leu
            20                  25                  30

Pro Tyr Pro Leu Val Ile Trp Gly Val Ala Thr Leu Cys Leu Gln
        35                  40                  45

<210> SEQ ID NO 158
<211> LENGTH: 114
<212> TYPE: DNA
<213> ORGANISM: Unknown
<220> FEATURE:
<223> OTHER INFORMATION: Description of Unknown: Bacteria; environmental
      sample sequence

<400> SEQUENCE: 158
atgagacgtc gtcgtctatc ccgcagaact tcccgccgtt ttttccgtaa aggacttaag     60
gttcgccgtc gtaacctccg cgcgagaccc atgagaggcg gattcagaat ttga          114

<210> SEQ ID NO 159
<211> LENGTH: 37
<212> TYPE: PRT
<213> ORGANISM: Unknown
<220> FEATURE:
<223> OTHER INFORMATION: Description of Unknown: Bacteria; environmental
      sample sequence

<400> SEQUENCE: 159

Met Arg Arg Arg Arg Leu Ser Arg Arg Thr Ser Arg Arg Phe Phe Arg
1               5                   10                  15

Lys Gly Leu Lys Val Arg Arg Arg Asn Leu Arg Ala Arg Pro Met Arg
            20                  25                  30

Gly Gly Phe Arg Ile
        35

<210> SEQ ID NO 160
<211> LENGTH: 120
<212> TYPE: DNA
<213> ORGANISM: Unknown
<220> FEATURE:
<223> OTHER INFORMATION: Description of Unknown: Bacteria; environmental
      sample sequence

<400> SEQUENCE: 160
atggcacgac gcaagaagat gaaaggcaag cgggataaac gggtgtttaa gcagacagcc     60
aacaaaacca aggctatcaa catcagccca aaaaacatga gaggggtac gagactgtga    120

<210> SEQ ID NO 161
<211> LENGTH: 39
<212> TYPE: PRT
<213> ORGANISM: Unknown
<220> FEATURE:
<223> OTHER INFORMATION: Description of Unknown: Bacteria; environmental
      sample sequence

<400> SEQUENCE: 161

Met Ala Arg Arg Lys Lys Met Lys Gly Lys Arg Asp Lys Arg Val Phe
1               5                   10                  15

Lys Gln Thr Ala Asn Lys Thr Lys Ala Ile Asn Ile Ser Pro Lys Asn

```
                    20                  25                  30

Met Arg Gly Gly Thr Arg Leu
            35

<210> SEQ ID NO 162
<211> LENGTH: 162
<212> TYPE: DNA
<213> ORGANISM: Marine gokushovirus

<400> SEQUENCE: 162
atgttaactg tgtggagtga caccctacc ataaaaagga gaaagacat gtatagaaag      60 agaatgtcaa gaaagaaaag taaaaggtt tttgcaaaaa ccgcaatgaa agtaaataaa    120
agaaaccacg ttaaacctat gcgtggtgga tatagaatat aa                      162

<210> SEQ ID NO 163
<211> LENGTH: 53
<212> TYPE: PRT
<213> ORGANISM: Marine gokushovirus

<400> SEQUENCE: 163

Met Leu Thr Val Trp Ser Asp Thr Pro Thr Ile Lys Arg Arg Lys Asp
1               5                   10                  15

Met Tyr Arg Lys Arg Met Ser Arg Lys Lys Ser Lys Lys Val Phe Ala
            20                  25                  30

Lys Thr Ala Met Lys Val Asn Lys Arg Asn His Val Lys Pro Met Arg
        35                  40                  45

Gly Gly Tyr Arg Ile
    50

<210> SEQ ID NO 164
<211> LENGTH: 120
<212> TYPE: DNA
<213> ORGANISM: Marine gokushovirus

<400> SEQUENCE: 164
atgatgaagt acagaaaaaa aatgagcgct aaaagtagcc gaaagcaatt tacaaaaggc     60
gccatgaaag tgaagggtaa aaacttcaca aaaccaatgc gcggaggcat ccgtctatag    120

<210> SEQ ID NO 165
<211> LENGTH: 39
<212> TYPE: PRT
<213> ORGANISM: Marine gokushovirus

<400> SEQUENCE: 165

Met Met Lys Tyr Arg Lys Lys Met Ser Ala Lys Ser Ser Arg Lys Gln
1               5                   10                  15

Phe Thr Lys Gly Ala Met Lys Val Lys Gly Lys Asn Phe Thr Lys Pro
            20                  25                  30

Met Arg Gly Gly Ile Arg Leu
            35

<210> SEQ ID NO 166
<211> LENGTH: 117
<212> TYPE: DNA
<213> ORGANISM: Marine gokushovirus

<400> SEQUENCE: 166
atgcgacgtt acaatgtaaa taaggtaaa tctgctaaga agtttcgaaa gcaggtaagt     60
aagacgaagg ttgcaaacct acgttctaat ccaatgcgag gtggttggag actctaa      117
```

<210> SEQ ID NO 167
<211> LENGTH: 38
<212> TYPE: PRT
<213> ORGANISM: Marine gokushovirus

<400> SEQUENCE: 167

Met Arg Arg Tyr Asn Val Asn Lys Gly Lys Ser Ala Lys Lys Phe Arg
1               5                   10                  15

Lys Gln Val Ser Lys Thr Lys Val Ala Asn Leu Arg Ser Asn Pro Met
            20                  25                  30

Arg Gly Gly Trp Arg Leu
        35

<210> SEQ ID NO 168
<211> LENGTH: 87
<212> TYPE: DNA
<213> ORGANISM: Spiroplasma virus SpV4

<400> SEQUENCE: 168
atggcttatc gtggttttaa aacgagtcgt gttgtaaaac atagagtacg tagaagatgg      60
tttaatcata gaagacgtta tagatag                                         87

<210> SEQ ID NO 169
<211> LENGTH: 28
<212> TYPE: PRT
<213> ORGANISM: Spiroplasma virus SpV4

<400> SEQUENCE: 169

Met Ala Tyr Arg Gly Phe Lys Thr Ser Arg Val Val Lys His Arg Val
1               5                   10                  15

Arg Arg Arg Trp Phe Asn His Arg Arg Arg Tyr Arg
            20                  25

<210> SEQ ID NO 170
<211> LENGTH: 117
<212> TYPE: DNA
<213> ORGANISM: Spiroplasma virus SpV4

<400> SEQUENCE: 170
gtgagacgca aggttaagaa cacaaagcgt catcagtgga ggttgactca ttctgcacgt      60
tcaattaaac gtgctaatat aatgccgtca aatcctcgtg gtggacgtcg tttttag        117

<210> SEQ ID NO 171
<211> LENGTH: 38
<212> TYPE: PRT
<213> ORGANISM: Spiroplasma virus SpV4

<400> SEQUENCE: 171

Met Arg Arg Lys Val Lys Asn Thr Lys Arg His Gln Trp Arg Leu Thr
1               5                   10                  15

His Ser Ala Arg Ser Ile Lys Arg Ala Asn Ile Met Pro Ser Asn Pro
            20                  25                  30

Arg Gly Gly Arg Arg Phe
        35

<210> SEQ ID NO 172
<211> LENGTH: 798
<212> TYPE: DNA
<213> ORGANISM: Pseudomonas phage PhiPA3

-continued

<400> SEQUENCE: 172

```
atgacattac tgaagaaagg cgacaagggt gacgccgtaa acaactaca gcagaaactc      60
aaagaccttg gtatacccct gggtgtcgat ggcaacttcg gtaatggcac cgatactgtc    120
gttcgttctt tccaaaccaa aatgaagctt agtgttgatg gtgtggttgg taatggtact    180
atgagtacta ttgactctac tctagcaggc attaaagcgt ggaagactag tgtacctttc    240
cctgcgacga caaatcccg agcaatggca atgccaacgt tgactgaaat aggtcgactg    300
acaaacgttg atcctaaatt gctagcgaca ttctgttcta tcgaaagcgc gtttgattac    360
acagctaaac cctacaagcc cgatggcaca gtgtacagct ccgccgaagg ttggttccag    420
ttcctggatg caacatggga tgacgaagtg cgtaaacacg gtaagcaata tagcttccct    480
gttgatcctg gtcgttcttt gcgtaaagat ccacgggcta atggcttgat gggcgctgag    540
ttcctcaaag ggaatgctgc tattctgcgg ccagtactgg gtcatgaacc gagcgacaca    600
gatctttatc tagcccattt catgggagca ggtggcgcaa acagttcct tatggccgat    660
caaaataaat tggctgccga attgttccct ggtccagcta aggctaatcc taacatcttc    720
tataaatccg gaaatattgc ccgcacttta gcagaggtct atgcagtcct cgatgctaag    780
gtagccaagc atagagct                                                  798
```

<210> SEQ ID NO 173
<211> LENGTH: 266
<212> TYPE: PRT
<213> ORGANISM: Pseudomonas phage PhiPA3

<400> SEQUENCE: 173

```
Met Thr Leu Leu Lys Lys Gly Asp Lys Gly Asp Ala Val Lys Gln Leu
1               5                   10                  15

Gln Gln Lys Leu Lys Asp Leu Gly Tyr Thr Leu Gly Val Asp Gly Asn
            20                  25                  30

Phe Gly Asn Gly Thr Asp Thr Val Val Arg Ser Phe Gln Thr Lys Met
        35                  40                  45

Lys Leu Ser Val Asp Gly Val Val Gly Asn Gly Thr Met Ser Thr Ile
    50                  55                  60

Asp Ser Thr Leu Ala Gly Ile Lys Ala Trp Lys Thr Ser Val Pro Phe
65                  70                  75                  80

Pro Ala Thr Asn Lys Ser Arg Ala Met Ala Met Pro Thr Leu Thr Glu
                85                  90                  95

Ile Gly Arg Leu Thr Asn Val Asp Pro Lys Leu Leu Ala Thr Phe Cys
            100                 105                 110

Ser Ile Glu Ser Ala Phe Asp Tyr Thr Ala Lys Pro Tyr Lys Pro Asp
        115                 120                 125

Gly Thr Val Tyr Ser Ser Ala Glu Gly Trp Phe Gln Phe Leu Asp Ala
    130                 135                 140

Thr Trp Asp Asp Glu Val Arg Lys His Gly Lys Gln Tyr Ser Phe Pro
145                 150                 155                 160

Val Asp Pro Gly Arg Ser Leu Arg Lys Asp Pro Arg Ala Asn Gly Leu
                165                 170                 175

Met Gly Ala Glu Phe Leu Lys Gly Asn Ala Ala Ile Leu Arg Pro Val
            180                 185                 190

Leu Gly His Glu Pro Ser Asp Thr Asp Leu Tyr Leu Ala His Phe Met
        195                 200                 205

Gly Ala Gly Gly Ala Lys Gln Phe Leu Met Ala Asp Gln Asn Lys Leu
    210                 215                 220
```

```
Ala Ala Glu Leu Phe Pro Gly Pro Ala Lys Ala Asn Pro Asn Ile Phe
225                 230                 235                 240

Tyr Lys Ser Gly Asn Ile Ala Arg Thr Leu Ala Glu Val Tyr Ala Val
                245                 250                 255

Leu Asp Ala Lys Val Ala Lys His Arg Ala
            260                 265

<210> SEQ ID NO 174
<211> LENGTH: 435
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(435)
<223> OTHER INFORMATION: GN37 and RI18

<400> SEQUENCE: 174
atgacataca ccctgagcaa agaagcctg gataacctaa aaggcgttca tcccgatctg      60
gttgccgttg tccatcgcgc catccagctt acaccggttg atttcgcggt gatcgaaggc    120
ctgcgctccg tatcccgcca aaaggaactg gtggccgccg gcgccagcaa gaccatgaac    180
agccgacacc tgacaggcca tgcggttgat ctagccgctt acgtcaatgg catccgctgg    240
gactggcccc tgtatgacgc catcgccgtg gctgtgaaag ccgcagcaaa ggaattgggt    300
gtggccatcg tgtggggcgg tgactggacc acgtttaagg atggcccgca ctttgaactg    360
gatcggagca aatacagatg acgtaaaaaa acccgtaaac gtctgaaaaa aatcggtaaa    420
gttctgaaat ggatc                                                    435

<210> SEQ ID NO 175
<211> LENGTH: 144
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 175

Met Thr Tyr Thr Leu Ser Lys Arg Ser Leu Asp Asn Leu Lys Gly Val
1               5                   10                  15

His Pro Asp Leu Val Ala Val Val His Arg Ala Ile Gln Leu Thr Pro
            20                  25                  30

Val Asp Phe Ala Val Ile Glu Gly Leu Arg Ser Val Ser Arg Gln Lys
        35                  40                  45

Glu Leu Val Ala Ala Gly Ala Ser Lys Thr Met Asn Ser Arg His Leu
    50                  55                  60

Thr Gly His Ala Val Asp Leu Ala Ala Tyr Val Asn Gly Ile Arg Trp
65                  70                  75                  80

Asp Trp Pro Leu Tyr Asp Ala Ile Ala Val Ala Val Lys Ala Ala Ala
                85                  90                  95

Lys Glu Leu Gly Val Ala Ile Val Trp Gly Gly Asp Trp Thr Thr Phe
            100                 105                 110

Lys Asp Gly Pro His Phe Glu Leu Asp Arg Ser Lys Tyr Arg Arg Lys
        115                 120                 125

Lys Thr Arg Lys Arg Leu Lys Lys Ile Gly Lys Val Leu Lys Trp Ile
    130                 135                 140
```

<210> SEQ ID NO 176
<211> LENGTH: 120
<212> TYPE: DNA
<213> ORGANISM: Escherichia sp.

<400> SEQUENCE: 176

```
atggctcgtt ctcgtcgtcg tatgtctaaa cgttcttctc gtcgttcttt tcgtaaatat      60
gctaaaactc ataaaaaaaa ttttaaagct cgttctatgc gtggaggaat cgtttataa     120
```

<210> SEQ ID NO 177
<211> LENGTH: 39
<212> TYPE: PRT
<213> ORGANISM: Escherichia sp.

<400> SEQUENCE: 177

Met Ala Arg Ser Arg Arg Arg Met Ser Lys Arg Ser Ser Arg Arg Ser
1               5                   10                  15

Phe Arg Lys Tyr Ala Lys Thr His Lys Lys Asn Phe Lys Ala Arg Ser
            20                  25                  30

Met Arg Gly Gly Ile Arg Leu
        35

<210> SEQ ID NO 178
<211> LENGTH: 117
<212> TYPE: DNA
<213> ORGANISM: Escherichia coli

<400> SEQUENCE: 178

```
atggcgcgca gccgccgccg catgagcaaa cgcagcagcc gccgcagctt tcgcaaatat      60
gcgaaaagcc ataaaaaaaa ctttaaagcg cgcagcatgc gcggcggcat tcgcctg        117
```

<210> SEQ ID NO 179
<211> LENGTH: 39
<212> TYPE: PRT
<213> ORGANISM: Escherichia coli

<400> SEQUENCE: 179

Met Ala Arg Ser Arg Arg Arg Met Ser Lys Arg Ser Ser Arg Arg Ser
1               5                   10                  15

Phe Arg Lys Tyr Ala Lys Ser His Lys Lys Asn Phe Lys Ala Arg Ser
            20                  25                  30

Met Arg Gly Gly Ile Arg Leu
        35

<210> SEQ ID NO 180
<211> LENGTH: 117
<212> TYPE: DNA
<213> ORGANISM: Alces alces faeces associated microvirus MP12 5423

<400> SEQUENCE: 180

```
atggcaaaga aaattagaaa caaagcacgt gatagacgta tcttcacaag aacagcttca      60
cgcatgcaca aggcaaaccg cacaccaaga tttatgagag gcggtattag gttatga        117
```

<210> SEQ ID NO 181
<211> LENGTH: 38
<212> TYPE: PRT
<213> ORGANISM: Alces alces faeces associated microvirus MP12 5423

<400> SEQUENCE: 181

Met Ala Lys Lys Ile Arg Asn Lys Ala Arg Asp Arg Arg Ile Phe Thr

```
1               5                   10                  15
Arg Thr Ala Ser Arg Met His Lys Ala Asn Arg Thr Pro Arg Phe Met
            20                  25                  30

Arg Gly Gly Ile Arg Leu
            35

<210> SEQ ID NO 182
<211> LENGTH: 117
<212> TYPE: DNA
<213> ORGANISM: Unknown
<220> FEATURE:
<223> OTHER INFORMATION: Description of Unknown: Gokushovirinae
      environmental sample sequence

<400> SEQUENCE: 182
atgcgtcgta aaaaaatgtc acgcggtaaa tcaaaaaaac tctttcgccg aacagcaaaa     60
cgcgttcatc gaaaaaacct acgagctcgc ccaatgcgtg gcggcatacg catgtag       117

<210> SEQ ID NO 183
<211> LENGTH: 38
<212> TYPE: PRT
<213> ORGANISM: Unknown
<220> FEATURE:
<223> OTHER INFORMATION: Description of Unknown: Gokushovirinae
      environmental sample sequence

<400> SEQUENCE: 183

Met Arg Arg Lys Lys Met Ser Arg Gly Lys Ser Lys Lys Leu Phe Arg
1               5                   10                  15

Arg Thr Ala Lys Arg Val His Arg Lys Asn Leu Arg Ala Arg Pro Met
            20                  25                  30

Arg Gly Gly Ile Arg Met
            35

<210> SEQ ID NO 184
<211> LENGTH: 120
<212> TYPE: DNA
<213> ORGANISM: Unknown
<220> FEATURE:
<223> OTHER INFORMATION: Description of Unknown: Gokushovirinae
      environmental sample sequence

<400> SEQUENCE: 184
atggcgaagc gacacaaaat cccgcaacgc gcgtcacaac attccttcac gcgccatgcg     60
caaaaggtcc accctaagaa cgttccccgc ctgccaatgc gaggcggtat ccgtctctaa   120

<210> SEQ ID NO 185
<211> LENGTH: 39
<212> TYPE: PRT
<213> ORGANISM: Unknown
<220> FEATURE:
<223> OTHER INFORMATION: Description of Unknown: Gokushovirinae
      environmental sample sequence

<400> SEQUENCE: 185

Met Ala Lys Arg His Lys Ile Pro Gln Arg Ala Ser Gln His Ser Phe
1               5                   10                  15

Thr Arg His Ala Gln Lys Val His Pro Lys Asn Val Pro Arg Leu Pro
            20                  25                  30

Met Arg Gly Gly Ile Arg Leu
            35
```

-continued

```
<210> SEQ ID NO 186
<211> LENGTH: 114
<212> TYPE: DNA
<213> ORGANISM: Unknown
<220> FEATURE:
<223> OTHER INFORMATION: Description of Unknown: uncultured bacterium
      sequence

<400> SEQUENCE: 186
atgcgtaaaa aaatgcacaa atcattagac aagcgagtgt ttaaccgcac tgcaaaaaaa      60
tcaaaaaaaa taaatgttaa tcctgtagtt tatcgtggag gtattagatt atga           114

<210> SEQ ID NO 187
<211> LENGTH: 37
<212> TYPE: PRT
<213> ORGANISM: Unknown
<220> FEATURE:
<223> OTHER INFORMATION: Description of Unknown: uncultured bacterium
      sequence

<400> SEQUENCE: 187

Met Arg Lys Lys Met His Lys Ser Leu Asp Lys Arg Val Phe Asn Arg
1               5                   10                  15

Thr Ala Lys Lys Ser Lys Lys Ile Asn Val Asn Pro Val Val Tyr Arg
            20                  25                  30

Gly Gly Ile Arg Leu
        35

<210> SEQ ID NO 188
<211> LENGTH: 117
<212> TYPE: DNA
<213> ORGANISM: Marine gokushovirus

<400> SEQUENCE: 188
atgcgacgtt acaatgtaaa taaaggtaaa tctgctaaga agtttcgaaa gcaggtaagt      60
aagacgaagg ttgcaaacct acgttctaat ccaatgcgag gtggttggag actctaa        117

<210> SEQ ID NO 189
<211> LENGTH: 38
<212> TYPE: PRT
<213> ORGANISM: Marine gokushovirus

<400> SEQUENCE: 189

Met Arg Arg Tyr Asn Val Asn Lys Gly Lys Ser Ala Lys Lys Phe Arg
1               5                   10                  15

Lys Gln Val Ser Lys Thr Lys Val Ala Asn Leu Arg Ser Asn Pro Met
            20                  25                  30

Arg Gly Gly Trp Arg Leu
        35

<210> SEQ ID NO 190
<211> LENGTH: 126
<212> TYPE: DNA
<213> ORGANISM: Richelia intracellularis HH01

<400> SEQUENCE: 190
atgcgtccag ttaaaagatc aagagtaaat aaggcccgat ctgcaggcaa gtttcgtaag      60
caggtcggta aaacaaagat ggcaaatctg cgtagtaatc cgatgcgcgg cggatggcgg     120
ctgtga                                                                126

<210> SEQ ID NO 191
```

```
<211> LENGTH: 41
<212> TYPE: PRT
<213> ORGANISM: Richelia intracellularis HH01

<400> SEQUENCE: 191

Met Arg Pro Val Lys Arg Ser Arg Val Asn Lys Ala Arg Ser Ala Gly
1               5                   10                  15

Lys Phe Arg Lys Gln Val Gly Lys Thr Lys Met Ala Asn Leu Arg Ser
            20                  25                  30

Asn Pro Met Arg Gly Gly Trp Arg Leu
        35                  40

<210> SEQ ID NO 192
<211> LENGTH: 126
<212> TYPE: DNA
<213> ORGANISM: Gokushovirinae Fen7875_21

<400> SEQUENCE: 192
atgaagccat tgaagcgtaa gccggttcag aaggcgcggt cagcagccaa gttccgtcga      60
aatgtgtcta ccgttaaggc tgccaatatg gcggtgaagc cgatgcgcgg cggttggcgg     120
ttctga                                                               126

<210> SEQ ID NO 193
<211> LENGTH: 41
<212> TYPE: PRT
<213> ORGANISM: Gokushovirinae Fen7875_21

<400> SEQUENCE: 193

Met Lys Pro Leu Lys Arg Lys Pro Val Gln Lys Ala Arg Ser Ala Ala
1               5                   10                  15

Lys Phe Arg Arg Asn Val Ser Thr Val Lys Ala Ala Asn Met Ala Val
            20                  25                  30

Lys Pro Met Arg Gly Gly Trp Arg Phe
        35                  40

<210> SEQ ID NO 194
<211> LENGTH: 135
<212> TYPE: DNA
<213> ORGANISM: Mycobacterium phage BabyRay

<400> SEQUENCE: 194
atgaccaaga gagacatcga gtaccggaaa gctttggggc tcaacccatc tgagccgctc      60
ccgaagattg tgggtgccgt cacccgccac ggggccactc tgaaacgccc acgggtcacc     120
gcactggccc gatag                                                     135

<210> SEQ ID NO 195
<211> LENGTH: 44
<212> TYPE: PRT
<213> ORGANISM: Mycobacterium phage BabyRay

<400> SEQUENCE: 195

Met Thr Lys Arg Asp Ile Glu Tyr Arg Lys Ala Leu Gly Leu Asn Pro
1               5                   10                  15

Ser Glu Pro Leu Pro Lys Ile Val Gly Ala Val Thr Arg His Gly Ala
            20                  25                  30

Thr Leu Lys Arg Pro Arg Val Thr Ala Leu Ala Arg
        35                  40

<210> SEQ ID NO 196
```

```
<211> LENGTH: 117
<212> TYPE: DNA
<213> ORGANISM: Bdellovibrio phage phiMH2K

<400> SEQUENCE: 196
atgaaaagaa aaccaatgag ccgcaaggcc tctcaaaaaa ccttcaaaaa gaacacaggc    60
gttcaacgca tgaaccatct caacccacgc gccatgcgtg gtggcattag actataa     117

<210> SEQ ID NO 197
<211> LENGTH: 38
<212> TYPE: PRT
<213> ORGANISM: Bdellovibrio phage phiMH2K

<400> SEQUENCE: 197

Met Lys Arg Lys Pro Met Ser Arg Lys Ala Ser Gln Lys Thr Phe Lys
1               5                   10                  15

Lys Asn Thr Gly Val Gln Arg Met Asn His Leu Asn Pro Arg Ala Met
            20                  25                  30

Arg Gly Gly Ile Arg Leu
        35

<210> SEQ ID NO 198
<211> LENGTH: 168
<212> TYPE: DNA
<213> ORGANISM: Pseudomonas phage PP7

<400> SEQUENCE: 198
ttgtcgtcaa ccttgtgccg ctgggccgtt aaggccctgc ggtgtacccg tgtgtataag    60
gagtttatat ggaaacccct tagtagcgct cagttacgtga cgttgtatct tctgagctcg   120
gtcttcctgt cccaactcag ctaccccatc gggagctggg cggtgtag              168

<210> SEQ ID NO 199
<211> LENGTH: 55
<212> TYPE: PRT
<213> ORGANISM: Pseudomonas phage PP7

<400> SEQUENCE: 199

Met Ser Ser Thr Leu Cys Arg Trp Ala Val Lys Ala Leu Arg Cys Thr
1               5                   10                  15

Arg Val Tyr Lys Glu Phe Ile Trp Lys Pro Leu Val Ala Leu Ser Tyr
            20                  25                  30

Val Thr Leu Tyr Leu Leu Ser Ser Val Phe Leu Ser Gln Leu Ser Tyr
        35                  40                  45

Pro Ile Gly Ser Trp Ala Val
    50                  55

<210> SEQ ID NO 200
<211> LENGTH: 108
<212> TYPE: DNA
<213> ORGANISM: Acinetobacter phage AP205

<400> SEQUENCE: 200
atgaagaaaa ggacaaaagc cttgcttccc tatgcggttt tcatcatact cagctttcaa    60
ctaacattgt tgactgcctt gtttatgtat taccattata cctttttag               108

<210> SEQ ID NO 201
<211> LENGTH: 35
<212> TYPE: PRT
<213> ORGANISM: Acinetobacter phage AP205
```

<400> SEQUENCE: 201

Met Lys Lys Arg Thr Lys Ala Leu Leu Pro Tyr Ala Val Phe Ile Ile
1               5                   10                  15

Leu Ser Phe Gln Leu Thr Leu Leu Thr Ala Leu Phe Met Tyr Tyr His
            20                  25                  30

Tyr Thr Phe
        35

<210> SEQ ID NO 202
<211> LENGTH: 558
<212> TYPE: DNA
<213> ORGANISM: Acinetobacter phage vB_AbaP_CEB1

<400> SEQUENCE: 202

```
atgattctga ctaaagatgg gtttggtatt atccgtaatg aactattcgg aggtaagtta    60
gatcaaactc aagtagatgc aataaacttt attgtagaga aagctactga gtctggttta   120
tcttatccag aggcagccta tttactagct accatctatc atgagactgg tctaccaagc   180
ggttatcgaa ctatgcaacc tattaaagaa gctggttctg ataactacct tcgatctaag   240
aagtactacc cgtacattgg ttatggttat gtacagttaa cttggaagga aactatggaa   300
cggattggta aacttattgg aattgaccta attaagaatc tgagaaagc gctagaacct   360
ttaattgcta ttcagattgc tatcaaaggc atgttaatg gttggttcac aggtgttgga   420
ttccgacgta acgtccagt tagtaaatac aacaaacagc agtacatagc tgcgcgtaat   480
atcattaatg ggaaagataa ggctgagctt atagcgaagt acgctattat ctttgaacgc   540
gctctacgga gcttataa                                                 558
```

<210> SEQ ID NO 203
<211> LENGTH: 185
<212> TYPE: PRT
<213> ORGANISM: Acinetobacter phage vB_AbaP_CEB1

<400> SEQUENCE: 203

Met Ile Leu Thr Lys Asp Gly Phe Gly Ile Ile Arg Asn Glu Leu Phe
1               5                   10                  15

Gly Gly Lys Leu Asp Gln Thr Gln Val Asp Ala Ile Asn Phe Ile Val
            20                  25                  30

Glu Lys Ala Thr Glu Ser Gly Leu Ser Tyr Pro Glu Ala Ala Tyr Leu
        35                  40                  45

Leu Ala Thr Ile Tyr His Glu Thr Gly Leu Pro Ser Gly Tyr Arg Thr
    50                  55                  60

Met Gln Pro Ile Lys Glu Ala Gly Ser Asp Asn Tyr Leu Arg Ser Lys
65                  70                  75                  80

Lys Tyr Tyr Pro Tyr Ile Gly Tyr Gly Tyr Val Gln Leu Thr Trp Lys
                85                  90                  95

Glu Asn Tyr Gly Arg Ile Gly Lys Leu Ile Gly Ile Asp Leu Ile Lys
            100                 105                 110

Asn Pro Glu Lys Ala Leu Glu Pro Leu Ile Ala Ile Gln Ile Ala Ile
        115                 120                 125

Lys Gly Met Leu Asn Gly Trp Phe Thr Gly Val Gly Phe Arg Arg Lys
    130                 135                 140

Arg Pro Val Ser Lys Tyr Asn Lys Gln Gln Tyr Ile Ala Ala Arg Asn
145                 150                 155                 160

Ile Ile Asn Gly Lys Asp Lys Ala Glu Leu Ile Ala Lys Tyr Ala Ile
                165                 170                 175

Ile Phe Glu Arg Ala Leu Arg Ser Leu
            180                 185

<210> SEQ ID NO 204
<211> LENGTH: 36
<212> TYPE: PRT
<213> ORGANISM: Sus scrofa
<220> FEATURE:
<221> NAME/KEY: MISC_FEATURE
<222> LOCATION: (1)..(36)
<223> OTHER INFORMATION: PMAP-36

<400> SEQUENCE: 204

Gly Arg Phe Arg Arg Leu Arg Lys Lys Thr Arg Lys Arg Leu Lys Lys
1               5                   10                  15

Ile Gly Lys Val Leu Lys Trp Ile Pro Pro Ile Val Gly Ser Ile Pro
            20                  25                  30

Leu Gly Cys Gly
        35

<210> SEQ ID NO 205
<211> LENGTH: 519
<212> TYPE: DNA
<213> ORGANISM: Unknown
<220> FEATURE:
<223> OTHER INFORMATION: GOS_4958713 hypothetical protein GOS_4958713,
      partial [marine metagenome]

<400> SEQUENCE: 205 atgacccat tgaccacgc cctcgagctc accctcggat ggagggtgg atactccaat      60 catttaatgg accgtggcgg agagaccatg tgcggtataa cggaggccgt agcacggagg   120
cacggatggg agggtgagat gcgagaccta cccatcgaaa tggtccggca tatttacaag   180
gtggattatt gggacccatt gatgggtgat tacctgggag aacacaaccc ggagctcgcg   240
gaggaattat ttgatacggc cgttaattgt ggcgtgggtt ttgcgtccaa gattctccaa   300
aagagcatca acgtattaaa ccgcaaccgg accgaggaca ttgcggagga tggccaaatc   360
ggtccacaaa ccctcaaggc tttacgggat ttggctcggc gtgattatga ttatttactc   420
gagtgttgca agattctcca gggtaaccat tatataagcc tagcccatcg cgaccccacc   480
caacggatat tcattcgagg atggttgacc agggtatga                         519

<210> SEQ ID NO 206
<211> LENGTH: 172
<212> TYPE: PRT
<213> ORGANISM: Unknown
<220> FEATURE:
<223> OTHER INFORMATION: GOS_4958713 hypothetical protein GOS_4958713,
      partial [marine metagenome]

<400> SEQUENCE: 206

Met Thr Pro Phe Asp His Ala Leu Glu Leu Thr Leu Gly Leu Glu Gly
1               5                   10                  15

Gly Tyr Ser Asn His Leu Met Asp Arg Gly Gly Glu Thr Met Cys Gly
            20                  25                  30

Ile Thr Glu Ala Val Ala Arg Arg His Gly Trp Glu Gly Glu Met Arg
        35                  40                  45

Asp Leu Pro Ile Glu Met Val Arg His Ile Tyr Lys Val Asp Tyr Trp
    50                  55                  60

Asp Pro Leu Met Gly Asp Tyr Leu Gly Glu His Asn Pro Glu Leu Ala
65                  70                  75                  80

Glu Leu Phe Asp Thr Ala Val Asn Cys Gly Val Gly Phe Ala Ser
                85                  90                  95

Lys Ile Leu Gln Lys Ser Ile Asn Val Leu Asn Arg Asn Arg Thr Glu
            100                 105                 110

Asp Ile Ala Glu Asp Gly Gln Ile Gly Pro Gln Thr Leu Lys Ala Leu
            115                 120                 125

Arg Asp Leu Ala Arg Asp Tyr Asp Tyr Leu Leu Glu Cys Cys Lys
    130                 135                 140

Ile Leu Gln Gly Asn His Tyr Ile Ser Leu Ala His Arg Asp Pro Thr
145                 150                 155                 160

Gln Arg Ile Phe Ile Arg Gly Trp Leu Thr Arg Val
                165                 170

<210> SEQ ID NO 207
<211> LENGTH: 450
<212> TYPE: DNA
<213> ORGANISM: Pseudomonas putida

<400> SEQUENCE: 207
atgacataca acgctggaac gaaaccccgc gctgagacgg actacctggt agttcactgt      60
agcgccacgc gaccatccca agacatcggg gctgctgaca tcaaccgctg gcatcgcgcc     120
aaaggttggc ggtgcatcgg ctatcacttt gtcatccgcc gcaatggcgt ggtggaggag     180
ggccgcgagc tggatcaaat cggcgcccac gtagagggcc ataacatcaa ctccgtaggc     240
atttgcatgg ccggtggagt caccgaggcg gacatcaacg tccccgaaaa caacttcacg     300
cccgagcagt ttgcaagtct caagcacctg ctgggcgagc tgaaagagaa ataccccagc     360
gcgacaatcc aaggccaccg ggacttcccg aaagtagcca aggcttgccc gagcttcgac     420
gttaaaccgt gggtagcggc caacttataa                                     450

<210> SEQ ID NO 208
<211> LENGTH: 149
<212> TYPE: PRT
<213> ORGANISM: Pseudomonas putida

<400> SEQUENCE: 208

Met Thr Tyr Asn Ala Gly Thr Lys Pro Arg Ala Glu Thr Asp Tyr Leu
1               5                   10                  15

Val Val His Cys Ser Ala Thr Arg Pro Ser Gln Asp Ile Gly Ala Ala
                20                  25                  30

Asp Ile Asn Arg Trp His Arg Ala Lys Gly Trp Arg Cys Ile Gly Tyr
            35                  40                  45

His Phe Val Ile Arg Arg Asn Gly Val Val Glu Glu Gly Arg Glu Leu
        50                  55                  60

Asp Gln Ile Gly Ala His Val Glu Gly His Asn Ile Asn Ser Val Gly
65                  70                  75                  80

Ile Cys Met Ala Gly Gly Val Thr Glu Ala Asp Ile Asn Val Pro Glu
                85                  90                  95

Asn Asn Phe Thr Pro Glu Gln Phe Ala Ser Leu Lys His Leu Leu Gly
            100                 105                 110

Glu Leu Lys Glu Lys Tyr Pro Ser Ala Thr Ile Gln Gly His Arg Asp
        115                 120                 125

Phe Pro Lys Val Ala Lys Ala Cys Pro Ser Phe Asp Val Lys Pro Trp
    130                 135                 140

Val Ala Ala Asn Leu
145

<210> SEQ ID NO 209
<211> LENGTH: 636
<212> TYPE: DNA
<213> ORGANISM: Micavibrio aeruginosavorus

<400> SEQUENCE: 209

```
atgtttagac catcttatat tttgcccggt gtggcggcgg tgatgctgtt ggcatcgacg    60
gcggcgcatg cggccggata tgaatggaaa cgcgttgatt accaatacct gcaaagcgtt   120
tccgaaaaag agcgcggcat gttgcgtatt tataaagatt acgaagaacg cgagccgtgc   180
caaaattacc gcgagcttcc gcccgaggta aaatacgtgg attgtaaatt gtatcaccgc   240
gtagcaatcc cagatccacc accccaccc gctccgccac cggctccga gcctccgaaa   300
gttgtgtcca gctatgaaat cttcttccca ctggacagca cggctctgga tctgcaggcc   360
aatgccatgg ttgataaagc cgctgccgac attgcgctgt atcaacccag caccgtgatt   420
gtggccgggt ataccgacac gtccggcgcg gcggattata atgaccagtt gtctgccaac   480
cgggccatgg cggtgtctgc cgcgttgagc cagcgtggca tcccgaacac ggcgatggac   540
ctggaggctc acggtcagaa tgacctgaaa gtgccgacag cggacgatgt tcacgagccg   600
caaaaccgcc gcacggtcat tcatttcatg aaatag                             636
```

<210> SEQ ID NO 210
<211> LENGTH: 211
<212> TYPE: PRT
<213> ORGANISM: Micavibrio aeruginosavorus

<400> SEQUENCE: 210

Met Phe Arg Pro Ser Tyr Ile Leu Pro Gly Val Ala Ala Val Met Leu
1               5                   10                  15

Leu Ala Ser Thr Ala Ala His Ala Ala Gly Tyr Glu Trp Lys Arg Val
            20                  25                  30

Asp Tyr Gln Tyr Leu Gln Ser Val Ser Glu Lys Glu Arg Gly Met Leu
        35                  40                  45

Arg Ile Tyr Lys Asp Tyr Glu Glu Arg Glu Pro Cys Gln Asn Tyr Arg
    50                  55                  60

Glu Leu Pro Pro Glu Val Lys Tyr Val Asp Cys Lys Leu Tyr His Arg
65                  70                  75                  80

Val Ala Ile Pro Asp Pro Pro Pro Ala Pro Pro Ala Pro
                85                  90                  95

Glu Pro Pro Lys Val Val Ser Ser Tyr Glu Ile Phe Phe Pro Leu Asp
            100                 105                 110

Ser Thr Ala Leu Asp Leu Gln Ala Asn Ala Met Val Asp Lys Ala Ala
        115                 120                 125

Ala Asp Ile Ala Leu Tyr Gln Pro Ser Thr Val Ile Val Ala Gly Tyr
    130                 135                 140

Thr Asp Thr Ser Gly Ala Ala Asp Tyr Asn Asp Gln Leu Ser Ala Asn
145                 150                 155                 160

Arg Ala Met Ala Val Ser Ala Ala Leu Ser Gln Arg Gly Ile Pro Asn
                165                 170                 175

Thr Ala Met Asp Leu Glu Ala His Gly Gln Asn Asp Leu Lys Val Pro
            180                 185                 190

Thr Ala Asp Asp Val His Glu Pro Gln Asn Arg Arg Thr Val Ile His
        195                 200                 205

Phe Met Lys
   210

<210> SEQ ID NO 211
<211> LENGTH: 723
<212> TYPE: DNA
<213> ORGANISM: Artificial Sequence
<220> FEATURE:
<223> OTHER INFORMATION: SMAP29-KZ144 (Artilysin) AMP fusion to
      N-terminus

<400> SEQUENCE: 211

```
ggagaattca ccatgagggg acttcgaaga ctgggtagga agatagcaca tggtgtgaag    60
aagtatggcc caactgttct ccgaataatc agaatagctt ctgataaacg cgttgaaatt   120
accggaaacg tttccggttt tttcgagtcc ggtggccgtg gtgtaaaaac cgtttctacc   180
ggcaaaggtg acaacggcgg tgtgagctac ggcaagcatc agctggcgtc gaataacggc   240
tctatggctc tgttccttga atctccgttc ggtgctccgt accgtgcgca attcgcagga   300
ctgaaaccgg gaaccgctgc gtttacttcc gtgtacaaca aatcgcaaa tgaaacgccg   360
accgcgtttg aacgggacca gttccaatac atcgcggctt cgcactacga tccacaagcg   420
gccaagctga aagccgaagg cattaacgtc gatgaccgac atgtcgcggt gcgtgaatgc   480
gtgttcagcg tagccgtgca atatggtcga aatacttcga tcattatcaa agcactcggc   540
agtaatttcc ggggcagcga caaagacttc atcgaaaagg tgcaggacta tcgcggtgcc   600
acggttaaca cctactttaa atccagtagc cagcaaactc gcgacagcgt gaaaaaccgc   660
tcgcagcaag aaaagcaaat gctgctgaaa ctcctgaata gttaataagc ttggctgttt   720
tgg                                                                723
```

<210> SEQ ID NO 212
<211> LENGTH: 230
<212> TYPE: PRT
<213> ORGANISM: Artificial Sequence
<220> FEATURE:
<223> OTHER INFORMATION: SMAP29-GN13, (Artilysin) AMP fusion to
      N-terminus

<400> SEQUENCE: 212

Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Ser Asp Lys
                20                  25                  30

Arg Val Glu Ile Thr Gly Asn Val Ser Gly Phe Phe Glu Ser Gly Gly
            35                  40                  45

Arg Gly Val Lys Thr Val Ser Thr Gly Lys Gly Asp Asn Gly Gly Val
        50                  55                  60

Ser Tyr Gly Lys His Gln Leu Ala Ser Asn Asn Gly Ser Met Ala Leu
65                  70                  75                  80

Phe Leu Glu Ser Pro Phe Gly Ala Pro Tyr Arg Ala Gln Phe Ala Gly
                85                  90                  95

Leu Lys Pro Gly Thr Ala Ala Phe Thr Ser Val Tyr Asn Lys Ile Ala
                100                 105                 110

Asn Glu Thr Pro Thr Ala Phe Glu Arg Asp Gln Phe Gln Tyr Ile Ala
            115                 120                 125

Ala Ser His Tyr Asp Pro Gln Ala Ala Lys Leu Lys Ala Glu Gly Ile
        130                 135                 140

Asn Val Asp Asp Arg His Val Ala Val Arg Glu Cys Val Phe Ser Val

```
                            145                 150                 155                 160
Ala Val Gln Tyr Gly Arg Asn Thr Ser Ile Ile Lys Ala Leu Gly
                165                 170                 175

Ser Asn Phe Arg Gly Ser Asp Lys Asp Phe Ile Glu Lys Val Gln Asp
                180                 185                 190

Tyr Arg Gly Ala Thr Val Asn Thr Tyr Phe Lys Ser Ser Gln Gln
                195                 200                 205

Thr Arg Asp Ser Val Lys Asn Arg Ser Gln Gln Glu Lys Gln Met Leu
        210                 215                 220

Leu Lys Leu Leu Asn Ser
225                 230

<210> SEQ ID NO 213
<211> LENGTH: 1005
<212> TYPE: DNA
<213> ORGANISM: Staphylococcus sciuri

<400> SEQUENCE: 213
ggagaattca ccatggaaaa tatacaaaaa ggtatcaccg tagacatcgc aagaaaatca        60
tattccttag aactttaaa aaccatcgtt aaacatatac atgatcacaa tggtcaatac       120
cttcaattac attttcaga tgatgaaaat tacgcaattg aatcagaata ttttgatcgt       180
aaaagttttt ctaatccata ttatttaaca aaaacagaag tgaaatcact tattgagtat       240
agtaatgatt taaatgtaat ggtcattcca gatatggatt ttccctctca ttccaaagct       300
tttttatctt tgattaaaca aaatgataaa tcattatatc aagaaataat cagtgattat       360
agtgataaca ctttagattt tttctcaaat cgtaaagcag tagatgttac aaatagacaa       420
attgatgaaa taacagagtt gtttaaacaa cctcaatttg cagaacaaca acgaattgta       480
ctcggtgggg atgaagtagc aggtggaggt gcgcatcaaa atagctttat agaatatatg       540
aatcaaatag gtgactatgc atttcaacaa ggatatgagc cacagatgtg gaatgatatg       600
gtcacgcatg aaggggtgaa gtctttaaat aaccattatt caatattata ttggaagcaa       660
aatgaagaca taaatctaa tttaactgta gaagattttg ataaatatta ttttgatgta       720
tataactata attattattc gttatatttc ttgccttcaa acagtttag ccaggacgat       780
attaatgaac aggctgaata taggttgg gcatatgcat ataacaaatt ttattataat       840
aagaatcctt atagtgaagt gaatagtcaa atgttaaag gatctgcatt atcattttgg       900
ggtgaacatg caactgatat gacacaagaa gaattaatca atcaagaagt gcctttgatt       960
aaagtatatt ttaatcttaa gaagtgataa gcctggctgt tctgg                     1005

<210> SEQ ID NO 214
<211> LENGTH: 324
<212> TYPE: PRT
<213> ORGANISM: Staphylococcus sciuri

<400> SEQUENCE: 214

Met Glu Asn Ile Gln Lys Gly Ile Thr Val Asp Ile Ala Arg Lys Ser
1               5                   10                  15

Tyr Ser Leu Glu Thr Leu Lys Thr Ile Val Lys His Ile His Asp His
            20                  25                  30

Asn Gly Gln Tyr Leu Gln Leu His Phe Ser Asp Asp Glu Asn Tyr Ala
        35                  40                  45

Ile Glu Ser Glu Tyr Phe Asp Arg Lys Ser Phe Ser Asn Pro Tyr Tyr
    50                  55                  60
```

Leu Thr Lys Thr Glu Val Lys Ser Leu Ile Glu Tyr Ser Asn Asp Leu
 65                  70                  75                  80

Asn Val Met Val Ile Pro Asp Met Asp Phe Pro Ser His Ser Lys Ala
             85                  90                  95

Phe Leu Ser Leu Ile Lys Gln Asn Asp Lys Ser Leu Tyr Gln Glu Ile
            100                 105                 110

Ile Ser Asp Tyr Ser Asp Asn Thr Leu Asp Phe Phe Ser Asn Arg Lys
            115                 120                 125

Ala Val Asp Val Thr Asn Arg Gln Ile Asp Glu Ile Thr Glu Leu Phe
            130                 135                 140

Lys Gln Pro Gln Phe Ala Glu Gln Gln Arg Ile Val Leu Gly Gly Asp
145                 150                 155                 160

Glu Val Ala Gly Gly Gly Ala His Gln Asn Ser Phe Ile Glu Tyr Met
                165                 170                 175

Asn Gln Ile Gly Asp Tyr Ala Phe Gln Gln Gly Tyr Glu Pro Gln Met
            180                 185                 190

Trp Asn Asp Met Val Thr His Glu Gly Val Lys Ser Leu Asn Asn His
            195                 200                 205

Tyr Ser Ile Leu Tyr Trp Lys Gln Asn Glu Asp Asn Lys Ser Asn Leu
210                 215                 220

Thr Val Glu Asp Phe Asp Lys Tyr Tyr Phe Asp Val Tyr Asn Tyr Asn
225                 230                 235                 240

Tyr Tyr Ser Leu Tyr Phe Leu Pro Ser Lys Gln Phe Ser Gln Asp Asp
                245                 250                 255

Ile Asn Glu Gln Ala Glu Tyr Ile Gly Trp Ala Tyr Ala Tyr Asn Lys
            260                 265                 270

Phe Tyr Tyr Asn Lys Asn Pro Tyr Ser Glu Val Asn Ser Gln Asn Val
            275                 280                 285

Lys Gly Ser Ala Leu Ser Phe Trp Gly Glu His Ala Thr Asp Met Thr
            290                 295                 300

Gln Glu Glu Leu Ile Asn Gln Glu Val Pro Leu Ile Lys Val Tyr Phe
305                 310                 315                 320

Asn Leu Lys Lys

<210> SEQ ID NO 215
<211> LENGTH: 834
<212> TYPE: DNA
<213> ORGANISM: Artificial Sequence
<220> FEATURE:
<223> OTHER INFORMATION: OBG_GN4_2 (Lyzterm)

<400> SEQUENCE: 215
ggagaattca ccatgaaaaa tagcgagaag aatgcatcga taattatgtc gatacagaga      60
acgctcgctt cactctcact ctatggaggc cgcatcgacg gcctctttgg agagaagtgt     120 cgtgggggcta tcatcttgat gctgaataag gtctatccta atttcagcac caacaaactt     180
ccgagtaaca catatgaagc ggaatccgtg ttcacgtttc tccagactgc tttggctggt     240
gttggtcttt ataccattac tattgatggt aaatggggtg gtacttctca aggtgctatt     300
gacgccctcg tcaagtctta ccgtcaaatt accgaagcgg agcgagctgg gtcgacgttg     360
ccattaggtc ttgctactgt gatgtctaca tcccaacgag gcatcgacct catcaaatcc     420
ttcgagggcc tgcgcctgtc cgcttaccag gactcggtgg tgtctggac ataggttac      480 ggcaccactc ggggcgtcac ccgctacatg acgatcaccg tcgagcaggc cgagcggatg     540
ctgtcgaacg acattcagcg cttcgagcca gagctagaca ggctggcgaa ggtgccactg     600

```
aaccagaacc agtgggatgc cctgatgagc ttcgtgtaca acctgggcgc ggccaatctg    660
gcgtcgtcca cgctgctcaa gctgctgaac aagggtgact accagggagc agcggaccag    720
ttcccgcgct gggtgaatgc gggcggtaag cgcttggatg gtctggttaa cgtcgagca     780 gccgagcgtg cgctgttcct ggagccacta tcgtaataag cttggctgtt ttgg          834
```

<210> SEQ ID NO 216
<211> LENGTH: 267
<212> TYPE: PRT
<213> ORGANISM: Artificial Sequence
<220> FEATURE:
<223> OTHER INFORMATION: OBG_GN4_2 (Lyzterm)

<400> SEQUENCE: 216

```
Met Lys Asn Ser Glu Lys Asn Ala Ser Ile Ile Met Ser Ile Gln Arg
1               5                   10                  15

Thr Leu Ala Ser Leu Ser Leu Tyr Gly Gly Arg Ile Asp Gly Leu Phe
            20                  25                  30

Gly Glu Lys Cys Arg Gly Ala Ile Ile Leu Met Leu Asn Lys Val Tyr
        35                  40                  45

Pro Asn Phe Ser Thr Asn Lys Leu Pro Ser Asn Thr Tyr Glu Ala Glu
    50                  55                  60

Ser Val Phe Thr Phe Leu Gln Thr Ala Leu Ala Gly Val Gly Leu Tyr
65                  70                  75                  80

Thr Ile Thr Ile Asp Gly Lys Trp Gly Gly Thr Ser Gln Gly Ala Ile
                85                  90                  95

Asp Ala Leu Val Lys Ser Tyr Arg Gln Ile Thr Glu Ala Glu Arg Ala
            100                 105                 110

Gly Ser Thr Leu Pro Leu Gly Leu Ala Thr Val Met Ser Thr Ser Gln
        115                 120                 125

Arg Gly Ile Asp Leu Ile Lys Ser Phe Glu Gly Leu Arg Leu Ser Ala
    130                 135                 140

Tyr Gln Asp Ser Val Gly Val Trp Thr Ile Gly Tyr Gly Thr Thr Arg
145                 150                 155                 160

Gly Val Thr Arg Tyr Met Thr Ile Thr Val Glu Gln Ala Glu Arg Met
                165                 170                 175

Leu Ser Asn Asp Ile Gln Arg Phe Glu Pro Glu Leu Asp Arg Leu Ala
            180                 185                 190

Lys Val Pro Leu Asn Gln Asn Gln Trp Asp Ala Leu Met Ser Phe Val
        195                 200                 205

Tyr Asn Leu Gly Ala Ala Asn Leu Ala Ser Ser Thr Leu Leu Lys Leu
    210                 215                 220

Leu Asn Lys Gly Asp Tyr Gln Gly Ala Ala Asp Gln Phe Pro Arg Trp
225                 230                 235                 240

Val Asn Ala Gly Gly Lys Arg Leu Asp Gly Leu Val Lys Arg Arg Ala
                245                 250                 255

Ala Glu Arg Ala Leu Phe Leu Glu Pro Leu Ser
            260                 265
```

<210> SEQ ID NO 217
<211> LENGTH: 438
<212> TYPE: DNA
<213> ORGANISM: Pseudomonas putida

<400> SEQUENCE: 217

```
atgagcattt tcagtttcgt caaagaagca ggcgagaaac ttatcgacct gttgaccccg    60
```

```
ggtaatgcca atgccagcga gcagttgaag gagcatgtct ccaaggtagg cttgggcaat    120
ccgaacattc agacaactgt cgagggcagc aaggtgacgg tcaccggcga ggtggccagc    180
caggaagaga aggagaaaat cctgctggcg ctgggcaaca ttgccggtgt ggagtcggtg    240
gatgatcaga tcactgttac cgggcctctg gttgccgctg cccgttttgt cgtggtgaag    300
aagggcgaca ccctcagtgc catttccctg gctgtgtacg gcaacgccaa ccagtacaac    360
aagattttcg aagccaacaa gccgctgctc agccacccgg acaagatcta cccgggccag    420
accctgcgca tccctgaa                                                  438
```

<210> SEQ ID NO 218
<211> LENGTH: 146
<212> TYPE: PRT
<213> ORGANISM: Pseudomonas putida

<400> SEQUENCE: 218

```
Met Ser Ile Phe Ser Phe Val Lys Glu Ala Gly Glu Lys Leu Ile Asp
1               5                   10                  15

Leu Leu Thr Pro Gly Asn Ala Asn Ala Ser Glu Gln Leu Lys Glu His
            20                  25                  30

Val Ser Lys Val Gly Leu Gly Asn Pro Asn Ile Gln Thr Thr Val Glu
        35                  40                  45

Gly Ser Lys Val Thr Val Thr Gly Glu Val Ala Ser Gln Glu Lys
    50                  55                  60

Glu Lys Ile Leu Leu Ala Leu Gly Asn Ile Ala Gly Val Glu Ser Val
65                  70                  75                  80

Asp Asp Gln Ile Thr Val Thr Gly Pro Leu Val Ala Ala Ala Arg Phe
                85                  90                  95

Val Val Val Lys Lys Gly Asp Thr Leu Ser Ala Ile Ser Leu Ala Val
            100                 105                 110

Tyr Gly Asn Ala Asn Gln Tyr Asn Lys Ile Phe Glu Ala Asn Lys Pro
        115                 120                 125

Leu Leu Ser His Pro Asp Lys Ile Tyr Pro Gly Gln Thr Leu Arg Ile
    130                 135                 140

Pro Glu
145
```

<210> SEQ ID NO 219
<211> LENGTH: 891
<212> TYPE: DNA
<213> ORGANISM: Pseudomonas protegens

<400> SEQUENCE: 219

```
gtttaacttt aagaaggaga attcaccatg aacacactcc ggcacggcga tcgctcgcaa     60
gcggtacgca gcctgcagaa gaacctcaac agccacgggg ccatcctggt ggtggacggc    120
gactacggcg acgccaccga agcggccgtg cgcgcctacc agctcaaggc cggcctggtg    180
gtggacggta tcgccggcga gaaaacccaa accagcctgg tcggtggcga ttgcgctctg    240
ctgctgaaga cgccgacct ggtcagcgcg cccagcgcc tggatctgcc cctcgccagt    300
gtctacgcgg tcaatgaggt cgaatcgaac ggcaagggct tcttcgccaa cggcaagccg    360
gcgatcctgt ttgagcggca catcatgtac cgccaattga agacgccacg ctacccaggc    420
gacgacccgg cagaactcaa cgccacgccc gacgagcttg cggcgcagta cccgccatc    480 atcaatccga acccgggtgg ttatgccggc ggccctgctg agcatcagcg cctggccacg    540
```

```
gcccgcctga tcgatgacac cgcggccctg gagtctgcct cctggggcgc cttccagatc    600
atgggctttc actggaagcg cctcggctat gccagcgtgc aggacttcgt gacggccatg    660
agcgcgagcg agccccgcca gtttgaggcc ttcgtccgct tcatcgagac cgatccggcc    720
ctccacaaag cgctgaaggc cgcaagtgg tccgacttcg ccaggcagta caacgggccg     780
aactaccaac gcaacctgta cgacaccaag ctccagcgcg cctatgagcg acatagcgcc    840
tgcagctgcg gtcaggaggt accggcatga taaaagcttg gctgttttgg c             891
```

<210> SEQ ID NO 220
<211> LENGTH: 280
<212> TYPE: PRT
<213> ORGANISM: Pseudomonas protegens

<400> SEQUENCE: 220

```
Met Asn Thr Leu Arg His Gly Asp Arg Ser Gln Ala Val Arg Ser Leu
1               5                   10                  15

Gln Lys Asn Leu Asn Ser His Gly Ala Ile Leu Val Val Asp Gly Asp
            20                  25                  30

Tyr Gly Asp Ala Thr Glu Ala Ala Val Arg Ala Tyr Gln Leu Lys Ala
        35                  40                  45

Gly Leu Val Val Asp Gly Ile Ala Gly Glu Lys Thr Gln Thr Ser Leu
    50                  55                  60

Val Gly Gly Asp Cys Ala Leu Leu Lys Asn Ala Asp Leu Val Ser
65                  70                  75                  80

Ala Ala Gln Arg Leu Asp Leu Pro Leu Ala Ser Val Tyr Ala Val Asn
                85                  90                  95

Glu Val Glu Ser Asn Gly Lys Gly Phe Phe Ala Asn Gly Lys Pro Ala
            100                 105                 110

Ile Leu Phe Glu Arg His Ile Met Tyr Arg Gln Leu Lys Thr Pro Arg
        115                 120                 125

Tyr Pro Gly Asp Asp Pro Ala Glu Leu Lys Arg His Ala Asp Glu Leu
    130                 135                 140

Ala Ala Gln Tyr Pro Ala Ile Ile Asn Pro Asn Pro Gly Gly Tyr Ala
145                 150                 155                 160

Gly Gly Pro Ala Glu His Gln Arg Leu Ala Thr Ala Arg Leu Ile Asp
                165                 170                 175

Asp Thr Ala Ala Leu Glu Ser Ala Ser Trp Gly Ala Phe Gln Ile Met
            180                 185                 190

Gly Phe His Trp Lys Arg Leu Gly Tyr Ala Ser Val Gln Asp Phe Val
        195                 200                 205

Thr Ala Met Ser Ala Ser Glu Pro Arg Gln Phe Glu Ala Phe Val Arg
    210                 215                 220

Phe Ile Glu Thr Asp Pro Ala Leu His Lys Leu Lys Ala Arg Lys
225                 230                 235                 240

Trp Ser Asp Phe Ala Arg Gln Tyr Asn Gly Pro Asn Tyr Gln Arg Asn
                245                 250                 255

Leu Tyr Asp Thr Lys Leu Gln Arg Ala Tyr Glu Arg His Ser Ala Cys
            260                 265                 270

Ser Cys Gly Gln Glu Val Pro Ala
        275                 280
```

<210> SEQ ID NO 221
<211> LENGTH: 897
<212> TYPE: DNA
<213> ORGANISM: Artificial Sequence
<220> FEATURE:
<223> OTHER INFORMATION: SMAP29-KZ144, (Artilysin) AMP fusion to N-terminus

<400> SEQUENCE: 221

```
ggagaattca ccatgagggg acttcgaaga ctgggtagga agatagcaca tggtgtgaag      60
aagtatggcc caactgttct ccgaataatc agaatagcta agtattacg caaaggcgat     120
aggggtgatg aggtaagcca actccagaca ctcttaaatt taagcggcta tgatgttgga    180
aagccagatg gtattttgg aaataacacc tttaatcagg tagttaaatt tcaaaaagat     240
aatagcctag atagtgatgg tattgtaggt aagaatactt gggctgaatt attcagtaaa    300
tattctccac ctattcctta taaaactatc cctatgccaa ctgcaaataa atcacgtgca    360
gctgcaactc cagttatgaa tgcagtagaa aatgctactg gcgttcgtag ccagttgcta    420
ctaacatttg cttctattga atcagcattc gattacgaaa taaaagctaa gacttcatca    480
gctactggtt ggttccaatt ccttactgga acatggaaaa caatgattga aaattatggc    540
atgaagtatg gcgtacttac tgatccaact ggggcattac gtaaagatcc acgtataagt    600
gctttaatgg gtgccgaact aattaaagag aatatgaata ttcttcgtcc tgtccttaaa    660
cgtgaaccaa ctgatactga tctttatta gctcacttct ttgggcctgg tgcagcccgt    720
cgtttcctga ccactggcca gaatgaatta gctgctaccc atttcccaaa agaagctcag    780
gcaaacccat ctattttta taacaaagat gggtcaccta aaaccattca agaagtttat    840
aacttaatgg atggtaaagt tgcagcacat agaaaataat aagcttggct gttttgg      897
```

<210> SEQ ID NO 222
<211> LENGTH: 288
<212> TYPE: PRT
<213> ORGANISM: Artificial Sequence
<220> FEATURE:
<223> OTHER INFORMATION: SMAP29-KZ144, (Artilysin) AMP fusion to N-terminus

<400> SEQUENCE: 222

```
Met Arg Gly Leu Arg Arg Leu Gly Arg Lys Ile Ala His Gly Val Lys
1               5                   10                  15

Lys Tyr Gly Pro Thr Val Leu Arg Ile Ile Arg Ile Ala Lys Val Leu
                20                  25                  30

Arg Lys Gly Asp Arg Gly Asp Glu Val Ser Gln Leu Gln Thr Leu Leu
            35                  40                  45

Asn Leu Ser Gly Tyr Asp Val Gly Lys Pro Asp Gly Ile Phe Gly Asn
        50                  55                  60

Asn Thr Phe Asn Gln Val Val Lys Phe Gln Lys Asp Asn Ser Leu Asp
65                  70                  75                  80

Ser Asp Gly Ile Val Gly Lys Asn Thr Trp Ala Glu Leu Phe Ser Lys
                85                  90                  95

Tyr Ser Pro Pro Ile Pro Tyr Lys Thr Ile Pro Met Pro Thr Ala Asn
                100                 105                 110

Lys Ser Arg Ala Ala Ala Thr Pro Val Met Asn Ala Val Glu Asn Ala
            115                 120                 125

Thr Gly Val Arg Ser Gln Leu Leu Leu Thr Phe Ala Ser Ile Glu Ser
        130                 135                 140

Ala Phe Asp Tyr Glu Ile Lys Ala Lys Thr Ser Ser Ala Thr Gly Trp
145                 150                 155                 160

Phe Gln Phe Leu Thr Gly Thr Trp Lys Thr Met Ile Glu Asn Tyr Gly
                165                 170                 175
```

```
Met Lys Tyr Gly Val Leu Thr Asp Pro Thr Gly Ala Leu Arg Lys Asp
            180                 185                 190

Pro Arg Ile Ser Ala Leu Met Gly Ala Glu Leu Ile Lys Glu Asn Met
        195                 200                 205

Asn Ile Leu Arg Pro Val Leu Lys Arg Glu Pro Thr Asp Thr Asp Leu
210                 215                 220

Tyr Leu Ala His Phe Phe Gly Pro Gly Ala Ala Arg Arg Phe Leu Thr
225                 230                 235                 240

Thr Gly Gln Asn Glu Leu Ala Ala Thr His Phe Pro Lys Glu Ala Gln
            245                 250                 255

Ala Asn Pro Ser Ile Phe Tyr Asn Lys Asp Gly Ser Pro Lys Thr Ile
            260                 265                 270

Gln Glu Val Tyr Asn Leu Met Asp Gly Lys Val Ala Ala His Arg Lys
            275                 280                 285

<210> SEQ ID NO 223
<211> LENGTH: 945
<212> TYPE: DNA
<213> ORGANISM: Artificial Sequence
<220> FEATURE:
<223> OTHER INFORMATION: SMAP29-KZ144 (1440) C Term His, HisTagged
      Art175 (SMAP29-KZ144)

<400> SEQUENCE: 223
gtttaacttt aagaaggaga attcaccatg cgtggtctgc gtcgtctggg tcgtaaaatc      60
gctcacggtg ttaaaaaata cggtccgacc gttctgcgta tcatccgtat cgctggtgga     120
tccaaagtat tacgcaaagg cgatagggt gatgaggtaa gccaactcca gacactctta     180
aatttaagcg ctatgatgt tggaaagcca gatggtattt ttggaaataa cacctttaat     240
caggtagtta aatttcaaaa agataatagc ctagatagta atggtattgt aggtaagaat     300
acttgggctg aattattcag taaatattct ccacctattc cttataaaac tatccctatg     360
ccaactgcaa ataaatcacg tgcagctgca actccagtta tgaatgcagt agaaaatgct     420
actggcgttc gtagccagtt gctactaaca tttgcttcta ttgaatcagc attcgattac     480
gaaataaaag ctaagacttc atcagctact ggttggttcc aattccttac tggaacatgg     540
aaaacaatga ttgaaaatta tggcatgaag tatggcgtac ttactgatcc aactggggca     600
ttacgtaaag atccacgtat aagtgctttta atgggtgccg aactaattaa agagaatatg     660
aatattcttc gtcctgtcct taaacgtgaa ccaactgata ctgatcttta tttagctcac     720
ttctttgggc ctggtgcagc ccgtcgtttc ctgaccactg gccagaatga attagctgct     780
acccatttcc caaaagaagc tcaggcaaac ccatctattt tttataacaa agatgggtca     840
cctaaaacca ttcaagaagt ttataactta atggatggta agttgcagc acatagaaaa     900 ctcgagcatc accatcatca ccactagtaa gcttggctgt tttgg                    945

<210> SEQ ID NO 224
<211> LENGTH: 299
<212> TYPE: PRT
<213> ORGANISM: Artificial Sequence
<220> FEATURE:
<223> OTHER INFORMATION: SMAP29-KZ144 (1440) C Term His, HisTagged
      Art175 (SMAP29-KZ144)

<400> SEQUENCE: 224

Met Arg Gly Leu Arg Arg Leu Gly Arg Lys Ile Ala His Gly Val Lys
1               5                   10                  15
```

Lys Tyr Gly Pro Thr Val Leu Arg Ile Ile Arg Ile Ala Gly Gly Ser
              20                  25                  30

Lys Val Leu Arg Lys Gly Asp Arg Gly Asp Glu Val Ser Gln Leu Gln
         35                  40                  45

Thr Leu Leu Asn Leu Ser Gly Tyr Asp Val Gly Lys Pro Asp Gly Ile
     50                  55                  60

Phe Gly Asn Asn Thr Phe Asn Gln Val Val Lys Phe Gln Lys Asp Asn
65                  70                  75                  80

Ser Leu Asp Ser Asp Gly Ile Val Gly Lys Asn Thr Trp Ala Glu Leu
                 85                  90                  95

Phe Ser Lys Tyr Ser Pro Pro Ile Pro Tyr Lys Thr Ile Pro Met Pro
             100                 105                 110

Thr Ala Asn Lys Ser Arg Ala Ala Thr Pro Val Met Asn Ala Val
         115                 120                 125

Glu Asn Ala Thr Gly Val Arg Ser Gln Leu Leu Thr Phe Ala Ser
     130                 135                 140

Ile Glu Ser Ala Phe Asp Tyr Glu Ile Lys Ala Lys Thr Ser Ser Ala
145                 150                 155                 160

Thr Gly Trp Phe Gln Phe Leu Thr Gly Thr Trp Lys Thr Met Ile Glu
                 165                 170                 175

Asn Tyr Gly Met Lys Tyr Gly Val Leu Thr Asp Pro Thr Gly Ala Leu
             180                 185                 190

Arg Lys Asp Pro Arg Ile Ser Ala Leu Met Gly Ala Glu Leu Ile Lys
         195                 200                 205

Glu Asn Met Asn Ile Leu Arg Pro Val Leu Lys Arg Glu Pro Thr Asp
210                 215                 220

Thr Asp Leu Tyr Leu Ala His Phe Phe Gly Pro Gly Ala Ala Arg Arg
225                 230                 235                 240

Phe Leu Thr Thr Gly Gln Asn Glu Leu Ala Ala Thr His Phe Pro Lys
                 245                 250                 255

Glu Ala Gln Ala Asn Pro Ser Ile Phe Tyr Asn Lys Asp Gly Ser Pro
             260                 265                 270

Lys Thr Ile Gln Glu Val Tyr Asn Leu Met Asp Gly Lys Val Ala Ala
         275                 280                 285

His Arg Lys Leu Glu His His His His His His
     290                 295

<210> SEQ ID NO 225
<211> LENGTH: 1086
<212> TYPE: DNA
<213> ORGANISM: Actinobacillus pleuropneumoniae

<400> SEQUENCE: 225

```
ggagaattca ccatggactt acctaaaaaa gaaagcggtc tgacgttaga tatcgcacgt      60
cgtttctata ccgttgatac gataaaacaa tttatcgata cgattcatca ggcgggcggc     120
acttttctgc atttacattt ttccgatcac gagaattatg cattggaaag ttcttatttg     180
gaacaacgag aagaaaatgc gaccgagaaa acggaacct atttcaatcc gaaaacaaat      240
aagccgtttc tcacttataa acagctcaat gaattatct attatgccaa gaacgaaat      300 attgaaattg tgcctgaagt cgatagcccg aatcatatga cggcgatttt tgatctttta     360
acccttaagc acggaaagga atacgtaaaa gggctaaaat cgccttatat cgccgaggaa     420
atcgatatta ataccccga agcggttgaa gttattaaaa ccttaatcgg tgaagtgatc      480
tatattttcg acattcaag ccggcatttc catatcggcg agatgaatt tagctatgcg       540
```

```
gtcgaaaata atcatgaatt tattcggtat gtgaatacct taaatgattt tatcaattcc    600
aaagggctaa ttacccgtgt ttggaatgac ggtttgatca aaaacaactt aagcgaactc    660
aataaaaaca ttgaaatcac ttactggagc tacgacggtg acgctcaagc caaagaagat    720
attcaatatc gacgtgaaat aagagccgat ttgcccgaac tgctggcaaa cggttttaag    780
gttttaaact ataattctta ttatttatac tttgtgccta atccggttc taatattcac     840 aatgacggta aatatgcggc tgaagacgta ttaaataact ggacattagg taaatgggac    900
ggaaaaaaca gctcaaatca cgtacaaaat acgcagaata ttatcggttc ttctttgtcg    960
atttgggggg aacgttccag cgcattaaat gaacaaacta ttcagcaagc ctctaaaaat   1020
ttattaaaag cggtgatcca aaaaactaat gatccgaaat cgcattaata agcttggctg   1080
ttttgg                                                              1086
```

<210> SEQ ID NO 226
<211> LENGTH: 351
<212> TYPE: PRT
<213> ORGANISM: Actinobacillus pleuropneumoniae

<400> SEQUENCE: 226

```
Met Asp Leu Pro Lys Lys Glu Ser Gly Leu Thr Leu Asp Ile Ala Arg
1               5                   10                  15

Arg Phe Tyr Thr Val Asp Thr Ile Lys Gln Phe Ile Asp Thr Ile His
                20                  25                  30

Gln Ala Gly Gly Thr Phe Leu His Leu His Phe Ser Asp His Glu Asn
            35                  40                  45

Tyr Ala Leu Glu Ser Ser Tyr Leu Glu Gln Arg Glu Glu Asn Ala Thr
        50                  55                  60

Glu Lys Asn Gly Thr Tyr Phe Asn Pro Lys Thr Asn Lys Pro Phe Leu
65                  70                  75                  80

Thr Tyr Lys Gln Leu Asn Glu Ile Ile Tyr Tyr Ala Lys Glu Arg Asn
                85                  90                  95

Ile Glu Ile Val Pro Glu Val Asp Ser Pro Asn His Met Thr Ala Ile
            100                 105                 110

Phe Asp Leu Leu Thr Leu Lys His Gly Lys Glu Tyr Val Lys Gly Leu
        115                 120                 125

Lys Ser Pro Tyr Ile Ala Glu Glu Ile Asp Ile Asn Asn Pro Glu Ala
    130                 135                 140

Val Glu Val Ile Lys Thr Leu Ile Gly Glu Val Ile Tyr Ile Phe Gly
145                 150                 155                 160

His Ser Ser Arg His Phe His Ile Gly Gly Asp Glu Phe Ser Tyr Ala
                165                 170                 175

Val Glu Asn Asn His Glu Phe Ile Arg Tyr Val Asn Thr Leu Asn Asp
            180                 185                 190

Phe Ile Asn Ser Lys Gly Leu Ile Thr Arg Val Trp Asn Asp Gly Leu
        195                 200                 205

Ile Lys Asn Asn Leu Ser Glu Leu Asn Lys Asn Ile Glu Ile Thr Tyr
    210                 215                 220

Trp Ser Tyr Asp Gly Asp Ala Gln Ala Lys Glu Asp Ile Gln Tyr Arg
225                 230                 235                 240

Arg Glu Ile Arg Ala Asp Leu Pro Glu Leu Leu Ala Asn Gly Phe Lys
                245                 250                 255

Val Leu Asn Tyr Asn Ser Tyr Tyr Leu Tyr Phe Val Pro Lys Ser Gly
            260                 265                 270
```

```
Ser Asn Ile His Asn Asp Gly Lys Tyr Ala Ala Glu Asp Val Leu Asn
        275             280                 285

Asn Trp Thr Leu Gly Lys Trp Asp Gly Lys Asn Ser Ser Asn His Val
    290             295                 300

Gln Asn Thr Gln Asn Ile Ile Gly Ser Ser Leu Ser Ile Trp Gly Glu
305             310             315                     320

Arg Ser Ser Ala Leu Asn Glu Gln Thr Ile Gln Gln Ala Ser Lys Asn
                325             330                 335

Leu Leu Lys Ala Val Ile Gln Lys Thr Asn Asp Pro Lys Ser His
                340             345             350
```

US 10,988,520 B2

LYSIN-ANTIMICROBIAL PEPTIDE (AMP) POLYPEPTIDE CONSTRUCTS, LYSINS, ISOLATED POLYNUCLEOTIDES ENCODING SAME AND USES THEREOF

CROSS-REFERENCE TO RELATED APPLICATIONS

This application is a continuation-in-part, which claims the benefit of, and relies on the filing date of PCT Application No. PCT/US19/47916, filed on 23 Aug. 2019, which claims the benefit of priority of PCT/US2019/024912, filed on 29 Mar. 2019, which claims the benefit of priority of U.S. provisional Application No. 62/722,793, filed 24 Aug. 2018, U.S. Provisional Application No. 62/650,235, filed on 29 Mar. 2018, and U.S. Provisional Application No. 62/721,969, filed on 23 Aug. 2018, and also relies on the filing date of U.S. Provisional Application No. 62/849,320 filed on 17 May 2019, U.S. Provisional Application No. 62/860,836 filed 13 Jun. 2019 and U.S. Provisional Application No. 62/935,479 filed 14 Nov. 2019, each of which is herein incorporated by reference in its entirety.

GOVERNMENT INTEREST

This invention was made with government support under grant 5 IDSEP160030-03-00 from the Department of Health and Human Services. The U.S. government has certain rights in this invention.

SEQUENCE LISTING

The instant application contains a Sequence Listing which has been submitted electronically in ASCII format and is hereby incorporated by reference in its entirety. Said ASCII copy, created on Jan. 28, 2020, is named 0341_0021-00-CIP_ST25.txt and is 286,955 bytes in size.

FIELD OF THE DISCLOSURE

The present disclosure relates to the field of antibacterial agents and more specifically to polypeptides having lysin activity against Gram-negative bacteria and the use of these agents in killing Gram-negative bacteria and combating bacterial infection and contamination.

BACKGROUND

Gram-negative bacteria, in particular, members of the genus *Pseudomonas* and the emerging multi-drug resistant pathogen *Acinetobacter baumannii*, are an important cause of serious and potentially life-threatening invasive infections. *Pseudomonas* infection presents a major problem in burn wounds, chronic wounds, chronic obstructive pulmonary disorder (COPD), cystic fibrosis, surface growth on implanted biomaterials, and within hospital surfaces and water supplies where it poses a host of threats to vulnerable patients.

Once established in a patient, *P. aeruginosa* can be especially difficult to treat. The genome encodes a host of resistance genes, including multidrug efflux pumps and enzymes conferring resistance to beta-lactam and aminoglycoside antibiotics, making therapy against this Gram-negative pathogen particularly challenging due to the lack of novel antimicrobial therapeutics. This challenge is compounded by the ability of *P. aeruginosa* to grow in a biofilm, which may enhance its ability to cause infections by protecting bacteria from host defenses and chemotherapy.

In the healthcare setting, the incidence of drug-resistant strains of *Pseudomonas aeruginosa* is increasing. In an observational study of health care-associated bloodstream infections (BSIs) in community hospitals, *P. aeruginosa* was one of the top four Multiple Drug Resistant (MDR) pathogens, contributing to an overall hospital mortality of 18%. Additionally, outbreaks of MDR *P. aeruginosa* are well-documented. Poor outcomes are associated with MDR stains of *P. aeruginosa* that frequently require treatment with drugs of last resort, such as colistin.

Moreover, reduced effectiveness of certain antibiotics is observed in combating both Gram-negative and Gram-positive infections due to factors in the environment of the infection, such as the pulmonary surfactant, rather than to antibiotic resistance developments. Certain antibiotics, such as daptomycin, for example, have failed to meet criteria in a clinical trial for severe community-acquired pneumonia. This deficiency has been shown to be due to an interaction between daptomycin and pulmonary surfactant, which inhibits the activity of this antibiotic against Gram-positive organisms, specifically in the lung environment and more generally in the airway environment wherein pulmonary surfactant is present. Silverman, J. A. et al., "Surfactant Inhibition of Daptomycin," *JID*, 191: 2149-2152 (2005). Thus, daptomycin is not indicated for treatment of lung and more generally airway (especially lower respiratory tract) infections and those of skill in the art would not employ a treatment regimen including daptomycin to treat such infections. The inability of daptomycin to combat infection in the presence of pulmonary surfactants has been shown dramatically in, for example, Koplowicz, Y. B. et al., "Development of daptomycin-susceptible methicillin-resistant *Staphylococcus aureus* Pneumonia during high-dose daptomycin therapy", *Clin Infect Dis.* 49(8):1286-7 (2009). Recent studies have focused on overcoming daptomycin inactivity in the presence of surfactant by testing and evaluating antibacterial activity of hybrid molecules of the structurally related lipopeptide A54145. Nguyen, K. T. et al., "Genetically engineered lipopeptide antibiotics related to A54145 and daptomycin with improved properties", *Antimicrob. Agents Chemother.* 2010 April; 54(4):1404-1413.

Pulmonary surfactant, a primary component of epithelial lining fluid, is a complex lipid-and-protein mixture that coats the interior surface of the airway, reducing surface tension within the alveoli. Surfactant is composed primarily of dipalmitoylphosphatidylcholine (~80% in all mammalian species), along with significant amounts of phosphatidylglycerol (PG) and smaller amounts of minor phospholipids, neutral lipids, and cholesterol. There are 4 protein components: hydrophilic proteins SP-A and SP-D and hydrophobic proteins SP-B and SP-C. Goerke, J., "Pulmonary Surfactant: functions and molecular composition", *Biochim. Biophys. Acta.* 1998; 1408:79-89. Daptomycin is inserted into artificial membrane vesicles composed of phosphatidylcholine (PC) and PC/PG. Lakey J. H. et al., "Fluorescence indicates a calcium-dependent interaction between the lipopeptide antibiotic LY146032 and phospholipid membranes," *Biochemistry* 1988; 27:4639-45; Jung, D. et al., "Structural transitions as determinants of the action of the calcium-dependent antibiotic daptomycin", *Chem. Biol.* 2004; 11:949-57.

Thus, to the extent that otherwise effective antibiotics are inhibited by factors present in the organ or tissue that is the site of the infection, such as pulmonary surfactant in the case of infections of the lungs or other airways and more generally of the respiratory tract, a treatment regimen that would restore and even augment activity of such antibiotics would be of commercial and public health value.

In addition to daptomycin discussed above, other antibiotics that are known to be inhibited by pulmonary surfactant include without limitation: tobramycin, an aminoglycoside used to treat infections caused by the gram-negative bacterium *Pseudomonas aeruginosa*, a common cause of pneumonia (van't Veen, A. et al., "Influence of pulmonary surfactant on in vitro bactericidal activities of amoxicillin, ceftazidime, and tobramycin", *Antimicrob. Agents Chemother.* 39:329-333 (1995)), and colistin, a cyclic lipopeptide (polymyxin) broadly active against gram-negative bacteria, including *P. aeruginosa*. Schwameis, R. et al., "Effect of Pulmonary surfactant on antimicrobial activity in vitro", *Antimicrob. Agents Chemother.* 57(10):5151-54 (2013).

To address the need for new antimicrobials with novel mechanisms, researchers are investigating a variety of drugs and biologics. One such class of antimicrobial agents includes lysins. Lysins are cell wall peptidoglycan hydrolases, which act as "molecular scissors" to degrade the peptidoglycan meshwork responsible for maintaining cell shape and for withstanding internal osmotic pressure. Degradation of peptidoglycan results in osmotic lysis. However, lysins, typically, have not been effective against Gram-negative bacteria, at least in part, due to the presence of an outer membrane (OM), which is absent in Gram-positive bacteria and which limits access to subjacent peptidoglycan. Modified lysins ("artilysins") have also been developed. These agents, which contain lysins fused to specific α-helical domains with polycationic, amphipathic, and hydrophobic features, are capable of translocating across the OM. However, artilysins typically exhibit low in vivo activity.

Although recent publications have described novel lysins that may be used against Gram-negative bacteria with varying levels of efficacy in vivo, there remains a continuing medical need for additional antibacterials that retain activity in human blood matrices or pulmonary surfactant to target MDR *P. aeruginosa* and other Gram-negative bacteria for the treatment of invasive infections.

SUMMARY

The present application is directed to novel polypeptide constructs comprising lysins and antimicrobial peptides (AMP) that can be used, for example, to treat bacterial infections, including infections caused by Gram-negative bacteria, particularly multi-drug resistant Gram-negative bacteria, including, but not limited to *Pseudomonas aeruginosa*. Newly identified lysins and variants thereof, as well as variants of other lysins are also provided. As described herein, the lysin-AMP polypeptide constructs, newly obtained lysins and variant lysins may be included in pharmaceutical compositions that can be used, for example, to treat bacterial infections. Also provided herein, inter alia, are methods for using the lysin-AMP polypeptide constructs, newly identified lysins and variant lysins for treating bacterial infections, augmenting the efficacy of antibiotics and, generally, inhibiting the growth, reducing the population, or killing Gram-negative bacteria, such as *P. aeruginosa*. Lysin variant polypeptides and polynucleotides encoding the constructs and lysin variants are also provided. In certain embodiments, the lysin-AMP polypeptide constructs, newly obtained lysins and variant lysins may be used to treat bacterial infections in an organ or tissue in which pulmonary surfactant is present, such as, for example, pneumonia (including hospital acquired pneumonia) and cystic fibrosis. In other embodiments, the lysin-AMP polypeptide constructs, newly obtained lysins and variant lysins may be used to treat Gram-negative bacterial infections that are associated with biofilms.

In one aspect, the present disclosure is directed to a lysin-AMP polypeptide construct comprising: (a) a first component comprising the polypeptide sequence of: (i) SEQ ID NO: 118 (GN202); or (ii) a polypeptide having lysin activity and having at least 80% sequence identity with the polypeptide sequence of SEQ ID NO: 118; or (iii) an active fragment of SEQ ID NO: 118 (GN202); and (b) a second component comprising the polypeptide sequence of: (i) at least one antimicrobial peptide (AMP), wherein the at least one AMP comprises the polypeptide sequence of SEQ ID NO: 114 (FIRL).

The present disclosure also provides an isolated polynucleotide comprising a nucleic acid molecule encoding a lysin-antimicrobial peptide (AMP) polypeptide construct, the nucleic acid molecule comprising: (a) a first nucleic acid encoding the polypeptide sequence of: (i) SEQ ID NO: 118 (GN202); or (ii) a polypeptide having lysin activity and having at least 80% sequence identity with the polypeptide sequence of SEQ ID NO: 118; or (iii) an active fragment of SEQ ID NO: 118 (GN202); and (b) a second nucleic acid encoding the polypeptide sequence of: (i) at least one antimicrobial peptide (AMP), wherein the at least one AMP comprises the polypeptide sequence of SEQ ID NO: 114 (FIRL).

In another aspect, the present disclosure is directed to a method of treating a bacterial infection caused by a Gram-negative bacteria, which method comprises: administering to a subject diagnosed with, at risk for, or exhibiting symptoms of a bacterial infection, a pharmaceutical composition comprising a lysin-antimicrobial peptide (AMP) polypeptide construct and a pharmaceutically acceptable carrier, wherein the lysin-AMP polypeptide construct comprises: (a) a first component comprising the polypeptide sequence of: (i) SEQ ID NO: 118 (GN202); or (ii) a polypeptide having lysin activity and having at least 80% sequence identity with the polypeptide sequence of SEQ ID NO: 118; or (iii) an active fragment of SEQ ID NO: 118 (GN202); and (b) a second component comprising the polypeptide sequence of: (i) at least one antimicrobial peptide (AMP), wherein the at least one AMP comprises the polypeptide sequence of SEQ ID NO: 114 (FIRL).

The present disclosure also provides a method of preventing, disrupting or eradicating a Gram-negative bacterial biofilm comprising: administering a lysin-AMP polypeptide construct in an amount effective to kill Gram-negative bacteria in a biofilm to a subject in need thereof, wherein the lysin-AMP polypeptide construct comprises (a) a first component comprising the polypeptide sequence of: (i) SEQ ID NO: 118 (GN202); or (ii) a polypeptide having lysin activity and having at least 80% sequence identity with the polypeptide sequence of SEQ ID NO: 118; or (iii) an active fragment of SEQ ID NO: 118 (GN202); and (b) a second component comprising the polypeptide sequence of: (i) at least one antimicrobial peptide (AMP), wherein the at least one AMP comprises the polypeptide sequence of SEQ ID NO: 114 (FIRL).

In another aspect, the present disclosure is directed to a lysin-AMP polypeptide construct comprising: (a) a first component comprising the polypeptide sequence of: (i) a lysin selected from the group consisting of GN7 (SEQ ID NO: 206), GN11 (SEQ ID NO: 208), GN40 (SEQ ID NO: 210), GN122 (SEQ ID NO: 218), GN328 (SEQ ID NO:

220), GN76 (SEQ ID NO: 203), GN4 (SEQ ID NO: 74), GN146 (SEQ ID NO: 78), GN14 (SEQ ID NO: 124), GN37 (SEQ ID NO: 84) optionally with a single pI-increasing mutation, GN316 (SEQ ID NO: 22) optionally with a single point mutation, lysin Pap2_gp17 (SEQ ID NO: 96), GN329 (SEQ ID NO: 26), GN424 (SEQ ID NO: 56), GN202 (SEQ ID NO: 118), GN425 (SEQ ID NO: 58), GN428 (SEQ ID NO: 60), GN431 (SEQ ID NO: 64), GN486 (SEQ ID NO: 66), GN333 (SEQ ID NO: 28), GN485 (SEQ ID NO: 68), GN123 (SEQ ID NO: 173) and GN121 (SEQ ID NO: 175); or (ii) a polypeptide having lysin activity and having at least 80% sequence identity with the polypeptide sequence of at least one of SEQ ID NOS: 206, 208, 210, 218, 220, 203, 74, 78, 124, 84, 22, 96, 26, 56, 118, 58, 60, 64, 66, 28, 68, 173 or 175; or (iii) an active fragment of the lysin; and (b) a second component comprising the polypeptide sequence of: (i) at least one antimicrobial peptide (AMP) selected from the group consisting of Chp1 (SEQ ID NO: 133), Chp2 (SEQ ID NO: 70), CPAR39 (SEQ ID NO: 135), Chp3 (SEQ ID NO: 137), Chp4 (SEQ ID NO: 102), Chp6 (SEQ ID NO: 106), Chp7 (SEQ ID NO: 139), Chp8 (SEQ ID NO: 141), Chp9 (SEQ ID NO: 143), Chp10 (SEQ ID NO: 145), Chp11 (SEQ ID NO: 147), Chp12 (SEQ ID NO: 149), Gkh1 (SEQ ID NO: 151), Gkh2 (SEQ ID NO: 90), Unp1 (SEQ ID NO: 153), Ecp1 (SEQ ID NO: 155), Ecp2 (SEQ ID NO: 104), Tma1 (SEQ ID NO: 157), Osp1 (SEQ ID NO: 108), Unp2 (SEQ ID NO: 159), Unp3 (SEQ ID NO: 161), Gkh3 (SEQ ID NO: 163), Unp5 (SEQ ID NO: 165), Unp6 (SEQ ID NO: 167), Spi1 (SEQ ID NO: 169), Spi2 (SEQ ID NO: 171), Ecp3 (SEQ ID NO: 177), Ecp4 (SEQ ID NO: 179), ALCES1 (SEQ ID NO: 181), AVQ206 (SEQ ID NO: 183), AVQ244 (SEQ ID NO: 185), CDL907 (SEQ ID NO: 187), AGT915 (SEQ ID NO: 189), HH3930 (SEQ ID NO: 191), Fen7875 (SEQ ID NO: 193), SBR77 (SEQ ID NO: 195), Bdp1 (SEQ ID NO: 197), LVP1 (SEQ ID NO: 199), Lvp2 (SEQ ID NO: 201), an esculentin fragment (SEQ ID NO: 80), RI12 (SEQ ID NO: 88), TI15 (SEQ ID NO: 94), RI18 (SEQ ID NO: 92), FIRL (SEQ ID NO: 114), a fragment of LPS binding protein (SEQ ID NO: 76), RR12whydro (SEQ ID NO: 110), RI18 peptide derivative (SEQ ID NO: 131) and cationic peptide (SEQ ID NO: 120) or (ii) a polypeptide having AMP activity, wherein the polypeptide is at least 80% identical to at least one of SEQ ID NOS: 133, 70, 135, 137, 102, 106, 139, 141, 143, 145, 147, 149, 151, 90, 153, 155, 104, 157, 108, 159, 161, 163, 165, 167, 169, 171, 177, 179, 181, 183, 185, 187, 189, 191, 193, 195, 197, 199, 201, 80, 88, 94, 92, 114, 76, 110, 131 and 120, wherein the lysin-AMP polypeptide construct comprises at least one activity selected from inhibiting *P. aeruginosa* bacterial growth, reducing a *P. aeruginosa* bacterial population and/or killing *P. aeruginosa* in the absence and/or presence of human serum or in the presence of pulmonary surfactant.

In another aspect, the present disclosure is directed to an isolated polypeptide comprising a lysin selected from the group consisting of GN121 (SEQ ID NO: 175), GN217 lysin (SEQ ID NO: 8), GN394 lysin (SEQ ID NO: 48), GN396 lysin (SEQ ID NO: 50), GN408 lysin (SEQ ID NO: 52), GN418 lysin (SEQ ID NO: 54), GN428 (SEQ ID NO: 60), and GN486 (SEQ ID NO: 66) or an active fragment thereof, wherein the lysin or active fragment thereof inhibits *P. aeruginosa* bacterial growth, reduces a *P. aeruginosa* bacterial population and/or kills *P. aeruginosa* in the absence and/or presence of human serum or in the presence of pulmonary surfactant.

In another aspect, the present disclosure is directed to (i) a lysin-AMP polypeptide construct comprising GN75 (SEQ ID NO: 212), GN83 (SEQ ID NO: 216) or a dispersin-like molecule, such as GN80 (SEQ ID NO: 214) or (ii) a polypeptide having lysin activity and having at least 80% sequence identity with the polypeptide sequence of SEQ ID NOS: 212, 216 or 214 (iii) an active fragment thereof, wherein the lysin or active fragment thereof inhibits *P. aeruginosa* bacterial growth, reduces a *P. aeruginosa* bacterial population and/or kills *P. aeruginosa* in the absence and/or presence of human serum or in the presence of pulmonary surfactant.

The present disclosure is also directed to an isolated polynucleotide comprising a nucleic acid molecule encoding a lysin-antimicrobial peptide (AMP) polypeptide construct, the nucleic acid molecule comprising:

(a) a first nucleic acid molecule encoding a first component comprising: (i) a lysin selected from the group consisting of GN7 (SEQ ID NO: 206), GN11 (SEQ ID NO: 208), GN40 (SEQ ID NO: 210), GN122 (SEQ ID NO: 218), GN328 (SEQ ID NO: 220), GN76 (SEQ ID NO: 203), GN4 (SEQ ID NO: 74), GN146 (SEQ ID NO: 78), GN14 (SEQ ID NO: 124), GN37 (SEQ ID NO: 84) optionally with a single pI-increasing mutation, GN316 (SEQ ID NO: 22) optionally with a single point mutation, lysin Pap2_gp17 (SEQ ID NO: 96), GN329 (SEQ ID NO: 26), GN424 (SEQ ID NO: 56), GN202 (SEQ ID NO: 118), GN425 (SEQ ID NO: 58), GN428 (SEQ ID NO: 60), GN431 (SEQ ID NO: 64), GN486 (SEQ ID NO: 66), GN333 (SEQ ID NO: 28), GN485 (SEQ ID NO: 68), GN123 (SEQ ID NO: 173) and GN121 (SEQ ID NO: 175); or (ii) a polypeptide having lysin activity, wherein the polypeptide is at least 80% identical to at least one of SEQ ID NOS: 206, 208, 210, 218, 220, 203, 74, 78, 124, 84, 22, 96, 26, 56, 118, 58, 60, 64, 66, 28, 68, 173 or 175; or (iii) an active fragment of the lysin; and (b) a second nucleic acid molecule encoding a second component comprising: (i) at least one antimicrobial peptide (AMP) selected from the group consisting of Chp1 (SEQ ID NO: 133), Chp2 (SEQ ID NO: 70), CPAR39 (SEQ ID NO: 135), Chp3 (SEQ ID NO: 137), Chp4 (SEQ ID NO: 102), Chp6 (SEQ ID NO: 106), Chp7 (SEQ ID NO: 139), Chp8 (SEQ ID NO: 141), Chp9 (SEQ ID NO: 143), Chp10 (SEQ ID NO: 145), Chp11 (SEQ ID NO: 147), Chp12 (SEQ ID NO: 149), Gkh1 (SEQ ID NO: 151), Gkh2 (SEQ ID NO: 90), Unp1 (SEQ ID NO: 153), Ecp1 (SEQ ID NO: 155), Ecp2 (SEQ ID NO: 104), Tma1 (SEQ ID NO: 157), Osp1 (SEQ ID NO: 108), Unp2 (SEQ ID NO: 159), Unp3 (SEQ ID NO: 161), Gkh3 (SEQ ID NO: 163), Unp5 (SEQ ID NO: 165), Unp6 (SEQ ID NO: 167), Spi1 (SEQ ID NO: 169), Spi2 (SEQ ID NO: 171), Ecp3 (SEQ ID NO: 177), Ecp4 (SEQ ID NO: 179), ALCES1 (SEQ ID NO: 181), AVQ206 (SEQ ID NO: 183), AVQ244 (SEQ ID NO: 185), CDL907 (SEQ ID NO: 187), AGT915 (SEQ ID NO: 189), HH3930 (SEQ ID NO: 191), Fen7875 (SEQ ID NO: 193), SBR77 (SEQ ID NO: 195), Bdp1 (SEQ ID NO: 197), LVP1 (SEQ ID NO: 199), Lvp2 (SEQ ID NO: 201), an esculentin fragment (SEQ ID NO: 80), RI12 (SEQ ID NO: 88), TI15 (SEQ ID NO: 94), RI18 (SEQ ID NO: 92), FIRL (SEQ ID NO: 114), a fragment of LPS binding protein (SEQ ID NO: 76), RR12whydro (SEQ ID NO: 110), RI18 peptide derivative (SEQ ID NO: 131) and cationic peptide (SEQ ID NO: 120) or (ii) a polypeptide having AMP activity, wherein the polypeptide is at least 80% identical to at least one of SEQ ID NOS: 133, 70, 135, 137, 102, 106, 139, 141, 143, 145, 147, 149, 151, 90, 153, 155, 104, 157, 108, 159, 161, 163, 165, 167, 169, 171, 177, 179, 181, 183, 185, 187, 189, 191, 193, 195, 197, 199, 201, 80, 88, 94, 92, 114, 76, 110, 131 and 120, wherein the lysin-AMP polypeptide construct comprises at least one activity selected from inhibiting *P. aeruginosa* bacterial growth, reducing a *P. aeruginosa* bacterial population and/or killing *P. aeruginosa* in the absence and/or presence of human serum or in the presence of pulmonary surfactant.

In yet another aspect, the present disclosure is directed to an isolated polynucleotide sequence comprising a nucleic acid molecule encoding a lysin selected from the group consisting of GN121 (SEQ ID NO: 175), GN217 lysin (SEQ ID NO: 8), GN394 lysin (SEQ ID NO: 48), GN396 lysin (SEQ ID NO: 50), GN408 lysin (SEQ ID NO: 52), GN418 lysin (SEQ ID NO: 54), GN428 (SEQ ID NO: 60), and GN486 (SEQ ID NO: 66) or an active fragment thereof, wherein the lysin or active fragment thereof inhibits *P. aeruginosa* bacterial growth, reduces a *P. aeruginosa* bacterial population and/or kills *P. aeruginosa* in the absence and/or presence of human serum or in the presence of pulmonary surfactant.

In another aspect, the present disclosure is directed to (i) an isolated polynucleotide comprising a nucleic acid molecule encoding a lysin-AMP polypeptide construct comprising GN75 (SEQ ID NO: 212), GN83 (SEQ ID NO: 216) or a dispersin-like molecule, such as GN80 (SEQ ID NO: 214) or (ii) a polypeptide having lysin activity and having at least 80% identity to SEQ ID NOS: 212, 216 or 214 or (iii) an active fragment of SEQ ID NOS: 212, 216 or 214, wherein the lysin-AMP polypeptide construct comprises at least one activity selected from inhibiting *P. aeruginosa* bacterial growth, reducing a *P. aeruginosa* bacterial population and/or killing *P. aeruginosa* in the absence and/or presence of human serum or in the presence of pulmonary surfactant.

In one aspect, the present disclosure is directed to a pharmaceutical composition comprising an isolated lysin and/or a lysin-antimicrobial peptide (AMP) polypeptide construct and a pharmaceutically acceptable carrier, wherein the isolated lysin comprises at least one of: (i) GN7 (SEQ ID NO: 206), GN11 (SEQ ID NO: 208), GN40 (SEQ ID NO: 210), GN122 (SEQ ID NO: 218), GN328 (SEQ ID NO: 220), GN121 (SEQ ID NO: 175), GN123 (SEQ ID NO: 173), GN217 (SEQ ID NO: 8), GN316 variant (SEQ ID NO: 24), GN316 (SEQ ID NO: 22), GN329 (SEQ ID NO: 26), GN333 (SEQ ID NO: 28), GN394 (SEQ ID NO: 48), GN396 (SEQ ID NO: 50), GN408 (SEQ ID NO: 52), GN418 (SEQ ID NO: 54), GN424 (SEQ ID NO: 56), GN425 (SEQ ID NO: 58), GN428 (SEQ ID NO: 60), GN431 (SEQ ID NO: 64), GN486 (SEQ ID NO: 66), GN485 (SEQ ID NO: 68), Lysin PaP2_gp17 (SEQ ID NO: 96), (ii) an active fragment thereof, or (iii) a polypeptide having lysin activity and at least 80% sequence identity with the polypeptide sequence of at least one of SEQ ID NOS: 206, 208, 210, 218, 220, 212, 216, 175, 173, 8, 24, 22, 26, 28, 48, 50, 52, 54, 56, 58, 60, 64, 66, 68, or 96;

wherein the lysin-AMP polypeptide construct comprises: (a) a first component comprising the polypeptide sequence of: (i) a lysin selected from the group consisting of GN7 (SEQ ID NO: 206), GN11 (SEQ ID NO: 208), GN40 (SEQ ID NO: 210), GN122 (SEQ ID NO: 218), GN328 (SEQ ID NO: 220), GN76 (SEQ ID NO: 203), GN4 (SEQ ID NO: 74), GN146 (SEQ ID NO: 78), GN14 (SEQ ID NO: 124), GN37 (SEQ ID NO: 84) optionally with a single pI-increasing mutation, GN316 (SEQ ID NO: 22) optionally with a single point mutation, lysin Pap2_gp17 (SEQ ID NO: 96), GN329 (SEQ ID NO: 26), GN424 (SEQ ID NO: 56), GN202 (SEQ ID NO: 118), GN425 (SEQ ID NO: 58), GN428 (SEQ ID NO: 60), GN431 (SEQ ID NO: 64), GN486 (SEQ ID NO: 66), GN333 (SEQ ID NO: 28), GN485 (SEQ ID NO: 68), GN123 (SEQ ID NO: 173) and GN121 (SEQ ID NO: 175); or (ii) a polypeptide having lysin activity and having at least 80% sequence identity with the polypeptide sequence of at least one of SEQ ID NOS: 206, 208, 210, 218, 220, 203, 74, 78, 124, 84, 22, 96, 26, 56, 118, 58, 60, 64, 66, 28, 68, 173 or 175; or (iii) an active fragment of the lysin; and (b) a second component comprising the polypeptide sequence of: (i) at least one antimicrobial peptide (AMP) selected from the group consisting of Chp1 (SEQ ID NO: 133), Chp2 (SEQ ID NO: 70), CPAR39 (SEQ ID NO: 135), Chp3 (SEQ ID NO: 137), Chp4 (SEQ ID NO: 102), Chp6 (SEQ ID NO: 106), Chp7 (SEQ ID NO: 139), Chp8 (SEQ ID NO: 141), Chp9 (SEQ ID NO: 143), Chp10 (SEQ ID NO: 145), Chp11 (SEQ ID NO: 147), Chp12 (SEQ ID NO: 149), Gkh1 (SEQ ID NO: 151), Gkh2 (SEQ ID NO: 90), Unp1 (SEQ ID NO: 153), Ecp1 (SEQ ID NO: 155), Ecp2 (SEQ ID NO: 104), Tma1 (SEQ ID NO: 157), Osp1 (SEQ ID NO: 108), Unp2 (SEQ ID NO: 159), Unp3 (SEQ ID NO: 161), Gkh3 (SEQ ID NO: 163), Unp5 (SEQ ID NO: 165), Unp6 (SEQ ID NO: 167), Spi1 (SEQ ID NO: 169), Spi2 (SEQ ID NO: 171), Ecp3 (SEQ ID NO: 177), Ecp4 (SEQ ID NO: 179), ALCES1 (SEQ ID NO: 181), AVQ206 (SEQ ID NO: 183), AVQ244 (SEQ ID NO: 185), CDL907 (SEQ ID NO: 187), AGT915 (SEQ ID NO: 189), HH3930 (SEQ ID NO: 191), Fen7875 (SEQ ID NO: 193), SBR77 (SEQ ID NO: 195), Bdp1 (SEQ ID NO: 197), LVP1 (SEQ ID NO: 199), Lvp2 (SEQ ID NO: 201), an esculentin fragment (SEQ ID NO: 80), RI12 (SEQ ID NO: 88), TI15 (SEQ ID NO: 94), RI18 (SEQ ID NO: 92), FIRL (SEQ ID NO: 114), a fragment of LPS binding protein (SEQ ID NO: 76), RR12whydro (SEQ ID NO: 110), RI18 peptide derivative (SEQ ID NO: 131) and cationic peptide (SEQ ID NO: 120) or (ii) a polypeptide having AMP activity, wherein the polypeptide is at least 80% identical to at least one of SEQ ID NOS: 133, 70, 135, 137, 102, 106, 139, 141, 143, 145, 147, 149, 151, 90, 153, 155, 104, 157, 108, 159, 161, 163, 165, 167, 169, 171, 177, 179, 181, 183, 185, 187, 189, 191, 193, 195, 197, 199, 201, 80, 88, 94, 92, 114, 76, 110, 131 and 120, wherein the pharmaceutical composition comprises at least one activity selected from inhibiting *P. aeruginosa* bacterial growth, reducing a *P. aeruginosa* bacterial population and/or killing *P. aeruginosa* in the absence and/or presence of human serum or in the presence of pulmonary surfactant.

In another aspect, the present disclosure is directed to a pharmaceutical composition comprising (i) a lysin-AMP polypeptide construct comprising GN75 (SEQ ID NO: 212), GN83 (SEQ ID NO: 216) or a dispersin-like molecule, such as GN80 (SEQ ID NO: 214) or (ii) a polypeptide having lysin activity and having at least 80% identity to SEQ ID NOS: 212, 216 or 214 or (iii) an active fragment of SEQ ID NOS: 212, 216 or 214, wherein the lysin-AMP polypeptide construct comprises at least one activity selected from inhibiting *P. aeruginosa* bacterial growth, reducing a *P. aeruginosa* bacterial population and/or killing *P. aeruginosa* in the absence and/or presence of human serum or in the presence of pulmonary surfactant.

In yet another aspect, the present disclosure is directed to a method of treating a bacterial infection caused by a Gram-negative bacteria, wherein the Gram-negative bacteria comprises *P. aeruginosa* and optionally one or more additional species of Gram-negative bacteria, which method comprises: administering to a subject diagnosed with, at risk for, or exhibiting symptoms of a bacterial infection, a pharmaceutical composition as described herein. In certain embodiments, the bacterial infection is in an organ or tissue in which pulmonary surfactant is present, such as in the lungs or the airways.

In yet another aspect, the present disclosure is directed to a method of preventing or treating a bacterial infection comprising: co-administering to a subject diagnosed with, at risk for, or exhibiting symptoms of a bacterial infection, a combination of a first effective amount of a pharmaceutical composition as described herein, and a second effective amount of an antibiotic suitable for the treatment of a Gram-negative bacterial infection.

In one aspect, the present disclosure is directed to a method for augmenting the efficacy of an antibiotic suitable for the treatment of a Gram-negative bacterial infection, comprising: co-administering the antibiotic in combination with a composition containing an effective amount of an isolated lysin and/or a lysin-antimicrobial peptide (AMP) polypeptide construct, wherein the isolated lysin comprises at least one of: (i) GN7 (SEQ ID NO: 206), GN11 (SEQ ID NO: 208), GN40 (SEQ ID NO: 210), GN122 (SEQ ID NO: 218), GN328 (SEQ ID NO: 220), GN121 (SEQ ID NO: 175), GN123 (SEQ ID NO: 173), GN217 (SEQ ID NO: 8), GN316 variant (SEQ ID NO: 24), GN316 (SEQ ID NO: 22), GN329 (SEQ ID NO: 26), GN333 (SEQ ID NO: 28), GN394 (SEQ ID NO: 48), GN396 (SEQ ID NO: 50), GN408 (SEQ ID NO: 52), GN418 (SEQ ID NO: 54), GN424 (SEQ ID NO: 56), GN425 (SEQ ID NO:58), GN428 (SEQ ID NO: 60), GN431 (SEQ ID NO: 64), GN486 (SEQ ID NO: 66), GN485 (SEQ ID NO: 68), Lysin PaP2_gp17 (SEQ ID NO: 96), or (ii) an active fragment thereof, or (iii) a polypeptide having lysin activity and at least 80% sequence identity with the polypeptide sequence of at least one of SEQ ID NOS: 206, 208, 210, 218, 220, 175, 173, 8, 24, 22, 26, 28, 48, 50, 52, 54, 56, 58, 60, 64, 66, 68, or 96;

wherein the lysin-AMP polypeptide construct comprises: (a) a first component comprising the polypeptide sequence of: (i) a lysin selected from the group consisting of GN7 (SEQ ID NO: 206), GN11 (SEQ ID NO: 208), GN40 (SEQ ID NO: 210), GN122 (SEQ ID NO: 218), GN328 (SEQ ID NO: 220), GN76 (SEQ ID NO: 203), GN4 (SEQ ID NO: 74), GN146 (SEQ ID NO: 78), GN14 (SEQ ID NO: 124), GN37 (SEQ ID NO: 84) optionally with a single pI-increasing mutation, GN316 (SEQ ID NO: 22) optionally with a single point mutation, lysin Pap2_gp17 (SEQ ID NO: 96), GN329 (SEQ ID NO: 26), GN424 (SEQ ID NO: 56), GN202 (SEQ ID NO: 118), GN425 (SEQ ID NO: 58), GN428 (SEQ ID NO: 60), GN431 (SEQ ID NO: 64), GN486 (SEQ ID NO: 66), GN333 (SEQ ID NO: 28), GN485 (SEQ ID NO: 68), GN123 (SEQ ID NO: 173) and GN121 (SEQ ID NO: 175); or (ii) a polypeptide having lysin activity and having at least 80% sequence identity with the polypeptide sequence of at least one of SEQ ID NOS: 206, 208, 210, 218, 220, 203, 74, 78, 124, 84, 22, 26, 56, 118, 58, 60, 64, 66, 28, 68, 173 or 175; or (iii) an active fragment of the lysin; and (b) a second component comprising the polypeptide sequence of: (i) at least one antimicrobial peptide (AMP) selected from the group consisting of Chp1 (SEQ ID NO: 133), Chp2 (SEQ ID NO: 70), CPAR39 (SEQ ID NO: 135), Chp3 (SEQ ID NO: 137), Chp4 (SEQ ID NO: 102), Chp6 (SEQ ID NO: 106), Chp7 (SEQ ID NO: 139), Chp8 (SEQ ID NO: 141), Chp9 (SEQ ID NO: 143), Chp10 (SEQ ID NO: 145), Chp11 (SEQ ID NO: 147), Chp12 (SEQ ID NO: 149), Gkh1 (SEQ ID NO: 151), Gkh2 (SEQ ID NO: 90), Unp1 (SEQ ID NO: 153), Ecp1 (SEQ ID NO: 155), Ecp2 (SEQ ID NO: 104), Tma1 (SEQ ID NO: 157), Osp1 (SEQ ID NO: 108), Unp2 (SEQ ID NO: 159), Unp3 (SEQ ID NO: 161), Gkh3 (SEQ ID NO: 163), Unp5 (SEQ ID NO: 165), Unp6 (SEQ ID NO: 167), Spi1 (SEQ ID NO: 169), Spi2 (SEQ ID NO: 171), Ecp3 (SEQ ID NO: 177), Ecp4 (SEQ ID NO: 179), ALCES1 (SEQ ID NO: 181), AVQ206 (SEQ ID NO: 183), AVQ244 (SEQ ID NO: 185), CDL907 (SEQ ID NO: 187), AGT915 (SEQ ID NO: 189), HH3930 (SEQ ID NO: 191), Fen7875 (SEQ ID NO: 193), SBR77 (SEQ ID NO: 195), Bdp1 (SEQ ID NO: 197), LVP1 (SEQ ID NO: 199), Lvp2 (SEQ ID NO: 201), an esculentin fragment (SEQ ID NO: 80), RI12 (SEQ ID NO: 88), TI15 (SEQ ID NO: 94), RI18 (SEQ ID NO: 92), FIRL (SEQ ID NO: 114), a fragment of LPS binding protein (SEQ ID NO: 76), RR12whydro (SEQ ID NO: 110), RI18 peptide derivative (SEQ ID NO: 131) and cationic peptide (SEQ ID NO: 120) or (ii) a polypeptide having AMP activity, wherein the polypeptide is at least 80% identical to at least one of SEQ ID NOS: 133, 70, 135, 137, 102, 106, 139, 141, 143, 145, 147, 149, 151, 90, 153, 155, 104, 157, 108, 159, 161, 163, 165, 167, 169, 171, 177, 179, 181, 183, 185, 187, 189, 191, 193, 195, 197, 199, 201, 80, 88, 94, 92, 114, 76, 110, 131 and 120, wherein the composition comprises at least one activity selected from inhibiting *P. aeruginosa* bacterial growth, reducing a *P. aeruginosa* bacterial population and/or killing *P. aeruginosa* in the absence and/or presence of human serum or in the presence of pulmonary surfactant, and wherein administration of the combination is more effective in inhibiting the growth, or reducing the population, or killing the Gram-negative bacteria in the presence or absence or both in the presence and absence of human serum or in the presence of pulmonary surfactant than administration of either the antibiotic or the lysin or lysin-AMP polypeptide construct individually.

In another aspect, the present disclosure is directed to a method for augmenting the efficacy of an antibiotic suitable for the treatment of a Gram-negative bacterial infection, comprising: co-administering the antibiotic in combination with a composition containing an effective amount of (i) a lysin-AMP polypeptide construct comprising GN75 (SEQ ID NO: 212), GN83 (SEQ ID NO: 216) or a dispersin-like molecule, such as GN80 (SEQ ID NO: 214) or (ii) a polypeptide having lysin activity and having at least 80% identity to SEQ ID NOS: 212, 216 or 214 or (iii) an active fragment of SEQ ID NOS: 212, 216 or 214, wherein the lysin-AMP polypeptide construct comprises at least one activity selected from inhibiting *P. aeruginosa* bacterial growth, reducing a *P. aeruginosa* bacterial population and/or killing *P. aeruginosa* in the absence and/or presence of human serum or in the presence of pulmonary surfactant, and wherein administration of the combination is more effective in inhibiting the growth, or reducing the population, or killing the Gram-negative bacteria in the presence or absence or both in the presence and absence of human serum or in the presence of pulmonary surfactant than administration of either the antibiotic or the lysin or lysin-AMP polypeptide construct individually.

In another aspect, the present disclosure is directed to a method of inhibiting the growth, or reducing the population, or killing of at least one species of Gram-negative bacteria, wherein the at least one species of Gram-negative bacteria is *P. aeruginosa* and optionally one or more additional species of Gram-negative bacteria, which method comprises: contacting the bacteria with a composition containing an effective amount an isolated lysin and/or a lysin-antimicrobial peptide (AMP) polypeptide construct, wherein the isolated lysin comprises at least one of: (i) GN7 (SEQ ID NO: 206), GN11 (SEQ ID NO: 208), GN40 (SEQ ID NO: 210), GN122 (SEQ ID NO: 218), GN328 (SEQ ID NO: 220), GN121 (SEQ ID NO: 175), GN123 (SEQ ID NO: 173), GN217 (SEQ ID NO: 8), GN316 variant (SEQ ID NO: 24), GN316 (SEQ ID NO: 22), GN329 (SEQ ID NO: 26), GN333 (SEQ ID NO: 28), GN394 (SEQ ID NO: 48), GN396 (SEQ ID NO: 50), GN408 (SEQ ID NO: 52), GN418 (SEQ ID NO: 54), GN424 (SEQ ID NO: 56), GN425 (SEQ ID NO:58), GN428 (SEQ ID NO: 60), GN431 (SEQ ID NO: 64), GN486 (SEQ ID NO: 66), GN485 (SEQ ID NO: 68), Lysin PaP2_gp17 (SEQ ID NO: 96), or (ii) an active fragment thereof, or (iii) a polypeptide having lysin activity and at least 80% sequence identity with the polypeptide sequence of at least one of SEQ ID NOS: 206, 208, 210, 218, 220, 175, 173, 8, 24, 22, 26, 28, 48, 50, 52, 54, 56, 58, 60, 64, 66, 68, or 96;

wherein the lysin-AMP polypeptide construct comprises: (a) a first component comprising the polypeptide sequence of: (i) a lysin selected from the group consisting of GN7 (SEQ ID NO: 206), GN11 (SEQ ID NO: 208), GN40 (SEQ ID NO: 210), GN122 (SEQ ID NO: 218), GN328 (SEQ ID NO: 220), GN76 (SEQ ID NO: 203), GN4 (SEQ ID NO: 74), GN146 (SEQ ID NO: 78), GN14 (SEQ ID NO: 124), GN37 (SEQ ID NO: 84) optionally with a single pI-increasing mutation, GN316 (SEQ ID NO: 22) optionally with a single point mutation, lysin Pap2_gp17 (SEQ ID NO: 96), GN329 (SEQ ID NO: 26), GN424 (SEQ ID NO: 56), GN202 (SEQ ID NO: 118), GN425 (SEQ ID NO: 58), GN428 (SEQ ID NO: 60), GN431 (SEQ ID NO: 64), GN486 (SEQ ID NO: 66), GN333 (SEQ ID NO: 28), GN485 (SEQ ID NO: 68), GN123 (SEQ ID NO: 173) and GN121 (SEQ ID NO: 175); or (ii) a polypeptide having lysin activity and having at least 80% sequence identity with the polypeptide sequence of at least one of SEQ ID NOS: 206, 208, 210, 218, 220, 203, 74, 78, 124, 84, 22, 96, 26, 56, 118, 58, 60, 64, 66, 28, 68, 173 or 175; or (iii) an active fragment of the lysin; and (b) a second component comprising the polypeptide sequence of: (i) at least one antimicrobial peptide (AMP) selected from the group consisting of Chp1 (SEQ ID NO: 133), Chp2 (SEQ ID NO: 70), CPAR39 (SEQ ID NO: 135), Chp3 (SEQ ID NO: 137), Chp4 (SEQ ID NO: 102), Chp6 (SEQ ID NO: 106), Chp7 (SEQ ID NO: 139), Chp8 (SEQ ID NO: 141), Chp9 (SEQ ID NO: 143), Chp10 (SEQ ID NO: 145), Chp11 (SEQ ID NO: 147), Chp12 (SEQ ID NO: 149), Gkh1 (SEQ ID NO: 151), Gkh2 (SEQ ID NO: 90), Unp1 (SEQ ID NO: 153), Ecp1 (SEQ ID NO: 155), Ecp2 (SEQ ID NO: 104), Tma1 (SEQ ID NO: 157), Osp1 (SEQ ID NO: 108), Unp2 (SEQ ID NO: 159), Unp3 (SEQ ID NO: 161), Gkh3 (SEQ ID NO: 163), Unp5 (SEQ ID NO: 165), Unp6 (SEQ ID NO: 167), Spi1 (SEQ ID NO: 169), Spi2 (SEQ ID NO: 171), Ecp3 (SEQ ID NO: 177), Ecp4 (SEQ ID NO: 179), ALCES1 (SEQ ID NO: 181), AVQ206 (SEQ ID NO: 183), AVQ244 (SEQ ID NO: 185), CDL907 (SEQ ID NO: 187), AGT915 (SEQ ID NO: 189), HH3930 (SEQ ID NO: 191), Fen7875 (SEQ ID NO: 193), SBR77 (SEQ ID NO: 195), Bdp1 (SEQ ID NO: 197), LVP1 (SEQ ID NO: 199), Lvp2 (SEQ ID NO: 201), an esculentin fragment (SEQ ID NO: 80), RI12 (SEQ ID NO: 88), TI15 (SEQ ID NO: 94), RI18 (SEQ ID NO: 92), FIRL (SEQ ID NO: 114), a fragment of LPS binding protein (SEQ ID NO: 76), RR12whydro (SEQ ID NO: 110), RI18 peptide derivative (SEQ ID NO: 131) and cationic peptide (SEQ ID NO: 120) or (ii) a polypeptide having AMP activity, wherein the polypeptide is at least 80% identical to at least one of SEQ ID NOS: 133, 70, 135, 137, 102, 106, 139, 141, 143, 145, 147, 149, 151, 90, 153, 155, 104, 157, 108, 159, 161, 163, 165, 167, 169, 171, 177, 179, 181, 183, 185, 187, 189, 191, 193, 195, 197, 199, 201, 80, 88, 94, 92, 114, 76, 110, 131 and 120, and wherein the composition comprises at least one activity selected from inhibiting P. aeruginosa bacterial growth, reducing a P. aeruginosa bacterial population and/or killing P. aeruginosa in the absence and/or presence of human serum or in the presence of pulmonary surfactant.

In another aspect, the present disclosure is directed to a method of inhibiting the growth, or reducing the population, or killing of at least one species of Gram-negative bacteria, wherein the at least one species of Gram-negative bacteria is P. aeruginosa and optionally one or more additional species of Gram-negative bacteria, which method comprises: contacting the bacteria with a composition containing an effective amount (i) a lysin-AMP polypeptide construct comprising GN75 (SEQ ID NO: 212), GN83 (SEQ ID NO: 216) or a dispersin-like molecule, such as GN80 (SEQ ID NO: 214) or (ii) a polypeptide having lysin activity and having at least 80% identity to SEQ ID NOS: 212, 216 or 214 or (iii) an active fragment of SEQ ID NOS: 212, 216 or 214, wherein the lysin-AMP polypeptide construct comprises at least one activity selected from inhibiting P. aeruginosa bacterial growth, reducing a P. aeruginosa bacterial population and/or killing P. aeruginosa in the absence and/or presence of human serum or in the presence of pulmonary surfactant.

DETAILED DESCRIPTION

Definitions

Figure 1:
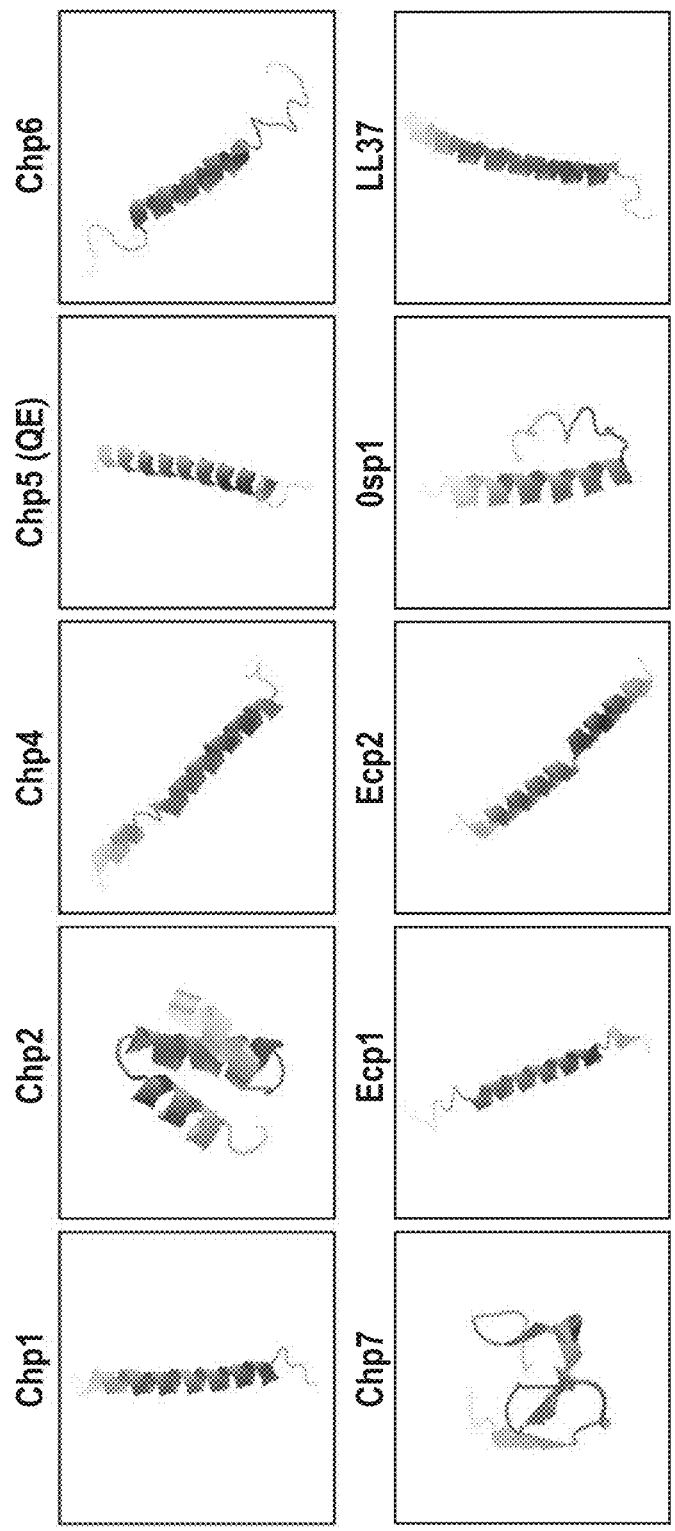
FIG. 1 depicts three-dimensional models predicted by I-Tasser for structures of Chlamydia phage peptide (Chp) family members Chp1, Chp 2, Chp4, Chp5, Chp6, Chp7, Ecp1, Ecp2, and Osp1. The human innate immune effector peptide LL-37 is included for comparison. Alpha helical structures are evident, and the top terminal is generally the N-terminal.

As used herein, the following terms and cognates thereof shall have the following meanings unless the context clearly indicates otherwise:

"Carrier" refers to a solvent, additive, excipient, dispersion medium, solubilizing agent, coating, preservative, isotonic and absorption delaying agent, surfactant, propellant, diluent, vehicle and the like with which an active compound is administered. Such carriers can be sterile liquids, such as water, saline solutions, aqueous dextrose solutions, aqueous glycerol solutions, and oils, including those of petroleum, animal, vegetable or synthetic origin, such as peanut oil, soybean oil, mineral oil, sesame oil, and the like.

"Pharmaceutically acceptable carrier" refers to any and all solvents, additives, excipients, dispersion media, solubilizing agents, coatings, preservatives, isotonic and absorption delaying agents, surfactants, propellants, diluents, vehicles and the like that are physiologically compatible. The carrier (s) must be "acceptable" in the sense of not being deleterious to the subject to be treated in amounts typically used in medicaments. Pharmaceutically acceptable carriers are compatible with the other ingredients of the composition without rendering the composition unsuitable for its intended purpose. Furthermore, pharmaceutically acceptable carriers are suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers or excipients include any of the standard pharmaceutical carriers such as phosphate buffered saline solutions, water, and emulsions such as oil/water emulsions and microemulsions. Suitable pharmaceutical carriers are described, for example, in Remington's Pharmaceutical Sciences by E. W. Martin, 18th Edition. The pharmaceutically acceptable carrier may be a carrier that does not exist in nature.

"Bactericidal" or "bactericidal activity" refers to the property of causing the death of bacteria or capable of killing bacteria to an extent of at least a 3-log 10 (99.9%) or better reduction among an initial population of bacteria over an 18-24 hour period.

"Bacteriostatic" or "bacteriostatic activity" refers to the property of inhibiting bacterial growth, including inhibiting growing bacterial cells, thus causing a 2-log 10 (99%) or better and up to just under a 3-log reduction among an initial population of bacteria over an 18-24 hour period.

"Antibacterial" refers to both bacteriostatic and bactericidal agents.

"Antibiotic" refers to a compound having properties that have a negative effect on bacteria, such as lethality or reduction of growth. An antibiotic can have a negative effect on Gram-positive bacteria, Gram-negative bacteria, or both. By way of example, an antibiotic can affect cell wall peptidoglycan biosynthesis, cell membrane integrity, or DNA or protein synthesis in bacteria. Nonlimiting examples of antibiotics active against Gram-negative bacteria include cephalosporins, such as ceftriaxone-cefotaxime, ceftazidime, cefepime, cefoperazone, and ceftobiprole; fluoroquinolones such as ciprofloxacin and levofloxacin; aminoglycosides such as gentamicin, tobramycin, and amikacin; piperacillin, ticarcillin, imipenem, meropenem, doripenem, broad spectrum penicillins with or without beta-lactamase inhibitors, rifampicin, polymyxin B, and colistin.

"Drug resistant" generally refers to a bacterium that is resistant to the antibacterial activity of a drug. When used in certain ways, drug resistance may specifically refer to antibiotic resistance. In some cases, a bacterium that is generally susceptible to a particular antibiotic can develop resistance to the antibiotic, thereby becoming a drug resistant microbe or strain. A "multi-drug resistant" ("MDR") pathogen is one that has developed resistance to at least two classes of antimicrobial drugs, each used as monotherapy. For example, certain strains of S. aureus have been found to be resistant to several antibiotics including methicillin and/or vancomycin (Antibiotic Resistant Threats in the United States, 2013, U.S. Department of Health and Services, Centers for Disease Control and Prevention). One skilled in the art can readily determine if a bacterium is drug resistant using routine laboratory techniques that determine the susceptibility or resistance of a bacterium to a drug or antibiotic.

"Effective amount" refers to an amount which, when applied or administered in an appropriate frequency or dosing regimen, is sufficient to prevent, reduce, inhibit, or eliminate bacterial growth or bacterial burden or to prevent, reduce, or ameliorate the onset, severity, duration, or progression of the disorder being treated (for example, Gram-negative bacterial pathogen growth or infection), prevent the advancement of the disorder being treated, cause the regression of the disorder being treated, or enhance or improve the prophylactic or therapeutic effect(s) of another therapy, such as antibiotic or bacteriostatic therapy.

"Co-administer" refers to the administration of two agents, such as a lysin or lysin-AMP polypeptide and an antibiotic or any other antibacterial agent, in a sequential manner, as well as administration of these agents in a substantially simultaneous manner, such as in a single mixture/composition or in doses given separately, but nonetheless administered substantially simultaneously to the subject, for example at different times in the same day or 24-hour period. Such co-administration of two agents, such as a lysin or lysin-AMP polypeptide with one or more additional antibacterial agents can be provided as a continuous treatment lasting up to days, weeks, or months. Additionally, depending on the use, the co-administration need not be continuous or coextensive. For example, if the use were as a topical antibacterial agent to treat, e.g., a bacterial ulcer or an infected diabetic ulcer, a lysin or lysin-AMP polypeptide could be administered only initially within 24 hours of an additional antibiotic, and then the additional antibiotic use may continue without further administration of the lysin or lysin-AMP polypeptide.

"Subject" refers to a mammal, a plant, a lower animal, a single cell organism, or a cell culture. For example, the term "subject" is intended to include organisms, e.g., prokaryotes and eukaryotes, which are susceptible to or afflicted with bacterial infections, for example Gram-positive or Gram-negative bacterial infections. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or susceptible to infection by Gram-negative bacteria, whether such infection be systemic, topical or otherwise concentrated or confined to a particular organ or tissue.

"Polypeptide" is used herein interchangeably with the term "peptide" or "protein" and refers to a polymer made from amino acid residues and generally having at least about 30 amino acid residues. The term includes not only polypeptides in isolated form, but also active fragments and derivatives thereof. The term "polypeptide" also encompasses fusion proteins or fusion polypeptides comprising a lysin or AMP as described herein and maintaining, for example a lytic function. Depending on context, a polypeptide can be a naturally occurring polypeptide or a recombinant, engineered, or synthetically produced polypeptide. A particular lysin polypeptide, for example, can be, for example, derived or removed from a native protein by enzymatic or chemical cleavage, or can be prepared using conventional peptide synthesis techniques (e.g., solid phase synthesis) or molecular biology techniques (such as those disclosed in Sambrook, J. et al., Molecular Cloning: A Laboratory Manual, Cold Spring Harbor Press, Cold Spring Harbor, N.Y. (1989)) or can be strategically truncated or segmented yielding active fragments, maintaining, e.g., lytic activity against the same or at least one common target bacterium.

"Fusion polypeptide" refers to an expression product resulting from the fusion of two or more nucleic acid segments, resulting in a fused expression product typically having two or more domains or segments, which typically have different properties or functionality. In a more particular sense, the term "fusion polypeptide" may also refer to a polypeptide or peptide comprising two or more heterologous polypeptides or peptides covalently linked, either directly or via an amino acid or peptide linker. The polypeptides forming the fusion polypeptide are typically linked C-terminus to N-terminus, although they can also be linked C-terminus to C-terminus, N-terminus to N-terminus, or N-terminus to C-terminus. The term "fusion polypeptide" can be used interchangeably with the term "fusion protein." The open-ended expression "a polypeptide comprising" a certain structure includes larger molecules than the recited structure, such as fusion polypeptides.

"Heterologous" refers to nucleotide, peptide, or polypeptide sequences that are not naturally contiguous. For example, in the context of the present disclosure, the term "heterologous" can be used to describe a combination or fusion of two or more peptides and/or polypeptides wherein the fusion peptide or polypeptide is not normally found in nature, such as for example a lysin or active fragment thereof and an antimicrobial peptide, including a cationic and/or a polycationic peptide, an amphipathic peptide, a sushi peptide (Ding et al. Cell Mol Life Sci., 65(7-8): 1202-19 (2008)), a defensin peptide (Ganz, T. Nature Reviews Immunology 3, 710-720 (2003)), a hydrophobic peptide, which may have enhanced lytic activity.

"Active fragment" refers to a portion of a polypeptide that retains one or more functions or biological activities of the isolated polypeptide from which the fragment was taken, for example bactericidal activity against one or more Gram-negative bacteria.

"Amphipathic peptide" refers to a peptide having both hydrophilic and hydrophobic functional groups. In certain embodiments, secondary structure may place hydrophobic and hydrophilic amino acid residues at opposite sides (e.g., inner side vs outer side when the peptide is in a solvent, such as water) of an amphipathic peptide. These peptides may in certain embodiments adopt a helical secondary structure, such as an alpha-helical secondary structure.

"Cationic peptide" refers to a peptide having a high percentage of positively charged amino acid residues. In certain embodiments, a cationic peptide has a pKa-value of 8.0 or greater. The term "cationic peptide" in the context of the present disclosure also encompasses polycationic peptides that are synthetically produced peptides composed of mostly positively charged amino acid residues, such as lysine (Lys) and/or arginine (Arg) residues. The amino acid residues that are not positively charged can be neutrally charged amino acid residues, negatively charged amino acid residues, and/or hydrophobic amino acid residues.

"Hydrophobic group" refers to a chemical group such as an amino acid side chain that has low or no affinity for water molecules but higher affinity for oil molecules. Hydrophobic substances tend to have low or no solubility in water or aqueous phases and are typically apolar but tend to have higher solubility in oil phases. Examples of hydrophobic amino acids include glycine (Gly), alanine (Ala), valine (Val), Leucine (Leu), isoleucine (Ile), proline (Pro), phenylalanine (Phe), methionine (Met), and tryptophan (Trp).

"Augmenting" refers to a degree of activity of an agent, such as antimicrobial activity, that is higher than it would be otherwise. "Augmenting" encompasses additive as well as synergistic (superadditive) effects.

"Synergistic" or "superadditive" refers to a beneficial effect brought about by two substances in combination that exceeds the sum of the effects of the two agents working independently. In certain embodiments the synergistic or superadditive effect significantly, i.e., statistically significantly, exceeds the sum of the effects of the two agents working independently. One or both active ingredients may be employed at a sub-threshold level, i.e., a level at which if the active substance is employed individually produces no or a very limited effect. The effect can be measured by assays such as the checkerboard assay, described here.

"Treatment" refers to any process, action, application, therapy, or the like, wherein a subject, such as a human being, is subjected to medical aid with the object of curing a disorder, eradicating a pathogen, or improving the subject's condition, directly or indirectly. Treatment also refers to reducing incidence, alleviating symptoms, eliminating recurrence, preventing recurrence, preventing incidence, reducing the risk of incidence, improving symptoms, improving prognosis, or combinations thereof. "Treatment" may further encompass reducing the population, growth rate, or virulence of a bacteria in the subject and thereby controlling or reducing a bacterial infection in a subject or bacterial contamination of an organ, tissue, or environment. Thus "treatment" that reduces incidence may, for example, be effective to inhibit growth of at least one Gram-negative bacterium in a particular milieu, whether it be a subject or an environment. On the other hand, "treatment" of an already established infection refers to inhibiting the growth, reducing the population, killing, including eradicating, a Gram-negative bacteria responsible for an infection or contamination.

"Preventing" refers to the prevention of the incidence, recurrence, spread, onset or establishment of a disorder such as a bacterial infection. It is not intended that the present disclosure be limited to complete prevention or to prevention of establishment of an infection. In some embodiments, the onset is delayed, or the severity of a subsequently contracted disease or the chance of contracting the disease is reduced, and such constitute examples of prevention.

"Contracted diseases" refers to diseases manifesting with clinical or subclinical symptoms, such as the detection of fever, sepsis, or bacteremia, as well as diseases that may be detected by growth of a bacterial pathogen (e.g., in culture) when symptoms associated with such pathology are not yet manifest.

The term "derivative" in the context of a peptide or polypeptide or active fragments thereof is intended to encompass, for example, a polypeptide modified to contain one or more chemical moieties other than an amino acid that do not substantially adversely impact or destroy the polypeptide's activity (e.g., lytic activity). The chemical moiety can be linked covalently to the peptide, e.g., via an amino terminal amino acid residue, a carboxy terminal amino acid residue, or at an internal amino acid residue. Such modifications may be natural or non-natural. In certain embodiments, a non-natural modification may include the addition of a protective or capping group on a reactive moiety, addition of a detectable label, such as antibody and/or fluorescent label, addition or modification of glycosylation, or addition of a bulking group such as PEG (pegylation) and other changes known to those skilled in the art. In certain embodiments, the non-natural modification may be a capping modification, such as N-terminal acetylations and C-terminal amidations. Exemplary protective groups that may be added to lysin polypeptides or AMPs include, but are not limited to, t-Boc and Fmoc. Commonly used fluorescent label proteins such as, but not limited to, green fluorescent protein (GFP), red fluorescent protein (RFP), cyan fluorescent protein (CFP), yellow fluorescent protein (YFP), and mCherry, are compact proteins that can be bound covalently or noncovalently to a polypeptide or fused to a polypeptide without interfering with normal functions of cellular proteins. In certain embodiments, a polynucleotide encoding a fluorescent protein may be inserted upstream or downstream of the lysin or AMP polynucleotide sequence. This will produce a fusion protein (e.g., Lysin Polypeptide::GFP) that does not interfere with cellular function or function of a polypeptide to which it is attached. Polyethylene glycol (PEG) conjugation to proteins has been used as a method for extending the circulating half-life of many pharmaceutical proteins. Thus, in the context of polypeptide derivatives, such as lysin polypeptide derivatives, the term "derivative" encompasses polypeptides, such as lysin polypeptides, chemically modified by covalent attachment of one or more PEG molecules. It is anticipated that lysin polypeptides, such as pegylated lysins, will exhibit prolonged circulation half-life compared to the unpegylated polypeptides, while retaining biological and therapeutic activity.

"Percent amino acid sequence identity" refers to the percentage of amino acid residues in a candidate sequence that are identical with the amino acid residues in the reference polypeptide sequence, such as a lysin polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for example, using publicly available software such as BLAST or software available commercially, for example from DNASTAR. Two or more polypeptide sequences can be anywhere from 0-100% identical, or any integer value there between. In the context of the present disclosure, two polypeptides are "substantially identical" when at least 80% of the amino acid residues (such as at least about 85%, at least about 90%, at least about 92.5%, at least about 95%, at least about 98%, or at least about 99%) are identical. The term "percent (%) amino acid sequence identity" as described herein applies to peptides as well. Thus, the term "substantially identical" will encompass mutated, truncated, fused, or otherwise sequence-modified variants of isolated lysin polypeptides and peptides and AMPs described herein, and active fragments thereof, as well as polypeptides with substantial sequence identity (e.g., at least 80%, at least 85%, at least 90%, at least 92.5%, at least 95%, at least 98%, or at least 99% identity as measured for example by one or more methods referenced above) as compared to the reference (wild type or other intact) polypeptide.

As used herein, two amino acid sequences are "substantially homologous" when at least about 80% of the amino acid residues (such as at least about 85%, at least about 90%, at least about 92.5%, at least about 95%, at least about 98%, or at least about 99%) are identical, or represent conservative substitutions. The sequences of the polypeptides of the present disclosure are substantially homologous when one or more, such as up to 10%, up to 15%, or up to 20% of the amino acids of the polypeptide, such as the lysin, AMP, and/or fusion polypeptides described herein, are substituted with a similar or conservative amino acid substitution, and wherein the resulting peptides have at least one activity (e.g., antibacterial effect) and/or bacterial specificities of the reference polypeptide, such as the lysin, AMP, and/or fusion polypeptides described herein.

As used herein, a "conservative amino acid substitution" is one in which the amino acid residue is replaced with an amino acid residue having a side chain with a similar charge. Families of amino acid residues having side chains with similar charges have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine).

"Inhalable composition" refers to pharmaceutical compositions of the present disclosure that are formulated for direct delivery to the respiratory tract during or in conjunction with routine or assisted respiration (e.g., by intratracheobronchial, pulmonary, and/or nasal administration), including, but not limited to, atomized, nebulized, dry powder, and/or aerosolized formulations.

"Biofilm" refers to bacteria that attach to surfaces and aggregate in a hydrated polymeric matrix that may be comprised of bacterial- and/or host-derived components. A biofilm is an aggregate of microorganisms in which cells adhere to each other on a biotic or abiotic surface. These adherent cells are frequently embedded within a matrix comprised of, but not limited to, extracellular polymeric substance (EPS). Biofilm EPS, which is also referred to as slime (although not everything described as slime is a biofilm) or plaque, is a polymeric conglomeration generally composed of extracellular DNA, proteins, and polysaccharides.

"Preventing biofilm formation" refers to the prevention of the incidence, recurrence, spread, onset or establishment of a biofilm. It is not intended that the present disclosure be limited to complete prevention or to prevention of establishment of biofilm. In some embodiments, the onset of a biofilm is delayed, or the establishment of a biofilm is reduced or the chance of formation of a new biofilm is reduced, and such constitute examples of prevention of a biofilm. Further, prevention of a biofilm may be due to any mechanism including 1) effectively killing planktonic bacteria; 2) killing "persister" bacterial cells in suspensions, i.e., bacteria that are metabolically inactive, tolerant of antibiotics, and highly associated with biofilm formation; and/or 3) preventing "aggregation", i.e., the ability of bacteria to attach to one another via proteins or polysaccharides.

"Eradication" in reference to a biofilm includes 1) effectively killing bacteria in a biofilm including persister bacterial cells in the biofilm and, optionally 2) effectively destroying and/or damaging the biofilm matrix.

"Disruption" in reference to a biofilm refers to a mechanism that falls between prevention and eradication. A biofilm, which is disrupted, may be "opened", or otherwise damaged, thus permitting, e.g., an antibiotic, to more readily penetrate the biofilm and kill the bacteria.

"Suitable" in the context of an antibiotic being suitable for use against certain bacteria refers to an antibiotic that was found to be effective against those bacteria even if resistance subsequently developed.

"Outer Membrane" or "OM" refers to a feature of Gram-negative bacteria. The outer membrane is comprised of a lipid bilayer with an internal leaflet of phospholipids and an external amphiphilic leaflet largely consisting of lipopolysaccharide (LPS). The LPS has three main sections: a hexa-acylated glucosamine-based phospholipid called lipid A, a polysaccharide core and an extended, external polysaccharide chain called O-antigen. The OM presents a non-fluid continuum stabilized by three major interactions, including: i) the avid binding of LPS molecules to each other, especially if cations are present to neutralize phosphate groups; ii) the tight packing of largely saturated acyl chains; and iii) hydrophobic stacking of the lipid A moiety. The resulting structure is a barrier for both hydrophobic and hydrophilic molecules. Below the OM, the peptidoglycan forms a thin layer that is very sensitive to hydrolytic cleavage—unlike the peptidoglycan of Gram-negative bacteria which is 30-100 nanometers (nm) thick and consists of up to 40 layers, the peptidoglycan of Gram-negative bacteria is only 2-3 nm thick and consists of only 1-3 layers.

Polypeptides

Lysins, Variant Lysins, Active Fragments Thereof or Derivatives

The present disclosure is directed to isolated polypeptides comprising lysins, variant lysins, active fragments thereof or derivatives. In some embodiments, the isolated polypeptides comprising the lysins, variant lysins, active fragments thereof or derivatives are combined with antimicrobial peptides ("AMPs") to form a lysin-AMP polypeptide construct, such as the lysin-AMP polypeptide construct of SEQ ID NO: 44 (GN370), wherein the lysin-AMP polypeptide construct has lysin activity. As used herein "lysin activity" encompasses the ability of a lysin to kill bacteria (e.g., *P. aeruginosa*), reduce the population of bacteria or inhibit bacterial growth (e.g., by penetrating the outer membrane of a Gram-negative bacteria), optionally in the presence of human serum or pulmonary surfactant. Lysin activity also encompasses the ability to remove or reduce a biofilm and/or the ability to reduce the minimum inhibitory concentration (MIC) of an antibiotic, optionally in the presence of human serum or pulmonary surfactant.

In some embodiments, the present isolated polypeptides comprising lysins, variant lysins, active fragments thereof or derivatives thereof are capable of penetrating the outer membrane of Gram-negative bacteria. Without being limited by theory, after penetration of the outer membrane, the present isolated polypeptides comprising lysins, variant lysins, active fragments thereof or derivatives thereof can degrade peptidoglycan, a major structural component of the bacterial cell wall, resulting in e.g., cell lysis or non-lethal damage that inhibits bacterial growth. In some embodiments, the present isolated polypeptides comprising lysins, variant lysins, active fragments thereof or derivatives disclosed herein contain positively charged (and amphipathic) N- and/or C-terminal α-helical domains that facilitate binding to the anionic outer membrane of a Gram-negative bacteria to effect translocation into the sub-adjacent peptidoglycan.

The ability of a lysin to penetrate an outer membrane of a Gram-negative bacteria may be assessed by any method known in the art, such as described in WO 2017/049233, which is herein incorporated by reference in its entirety. For example, the lysin may be incubated with Gram-negative bacteria and a hydrophobic compound. Most Gram-negative bacteria are strongly resistant to hydrophobic compounds, due to the presence of the outer membrane and, thus, do not allow the uptake of hydrophobic agents such as 1-N-phenylnaphthylamine (NPN), crystal violet, or 8-anilino-1-naphthalenesulfonic acid (ANS). NPN, for example, fluoresces strongly under hydrophobic conditions and weakly under aqueous conditions. Accordingly, NPN fluorescence can be used as a measurement of the outer membrane permeability.

More particularly, the ability of a lysin to penetrate an outer wall may be assessed by incubating, e.g., NPN with a Gram-negative bacteria, e.g., *P. aeruginosa* strain PA01, in the presence of the lysin to be tested for activity. A higher induction of fluorescence in comparison to the fluorescence emitted in the absence of a lysin (negative control) indicates outer membrane penetration. In addition, fluorescence induction can be compared to that of established permeabilizing agents, such as EDTA (ethylene diamine tetraacetate) or an antibiotic such as an antibiotic of last resort used in the treatment of *P. aeruginosa*, i.e., Polymyxin B (PMB) to assess the level of outer membrane permeability.

In some embodiments, the present isolated polypeptides comprising lysins, variant lysins, active fragments thereof or derivatives exhibit lysin activity in the presence and/or absence of human serum. Suitable methods for assessing the activity of a lysin in human serum are known in the art and described in the examples. Briefly, a MIC value (i.e., the minimum concentration of peptide sufficient to suppress at least 80% of the bacterial growth compared to control) may be determined for a lysin and compared to, e.g., a parent lysin or compound inactive in human serum, e.g., T4 phage lysozyme or artilysin GN126 (SEQ ID NO: 224, pI 9.8). T4 phage lysozyme is commercially available, e.g. from Sigma-Aldrich, Inc. GN126 (SEQ ID NO: 224) corresponds to Art-175, which is described in the literature and is obtained by fusing AMP SMAP-29 to GN lysin KZ144. See Briers et al. 2014, *Antimicrob, Agents Chemother.* 58:3774-3784, which is herein incorporated by reference in its entirety. Lysin GN65 (SEQ ID NO: 22, pI9.9) and dispersin B, which is an enzyme that degrades biofilm (GN81, SEQ ID NO: 226, pI 6.0), may also be used as controls.

More particularly, MIC values for a lysin may be determined against e.g., the laboratory *P. aeruginosa* strain PA01, in e.g., Mueller-Hinton broth, Mueller-Hinton broth supplemented with human serum, CAA as described herein, which includes physiological salt concentrations, and CAA supplemented with human serum. The use of PA01 enables testing in the presence of elevated serum concentrations since unlike most clinical isolates, PA01 is insensitive to the antibacterial activity of human blood matrices.

In some embodiments, the present isolated polypeptides comprising lysins, variant lysins, active fragments thereof or derivatives are capable of reducing a biofilm. Methods for assessing the Minimal Biofilm Eradicating Concentration (MBEC) of a lysin or AMP may be determined using a variation of the broth microdilution MIC method with modifications (See Ceri et al. 1999. *J. Clin. Microbial.* 37:1771-1776, which is herein incorporated by reference in its entirety and Schuch et al., 2017, *Antimicrob. Agents Chemother.* 61, pages 1-18, which is herein incorporated by reference in its entirety.) In this method, fresh colonies of e.g., a *P. aeruginosa* strain, such as ATCC 17647, are suspended in medium, e.g., phosphate buffer solution (PBS) diluted e.g., 1:100 in TSBg (tryptic soy broth supplemented with 0.2% glucose), added as e.g., 0.15 ml aliquots, to a Calgary Biofilm Device (96-well plate with a lid bearing 96 polycarbonate pegs; Innovotech Inc.) and incubated e.g., 24 hours at 37° C. Biofilms are then washed and treated with e.g., a 2-fold dilution series of the lysin in TSBg at e.g., 37° C. for 24 hours. After treatment, wells are washed, air-dried at e.g., 37° C. and stained with e.g., 0.05% crystal violet for 10 minutes. After staining, the biofilms are destained in e.g., 33% acetic acid and the OD600 of e.g., extracted crystal violet is determined. The MBEC of each sample is the minimum lysin concentration required to remove >95% of the biofilm biomass assessed by crystal violet quantitation.

In some embodiments, the present isolated polypeptides comprising lysins, variant lysins, active fragments thereof or derivatives reduce the minimum inhibitory concentration (MIC) of an antibiotic needed to inhibit bacteria in the presence and/or absence of human serum or in the presence of pulmonary surfactant. Any known method to assess MIC may be used. In some embodiments, a checkerboard assay is used to determine the effect of a lysin on antibiotic concentration. The checkerboard assay is based on a modification of the CLSI method for MIC determination by broth microdilution (See Clinical and Laboratory Standards Institute (CLSI), CLSI. 2015. Methods for Dilution Antimicrobial Susceptibility Tests for Bacteria That Grow Aerobically; Approved Standard-10th Edition. Clinical and Laboratory Standards Institute, Wayne, Pa., which is herein incorporated by reference in its entirety and Ceri et al. 1999. *J. Clin. Microbiol.* 37: 1771-1776, which is also herein incorporated by reference in its entirety).

Checkerboards are constructed by first preparing columns of e.g., a 96-well polypropylene microtiter plate, wherein each well has the same amount of antibiotic diluted 2-fold along the horizontal axis. In a separate plate, comparable rows are prepared in which each well has the same amount of lysin diluted e.g., 2-fold along the vertical axis. The lysin and antibiotic dilutions are then combined, so that each column has a constant amount of antibiotic and doubling dilutions of lysin, while each row has a constant amount of lysin and doubling dilutions of antibiotic. Each well thus has a unique combination of lysin and antibiotic. Bacteria are added to the drug combinations at concentrations of $1 \times 10^5$ CFU/ml in CAA, for example, with or without human serum or pulmonary surfactant (such as SURVANTA®). The MIC of each drug, alone and in combination, is then recorded after e.g., 16 hours at 37° C. in ambient air. Summation fractional inhibitory concentrations (ΣFICs) are calculated for each drug and the minimum ΣFIC value (ΣFICmin) is used to determine the effect of the lysin/antibiotic combination.

In some embodiments, the present lysins and lysin-AMP polypeptide constructs are able to synergize with antibiotics, such as imipenem and meropenem, and drive the resensitization of Gram-negative bacteria including MDR organisms, such as carbapenem-resistant *P. aeruginosa*. Such resensitization may be determined by combining the present lysins or lysin-AMP polypeptide constructs with an antibiotic in a checkerboard assay as described herein. Antibiotic-resistant bacteria, such as carbapenem-resistant *P. aeruginosa*, are added to the lysin or lysin-AMP polypeptide construct combination. Generally resensitization occurs in synergistic combinations in which the antibiotic MIC values fall below established breakpoints, e.g., a MIC value of ≤2 for antibiotic sensitive bacteria, a MIC value of 4 for intermediately sensitive bacteria and a MIC value of ≥8 for antibiotic resistant bacteria, e.g. carbapenem-resistant isolates. See Clinical and Laboratory Standards Institute (CLSI), CLSI. 2019. M100 Performance Standards for Antimicrobial Susceptibility Testing; 29th Edition. Clinical and Laboratory Standards Institute, Wayne, Pa., which is herein incorporated by reference in its entirety.

In some embodiments, the present isolated polypeptides comprising lysins, variant lysins, active fragments thereof or derivatives show low toxicity against erythrocytes. Any methodology known in the art may be used to assess the potential for hemolytic activity of the present isolated polypeptides comprising lysins, variant lysins, active fragments thereof or derivatives including the method described in the Examples.

Examples of suitable lysins of the present disclosure, particularly for use with the lysin-AMP polypeptide constructs described herein, include the GN316 lysin obtained from *Klebsiella* phage 0507-KN2-1 (NCBI Reference Sequence: YP_008531963.1, SEQ ID NO: 22), Lysin PaP2_gp17 obtained from *Pseudomonas* phage (NCBI Reference Sequence: YP_024745.1, SEQ ID NO: 96), GN333 obtained from *Delftia* sp. (NCBI Reference Sequence: WP_016064791.1, SEQ ID NO: 28), GN424 obtained from *Burkholderia pseudomultivorans* (NCBI Reference Sequence: WP_060250996.1, SEQ ID NO: 56), GN425 lysin obtained from *Pseudomonas flexibilis* (NCBI Reference Sequence: WP_039605935.1, SEQ ID NO: 58), GN428 obtained from *Escherichia* virus CBA120 (NCBI Reference Sequence: YP_004957781.1, SEQ ID NO: 60), GN431 obtained from *Dickeya* phage phiD3 (NCBI Reference Sequence: AIM51349.1, SEQ ID NO: 64), GN485 obtained from *Erwinia* sp. Leaf5 (NCBI Reference Sequence: WP_056233282.1, SEQ ID NO: 68) and GN123 obtained from *Pseudomonas* phage PhiPA3 (NCBI Reference Sequence: YP_009217242.1, SEQ ID NO: 173).

The above described lysins were identified by bioinformatics techniques. Although some of the identified sequences had been annotated as putative peptidoglycan binding proteins, no function had been previously definitively attributed to polypeptides having these sequences. The inventors have surprisingly recognized that the above-identified sequences are suitable for use as antibacterial agents, in particular, against Gram-negative bacteria as described in the examples.

Additional examples of suitable lysins of the present disclosure, particularly those for use with the present lysin-AMP polypeptide constructs, include the GN7 (SEQ ID NO: 206, pI 5.6), obtained from a marine metagenome, NCBI Accession Number ECF75988.1; GN11 (SEQ ID NO: 208, pI 7.3), obtained from *Pseudomonas putida* KT2440, NCBI Accession Number NP_744418.1; GN40 (SEQ ID NO: 210, pI 5.1), obtained from *Pseudomonas putida* strain PA14H7, NCBI Accession Number NZ_KN639176.1; GN122 (SEQ ID NO: 218, pI 5.4), obtained from *Pseudomonas putida* strain PA14H7, NCBI Accession Number NZ_KN639176.1; GN328 (SEQ ID NO: 220, pI 7.9), obtained from *Pseudomonas protegens*, NCBI Accession Number NC_021237.1; GN76 (SEQ ID NO: 203), obtained from *Acinetobacter* phage vB_AbaP_CEB1, NCBI Reference Sequence ALC76575.1, GenBank: ALC76575.1; GN4 (SEQ ID NO: 74), obtained from *Pseudomonas* phage PAJU2, NCBI Reference Sequence YP 002284361.1; GN14 (SEQ ID NO: 124), obtained from *Pseudomonas* phage Lull, NCBI Reference Sequence YP 006382555.1; and GN37 (SEQ ID NO: 84), obtained from *Micavibrio aeruginosavorus*, NCBI Reference Sequence WP_014102102.1. GN4, GN14 and GN37 are also disclosed in WO 2017/049233, which is herein incorporated by reference in its entirety.

Suitable lysin-AMP constructs of the present disclosure include GN75 (SEQ ID NO: 212, pI 10.1) and GN83 (SEQ ID NO: 216, pI 9.4). GN75 comprises the AMP OBPgpLYS (SEQ ID NO: 88 of U.S. Pat. No. 8,846,865) fused to the N-terminus of lysin GN13 described in WO 2019/118632. GN83 comprises the AMP OBPgpLYS (SEQ ID NO: 88 of U.S. Pat. No. 8,846,865) fused to the N-terminus of lysin GN4 described in WO 2019/118632. U.S. Pat. No. 8,846,865 and WO 2019/118632 are each incorporated herein by reference in its entirety.

In some embodiments, a suitable polypeptide of the disclosure is a dispersin B-like molecule, such as an enzyme, which is capable of disrupting biofilm formation. Suitable dispersin B-like molecules include GN80 (SEQ ID NO: 214, pI 4.6).

In some embodiments, the present isolated polypeptides comprise a lysin variant, e.g., a lysin containing one or more insertions, deletions and/or amino acid substitutions in comparison to a reference lysin polypeptide, e.g., a naturally occurring lysin or a parent lysin, which itself is a variant lysin. In some embodiments, an isolated polypeptide sequence comprising a variant lysin, active fragment thereof or derivative has at least 80%, such as at least 85%, such as at least 90%, such as at least 95%, such as at least 98% or such as at least 99% sequence identity with the reference lysin (e.g., GN202 (SEQ ID NO: 118) and/or active fragment thereof described herein.

The lysin variants of the present disclosure typically retain one or more functional or biological activities of a reference lysin. In some embodiments, the modification improves the antibacterial activity of the lysin. Typically, the lysin variant has improved in vitro antibacterial activity (e.g., in buffer and/or media) in comparison to the reference lysin. In other embodiments, the lysin variant has improved in vivo antibacterial activity (e.g., in an animal infection model). In some embodiments, the modification improves the antibacterial activity of the lysin in the absence and/or presence of human serum. In some embodiments, the modification improves the antibacterial activity of the lysin in the presence of pulmonary surfactant.

Suitable variant lysins, particularly those for use in the present lysin-AMP polypeptide constructs, include the GN146 lysin (SEQ ID NO: 78), GN156 lysin (SEQ ID NO: 126), the GN202 lysin (SEQ ID NO: 118) and GN121 lysin (SEQ ID NO: 175). Each of the foregoing lysins is also disclosed in U.S. Provisional Application No. 62/597,577, which was filed on Dec. 12, 2017 and U.S. Provisional Application No. 62/721,969, which was filed on 23 Aug. 2018, and is herein incorporated by reference in its entirety. The lysins described in U.S. Provisional Application No. 62/721,969, typically, are modified in reference to their naturally occurring counterpart to enhance the activity of the lysin in serum, e.g., by introducing amino acid substitutions and/or introducing amino acid fragments from larger antimicrobial peptides. For example, the amino acid sequence GPRRPRRPGRRAPV (residues 1-14 of SEQ ID NO: 126) described by Daniels and Scepartz, 2007, *J. Am. Chem. Soc.* 129:14578-14579, which is herein incorporated by reference in its entirety, is introduced, for example, at the N terminus of GN4 (SEQ ID NO: 74), to generate GN156 (SEQ ID NO: 126), a non-naturally occurring lysin-AMP polypeptide construct.

In some embodiments, the variant lysins are obtained by modifying a reference lysin to include a modification resulting in a change in the overall isoelectric point (pI) of the lysin, i.e., the pH at which a molecule has a net neutral charge by, for example, incorporating a single pI-increasing mutation, such as a single point mutation, into a reference lysin. Suitable reference lysin polypeptides include a lysin selected from the group consisting of GN7 (SEQ ID NO: 206), GN11 (SEQ ID NO: 208), GN40 (SEQ ID NO: 210), GN122 (SEQ ID NO: 218), GN328 (SEQ ID NO: 220), GN76 (SEQ ID NO: 203), GN4 (SEQ ID NO: 74), GN146 (SEQ ID NO: 78), GN14 (SEQ ID NO: 124), GN37 (SEQ ID NO: 84) GN316 (SEQ ID NO: 22) lysin Pap2_gp17 (SEQ ID NO: 96), GN329 (SEQ ID NO: 26), GN424 (SEQ ID NO: 56), GN202 (SEQ ID NO: 118), GN425 (SEQ ID NO: 58), GN428 (SEQ ID NO: 60), GN431 (SEQ ID NO: 64), GN486 (SEQ ID NO: 66), GN333 (SEQ ID NO: 28) GN485 (SEQ ID NO: 68) GN123 (SEQ ID NO: 173) and GN121 (SEQ ID NO: 175). In certain embodiments, the lysin variant has at least 80%, at least 85%, at least 90%, at least 95%, at least 98%, or at least 99% sequence identity to a reference lysin polypeptide having the amino acid sequence selected from the group consisting of SEQ ID NO: 206, 208, 210, 218, 220, 203, 74, 78, 124, 84, 22, 96, 26, 56, 118, 58, 60, 64, 66, 28, 68, 173 and 175. In some embodiments, the lysin variant has at least 80%, such as at least 85%, such as at least 90%, such as at least 95%, such as at least 98%, such as at least 99% sequence identity to a reference lysin polypeptide having the amino acid sequence of GN202 (SEQ ID NO: 118).

For example, the GN37 lysin (SEQ ID NO: 84) can be modified to increase the pI by introducing the amino acid substitution, R79H, to generate the GN217 lysin (SEQ ID NO: 8). In this embodiment, the potency of the GN217 lysin (SEQ ID NO: 8) is increased in both the presence and absence of human serum in comparison to that of the reference lysin, GN37 (SEQ ID NO: 84), as described in the examples.

Other examples of suitable pI modifying mutations include introducing an amino acid substitution such as K218D, K228D, R85H and/or K22D into a reference lysin, such as GN316 (SEQ ID NO: 22), to generate e.g., the GN394 lysin (SEQ ID NO: 48), the GN396 lysin (SEQ ID NO: 50), the GN408 lysin (SEQ ID NO: 52) and the GN418 lysin (SEQ ID NO: 54), respectively. In some embodiments, the foregoing pI modifying mutations improve the antibacterial activity of the lysin in the absence and/or presence of human serum as exemplified herein.

In some embodiments, the lysin variants of the present disclosure are typically designed to retain an α-helix domain, the presence or absence of which can be readily determined using various software programs, such as Jpred4 (compio.dundee.ac.uk/jpred), Helical Wheel (hael.net/helical.htm), HeliQuest (zhanglab.ccmb.med.umich.edu/I-TASSER/) and PEP-FOLD 3 (bioserv.rpbs.univ-paris-diderot.fr/services/PEP-FOLD3).

In some embodiments, the α-helix domain is located at the C terminus of a lysin. In other embodiments, the α-helix domain is located at the N-terminus of a lysin. More typically, the α-helix domain is located at the C terminus. The α-helix domain of the lysins of the present disclosure varies in size between about 20 and 40 amino acids, more typically between about 15 and 33 amino acid residues. For example, the GN14 α-helix domain, which is located at the N terminus, contains 15 amino acids (residues 66 to 80 of SEQ ID NO: 124). The GN37 α-helix domain, which is located at the C terminus, contains 14 amino acids (residues 113 to 126 of SEQ ID NO: 84). The GN4 α-helix domain, which is also located at the C terminus, contains 25 amino acids (residues 116 to 140 of SEQ ID NO: 74).

In some embodiments, the variant lysins, active fragments thereof or derivatives thereof disclosed herein are modified to include a purification tag, e.g. GSHHHHHG (SEQ ID NO: 100). The purification tag may be inserted anywhere within the lysin, such as the GN202 (SEQ ID NO: 118) lysin, typically between the first and second amino acids. For example, the purification tag may be inserted between the first methionine and first alanine at the N terminus of the GN316 lysin (SEQ ID NO: 22) to obtain a variant GN316 lysin (SEQ ID NO: 24) without adversely affecting the activity. In other embodiments, the purification tag may be inserted between the first methionine and the first glycine at the N terminus of the GN156 lysin (SEQ ID NO: 126) to obtain the variant GN486 (SEQ ID NO: 66).

Lysin variants may be formed by any method known in the art and as described in WO 2017/049233, which is herein incorporated by reference in its entirety, e.g., by modifying any of the lysins, active fragments thereof and derivatives described herein through site-directed mutagenesis or via mutations in hosts that produce the present lysins which retain one or more of the biological functions as described herein. The present lysin variants may be truncated, chimeric, shuffled or "natural," and may be in combination as described, for example, in U.S. Pat. No. 5,604,109, which is incorporated herein in its entirety by reference.

For example, one of skill in the art can reasonably make and test substitutions or replacements to, e.g., the α-helix domain or regions outside of the α-helix domain. Sequence comparisons to the Genbank database can be made with e.g., a full amino acid sequence as described herein, for instance, to identify amino acids for substitution.

Mutations can be made in the amino acid sequences, or in the nucleic acid sequences encoding the polypeptides and lysins, active fragments or derivatives, such that a particular codon is changed to a codon which codes for a different amino acid, an amino acid is substituted for another amino acid, or one or more amino acids are deleted.

Such a mutation is generally made by making the fewest nucleotide changes possible. A substitution mutation of this sort can be made to change an amino acid in the resulting protein in a non-conservative manner (for example, by changing the codon from an amino acid belonging to a grouping of amino acids having a particular size or characteristic to an amino acid belonging to another grouping) or in a conservative manner (for example, by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present disclosure should be considered to include sequences containing conservative changes which do not significantly alter the activity or binding characteristics of the resulting protein. Thus, one of skill in the art, based on a review of the sequence of lysins provided herein and on their knowledge and the public information available for other lysin polypeptides, can make amino acid changes or substitutions in the lysin polypeptide sequence. Amino acid changes can be made to replace or substitute one or more, one or a few, one or several, one to five, one to ten, or such other number of amino acids in the sequence of the lysin(s) provided herein to generate mutants or variants thereof. Such mutants or variants thereof may be predicted for function or tested for function or capability for antibacterial activity as described herein against, e.g., *P. aeruginosa*, and/or for having comparable activity to the lysin(s) as described and particularly provided herein. Thus, changes made to the sequence of lysin, and mutants or variants described herein can be tested using the assays and methods known in the art and described herein. One of skill in the art, on the basis of the domain structure of the lysin(s) hereof can predict one or more, one or several amino acids suitable for substitution or replacement and/or one or more amino acids which are not suitable for substitution or replacement, including reasonable conservative or non-conservative substitutions.

In some embodiments, the present isolated polypeptides comprise active fragments of lysins or derivatives. The term "active fragment" refers to a portion of a full-length lysin, which retains one or more biological activities of the reference lysin. Thus, as used herein, an active fragment of a lysin or variant lysin inhibits the growth, or reduces the population, or kills e.g., *P. aeruginosa* and and/or other Gram-negative bacteria as described herein in the absence or presence of, or in both the absence and presence of, human serum or in the presence of pulmonary surfactant. Suitable active fragments of lysins include, but are not limited, to those described in WO2017/049233, which is herein incorporated by reference in its entirety. The active lysin fragments typically retain an α-helix domain. Examples of active lysin fragments include those of the GN4 lysin (SEQ ID NO: 74) set forth in SEQ ID NOS: 127-129.

In some embodiments, the lysin, variant lysin, active fragment thereof or derivative included in the present isolated polypeptides is selected from the group consisting of GN217 (SEQ ID NO: 8), GN316 variant (SEQ ID NO: 24) GN316 (SEQ ID NO: 22), GN329 (SEQ ID NO: 26), GN333 (SEQ ID NO: 28), GN394 (SEQ ID NO: 48), GN396 (SEQ ID NO: 50), GN408 (SEQ ID NO: 52), (SEQ ID NO: 54), GN424 (SEQ ID NO: 56), GN425 (SEQ ID NO: 58), GN428 (SEQ ID NO: 60), GN431 (SEQ ID NO: 64), GN486 (SEQ ID NO: 66), GN485 (SEQ ID NO: 68), Lysin PaP2_gp17 (SEQ ID NO: 96), GN123 (SEQ ID NO: 173), GN121 (SEQ ID NO: 175), and GN202 (SEQ ID NO: 118) or an active fragment thereof, wherein the lysin or active fragment thereof inhibits the growth, or reduces the population, or kills *P. aeruginosa* and/or at least one other species of Gram-negative bacteria as described herein in the absence or presence of, or in both the absence and presence of, human serum or in the presence of pulmonary surfactant. In some embodiments, the lysin or active fragment thereof contains at least one amino acid substitution, deletion, or insertion relative to at least one of SEQ ID NOS: 8, 24, 22, 26, 28, 48, 50, 52, 54, 56, 58, 60, 64, 66, 68, 96, 118, 173 or 175. In certain embodiments, the at least one amino acid substitution is a conservative amino acid substitution.

In some embodiments, the lysin of the disclosure is selected from the group consisting of GN329 (SEQ ID NO: 26), GN333 (SEQ ID NO: 28), GN424 (SEQ ID NO: 56), GN425 (SEQ ID NO: 58), GN428 (SEQ ID NO: 60), GN431 (SEQ ID NO: 64), GN485 (SEQ ID NO: 68) and Lysin PaP2_gp17 (SEQ ID NO: 96) or an active fragment thereof, wherein the lysin or active fragment thereof inhibits the growth, or reduces the population, or kills *P. aeruginosa* and/or at least one other species of Gram-negative bacteria species of Gram-negative bacteria as described herein in the absence or presence of, or in both the absence and presence of, human serum or in the presence of pulmonary surfactant. In some embodiments, the lysin, derivative or active fragment thereof contains at least one substitution, deletion, or insertion modification relative to SEQ ID NOS: 26, 28, 56, 58, 60, 64, 68 or 96. In certain embodiments, the at least one amino acid substitution is a conservative amino acid substitution.

In some embodiments, the isolated polypeptide sequence comprises a lysin selected from the group consisting of GN217 lysin (SEQ ID NO: 8), GN394 lysin (SEQ ID NO: 48), GN396 lysin (SEQ ID NO: 50), GN408 lysin (SEQ ID NO: 52), GN418 lysin (SEQ ID NO: 54) and GN486 (SEQ ID NO: 66) or an active fragment thereof, wherein the lysin or active fragment thereof inhibits the growth, or reduces the population, or kills *P. aeruginosa* and/or at least one other species of Gram-negative bacteria as described herein in the absence or presence of, or in both the absence and presence of, human serum or in the presence of pulmonary surfactant. In some embodiments, the lysin or active fragment thereof contains at least one substitution, deletion, or insertion modification relative to SEQ ID NOS: 8, 48, 50, 52, 54, or 66. In certain embodiments, the at least one amino acid substitution is a conservative amino acid substitution.

Anti-Microbial Peptides

In some embodiments, the polypeptides of the present disclosure comprise lysin-Anti-Microbial Peptide (AMP) polypeptide constructs. The lysin-AMP polypeptide constructs comprise an isolated polypeptide comprising a lysin, variant lysin, active fragment thereof or derivative as described herein and an antimicrobial peptide or fragment thereof. The term "antimicrobial peptide" (AMP) as used herein refers to a member of a wide range of short (generally 3 to 50 amino acid residues in length) gene-encoded peptides, typically antibiotics, that can be found in virtually every organism. The term encompasses helical peptides, β-sheet peptides and those that display largely disordered random coil structures. AMPs include defensins, cathelicidins, sushi peptides, cationic peptides, polycationic peptides, amphipathic peptides, hydrophobic peptides and/or AMP-like peptides, e.g., amurin peptides as described herein. Fragments of AMPs, AMP variants and derivatives of AMPs are also encompassed by this term.

The term "AMP activity" as used herein encompasses the ability of an AMP or fragment thereof to kill bacteria, reduce the population of bacteria or inhibit bacterial growth e.g., by penetrating the outer membrane of a Gram-negative bacteria, e.g., in the presence and/or absence of human serum or pulmonary surfactant. Typically, translocation of the AMPs is driven by a primary electrostatic interaction with the lipopolysaccharide portion of the outer membrane followed by cation displacement, membrane disorganization and transient openings, and in some cases, internalization of the AMP.

AMP activity also encompasses the ability of an AMP or fragment thereof to reduce the minimum inhibitory concentration (MIC) of an antibiotic in the presence and/or absence of human serum or pulmonary surfactant. Suitable methods for assessing the ability of the present AMPs and fragments thereof to penetrate the outer membrane of Gram-negative bacteria and determining a reduction in the MIC of an antibiotic in the presence and absence of serum or pulmonary surfactant are known in the art and include those methods described above for the present lysins, derivatives and active fragments thereof.

In some embodiments, the present AMPs are variant AMPs having at least 50%, at least 60%, at least 75%, at least 80%, such as at least 85%, such as at least 90%, such as at least 95%, such as at least 98% or such as at least 99% sequence identity with any of the AMPs described herein (e.g., SEQ ID NO: 114), wherein the variant AMP thereof retains an AMP activity.

In some embodiments, the present AMPs comprise a helical domain, such as an α-helical domain. In some embodiments, the α-helical domain spans most of the molecule. See, for example, Chp1 and Chp4 of FIG. 1. In other embodiments, the α-helix domain is either interrupted (e.g., Chp2) or truncated (e.g., Chp6 and Osp1). The α-helix domain of the present AMPs, such as the Chps, described herein vary in size from between about 3 to 32 amino acids, more typically between about 10 and 25 amino acid residues. Generally, the helical domains are required for activity and typically must be retained when fused to a C- or N-terminus of a lysin.

Typically, helical peptides display amphipathic characteristics and contain a substantial proportion (e.g. 50%) of hydrophobic residues, frequently appearing in repeated patterns. Upon formation of an α-helical structure, the hydrophilic residues typically end up on the same side of the helix, thereby resulting in a conformation-dependent amphiphilicity. Frequently, these peptides are unstructured in an aqueous environment, but adopt a helical conformation upon encountering lipid membranes. Peptides belonging to this group typically display an overall positive charge ranging from +2 to +11 and usually kill microbes, such as Gram-negative bacteria, by creating membrane defects, leading to a loss of gradients in electrolytes, signal substances and other factors.

In some embodiments, the present AMPs are "AMP-like" peptides including phage lytic agents referred to herein as *Chlamydia* phage (Chp) peptides or amurin peptides. The amurin peptides of the present disclosure are distinguishable from amurins. As is known in the art, amurins, which are obtained from ssDNA or ssRNA phages (Microviridae and Leviviridae, respectively), are integral membrane proteins with a putative domain structure including an internal LS dipeptide immediately preceded by a stretch of 10-17 hydrophobic residues. Examples of amurins include the protein E amurin from phage <pX174 (Family Microviridae, genus *Microvints*), which is a 91 amino acid membrane protein that causes lysis by inhibiting the bacterial translocase Mra Y, an essential membrane-embedded enzyme that catalyzes the formation of the murein precursor, Lipid I; the A2 capsid protein of phage Q~ (Family Leviviridae, genus *Allolevivirus*), which is a 420-amino acid structural protein that causes lysis by interfering with MurA activity and dysregulating the process of peptidoglycan biosynthesis; the protein L amurin of phage MS2 (Family Levivirdae, genus *Levivirus*), which is a 75 amino acid integral membrane protein that causes lysis using a mechanism that requires the activity of host chaperone DnaJ. Typically, amurins cannot be purified and are not suitable for use as antibacterial therapeutics.

In contrast to amurins, the amurin peptides of the present disclosure are small cationic peptides with predicted α-helical structures similar to those of AMPs obtained from the innate immune systems of a variety of vertebrates (but with amino acid sequences dissimilar to AMPs). Amurin peptides are primarily found in Chlamydiamicroviruses and, to a lesser extent, in other related members of the subfamily Gokushovirinae. The amurin peptides from a variety of Microviridae phages exhibit 30-100% identity to each other and have no homology with other peptides. Unlike the amurins of Microviridae, which have cytoplasmic targets in the cell wall biosynthetic apparatus, and, accordingly, may not be easily accessed by externally applied proteins, the present amurin peptides can be used in purified form to exert bactericidal activity "from without."

Suitable amurin peptides for use in the present lysin-AMP polypeptide constructs include those described in U.S. Provisional Application No. 62/650,235, which was filed on 29 Mar. 2018, and which is herein incorporated by reference in its entirety. In some embodiments, amurin peptides such as the chlamydia phage (Chp)-derived lytic agents may be used. Such Chp-derived lytic agents include Chp1 (NCBI Reference Sequence: NP_044319.1, SEQ ID NO: 133), Chp2 (NCBI Reference Sequence: NP_0546521.1, SEQ ID NO: 70), CPAR39 (NCBI Reference Sequence: NP_063898.1, SEQ ID NO: 135), Chp3 (NCBI Reference Sequence: YP_022484.1, SEQ ID NO: 137), Chp4 (NCBI Reference Sequence: YP_338243.1, SEQ ID NO: 102), Chp6 (NCBI Reference Sequence: NP_510878.1, SEQ ID NO: 106), Chp7 (NCBI Reference Sequence: CRH73061.1, SEQ ID NO: 139), Chp8 (NCBI Reference Sequence: CRH64983.1, SEQ ID NO: 141), Chp9 (NCBI Reference Sequence: CRH84960.1, SEQ ID NO: 143), Chp10 (NCBI Reference Sequence: CRH73061.1, SEQ ID NO: 145), Chp11 (NCBI Reference Sequence: CRH59954.1, SEQ ID NO: 147) and Chp12 (NCBI Reference Sequence: CRH59965.1, SEQ ID NO: 149).

Additional, suitable Chp family members include Gkh1 (NCBI Reference Sequence: YP_008798245.1, SEQ ID NO: 151), Gkh2 (NCBI Reference Sequence: YP_009160382.1, SEQ ID NO: 90), Unp1 (NCBI Reference Sequence: CDL66944.1, SEQ ID NO: 153), Ecp1 (NCBI Reference Sequence: WP_100756432.1, SEQ ID NO: 155), Ecp2 (NCBI Reference Sequence: OAC1404.1, SEQ ID NO: 104), Tma1 (NCBI Reference Sequence: SHG47122.1, SEQ ID NO: 157), Osp1 (NCBI Reference Sequence: SFP13761.1, SEQ ID NO: 108), Unp2 (NCBI Reference Sequence: CDL65918.1, SEQ ID NO: 159), Unp3 (NCBI Reference Sequence: CDL65808.1, SEQ ID NO: 161), Gkh3 (NCBI Reference Sequence: AGT39941.1, SEQ ID NO: 163), Unp5 (NCBI Reference Sequence: AGT39924.1, SEQ ID NO: 165), Unp6 (NCBI Reference Sequence: AGT39915.1, SEQ ID NO: 167), Spi1 (NCBI Reference Sequence: NP_598337.1, SEQ ID NO: 169) and Spi2 (NCBI Reference Sequence: NP_598336.1, SEQ ID NO: 171), Ecp3 (NCBI Reference Sequence: WP_105269219.1, SEQ ID NO: 177), Ecp4 (NCBI Reference Sequence: WP_105466506.1, SEQ ID NO: 179), ALCES1 (NCBI Reference Sequence: AXB22573.1, SEQ ID NO: 181), AVQ206 (NCBI Reference Sequence: AVQ10236.1, SEQ ID NO: 183), AVQ244 (NCBI Reference Sequence: AVQ10244.1, SEQ ID NO: 185), CDL907 (NCBI Reference Sequence: CDL65907.1, SEQ ID NO: 187), AGT915 (NCBI Reference Sequence: AGT39915.1, SEQ ID NO: 189), HH3930 (NCBI Reference Sequence: CCH66548.1, SEQ ID NO: 191), Fen7875 (NCBI Reference Sequence: YP_009160399.1, SEQ ID NO: 193), SBR77 (NCBI Reference Sequence: AOT25441, SEQ ID NO: 195), Bdp1 NCBI Reference Sequence: NP_073546.1, SEQ ID NO: 197), LVP1 (NCBI Reference Sequence: NP_042306.1, SEQ ID NO: 199) and Lvp2 (NCBI Reference Sequence: NP_085469.1, SEQ ID NO: 201).

More typically, the AMPs are selected from one or more of the following amurin peptides, Chp2 (SEQ ID NO: 70), Gkh2 (SEQ ID NO: 90), Chp4 (SEQ ID NO: 102), Ecp2 (SEQ ID NO: 104), Chp6 (SEQ ID NO: 106) and Osp1 (SEQ ID NO: 108).

In some embodiments, the amurin peptides are modified to produce variant amurin peptides. As described herein, amurin peptides typically comprise a helical domain such as an α-helical domain. Typically, the variant amurin peptides retain the α-helical domain. The retention of the α-helical domain in any variant amurin peptide is typically accurately identified using various software programs, such as Jpred4 (compio.dundee.ac.uk/jpred), Helical Wheel (hael.net/helical.htm), HeliQuest (zhanglab.ccmb.med.umich.edu/I-TASSER/) and PEP-FOLD 3 (bioserv.rpbs.univ-paris-diderot.fr/services/PEP-FOLD3). In some embodiments, the amurin peptide variants are modified by converting (=) charged residues, such as arginine and lysine, within the amurin peptide to a "D" amino acid form. The utility of conversions to the D form is described in the literature, e.g., Manabe et al., *Sci. Rep.*, 2017, pages 1-10, which is herein incorporated by reference in its entirety. Variant AMPs may be prepared according to any method known in the art including as described herein above for the lysins, variants, active fragments thereof and derivatives.

In some embodiments, the AMPs for use in the lysin-AMP polypeptide constructs of the present disclosure include a fragment of a larger AMP that retains antibacterial activity. For example, in certain embodiments, the AMP portion of the lysin-AMP polypeptide construct may include a fragment of porcine myeloid antimicrobial peptide-36 ("PMAP-36", SEQ ID NO: 204) that retains antibacterial activity. PMAP-36 is a cathelicidin-related AMP deduced from porcine myeloid cDNA with an amphipathic α-helical conformation at the N-terminus. Accordingly, suitable PMAP-36 fragments are typically selected from the N-terminus to obtain fragments retaining antibacterial activity. In some embodiments, the PMAP-36 fragment of the present disclosure includes the hydrophobic amino acid (Trp) at position 23. In other embodiments, the random coil C-terminal is omitted from the PMAP-36 fragment to reduce or eliminate hemolysis that may be caused by PMAP-36. Further features of PMAP-36 fragments are described, for example, in Lyu et al., *Scientific Reports,* 2016, 6, pages 1-12, which is herein incorporated by reference in its entirety.

Particularly desirable PMAP-36 fragments include RI12 (SEQ ID NO: 88), RI18 (SEQ ID NO: 92) and TI15 (SEQ ID NO: 94). Other suitable AMP fragments include those from Esculentin (NCBI Reference Sequence: P40843.1), such as the fragment set forth in SEQ ID NO: 80 and anti-lipopolysaccharide factor isoform 2 (NCBI Reference Sequence: AFU61125.1), such as the fragment set forth in SEQ ID NO: 76.

In some embodiments, the AMPs of the present disclosure include synthetic peptides. In some embodiments, the synthetic peptide reduces the minimum inhibitory concentration (MIC) of an antibiotic, which prevents visible growth of bacterium, but does not itself exhibit antibacterial activity. A particularly desirable synthetic peptide for use with the lysin-AMP polypeptide constructs of the present disclosure includes the FIRL peptidomimetic (SEQ ID NO: 114). Without being limited by theory, FIRL (SEQ ID NO: 114), which is related to a sequence of a protein involved in outer membrane protein biogenesis, BamD, appears to increase the permeability of the outer membrane to antibiotics. Further information regarding the proposed mechanism is found, for example, in Mori et al., *Journal of Antimicrobial Chemotherapy,* 2012, 67: 2173-2181, which is herein incorporated by reference in its entirety.

Other synthetic peptides useful for sensitizing gram-negative bacteria to antibiotics, which may be incorporated into the lysin-AMP polypeptide construct of the present disclosure includes the cationic peptide KFFKFFKFFK (SEQ ID NO: 120) described in Vaara and Porro, *Antimicrobial agents and Chemotherapy,* 1996, 1801-1805, which is herein incorporated by reference in its entirety.

In some embodiments, the synthetic peptides are resistant to salts and serum inactivation as described, for example, in Monhanram et al., *Biopolymers,* 2016, 106: 345-346, which is herein incorporated by reference in its entirety. Particularly desirable salt and serum-resistant synthetic peptides include RR12Whydro (SEQ ID NO: 110) and RI18 peptide derivative (SEQ ID NO: 131).

Structure Stabilizing Components

In some embodiments, the lysin-AMP polypeptide constructs of the present disclosure further include at least one structure stabilizing component to maintain at least a portion of the structure of the first and/or second component in the construct, e.g., the lysin and/or AMP, substantially the same as in the unconjugated lysin and/or AMP. In some embodiments, the stabilizing structure is a linker. Typically, the at least one structure stabilizing component, such as a linker enables the lysin and AMP to substantially preserve the three-dimensional structure of the first and/or second protein moieties, such that at least one biological activity of the lysin and/or AMP is retained.

Suitable linkers for connecting two polypeptides are known in the art. In certain embodiments, the linker is a peptide, such as a peptide comprising glycine and serine residues. Specific suitable linkers include, but are not limited to, a TAGGTAGG linker (SEQ ID NO: 72), an IGEM linker GGSGSGSGSGSP (BBa_K1485002) (SEQ ID NO: 82). GGGSGGGGSGGGS (BBA_K1486037, (SEQ ID NO: 86), or a linker as described in Briers et al., mBio, 2014, 5:e01379-14, which is herein incorporated by reference in its entirety, i.e., AGAGAGAGAGAGAGAGAS (SEQ ID NO: 122).

In some embodiments, the structure stabilizing component is a peptide moiety, e.g., an RPP or PP moiety. Such peptide moieties may be included in the present lysin-AMP polypeptide constructs to assist in maintaining the structure of the lysin and/or AMP protein moieties. For example, the RPP or PP amino acid may be inserted at the C terminus or N terminus of a linker, e.g. at the N terminus of the BBA_K1486037 linker (RPPGGGSGGGGSGGGS residues 126 to 141 of SEQ ID NO: 12), at the N terminus of the BBA_K1486037 linker (PPGGGSGGGGSGGGS, residues 144-158 of SEQ ID NO: 16), at the N terminus of the TAGGTAGG linker (SEQ ID NO: 72), such as depicted in residues 137-144 of SEQ ID NO: 18) or at the C terminus of the BBA_K1486037 linker (GGGSGGGGSGGGSPP, residues 135-149 of SEQ ID NO: 20).

In other embodiments, the peptides MIDR (SEQ ID NO: 112) and/or NPTH (SEQ ID NO: 116) are included in the construct to assist in maintaining the structure of the lysin and/or AMP protein moieties. For example, in some embodiments an AMP structure, such as FIRL (SEQ ID NO: 114), is maintained by the addition of MIDR (SEQ ID NO: 112) and/or NPTH (SEQ ID NO: 116) such as depicted at residues 1-12 of SEQ ID NO: 46 (MIDRFIRLNPTH) and residues 1-12 of SEQ ID NO: 44.

Examples of Lysin-AMP Polypeptide Constructs

In some embodiments, the lysin-AMP construct comprises: (a) a first component comprising (i) at least one lysin selected from the group consisting of GN7 (SEQ ID NO: 206), GN11 (SEQ ID NO: 208), GN40 (SEQ ID NO: 210), GN122 (SEQ ID NO: 218), GN328 (SEQ ID NO: 220), GN76 (SEQ ID NO: 203), GN4 (SEQ ID NO: 74), GN146 (SEQ ID NO: 78), GN14 (SEQ ID NO: 124), GN37 (SEQ ID NO: 84) optionally with a single pI-increasing mutation, GN316 (SEQ ID NO: 22) optionally with a single point mutation, lysin Pap2_gp17 (SEQ ID NO: 96), GN329 (SEQ ID NO: 26), GN424 (SEQ ID NO: 56), GN202 (SEQ ID NO: 118), GN425 (SEQ ID NO: 58), GN428 (SEQ ID NO: 60), GN431 (SEQ ID NO: 64), GN486 (SEQ ID NO: 66), GN333 (SEQ ID NO: 28), GN485 (SEQ ID NO: 68), GN123 (SEQ ID NO: 173) and GN121 (SEQ ID NO: 175), typically GN202 (SEQ ID NO: 118) or (ii) a polypeptide having lysin activity and having at least 80%, such as at least such as at least 85%, such as at least 90%, such as at least 95%, such as at least 98%, or such as at least 99% sequence identity with the polypeptide sequence of any of SEQ ID NOs: 206, 208, 210, 218, 220, 203, 74, 78, 124, 84, 22, 96, 26, 56, 118, 58, 60, 64, 66, 28, 68, 173 or 175, typically SEQ ID NO: 118; or (iii) an active fragment of the lysin, said fragment including single point mutations and/or single pI increasing mutations if any; (b) a second component comprising (i) at least one antimicrobial peptide (AMP) selected from the group consisting of Chp1 (SEQ ID NO: 133), Chp2 (SEQ ID NO: 70), CPAR39 (SEQ ID NO: 135), Chp3 (SEQ ID NO: 137), Chp4 (SEQ ID NO: 102), Chp6 (SEQ ID NO: 106), Chp7 (SEQ ID NO: 139), Chp8 (SEQ ID NO: 141), Chp9 (SEQ ID NO: 143), Chp10 (SEQ ID NO: 145), Chp11 (SEQ ID NO: 147), Chp12 (SEQ ID NO: 149), Gkh1 (SEQ ID NO: 151), Gkh2 (SEQ ID NO: 90), Unp1 (SEQ ID NO: 153), Ecp1 (SEQ ID NO: 155), Ecp2 (SEQ ID NO: 104), Tma1 (SEQ ID NO: 157), Osp1 (SEQ ID NO: 108), Unp2 (SEQ ID NO: 159), Unp3 (SEQ ID NO: 161), Gkh3 (SEQ ID NO: 163), Unp5 (SEQ ID NO: 165), Unp6 (SEQ ID NO: 167), Spi1 (SEQ ID NO: 169), Spi2 (SEQ ID NO: 171), Ecp3 (SEQ ID NO: 177), Ecp4 (SEQ ID NO: 179), ALCES1 (SEQ ID NO: 181), AVQ206 (SEQ ID NO: 183), AVQ244 (SEQ ID NO: 185), CDL907 (SEQ ID NO: 187), AGT915 (SEQ ID NO: 189), HH3930 (SEQ ID NO: 191), Fen7875 (SEQ ID NO: 193), SBR77 (SEQ ID NO: 195), Bdp1 (SEQ ID NO: 197), LVP1 (SEQ ID NO: 199), Lvp2 (SEQ ID NO: 201), an esculentin fragment (SEQ ID NO: 80), RI12 (SEQ ID NO: 88), TI15 (SEQ ID NO: 94), RI18 (SEQ ID NO: 92), FIRL (SEQ ID NO: 114), a fragment of LPS binding protein (SEQ ID NO: 76), RR12whydro (SEQ ID NO: 110), RI18 peptide derivative (SEQ ID NO: 131) and cationic peptide (SEQ ID NO: 120), typically FIRL (SEQ ID NO: 114) or (ii) a polypeptide having AMP activity, wherein the polypeptide is at least 75%, such as at least 80% identical to at least one of SEQ ID NOS: 133, 70, 135, 137, 102, 106, 139, 141, 143, 145, 147, 149, 151, 90, 153, 155, 104, 157, 108, 159, 161, 163, 165, 167, 169, 171, 177, 179, 181, 183, 185, 187, 189, 191, 193, 195, 197, 199, 201, 80, 88, 94, 92, 114, 76, 110, 131 and 120, typically 114.

Typically, any of the AMP variants sharing at least 75%, such as at least 80% identity or more with the disclosed AMPs (e.g., SEQ ID NO: 114) or fragments thereof retain its alpha-helical structure and any residues associated with activity. For example, as noted above, fragments of PMAP-36 (SEQ ID NO: 204) typically retain the hydrophobic amino acid (Trp) at position 23.

In some embodiments, GN37 (SEQ ID NO: 84) comprises a single pI-increasing mutation, wherein the GN37 (SEQ ID NO: 84) with the single pI-increasing mutation is GN217 (SEQ ID NO: 8). In some embodiments, GN316 (SEQ ID NO: 22) comprises a single point mutation, wherein the GN37 (SEQ ID NO: 84) with the single point mutation is GN396 (SEQ ID NO: 50), GN408 (SEQ ID NO: 52), GN418 (SEQ ID NO: 54) and/or GN394 (SEQ ID NO: 48).

In some embodiments, the construct further comprises at least one structure stabilizing component. In some embodiments, the at least one structure stabilizing component is a peptide linker, such as a peptide comprising glycine and serine residues. In certain embodiments, the peptide linker is selected from the group consisting of TAGGTAGG (SEQ ID NO: 72), IGEM (BBa_K1485002) (SEQ ID NO: 82), PPTAGGTAGG (SEQ ID NO: 98), IGEM+PP (residues 44-58 of SEQ ID NO: 16) and AGAGAGAGAGAGAGA-GAS (SEQ ID NO: 122).

In some embodiments, the lysin-AMP polypeptide construct is selected from at least one of GN168 lysin (SEQ ID NO: 2), GN176 lysin (SEQ ID NO: 4), GN178 lysin (SEQ ID NO: 6), GN218 lysin (SEQ ID NO: 10), GN223 lysin (SEQ ID NO: 12), GN239 lysin (SEQ ID NO: 14), GN243 lysin (SEQ ID NO: 16), GN280 lysin (SEQ ID NO: 18), GN281 lysin (SEQ ID NO: 20), GN349 lysin (SEQ ID NO:

30), GN351 lysin (SEQ ID NO: 32), GN352 lysin (SEQ ID NO: 34), GN353 lysin (SEQ ID NO: 36), GN357 lysin (SEQ ID NO: 38), GN359 lysin (SEQ ID NO: 40), GN369 lysin (SEQ ID NO: 42), GN370 lysin (SEQ ID NO: 44), GN371 lysin (SEQ ID NO: 46) or GN93 lysin (SEQ ID NO: 62), typically GN370 lysin (SEQ ID NO: 44) or a polypeptide having lysin activity and having at least 80%, such as at least such as at least 85%, such as at least 90%, such as at least 95%, such as at least 98%, or such as at least 99% sequence identity with the polypeptide sequence of at least one of SEQ ID NOs: 2, 4, 6, 10, 12, 14, 16, 18, 20, 30, 32, 34, 36, 38, 40, 42, 44, 46, or 62, typically SEQ ID NO: 44.

More particularly, in some embodiments, the lysin-AMP polypeptide construct comprises a Chp2 amurin polypeptide (SEQ ID NO: 70) and a TAGGTAGG linker (SEQ ID NO: 72) introduced N-terminally to the GN4 lysin (SEQ ID NO: 74) to generate the GN168 lysin (SEQ ID NO: 2) or a polypeptide having lysin activity and having at least 80%, such as at least 85%, such as at least 90%, such as at least 95%, such as at least 98%, or such as at least 99% sequence identity to SEQ ID NO: 2.

In some embodiments, the encoded lysin-AMP polypeptide construct comprises a fragment of LPS binding protein (SEQ ID NO: 76) and a TAGGTAGG linker (SEQ ID NO: 72) introduced N-terminally to the GN146 lysin (SEQ ID NO: 78) to generate the GN176 lysin (SEQ ID NO: 4) or a polypeptide having lysin activity and having at least 80%, such as at least 85%, such as at least 90%, such as at least 95%, such as at least 98%, or such as at least 99% sequence identity to SEQ ID NO: 4.

In some embodiments, the lysin-AMP polypeptide construct comprises an Esculentin fragment (SEQ ID NO: 80) and an IGEM linker (SEQ ID NO: 82) introduced N-terminally to the GN146 lysin (SEQ ID NO: 78) to generate the GN178 lysin (SEQ ID NO: 6) or a polypeptide having at least 80%, such as at least 85%, such as at least 90%, such as at least 95%, such as at least 98%, or such as at least 99% sequence identity to SEQ ID NO: 6.

In some embodiments, the encoded lysin-AMP polypeptide construct comprises an IGEM linker (SEQ ID NO: 86) and an RI12 antimicrobial peptide (SEQ ID NO: 88) introduced C-terminally to the GN37 lysin (SEQ ID NO: 84) to generate the GN218 lysin (SEQ ID NO: 10) or a polypeptide having lysin activity and having at least 80%, such as at least 85%, such as at least 90%, such as at least 95%, such as at least 98%, or such as at least 99% sequence identity to SEQ ID NO: 10.

In some embodiments, the lysin-AMP polypeptide construct comprises an RPP moiety, an IGEM linker (SEQ ID NO: 86), and the antimicrobial amurin peptide Gkh2 (SEQ ID NO: 90) introduced C-terminally to the GN37 lysin (SEQ ID NO: 84) to generate the GN223 lysin (SEQ ID NO: 12) or a polypeptide having lysin activity and having at least 80%, such as at least 85%, such as at least 90%, such as at least 95%, such as at least 98% or such as at least 99% sequence identity to SEQ ID NO: 12.

In some embodiments, the lysin-AMP polypeptide construct comprises an IGEM linker (SEQ ID NO: 86) and an RI18 peptide (SEQ ID NO: 92) introduced C-terminally to the GN37 lysin (SEQ ID NO: 84) to generate the GN239 lysin (SEQ ID NO: 14) or a polypeptide having lysin activity and having at least 80%, such as at least 85%, such as at least 90%, such as at least 95%, such as at least 98%, or such as at least 99% sequence identity to SEQ ID NO: 14.

In some embodiments, the lysin-AMP polypeptide construct comprises a PP amino acid moiety, an IGEM linker (SEQ ID NO: 86) and a TI15 peptide (SEQ ID NO: 94), introduced C-terminally to the GN37 lysin (SEQ ID NO: 84) to generate the GN243 lysin (SEQ ID NO: 16) or a polypeptide having lysin activity and having at least 80%, such as at least 85%, such as at least 90%, such as at least 95%, such as at least 98%, or such as at least 99% sequence identity to SEQ ID NO: 16.

In some embodiments, the lysin-AMP polypeptide construct comprises an RI18 antimicrobial peptide (SEQ ID NO: 92), a linker having the amino acid sequence PPTAGGTAGG (SEQ ID NO: 98), and a TI15 antimicrobial peptide (SEQ ID NO: 94) introduced C terminally to a Lysin PaP2_gp17 (SEQ ID NO: 96) to generate GN280 lysin (SEQ ID NO: 18) or a polypeptide having lysin activity and having at least 80%, such as at least 85%, such as at least 90%, such as at least 95%, such as at least 98%, or such as at least 99% sequence identity to SEQ ID NO: 18.

In some embodiments, the lysin-AMP polypeptide construct comprises an RI18 peptide (SEQ ID NO: 92), an IGEM linker (SEQ ID NO: 86), a PP amino acid moiety (added to maintain structure of the lysin and/or the AMP), and a TI15 peptide (SEQ ID NO: 94) introduced C terminally to a Lysin PaP2_gp17 (SEQ ID NO: 96) to generate GN281 lysin (SEQ ID NO: 20) or a polypeptide having lysin activity and having at least 80%, such as at least 85%, such as at least 90%, such as at least 95%, such as at least 98%, or such as at least 99% sequence identity to SEQ ID NO: 20.

In some embodiments, the lysin-AMP polypeptide construct comprises a linker having the amino acid sequence TAGGTAGG (SEQ ID NO: 72), and an amurin peptide Chp4 (SEQ ID NO: 102) introduced C-terminally to the GN316 lysin (SEQ ID NO: 22) to generate the GN349 lysin (SEQ ID NO: 30) or a polypeptide having lysin activity and having at least 80%, such as at least 85%, such as at least 90%, such as at least 95%, such as at least 98%, or such as at least 99% sequence identity to SEQ ID NO: 30.

In some embodiments, the lysin-AMP polypeptide construct comprises a linker having the amino acid sequence TAGGTAGG (SEQ ID NO: 72), and an amurin peptide Ecp2 (SEQ ID NO: 104), introduced C-terminally to the GN316 lysin (SEQ ID NO: 22) to generate the GN351 lysin (SEQ ID NO: 32) or a polypeptide having lysin activity and having at least 80%, such as at least 85%, such as at least 90%, such as at least 95%, such as at least 98%, or such as at least 99% sequence identity to SEQ ID NO: 32.

In some embodiments, the lysin-AMP polypeptide construct comprises a linker having the amino acid sequence TAGGTAGG (SEQ ID NO: 72), and an amurin peptide Chp7 (SEQ ID NO: 139) introduced C-terminally to the GN316 lysin (SEQ ID NO: 22) to generate the GN352 lysin (SEQ ID NO: 34) or a polypeptide having lysin activity and having at least 80%, such as at least 85%, such as at least 90%, such as at least 95%, such as at least 98%, or such as at least 99% sequence identity to SEQ ID NO: 34.

In some embodiments, the lysin-AMP polypeptide construct comprises a linker having the amino acid sequence TAGGTAGG (SEQ ID NO: 72) and an amurin peptide Osp1 (SEQ ID NO: 108), introduced C-terminally to the GN316 lysin (SEQ ID NO: 22) to generate the GN353 lysin (SEQ ID NO: 36) or a polypeptide having lysin activity and having at least 80%, such as at least 85%, such as at least 90%, such as at least 95%, such as at least 98%, or such as at least 99% sequence identity to SEQ ID NO: 36.

In some embodiments, the lysin-AMP polypeptide construct comprises a linker having the amino acid sequence TAGGTAGG (SEQ ID NO: 72), and a RR12Whydro(SEQ ID NO: 110) introduced C-terminally to the GN316 lysin (SEQ ID NO: 22) to generate the GN357 lysin (SEQ ID NO:

38) or a polypeptide having lysin activity and having at least 80%, such as at least 85%, such as at least 90%, such as at least 95%, such as at least 98%, or such as at least 99% sequence identity to SEQ ID NO: 38.

In some embodiments, the lysin-AMP polypeptide construct comprises a linker having the amino acid sequence TAGGTAGG (SEQ ID NO: 72) and a TI15 peptide derivative of PMAP-36 (SEQ ID NO: 94), introduced C-terminally to the GN316 lysin (SEQ ID NO: 22) to generate the GN359 lysin (SEQ ID NO: 40) or a polypeptide having lysin activity and having at least 80%, such as at least 85%, such as at least 90%, such as at least 95%, such as at least 98%, or such as at least 99% sequence identity to SEQ ID NO: 40.

In some embodiments, the lysin-AMP polypeptide construct comprises RR18 (SEQ ID NO: 92), introduced C-terminally to the GN316 lysin (SEQ ID NO: 22) to generate the GN369 lysin (SEQ ID NO: 42) or a polypeptide having lysin activity and having at least 80%, such as at least 85%, such as at least 90%, such as at least 95%, such as at least 98%, or such as at least 99% sequence identity to SEQ ID NO: 42.

In some embodiments, the lysin-AMP polypeptide construct comprises a MIDR moiety (SEQ ID NO: 112), a FIRL moiety (SEQ ID NO:114) and an NPTH moiety (SEQ ID NO: 116) introduced N-terminally to the GN202 lysin (SEQ ID NO: 118) to generate the GN370 lysin (SEQ ID NO: 44) or a polypeptide having lysin activity and having at least 80%, such as at least 85%, such as at least 90%, such as at least 95%, such as at least 98%, or such as at least 99% sequence identity to SEQ ID NO: 44.

In some embodiments, the lysin-AMP polypeptide construct comprises a MIDR moiety (SEQ ID NO: 112), FIRL (SEQ ID NO: 114) and an NPTH moiety (SEQ ID NO: 116) introduced N-terminally to the GN146 lysin (SEQ ID NO: 78) to generate the GN371 lysin (SEQ ID NO: 46) or a polypeptide having lysin activity and having at least 80%, such as at least 85%, such as at least 90%, such as at least 95%, such as at least 98%, or such as at least 99% sequence identity to SEQ ID NO: 46.

In some embodiments, the lysin-AMP polypeptide construct comprises a cationic peptide (SEQ ID NO: 120) and a linker domain (SEQ ID NO: 122) introduced N-terminally to the GN14 lysin (SEQ ID NO: 124) to generate a GN93 lysin (SEQ ID NO: 62) or a polypeptide having lysin activity and having at least 80%, such as at least 85%, such as at least 90%, such as at least 95%, such as at least 98%, or such as at least 99% sequence identity to SEQ ID NO: 62.

Table 1, below, depicts specific examples of the lysins and lysin-AMP constructs described herein. The AMP portion of the construct is double-underlined for GN168 (SEQ ID NO: 2), GN176 (SEQ ID NO: 4), GN178 (SEQ ID NO: 6), GN370 (SEQ ID NO: 44), GN371 (SEQ ID NO: 46) and GN93 (SEQ ID NO: 62). For all other constructs, double underlines correspond to a lysin. Structure stabilizing components, such as linkers are italicized. The purification tag for GN486 (SEQ ID NO: 66) is italicized and bolded. Single point mutations are bolded.

TABLE 1

| GN # | Polypeptide Sequence |
|---|---|
| GN168 | MRLKMARRRYRLPRRRSRRLFSRTALRMHPRNRLRRIMRGGIRF*TAGGTA GGR*TSQRGIDLIKSFEGLRLSAYQDSVGVWTIGYGTTRGVTRYMTITVEQ AERMLSNDIQRFEPELDRLAKVPLNQNQWDALMSFVYNLGAANLASSTL LDLLNKGDYQGAADQFPHWVNAGGKRLDGLVKRRAAERALFLEPLS (SEQ ID NO: 2) |
| GN176 | MSFNVTPKFKRWQLYFRGRMW*TAGGTAGG*RTSQRGIDLIKSFEGLRLSAY QDSVGVWTIGYGTTRGVTRYMTITVEQAERMLSNDIQRFEPELDRLAKVP LNQNQWDALMSFVYNLGAANLASSTLLDLLNKGDYQGAADQFPHWVN AGGKRLDGLVKRRAAERALFLEPLS (SEQ ID NO: 4) |
| GN178 | MPPIFSKLAGKKIKNLLISGLK*GGSGSGSGSGS*PRTSQRGIDLIKSFEGLRLS AYQDSVGVWTIGYGTTRGVTRYMTITVEQAERMLSNDIQRFEPELDRLA KVPLNQNQWDALMSFVYNLGAANLASSTLLDLLNKGDYQGAADQFPH WVNAGGKRLDGLVKRRAAERALFLEPLS (SEQ ID NO: 6) |
| GN217 | MTYTLSKRSLDNLKGVHPDLVAVVHRAIQLTPVDFAVIEGLRSVSRQKEL VAAGASKTMNSRHLTGHAVDLAAYVNGIHWDWPLYDAIAVAVKAAAK ELGVAIVWGGDWTTFKDGPHFELDRSKYR (SEQ ID NO: 8) |
| GN218 | MTYTLSKRSLDNLKGVHPDLVAVVHRAIQLTPVDFAVIEGLRSVSRQKEL VAAGASKTMNSRHLTGHAVDLAAYVNGIRWDWPLYDAIAVAVKAAAK ELGVAIVWGGDWTTFKDGPHFELDRSKY*GGGSGGGGGGGS*RLKKIGKV LKWI (SEQ ID NO: 10) |
| GN223 | MTYTLSKRSLDNLKGVHPDLVAVVHRAIQLTPVDFAVIEGLRSVSRQKEL VAAGASKTMNSRHLTGHAVDLAAYVNGIRWDWPLYDAIAVAVKAAAK ELGVAIVWGGDWTTFKDGPHFELDRSKYRPP*GGGSGGGGSGGGGS*SKKAS RKSFTKGAVKVHKKNVPTRVPMRGGIRL (SEQ ID NO: 12) |
| GN239 | MTYTLSKRSLDNLKGVHPDLVAVVHRAIQLTPVDFAVIEGLRSVSRQKEL VAAGASKTMNSRHLTGHAVDLAAYVNGIRWDWPLYDAIAVAVKAAAK ELGVAIVWGGDWTTFKDGPHFELDRSKY*GGGSGGGGSGGGS*RKKTRKRL KKIGKVLKWI (SEQ ID NO: 14) |
| GN243 | MTYTLSKRSLDNLKGVHPDLVAVVHRAIQLTPVDFAVIEGLRSVSRQKEL VAAGASKTMNSRHLTGHAVDLAAYVNGIRWDWPLYDAIAVAVKAAAK ELGVAIVWGGDWTTFKDGPHFELDRSKYRKKTRKRLKKIGKVLKWIPP*G GGSGGGGSGGGS*TRKRLKKIGKVLKWI (SEQ ID NO: 16) |
| GN280 | MKLSEKRALFTQLLAQLILWAGTQDRVSVALDQVKRTQAEADANAKSG AGIRNSLHLLGLAGDLILYKDGKYMDKSEDYKFLGDYWKSLHPLCRWG |

TABLE 1-continued

| GN # | Polypeptide Sequence |
|---|---|
| | GDFKSRPDGNHFSLEHEGVQ*RKKTRKRLKKIGKVLKWI*PPTAGGTAGGTR<br>KRLKKIGKVLKWI (SEQ ID NO: 18) |
| GN281 | MKLSEKRALFTQLLAQLILWAGTQDRVSVALDQVKRTQAEADANAKSG<br>AGIRNSLHLLGLAGDLILYKDGKYMDKSEDYKFLGDYWKSLHPLCRWG<br>GDFKSRPDGNHFSLEHEGVQ*RKKTRKRLKKIGKVLKWI*GGGSGGGSGG<br>GSPPTRKRLKKIGKVLKWI (SEQ ID NO: 20) |
| GN316 | MAILKIGSKGLEVKNLQTSLNKIGFNLVADGIFGKATDNAVRAVQAGAGL<br>VVDGIAGPKTMYAIRNAGESHQDHLTEADLIDAARELSVDLASIKAVNQV<br>ESRGTGFTKSGKIKTLFERHIMYKKLNAKFGQAKANALAQLYPTLVNAK<br>AGGYTGGDAELERLHGAIAIDKDCAYESASYGLFQIMGFNCVICGYDNAE<br>EMFNDFLTGERAQLMAFVKFIKADANLWKALKDKNWAEFARRYNGPAY<br>AQNQYDTKLAAAYKSFS (SEQ ID NO: 22) |
| GN329 | MITDREYQQAAEMLGVDVPAIKAVTKVEAPVGGFQPTGEPTILYERHQM<br>YRQLQAKGLPTEGHPPDLVNKVAGGYGKYSEQHAKLARAVKIDRDSALE<br>SCSWGMFQIMGYHWKLMGYPTLQAFVNAMYASEGAQMDAFCRFIKAQP<br>TTHAALKAHDWAKFARLYNGPGYAKNKYDVKLEKAYAEASG (SEQ ID<br>NO: 26) |
| GN333 | MALTEQDFQSAADDLGVDVASVKAVTKVESRGSGFLLSGVPKILFERHW<br>MFKLLKRKLGRDPEINDVCNPKAGGYLGGQAEHERLDKAVKMDRDCAL<br>QSASWGLFQIMGFHWEALGYASVQAFVNAQYASEGSQLNTFVRFIKTNP<br>AIHKALKSKDWAEFARRYNGPDYKKNNYDVKLAEAYQSFK (SEQ ID<br>NO: 28) |
| GN349 | MAILKIGSKGLEVKNLQTSLNKIGFNLVADGIFGKATDNAVRAVQAGAGL<br>VVDGIAGPKTMYAIRNAGESHQDHLTEADLIDAARELSVDLASIKAVNQV<br>ESRGTGFTKSGKIKTLFERHIMYKKLNAKFGQAKANALAQLYPTLVNAK<br>AGGYTGGDAELERLHGAIAIDKDCAYESASYGLFQIMGFNCVICGYDNAE<br>EMFNDFLTGERAQLMAFVKFIKADANLWKALKDKNWAEFARRYNGPAY<br>AQNQYDTKLAAAYKSFS*TAGGTAGG*ARRYRLSRRRSRRLFSRTALRMHR<br>RNRLRRIMRGGIRF (SEQ ID NO: 30) |
| GN351 | MAILKIGSKGLEVKNLQTSLNKIGFNLVADGIFGKATDNAVRAVQAGAGL<br>VVDGIAGPKTMYAIRNAGESHQDHLTEADLIDAARELSVDLASIKAVNQV<br>ESRGTGFTKSGKIKTLFERHIMYKKLNAKFGQAKANALAQLYPTLVNAK<br>AGGYTGGDAELERLHGAIAIDKDCAYESASYGLFQIMGFNCVICGYDNAE<br>EMFNDFLTGERAQLMAFVKFIKADANLWKALKDKNWAEFARRYNGPAY<br>AQNQYDTKLAAAYKSFS*TAGGTAGG*ARSRRRMSKRSSRRSFRKYAKSHK<br>KNFKARSMRGGIRL (SEQ ID NO: 32) |
| GN352 | MAILKIGSKGLEVKNLQTSLNKIGFNLVADGIFGKATDNAVRAVQAGAGL<br>VVDGIAGPKTMYAIRNAGESHQDHLTEADLIDAARELSVDLASIKAVNQV<br>ESRGTGFTKSGKIKTLFERHIMYKKLNAKFGQAKANALAQLYPTLVNAK<br>AGGYTGGDAELERLHGAIAIDKDCAYESASYGLFQIMGFNCVICGYDNAE<br>EMFNDFLTGERAQLMAFVKFIKADANLWKALKDKNWAEFARRYNGPAY<br>AQNQYDTKLAAAYKSFS*TAGGTAGG*KRRKMTRKGSKRLFTATADKTKSI<br>NTAPPPMRGGIRL (SEQ ID NO: 34) |
| GN353 | MAILKIGSKGLEVKNLQTSLNKIGFNLVADGIFGKATDNAVRAVQAGAGL<br>VVDGIAGPKTMYAIRNAGESHQDHLTEADLIDAARELSVDLASIKAVNQV<br>ESRGTGFTKSGKIKTLFERHIMYKKLNAKFGQAKANALAQLYPTLVNAK<br>AGGYTGGDAELERLHGAIAIDKDCAYESASYGLFQIMGFNCVICGYDNAE<br>EMFNDFLTGERAQLMAFVKFIKADANLWKALKDKNWAEFARRYNGPAY<br>AQNQYDTKLAAAYKSFS*TAGGTAGG*RKRMSKRVDKKVFRRTAASAKKIN<br>IDPKIYRGGIRL (SEQ ID NO: 36) |
| GN357 | MAILKIGSKGLEVKNLQTSLNKIGFNLVADGIFGKATDNAVRAVQAGAGL<br>VVDGIAGPKTMYAIRNAGESHQDHLTEADLIDAARELSVDLASIKAVNQV<br>ESRGTGFTKSGKIKTLFERHIMYKKLNAKFGQAKANALAQLYPTLVNAK<br>AGGYTGGDAELERLHGAIAIDKDCAYESASYGLFQIMGFNCVICGYDNAE<br>EMFNDFLTGERAQLMAFVKFIKADANLWKALKDKNWAEFARRYNGPAY<br>AQNQYDTKLAAAYKSFS*TAGGTAGG*RRLIRLWLRLLR (SEQ ID NO: 38) |
| GN359 | MAILKIGSKGLEVKNLQTSLNKIGFNLVADGIFGKATDNAVRAVQAGAGL<br>VVDGIAGPKTMYAIRNAGESHQDHLTEADLIDAARELSVDLASIKAVNQV<br>ESRGTGFTKSGKIKTLFERHIMYKKLNAKFGQAKANALAQLYPTLVNAK<br>AGGYTGGDAELERLHGAIAIDKDCAYESASYGLFQIMGFNCVICGYDNAE<br>EMFNDFLTGERAQLMAFVKFIKADANLWKALKDKNWAEFARRYNGPAY<br>AQNQYDTKLAAAYKSFS*TAGGTAGG*TRKRLKKIGKVLKWI (SEQ ID NO:<br>40) |
| GN369 | MAILKIGSKGLEVKNLQTSLNKIGFNLVADGIFGKATDNAVRAVQAGAGL<br>VVDGIAGPKTMYAIRNAGESHQDHLTEADLIDAARELSVDLASIKAVNQV<br>ESRGTGFTKSGKIKTLFERHIMYKKLNAKFGQAKANALAQLYPTLVNAK<br>AGGYTGGDAELERLHGAIAIDKDCAYESASYGLFQIMGFNCVICGYDNAE |

TABLE 1-continued

| GN # | Polypeptide Sequence |
|---|---|
| | <u>EMFNDFLTGERAQLMAFVKFIKADANLWKALKDKNWAEFARRYNGPAY AQNQYDTKLAAAYKSFS</u>*RKKTRKRLKKIGKVLKWI* (SEQ ID NO: 42) |
| GN370 | *MIDRFIRLNPTH*GPRRPRRPGRRAPVRTSQRGIDLIKSFEGLRLSAYQDSVG VWTIGYGTTRGVTRYMTITVEQAERMLSNDIQRFEPELDRLAKVPLNQNQ WDALMSFVYNLGAANLASSTLLDLLNKGDYQGAADQFPHWVNAGGKR LDGLVKRRAAERALFLEPLS (SEQ ID NO: 44) |
| GN371 | *MIDRFIRLNPTH*RTSQRGIDLIKSFEGLRLSAYQDSVGVWTIGYGTTRGVTR YMTITVEQAERMLSNDIQRFEPELDRLAKVPLNQNQWDALMSFVYNLGA ANLASSTLLDLLNKGDYQGAADQFPHWVNAGGKRLDGLVKRRAAERAL FLEPLS (SEQ ID NO: 46) |
| GN394 | MAILKIGSKGLEVKNLQTSLNKIGFNLVADGIFGKATDNAVRAVQAGAGL VVDGIAGPKTMYAIRNAGESHQDHLTEADLIDAARELSVDLASIKAVNQV ESRGTGFTKSGKIKTLFERHIMYKKLNAKFGQAKANALAQLYPTLVNAK AGGYTGGDAELERLHGAIAIDKDCAYESASYGLFQIMGFNCVICGYDNAE EMFNDFLTGERAQLMAFVDFIKADANLWKALKDKNWAEFARRYNGPAY AQNQYDTKLAAAYKSFS (SEQ ID NO: 48) |
| GN396 | MAILKIGSKGLEVKNLQTSLNKIGFNLVADGIFGKATDNAVRAVQAGAGL VVDGIAGPKTMYAIRNAGESHQDHLTEADLIDAARELSVDLASIKAVNQV ESRGTGFTKSGKIKTLFERHIMYKKLNAKFGQAKANALAQLYPTLVNAK AGGYTGGDAELERLHGAIAIDKDCAYESASYGLFQIMGFNCVICGYDNAE EMFNDFLTGERAQLMAFVKFIKADANLWDALKDKNWAEFARRYNGPAY AQNQYDTKLAAAYKSFS (SEQ ID NO: 50) |
| GN408 | MAILKIGSKGLEVKNLQTSLNKIGFNLVADGIFGKATDNAVRAVQAGAGL VVDGIAGPKTMYAIRNAGESHQDHLTEADLIDAAHELSVDLASIKAVNQV ESRGTGFTKSGKIKTLFERHIMYKKLNAKFGQAKANALAQLYPTLVNAK AGGYTGGDAELERLHGAIAIDKDCAYESASYGLFQIMGFNCVICGYDNAE EMFNDFLTGERAQLMAFVKFIKADANLWKALKDKNWAEFARRYNGPAY AQNQYDTKLAAAYKSFS (SEQ ID NO: 52) |
| GN418 | MAILKIGSKGLEVKNLQTSLNDIGFNLVADGIFGKATDNAVRAVQAGAGL VVDGIAGPKTMYAIRNAGESHQDHLTEADLIDAARELSVDLASIKAVNQV ESRGTGFTKSGKIKTLFERHIMYKKLNAKFGQAKANALAQLYPTLVNAK AGGYTGGDAELERLHGAIAIDKDCAYESASYGLFQIMGFNCVICGYDNAE EMFNDFLTGERAQLMAFVKFIKADANLWKALKDKNWAEFARRYNGPAY AQNQYDTKLAAAYKSFS (SEQ ID NO: 54) |
| GN424 | MNTLRFNSRGAEVGVLQQRLVRAGYPIDVTHLYDEATEQAVKALQAAA GIVVDGIAGPNTYAVLSAGQRDRKHLTEADIARAADKLGVSPACVRAVN EVESRGSGFLADGRPVILFERHVMYNRLVAAKRAVDAASAAQRFPNVVS AKPGGYQGGAAEYVRLDTAARIDAAIAYESASWGAFQVMGYHWERLGY SSIDEFVARMETSEGEQLDAFVRFVAADSSLRTALKNRKWAAFAKGYNG PDYARNLYDAKLAQAYERYAGTKAAA (SEQ ID NO: 56) |
| GN425 | MTLRLDDVGLDVLHLQKRLNELGANPRLLPDGQFGEVTERAVRAFQQRA GLVVDGVAGPKTMAALSGHSTSRLLGQRDLQRAADRLGVPLASVMALN AVESRGEGFAANGRPVILFERHVMHERLQVNGLSEAEADALAARHPGLV SRRPGGYVGDTAEHQRLANARLLHDTAALESASWGLFQVMGYHWQAL GYDTTQDFTERMARHEAEHLEAFVRFIEADPALHKALKGRKWAEFARRY NGPAYARNLYDVKLARAFEQFSDALQAAA (SEQ ID NO: 58) |
| GN428 | MAILKLGNRGSEVKALQQSLNKIGFSLTADGIFGKATENAVKSVQAGAGL VIDGIAGPKTFYAIRNAGDAHQEHLTEADLVDAARELGVELASMKAVNQ VESRGTGFTKTGKIKTLFERHIMYKKVTAKFGQARANALYQLYPTLVNPN SGGYIGGDAELERLQGAIALDEDCAYESASYGLFQIMGFNCQICGYSNAK EMFTDFLTGERAHLLAFVKFIKADANMWKALKNKNWAEFARRYNGPAY AKNQYDTKLAAAYKSFC (SEQ ID NO: 60) |
| GN93 | <u>MKFFKFFKFFK</u>AGAGAGAGAGAGAGASNNELPWVAEARKYIGLREDTS KTSHNPKLLAMLDRMGEFSNESRAWWHDDETPWCGLFVGYCLGVAGR YVVREWYRARAWEAPQLTKLDRPAYGALVTFTRSGGGHVGFIVGKDAR GNLMVLGGNQSNAVSIAPFAVSRVTGYFWPSFWRNKTAVKSVPFEERYS LPLLKSNGELSTNEA (SEQ ID NO: 62) |
| GN431 | MAILKLGNRGTEVKALQDSLNKIGFTLVADGIFGKATENAVKTVQAGAG LVIDGIVGPKTSYAIRNAGEAHQDHLTEADLIEAANQLGVDLASVKAVNQ VESRGTGFTKSGKIKTLFERHIMYKKLMAKFGQARANAMGQMYPTLVSP VAGGYTGGDAELDRLHAAINIDEDCAYESASYGLFQIMGFNCQVCGYAN AKEMFNDFLTGERAHLMAFVKFIKADAKLWQALKDKNWAEFARRYNGP AYTKNQYDTKLAAAYNSFN (SEQ ID NO: 64) |
| GN486 | M*GSHHHHHHG*GPRRPRRPGRRAPVRTSQRGIDLIKSFEGLRLSAYQDSV GVWTIGYGTTRGVTRYMTITVEQAERMLSNDIQRFEPELDRLAKVPLNQN |

TABLE 1-continued

| GN # | Polypeptide Sequence |
|---|---|
| | QWDALMSFVYNLGAANLASSTLLKLLNKGDYQGAADQFPRWVNAGGK<br>RLDGLVKRRAAERALFLEPLS (SEQ ID NO: 66) |
| GN485 | MPGLSGFIRNADTPVTSLGSAGHVHVPEGPLIRINPDCLLGTPFKFFKFFKF<br>FKFFKFFKFFKFFKNECVLL (SEQ ID NO: 68) |

In some embodiment, the lysins and/or lysin-AMP polypeptide constructs of the present disclosure are chemically modified. A chemical modification includes but is not limited to, adding chemical moieties, creating new bonds, and removing chemical moieties. Chemical modifications can occur anywhere in a lysin and/or lysin-AMP polypeptide construct, including the amino acid side chains, as well as the amino or carboxyl termini. For example, in certain embodiments, the lysin or lysin-AMP polypeptide construct comprises an N-terminal acetylation modification. In certain embodiments, the lysin or lysin-AMP polypeptide construct comprises a C-terminal amidation modification. Such modification can be present at more than one site in a lysin and/or lysin-AMP polypeptide construct.

Furthermore, one or more side groups, or terminal groups of a lysin and/or lysin-AMP polypeptide construct may be protected by protective groups known to the person ordinarily-skilled in the art.

In some embodiments, the lysins and/or lysin-AMP polypeptide constructs are conjugated to a duration enhancing moiety. In some embodiment, the duration enhancing moiety is polyethylene glycol. Polyethylene glycol ("PEG") has been used to obtain therapeutic polypeptides of enhanced duration (Zalipsky, S., Bioconjugate Chemistry, 6:150-165 (1995); Mehvar, R., J. Pharm. Pharmaceut. Sci., 3:125-136 (2000), which is herein incorporated by reference in its entirety). The PEG backbone, (CH2CH2-0-)n, wherein n is a number of repeating monomers, is flexible and amphiphilic. When attached to another chemical entity, such as a lysin and/or lysin-AMP polypeptide construct, PEG polymer chains can protect such polypeptides from immune response and other clearance mechanisms. As a result, pegylation can lead to improved efficacy and safety by optimizing pharmacokinetics, increasing bioavailability, and decreasing immunogenicity and dosing amount and/or frequency.

Polynucleotides

In one aspect, the present disclosure is directed an isolated polynucleotide comprising a nucleic acid molecule encoding a lysin, a variant lysin, an active fragment thereof or derivative as described herein. In some embodiments, the isolated polynucleotide sequence is a DNA sequence. In other embodiments, the isolated polynucleotide is a cDNA sequence.

In some embodiments, the isolated polynucleotide comprises a nucleic acid molecule encoding a polypeptide having at least 80%, such as at least 85%, such as at least 90%, such as at least 95%, such as at least 98%, or such as at least 99% sequence identity with a lysin, a variant lysin, an active fragment thereof or derivative as described herein, wherein the encoded polypeptide inhibits the growth, or reduces the population, or kills P. aeruginosa and optionally at least one other species of Gram-negative bacteria as described herein in the absence or presence of, or in both the absence and presence of, human serum, or in the presence of pulmonary surfactant.

In some embodiments, the isolated polynucleotide comprises a nucleic acid molecule encoding a lysin selected from GN217 (SEQ ID NO: 8), GN316 variant (SEQ ID NO: 24) GN316 (SEQ ID NO: 22), GN329 (SEQ ID NO: 26), GN333 (SEQ ID NO: 28), GN394 (SEQ ID NO: 48), GN396 (SEQ ID NO: 50), GN408 (SEQ ID NO: 52), GN418 (SEQ ID NO: 54), GN424 (SEQ ID NO: 56), GN425 (SEQ ID NO:58), GN428 (SEQ ID NO: 60), GN431 (SEQ ID NO: 64), GN486 (SEQ ID NO: 66), GN485 (SEQ ID NO: 68), Lysin PaP2_gp17 (SEQ ID NO: 96), GN123 (SEQ ID NO: 173) or GN121 (SEQ ID NO: 175) or a variant or an active fragment thereof or derivative, wherein the lysin variant or an active fragment thereof or derivative encoded by the isolated polynucleotide inhibits the growth, or reduces the population, or kills P. aeruginosa and/or at least one other species of Gram-negative bacteria in the absence or presence of, or in both the absence and presence of, human serum, or in the presence of pulmonary surfactant. In certain embodiments, the isolated polynucleotide comprises a nucleic acid molecule encoding a lysin, variant or active fragment thereof or derivative that contains at least one modification relative to at least one of SEQ ID NOS: 8, 24, 22, 26, 28, 48, 50, 52, 54, 56, 58, 60, 64, 66, 68, 96, 173 and 175 such as at least one amino acid substitution, insertion or deletion. In certain embodiments, the isolated polynucleotide comprises a nucleic acid sequence selected from the group consisting of SEQ ID NOS: 7, 23, 21, 25, 27, 47, 49, 51, 53, 55, 57, 59, 63, 65, 67 95, 172 and 174 respectively, complements thereof or a nucleic acid sequence having at least 80%, such as at least 85%, such as at least 90%, such as at least 95%, such as at least 98%, or such as at least 99% sequence identity to one of SEQ ID NOS: 7, 23, 21, 25, 27, 47, 49, 51, 53, 55, 57, 59, 63, 65, 67 95, 172 and 174, or complements thereof, wherein the encoded polypeptide inhibits the growth, or reduces the population, or kills P. aeruginosa and/or at least one other species of Gram-negative bacteria in the absence or presence of, or in both the absence and presence of, human serum, or in the presence of pulmonary surfactant.

In some embodiments, the isolated polynucleotide comprises a nucleic acid molecule encoding a lysin selected from at least one of GN217 lysin (SEQ ID NO: 8), GN394 lysin (SEQ ID NO: 48), GN396 lysin (SEQ ID NO: 50), GN408 lysin (SEQ ID NO: 52), GN418 lysin (SEQ ID NO: 54) and GN486 (SEQ ID NO: 66) or a variant or an active fragment thereof or derivative. In certain embodiments, the polynucleotide comprises a nucleic acid sequence selected from the group consisting of SEQ ID NOS: 7, 47, 49, 51, 53, and 65 complements thereof or a nucleic acid sequence having at least 80%, such as at least 85%, such as at least 90%, such as at least 95%, such as at least 98%, or such as at least 99% sequence identity to one of SEQ ID NOS: 77, 47, 49, 51, 53, or 65, or complements thereof, wherein the encoded polypeptide inhibits the growth, or reduces the population, or kills P. aeruginosa and optionally at least one other species of Gram-negative bacteria in the absence or presence of, or in both the absence and presence of, human serum, or in the presence of pulmonary surfactant.

In some embodiments, the isolated polynucleotide comprises a nucleic acid molecule encoding a lysin selected from at least one of GN316 (SEQ ID NO: 22), GN329 (SEQ ID NO: 26), GN333 (SEQ ID NO: 28), GN424 (SEQ ID NO: 56), GN425 (SEQ ID NO:58), GN428 (SEQ ID NO: 60), GN431 (SEQ ID NO: 64), GN485 (SEQ ID NO: 68) or a variant or an active fragment thereof or derivative, wherein the encoded polypeptide inhibits the growth, or reduces the population, or kills *P. aeruginosa* and optionally at least one other species of Gram-negative bacteria in the absence or presence of, or in both the absence and presence of, human serum, or in the presence of pulmonary surfactant. In certain embodiments, the variant, active fragment thereof or derivative contains at least one modification relative to at least one of SEQ ID NOS: 22, 26, 28, 56, 58, 60, 64 or 68, such as at least one amino acid substitution, insertion or deletion. In certain embodiments, the polynucleotide comprises a nucleic acid sequence selected from the group consisting of SEQ ID NOS: 21, 25, 27, 55, 57, 59, 63 and 67, complements thereof or a nucleic acid sequence having at least 80%, such as at least 85%, such as at least 90%, such as at least 95%, such as at least 98%, or such as at least 99% sequence identity to one of SEQ ID NOS: 21, 25, 27, 55, 57, 59, 63 or 67, or complements thereof, wherein the encoded polypeptide inhibits the growth, or reduces the population, or kills *P. aeruginosa* and optionally at least one other species of Gram-negative bacteria in the absence or presence of, or in both the absence and presence of, human serum, or in the presence of pulmonary surfactant.

In another aspect, the present disclosure is directed to an isolated polynucleotide comprising a nucleic acid molecule encoding a lysin-AMP polypeptide construct comprising:

(a) a first nucleic acid molecule encoding a first component comprising: (i) a lysin selected from the group consisting of GN7 (SEQ ID NO: 206), GN11 (SEQ ID NO: 208), GN40 (SEQ ID NO: 210), GN122 (SEQ ID NO: 218), GN328 (SEQ ID NO: 220), GN76 (SEQ ID NO: 203), GN4 (SEQ ID NO: 74), GN146 (SEQ ID NO: 78), GN14 (SEQ ID NO: 124), GN37 (SEQ ID NO: 84) optionally with a single pI-increasing mutation, GN316 (SEQ ID NO: 22) optionally with a single point mutation, lysin Pap2_gp17 (SEQ ID NO: 96), GN329 (SEQ ID NO: 26), GN424 (SEQ ID NO: 56), GN202 (SEQ ID NO: 118), GN425 (SEQ ID NO: 58), GN428 (SEQ ID NO: 60), GN431 (SEQ ID NO: 64), GN486 (SEQ ID NO: 66), GN333 (SEQ ID NO: 28), and GN485 (SEQ ID NO: 68), GN123 (SEQ ID NO: 173) and GN121 (SEQ ID NO: 175); or (ii) a polypeptide having lysin activity, wherein the polypeptide is at least 80% identical to at least one of SEQ ID NOS: 206, 208, 210, 218, 220, 203, 74, 78, 124, 84, 22, 96, 26, 56, 118, 58, 60, 64, 66, 28, 68, 173 or 175; or (iii) an active fragment of the lysin;

(b) a second nucleic acid molecule encoding a second component comprising: (i) at least one antimicrobial peptide (AMP) selected from the group consisting of Chp1 (SEQ ID NO: 133), Chp2 (SEQ ID NO: 70), CPAR39 (SEQ ID NO: 135), Chp3 (SEQ ID NO: 137), Chp4 (SEQ ID NO: 102), Chp6 (SEQ ID NO: 106), Chp7 (SEQ ID NO: 139), Chp8 (SEQ ID NO: 141), Chp9 (SEQ ID NO: 143), Chp10 (SEQ ID NO: 145), Chp11 (SEQ ID NO: 147), Chp12 (SEQ ID NO: 149), Gkh1 (SEQ ID NO: 151), Gkh2 (SEQ ID NO: 90), Unp1 (SEQ ID NO: 153), Ecp1 (SEQ ID NO: 155), Ecp2 (SEQ ID NO: 104), Tma1 (SEQ ID NO: 157), Osp1 (SEQ ID NO: 108), Unp2 (SEQ ID NO: 159), Unp3 (SEQ ID NO: 161), Gkh3 (SEQ ID NO: 163), Unp5 (SEQ ID NO: 165), Unp6 (SEQ ID NO: 167), Spi1 (SEQ ID NO: 169), Spi2 (SEQ ID NO: 171), Ecp3 (SEQ ID NO: 177), Ecp4 (SEQ ID NO: 179), ALCES1 (SEQ ID NO: 181), AVQ206 (SEQ ID NO: 183), AVQ244 (SEQ ID NO: 185), CDL907 (SEQ ID NO: 187), AGT915 (SEQ ID NO: 189), HH3930 (SEQ ID NO: 191), Fen7875 (SEQ ID NO: 193), SBR77 (SEQ ID NO: 195), Bdp1 (SEQ ID NO: 197), LVP1 (SEQ ID NO: 199), Lvp2 (SEQ ID NO: 201), an esculentin fragment (SEQ ID NO: 80), RI12 (SEQ ID NO: 88), TI15 (SEQ ID NO: 94), RI18 (SEQ ID NO: 92), FIRL (SEQ ID NO: 114), a fragment of LPS binding protein (SEQ ID NO: 76), RR12whydro (SEQ ID NO: 110), RI18 peptide derivative (SEQ ID NO: 131) and cationic peptide (SEQ ID NO: 120) or (ii) a polypeptide having AMP activity, wherein the polypeptide is at least 80% identical to at least one of SEQ ID NOS: 133, 70, 135, 137, 102, 106, 139, 141, 143, 145, 147, 149, 151, 90, 153, 155, 104, 157, 108, 159, 161, 163, 165, 167, 169, 171, 177, 179, 181, 183, 185, 187, 189, 191, 193, 195, 197, 199, 201, 80, 88, 94, 92, 114, 76, 110, 131 and 120.

In some embodiments, the isolated polynucleotides of the present disclosure comprise a nucleic acid molecule encoding a first component of a lysin-AMP construct, wherein the first component is selected from the group consisting of GN394 (SEQ ID NO: 48), GN396 (SEQ ID NO: 50), GN408 (SEQ ID NO: 52) and GN418 (SEQ ID NO: 54).

In some embodiments, the isolated polynucleotides of the present disclosure comprise a nucleic acid molecule encoding a first component of a lysin-AMP construct, wherein the first component is GN202 (SEQ ID NO: 118).

In some embodiments, the isolated polynucleotides of the present disclosure comprise a nucleic acid molecule encoding a first component of a lysin-AMP construct, wherein the first component is GN202 (SEQ ID NO: 118) or has lysin activity and is at least 80% identical to SEQ ID NO: 118.

In some embodiments, the isolated polynucleotides of the present disclosure comprise a nucleic acid molecule encoding a second component of a lysin-AMP construct wherein the second component is selected from a from the group consisting of Chp1 (SEQ ID NO: 133), Chp2 (SEQ ID NO: 70), CPAR39 (SEQ ID NO: 135), Chp3 (SEQ ID NO: 137), Chp4 (SEQ ID NO: 102), Chp6 (SEQ ID NO: 106), Chp7 (SEQ ID NO: 139), Chp8 (SEQ ID NO: 141), Chp9 (SEQ ID NO: 143), Chp10 (SEQ ID NO: 145), Chp11 (SEQ ID NO: 147), Chp12 (SEQ ID NO: 149), Gkh1 (SEQ ID NO: 151), Gkh2 (SEQ ID NO: 90), Unp1 (SEQ ID NO: 153), Ecp1 (SEQ ID NO: 155), Ecp2 (SEQ ID NO: 104), Tma1 (SEQ ID NO: 157), Osp1 (SEQ ID NO: 108), Unp2 (SEQ ID NO: 159), Unp3 (SEQ ID NO: 161), Gkh3 (SEQ ID NO: 163), Unp5 (SEQ ID NO: 165), Unp6 (SEQ ID NO: 167), Spi1 (SEQ ID NO: 169), Spi2 (SEQ ID NO: 171), Ecp3 (SEQ ID NO: 177), Ecp4 (SEQ ID NO: 179), ALCES1 (SEQ ID NO: 181), AVQ206 (SEQ ID NO: 183), AVQ244 (SEQ ID NO: 185), CDL907 (SEQ ID NO: 187), AGT915 (SEQ ID NO: 189), HH3930 (SEQ ID NO: 191), Fen7875 (SEQ ID NO: 193), SBR77 (SEQ ID NO: 195), Bdp1 (SEQ ID NO: 197), LVP1 (SEQ ID NO: 199), Lvp2 (SEQ ID NO: 201), an esculentin fragment (SEQ ID NO: 80), RI12 (SEQ ID NO: 88), TI15 (SEQ ID NO: 94), RI18 (SEQ ID NO: 92), FIRL (SEQ ID NO: 114), a fragment of LPS binding protein (SEQ ID NO: 76), RR12whydro (SEQ ID NO: 110), RI18 peptide derivative (SEQ ID NO: 131) and cationic peptide (SEQ ID NO: 120) or (ii) a polypeptide having AMP activity, wherein the polypeptide is at least 80% identical to at least one of SEQ ID NOS: 133, 70, 135, 137, 102, 106, 139, 141, 143, 145, 147, 149, 151, 90, 153, 155, 104, 157, 108, 159, 161, 163, 165, 167, 169, 171, 177, 179, 181, 183, 185, 187, 189, 191, 193, 195, 197, 199, 201, 80, 88, 94, 92, 114, 76, 110, 131 and 120.

In some embodiments, the isolated polynucleotides of the present disclosure comprise a nucleic acid molecule encoding a second component of a lysin-AMP construct, wherein the second component is FIRL (SEQ ID NO: 114) or has AMP activity and is at least 75% identical to SEQ ID NO: 114.

In some embodiments, isolated polynucleotides of the present disclosure further comprise a nucleic acid molecule encoding at least one structure stabilizing component of a lysin-AMP polypeptide construct to maintain at least a portion of the structure of the first and/or second component in the construct substantially the same as in the unconjugated lysin and/or AMP. In some embodiments, the present isolated polynucleotides comprise a nucleic acid molecule encoding at least one structure stabilizing component, wherein the at least one structure stabilizing component is a peptide, such as a peptide comprising glycine and/or serine residues. In one embodiment, the peptide is selected from the group consisting of TAGGTAGG (SEQ ID NO: 72), IGEM (BBa_K1485002) (SEQ ID NO: 82), PPTAGGTAGG (SEQ ID NO: 98), IGEM+PP (residues 44-58 of SEQ ID NO: 16) and AGAGAGAGAGAGAGA-GAS (SEQ ID NO: 122).

More particularly, in some embodiments, the isolated polynucleotide comprises a nucleic acid molecule encoding a lysin-AMP polypeptide construct, wherein the lysin-AMP polypeptide construct is the GN168 lysin (SEQ ID NO: 2) or a polypeptide having lysin activity and having at least 80%, such as at least 85%, such as at least 90%, such as at least 95%, such as at least 98%, or such as at least 99% sequence identity to SEQ ID NO: 2.

In some embodiments, the nucleic acid molecule encoding the GN168 lysin comprises the nucleic acid sequence of SEQ ID NO: 1, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 1, or a complement thereof.

In some embodiments, the isolated polynucleotide comprises a nucleic acid molecule encoding a lysin-AMP polypeptide construct, wherein the lysin-AMP polypeptide construct is the GN176 lysin (SEQ ID NO: 4) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 4.

In some embodiments, the nucleic acid molecule encoding the GN176 lysin comprises the nucleic acid sequence of SEQ ID NO: 3, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 3, or a complement thereof.

In some embodiments, the isolated polynucleotide comprises a nucleic acid molecule encoding a lysin-AMP polypeptide construct, wherein the lysin-AMP polypeptide construct is the GN178 lysin (SEQ ID NO: 6) or a nucleic acid sequence encoding a polypeptide having at least 80%, such as at least 85%, such as at least 90%, such as at least 95%, such as at least 98%, or such as at least 99% sequence identity to SEQ ID NO: 6.

In some embodiments, the nucleic acid molecule encoding the GN178 lysin comprises the nucleic acid sequence of SEQ ID NO: 5, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 5, or a complement thereof.

In some embodiments, the isolated polynucleotide comprises a nucleic acid molecule encoding a lysin-AMP polypeptide construct, wherein the lysin-AMP polypeptide construct is the GN218 lysin (SEQ ID NO: 10) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 10.

In some embodiments, the nucleic acid molecule encoding the GN218 lysin comprises the nucleic acid sequence of SEQ ID NO: 9, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 9, or a complement thereof.

In some embodiments, the isolated polynucleotide comprises a nucleic acid molecule encoding a lysin-AMP polypeptide construct, wherein the lysin-AMP polypeptide construct is the GN223 lysin (SEQ ID NO: 12) or a nucleic acid molecule encoding a polypeptide having lysin activity and having at least 80%, such as at least 85%, such as at least 90%, such as at least 95%, such as at least 98% or such as at least 99% sequence identity to SEQ ID NO: 12.

In some embodiments, the nucleic acid molecule encoding the GN223 lysin comprises the nucleic acid sequence of SEQ ID NO: 11, a complement thereof or a nucleic acid sequence encoding a polypeptide having lysin activity and having at least 80%, such as at least 85%, such as at least 90%, such as at least 95%, such as at least 98% or such as at least 99% sequence identity to SEQ ID NO: 11, or a complement thereof.

In some embodiments, the isolated polynucleotide comprises a nucleic acid molecule encoding a lysin-AMP polypeptide construct, wherein the lysin-AMP polypeptide construct is the GN239 lysin (SEQ ID NO: 14) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 14.

In some embodiments, the nucleic acid molecule encoding the GN239 lysin comprises the nucleic acid sequence of SEQ ID NO: 13, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 13, or a complement thereof.

In some embodiments, the isolated polynucleotide comprises a nucleic acid molecule encoding a lysin-AMP polypeptide construct, wherein the lysin-AMP polypeptide construct is the GN243 lysin (SEQ ID NO: 16) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 16.

In some embodiments, the nucleic acid molecule encoding the GN243 lysin comprises the nucleic acid sequence of SEQ ID NO: 15, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 15, or a complement thereof.

In some embodiments, the isolated polynucleotide comprises a nucleic acid molecule encoding a lysin-AMP polypeptide construct, wherein the lysin-AMP polypeptide construct is the GN280 lysin (SEQ ID NO: 18) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 18.

In some embodiments, the nucleic acid molecule encoding the GN280 lysin comprises the nucleic acid sequence of SEQ ID NO: 17, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 17, or a complement thereof.

In some embodiments, the isolated polynucleotide comprises a nucleic acid molecule encoding a lysin-AMP polypeptide construct, wherein the lysin-AMP polypeptide construct is the GN281 lysin (SEQ ID NO: 20) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 20.

In some embodiments, the nucleic acid molecule encoding the GN281 lysin comprises the nucleic acid sequence of SEQ ID NO: 19, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 19, or a complement thereof.

In some embodiments, the isolated polynucleotide comprises a nucleic acid molecule encoding a lysin-AMP polypeptide construct, wherein the lysin-AMP polypeptide construct is the GN349 lysin (SEQ ID NO: 30) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 30.

In some embodiments, the nucleic acid molecule encoding the GN349 lysin comprises the nucleic acid sequence of SEQ ID NO: 29, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 29, or a complement thereof.

In some embodiments, the isolated polynucleotide comprises a nucleic acid molecule encoding a lysin-AMP polypeptide construct, wherein the lysin-AMP polypeptide construct is the GN351 lysin (SEQ ID NO: 32) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 32.

In some embodiments, the nucleic acid molecule encoding the GN351 lysin comprises the nucleic acid sequence of SEQ ID NO: 31, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 31, or a complement thereof.

In some embodiments, the isolated polynucleotide comprises a nucleic acid molecule encoding a lysin-AMP polypeptide construct, wherein the lysin-AMP polypeptide construct is the GN352 lysin (SEQ ID NO: 34) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 34.

In some embodiments, the nucleic acid molecule encoding the GN352 lysin comprises the nucleic acid sequence of SEQ ID NO: 33, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 33, or a complement thereof.

In some embodiments, the isolated polynucleotide comprises a nucleic acid molecule encoding a lysin-AMP polypeptide construct, wherein the lysin-AMP polypeptide construct is the GN353 lysin (SEQ ID NO: 36) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 36.

In some embodiments, the nucleic acid molecule encoding the GN353 lysin comprises the nucleic acid sequence of SEQ ID NO: 35, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 35, or a complement thereof.

In some embodiments, the isolated polynucleotide comprises a nucleic acid molecule encoding a lysin-AMP polypeptide construct, wherein the lysin-AMP polypeptide construct is the GN357 lysin (SEQ ID NO: 38) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 38.

In some embodiments, the nucleic acid molecule encoding the GN357 lysin comprises the nucleic acid sequence of SEQ ID NO: 37, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 37, or a complement thereof.

In some embodiments, the isolated polynucleotide comprises a nucleic acid molecule encoding a lysin-AMP polypeptide construct, wherein the lysin-AMP polypeptide construct is the GN359 lysin (SEQ ID NO: 40) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 40.

In some embodiments, the nucleic acid molecule encoding the GN359 lysin comprises the nucleic acid sequence of SEQ ID NO: 39, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 39, or a complement thereof.

In some embodiments, the isolated polynucleotide comprises a nucleic acid molecule encoding a lysin-AMP polypeptide construct, wherein the lysin-AMP polypeptide construct is the GN369 lysin (SEQ ID NO: 42) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 42.

In some embodiments, the nucleic acid molecule encoding the GN369 lysin comprises the nucleic acid sequence of SEQ ID NO: 41, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 41, or a complement thereof.

In some embodiments, the isolated polynucleotide comprises a nucleic acid molecule encoding a lysin-AMP polypeptide construct, wherein the lysin-AMP polypeptide construct is the GN370 lysin (SEQ ID NO: 44) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 44.

In some embodiments, the nucleic acid molecule encoding the GN370 lysin comprises the nucleic acid sequence of SEQ ID NO: 43, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 43, or a complement thereof.

In some embodiments, the isolated polynucleotide comprises a nucleic acid molecule encoding a lysin-AMP polypeptide construct, wherein the lysin-AMP polypeptide construct is the GN371 lysin (SEQ ID NO: 46) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 46.

In some embodiments, the nucleic acid molecule encoding the GN371 lysin comprises the nucleic acid sequence of SEQ ID NO: 45, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 45, or a complement thereof.

In some embodiments, the isolated polynucleotide comprises a nucleic acid molecule encoding a lysin-AMP polypeptide construct, wherein the lysin-AMP polypeptide construct is the GN93 lysin (SEQ ID NO: 62) or a nucleic acid molecule encoding a polypeptide having lysin activity and having at least 80%, such as at least 85%, such as at least 90%, such as at least 95%, such as at least 98%, or such as at least 99% sequence identity to SEQ ID NO: 62.

In some embodiments, the nucleic acid molecule encoding the GN93 comprises the nucleic acid sequence of SEQ ID NO: 61, a complement thereof or a nucleic acid sequence encoding a polypeptide having lysin activity and having at least 80%, such as at least 85%, such as at least 90%, such as at least 95%, such as at least 98%, or such as at least 99% sequence identity to SEQ ID NO: 61, or a complement thereof.

Vectors and Host Cells

In another aspect, the present disclosure is directed to a vector comprising an isolated polynucleotide comprising a nucleic acid molecule encoding any of the lysin-AMP polypeptides, lysin polypeptides, variants, active fragments thereof or derivatives disclosed herein, such as GN370 (SEQ ID NO: 44) or a complementary sequence of the present isolated polynucleotides. In some embodiments, the vector is a plasmid or cosmid. In other embodiments, the vector is a viral vector, wherein additional DNA segments can be ligated into the viral vector. In some embodiments, the vector can autonomously replicate in a host cell into which it is introduced. In some embodiments, the vector can be integrated into the genome of a host cell upon introduction into the host cell and thereby be replicated along with the host genome.

In some embodiments, particular vectors, referred to herein as "recombinant expression vectors" or "expression vectors", can direct the expression of genes to which they are operatively linked. A polynucleotide sequence is "operatively linked" when it is placed into a functional relationship with another nucleotide sequence. For example, a promoter or regulatory DNA sequence is said to be "operatively linked" to a DNA sequence that codes for an RNA and/or a protein if the two sequences are operatively linked, or situated such that the promoter or regulatory DNA sequence affects the expression level of the coding or structural DNA sequence. Operatively linked DNA sequences are typically, but not necessarily, contiguous.

Generally, any system or vector suitable to maintain, propagate or express a polypeptide in a host may be used for expression of the present lysin-AMP polypeptides, lysin polypeptides, variants, active fragments thereof or derivatives. The appropriate DNA/polynucleotide sequence may be inserted into the expression system by any of a variety of well-known and routine techniques, such as, for example, those set forth in Sambrook et al., eds., *Molecular Cloning: A Laboratory Manual* (3rd Ed.), Vols. 1-3, Cold Spring Harbor Laboratory (2001). Additionally, tags can also be added to the lysin-AMP polypeptides, lysin polypeptides, variants, active fragments thereof or derivatives of the present disclosure to provide convenient methods of isolation, e.g., c-myc, biotin, poly-His, etc. Kits for such expression systems are commercially available.

A wide variety of host/expression vector combinations may be employed in expressing the polynucleotide sequences encoding the present lysin-AMP polypeptides, lysin polypeptides, variants, active fragments thereof or derivatives. Large numbers of suitable vectors are known to those of skill in the art, and are commercially available. Examples of suitable vectors are provided, e.g., in Sambrook et al, eds., *Molecular Cloning: A Laboratory Manual* (3rd Ed.), Vols. 1-3, Cold Spring Harbor Laboratory (2001). Such vectors include, among others, chromosomal, episomal and virus derived vectors, e.g., vectors derived from bacterial plasmids, from bacteriophage, from transposons, from yeast episomes, from insertion elements, from yeast chromosomal elements, from viruses such as baculoviruses, papova viruses, such as SV40, vaccinia viruses, adenoviruses, fowl pox viruses, pseudorabies viruses and retroviruses, and vectors derived from combinations thereof, such as those derived from plasmid and bacteriophage genetic elements, such as cosmids and phagemids.

Furthermore, the vectors may provide for the constitutive or inducible expression of the lysin-AMP polypeptides, lysin polypeptides, variants, active fragments thereof or derivatives of the present disclosure. Suitable vectors include but are not limited to derivatives of SV40 and known bacterial plasmids, e.g., *E. coli* plasmids colE1, pCR1, pBR322, pMB9 and their derivatives, plasmids such as RP4, pBAD24 and pBAD-TOPO; phage DNAS, e.g., the numerous derivatives of phage A, e.g., NM989, and other phage DNA, e.g., M13 and filamentous single stranded phage DNA; yeast plasmids such as the 2 D plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like. Many of the vectors mentioned above are commercially available from vendors such as New England Biolabs Inc., Addgene, Takara Bio Inc., ThermoFisher Scientific Inc., etc.

Additionally, vectors may comprise various regulatory elements (including promoter, ribosome binding site, terminator, enhancer, various cis-elements for controlling the expression level) wherein the vector is constructed in accordance with the host cell. Any of a wide variety of expression control sequences (sequences that control the expression of a polynucleotide sequence operatively linked to it) may be used in these vectors to express the polynucleotide sequences encoding the lysin-AMP polypeptides, such as GN370 (SEQ ID NO: 44) lysin polypeptides, variants, active fragments thereof or derivatives thereof of the present disclosure. Useful control sequences include, but are not limited to: the early or late promoters of SV40, CMV, vaccinia, polyoma or adenovirus, the lac system, the trp system, the TAC system, the TRC system, the LTR system, the major operator and promoter regions of phage A, the control regions of fd coat protein, the promoter for 3-phosphoglycerate kinase or other glycolytic enzymes, the promoters of acid phosphatase (e.g., Pho5), the promoters of the yeast-mating factors, E. coli promoter for expression in bacteria, and other promoter sequences known to control the expression of genes of prokaryotic or eukaryotic cells or their viruses, and various combinations thereof. Typically, the polynucleotide sequences encoding the lysin-AMP polypeptides, lysin polypeptides, variants, active fragments thereof or derivatives is operatively linked to a heterologous promoter or regulatory element.

In another aspect, the present disclosure is directed to a host cell comprising any of the vectors disclosed herein including the expression vectors comprising the polynucleotide sequences encoding the lysin-AMP polypeptides, such as GN370 (SEQ ID NO: 44), lysin polypeptides, variants, active fragments thereof or derivatives of the present disclosure. A wide variety of host cells are useful in expressing the present polypeptides. Non-limiting examples of host cells suitable for expression of the present polypeptides include well known eukaryotic and prokaryotic hosts, such as strains of *E. coli, Pseudomonas, Bacillus, Streptomyces*, fungi such as yeasts, and animal cells, such as CHO, R1.1, B-W and L-M cells, African Green Monkey kidney cells (e.g., COS 1, COS 7, BSC1, BSC40, and BMT10), insect cells (e.g., Sf9), and human cells and plant cells in tissue culture. While the expression host may be any known expression host cell, in a typical embodiment the expression host is one of the strains of *E. coli*. These include, but are not limited to commercially available *E. coli* strains such as Top10 (ThermoFisher Scientific, Inc.), DH5a (Thermo Fisher Scientific, Inc.), XLI-Blue (Agilent Technologies, Inc.), SCSllO (Agilent Technologies, Inc.), JM109 (Promega, Inc.), LMG194 (ATCC), and BL21 (Thermo Fisher Scientific, Inc.).

There are several advantages of using *E. coli* as a host system including: fast growth kinetics, where under the optimal environmental conditions, its doubling time is about 20 min (Sezonov et al., *J. Bacteriol.* 189 8746-8749 (2007)), easily achieved high density cultures, easy and fast transformation with exogenous DNA, etc. Details regarding protein expression in *E. coli*, including plasmid selection as well as strain selection are discussed in details by Rosano, G. and Ceccarelli, E., *Front Microbial.*, 5: 172 (2014).

Efficient expression of the present lysin-AMP polypeptides, lysin polypeptides, variants, active fragments thereof or derivatives depends on a variety of factors such as optimal expression signals (both at the level of transcription and translation), correct protein folding, and cell growth characteristics. Regarding methods for constructing the vector and methods for transducing the constructed recombinant vector into the host cell, conventional methods known in the art can be utilized. While it is understood that not all vectors, expression control sequences, and hosts will function equally well to express the polynucleotide sequences encoding lysin-AMP polypeptides, such as GN370 (SEQ ID NO: 44), lysin polypeptides, variants, active fragments thereof or derivatives of the present disclosure, one skilled in the art will be able to select the proper vectors, expression control sequences, and hosts without undue experimentation to accomplish the desired expression without departing from the scope of this disclosure.

In some embodiments, the present inventors have found a correlation between level of expression and activity of the expressed polypeptide; in *E. coli* expression systems in particular, moderate levels of expression (for example between about 1 and 10 mg/liter) have produced lysin-AMP polypeptides, lysin polypeptides, variants, active fragments thereof or derivatives with higher levels of activity than those that were expressed at higher levels in *E. coli* (for example between about 20 and about 100 mg/liter), the latter having sometimes produced wholly inactive polypeptides.

Lysin-AMP polypeptides, lysin polypeptides, variants, active fragments thereof or derivatives of the present disclosure can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography, and lectin chromatography. High performance liquid chromatography can also employed for lysin polypeptide purification.

Alternatively, the vector system used for the production of lysin-AMP polypeptides, lysin polypeptides, variants, active fragments thereof or derivatives of the present disclosure may be a cell-free expression system. Various cell-free expression systems are commercially available, including, but are not limited to those available from Promega, LifeTechnologies, Clonetech, etc.

As indicated above, there is an array of choices when it comes to protein production and purification. Examples of suitable methods and strategies to be considered in protein production and purification are provided in WO 2017/049233, which is herein incorporated by reference in its entirety and further provided in Structural Genomics Consortium et al., *Nat. Methods.*, 5(2): 135-146 (2008).

Pharmaceutical Compositions

In another aspect, the present disclosure is directed to a pharmaceutical composition comprising an effective amount of lysin-AMP polypeptides, such as GN370 (SEQ ID NO: 44), lysin polypeptides, variants, active fragments thereof or derivatives as described herein and a pharmaceutically acceptable carrier. In some embodiments, the present pharmaceutical composition comprises at least one activity selected from inhibiting *P. aeruginosa* bacterial growth, reducing a *P. aeruginosa* bacterial population and/or killing *P. aeruginosa* in the absence and/or presence of human serum, or in the presence of pulmonary surfactant.

In some embodiments, the present pharmaceutical compositions further comprise one or more antibiotics suitable for the treatment of Gram-negative bacteria. Typical antibiotics include one or more of ceftazidime, cefepime, cefoperazone, ceftobiprole, ciprofloxacin, levofloxacin, aminoglycosides, imipenem, meropenem, doripenem, gentamicin, tobramycin, amikacin, piperacillin, ticarcillin, penicillin, rifampicin, polymyxin B, and colistin. Additional suitable antibiotics are described in Table 3.

In some embodiments, the pharmaceutical composition is a solution, a suspension, an emulsion, an inhalable powder, an aerosol, or a spray. The pharmaceutical compositions of the present disclosure can take the form of solutions, suspensions, emulsion, tablets, pills, pellets, capsules, capsules containing liquids, powders, sustained-release formulations, suppositories, tampon applications emulsions, aerosols, sprays, suspensions, lozenges, troches, candies, injectants, chewing gums, ointments, smears, time-release patches, liquid absorbed wipes, and combinations thereof.

Administration of the pharmaceutical compositions of the present disclosure may be topical, i.e., the pharmaceutical composition is applied directly where its action is desired (for example directly to a wound). The topical compositions of the present disclosure may further comprise a pharmaceutically or physiologically acceptable carrier, such as a dermatologically or an otically acceptable carrier. Such carriers, in the case of dermatologically acceptable carriers, are preferably compatible with skin, nails, mucous membranes, tissues and/or hair, and can include any conventionally used dermatological carrier meeting these requirements. In the case of otically acceptable carriers, the carrier is preferably compatible with all parts of the ear. Such carriers can be readily selected by one of ordinary skill in the art.

Carriers for topical administration of the lysin, active fragment thereof and/or lysin-AMP polypeptide construct of the present disclosure include, but are not limited to, mineral oil, liquid petroleum, white petroleum, propylene glycol, polyoxyethylene and/or polyoxypropylene compounds, emulsifying wax, sorbitan monostearate, polysorbate 60, cetyl esters wax, cetearyl alcohol, 2-octyldodecanol, benzyl alcohol, and water. In formulating skin ointments, the active components of the present disclosure may be formulated in an oleaginous hydrocarbon base, an anhydrous absorption base, a water-in-oil absorption base, an oil-in-water water-removable base and/or a water-soluble base. In formulating otic compositions, the active components of the present disclosure may be formulation in an aqueous polymeric suspension including such carriers as dextrans, polyethylene glycols, polyvinylpyrrolidone, polysaccharide gels, Gelrite®, cellulosic polymers like hydroxypropyl methylcellulose, and carboxy-containing polymers such as polymers or copolymers of acrylic acid, as well as other polymeric demulcents.

The topical compositions according to the present disclosure may be in any form suitable for topical application, including aqueous, aqueous-alcoholic or oily solutions, lotion or serum dispersions, aqueous, anhydrous or oily gels, emulsions obtained by dispersion of a fatty phase in an aqueous phase (OAV or oil in water) or, conversely, (W/O or water in oil), microemulsions or alternatively microcapsules, microparticles or lipid vesicle dispersions of ionic and/or nonionic type, creams, lotions, gels, foams (which will generally require a pressurized canister, a suitable applicator an emulsifier and an inert propellant), essences, milks, suspensions, or patches. Topical compositions of the present disclosure may also contain adjuvants such as hydrophilic or lipophilic gelling agents, hydrophilic or lipophilic active agents, preserving agents, antioxidants, solvents, fragrances, fillers, sunscreens, odor-absorbers and dyestuffs. In a further aspect, the topical compositions may be administered in conjunction with devices such as transdermal patches, dressings, pads, wraps, matrices and bandages capable of being adhered to or otherwise associated with the skin or other tissue of a subject, being capable of delivering a therapeutically effective amount of one or more antibacterial peptides in accordance with the present disclosure.

In one embodiment, the topical compositions of the present disclosure additionally comprise one or more components used to treat topical burns. Such components typically include, but are not limited to, a propylene glycol hydrogel; a combination of a glycol, a cellulose derivative and a water soluble aluminum salt; an antiseptic; an antibiotic; and a corticosteroid. Humectants (such as solid or liquid wax esters), absorption promoters (such as hydrophilic clays, or starches), viscosity building agents, and skin-protecting agents may also be added. Topical formulations may be in the form of rinses such as mouthwash. See, e.g., WO2004/004650.

In some embodiments, administration of the pharmaceutical compositions of the present disclosure may be systemic. Systemic administration can be enteral or oral, i.e., a substance is given via the digestive tract, parenteral, i.e., a substance is given by other routes than the digestive tract such as by injection or inhalation. Thus, the polypeptides including lysin-AMP polypeptides, lysin polypeptides, variants, active fragments thereof or derivatives of the present disclosure can be administered to a subject orally, parenterally, by inhalation, topically, rectally, nasally, buccally or via an implanted reservoir or by any other known method. The lysin-AMP polypeptides, lysin polypeptides, variants, active fragments thereof or derivatives of the present disclosure can also be administered by means of sustained release dosage forms.

For oral administration, the lysin-AMP polypeptides, lysin polypeptides, variants, active fragments thereof or derivatives of the present disclosure can be formulated into solid or liquid preparations, for example tablets, capsules, powders, solutions, suspensions and dispersions. The lysin, active fragment thereof and/or lysin-AMP polypeptide constructs can be formulated with excipients such as, e.g., lactose, sucrose, corn starch, gelatin, potato starch, alginic acid and/or magnesium stearate.

For preparing solid compositions such as tablets and pills, lysin-AMP polypeptides, lysin polypeptides, variants, active fragments thereof or derivatives of the present disclosure is mixed with a pharmaceutical excipient to form a solid pre-formulation composition. If desired, tablets may be sugar coated or enteric coated by standard techniques. The tablets or pills may be coated or otherwise compounded to provide a dosage form affording the advantage of prolonged action. For example, the tablet or pill can include an inner dosage and an outer dosage component, the latter being in the form of an envelope over the former. The two dosage components can be separated by an enteric layer, which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The pharmaceutical compositions of the present disclosure may also be administered by injection. For example, the pharmaceutical compositions can be administered intramuscularly, intrathecally, subdermally, subcutaneously, or intravenously to treat infections by Gram-negative bacteria, more specifically those caused by *P. aeruginosa*. The pharmaceutically acceptable carrier may be comprised of distilled water, a saline solution, albumin, a serum, or any combinations thereof. Additionally, pharmaceutical compositions of parenteral injections can comprise pH buffered solutions, adjuvants (e.g., preservatives, wetting agents, emulsifying agents, and dispersing agents), liposomal formulations, nanoparticles, dispersions, suspensions or emulsions as well as sterile powders for reconstitution into sterile injectable solutions or dispersions just prior to use.

In cases where parenteral injection is the chosen mode of administration, an isotonic formulation is preferably used. Generally, additives for isotonicity can include sodium chloride, dextrose, mannitol, sorbitol, and lactose. In some cases, isotonic solutions such as phosphate buffered saline are preferred. Stabilizers can include gelatin and albumin. A vasoconstriction agent can be added to the formulation. The pharmaceutical preparations according to this type of application are provided sterile and pyrogen free.

In another embodiment, the pharmaceutical compositions of the present disclosure are inhalable compositions. In some embodiments, the present pharmaceutical compositions are advantageously formulated as a dry, inhalable powder. In specific embodiments, the present pharmaceutical compositions may further be formulated with a propellant for aerosol delivery. Examples of suitable propellants include, but are not limited to: dichlorodifluoromethane, trichlorofluoromethane, dichloro-tetrafluoroethane and carbon dioxide. In certain embodiments, the formulations may be nebulized.

A surfactant can be added to an inhalable pharmaceutical composition of the present disclosure in order to lower the surface and interfacial tension between the medicaments and the propellant. The surfactant may be any suitable, non-toxic compound which is non-reactive with the present polypeptides.

Examples of suitable surfactants include, but are not limited to: oleic acid; sorbitan trioleate; cetyl pyridinium chloride; soya lecithin; polyoxyethylene(20) sorbitan monolaurate; polyoxyethylene (10) stearyl ether; polyoxyethylene (2) oleyl ether; polyoxypropylene-polyoxyethylene ethylene diamine block copolymers; polyoxyethylene(20) sorbitan monostearate; polyoxyethylene(20) sorbitan monooleate; polyoxypropylene-polyoxyethylene block copolymers; castor oil ethoxylate; and combinations thereof.

In some embodiments, the inhalable pharmaceutical compositions include excipients. Examples of suitable excipients include, but are not limited to: lactose, starch, propylene glycol diesters of medium chain fatty acids; triglyceride esters of medium chain fatty acids, short chains, or long chains, or any combination thereof; perfluorodimethylcyclobutane; perfluorocyclobutane; polyethylene glycol; menthol; lauroglycol; diethylene glycol monoethylether; polyglycolized glycerides of medium chain fatty acids; alcohols; eucalyptus oil; short chain fatty acids; and combinations thereof.

In some embodiments, the pharmaceutical compositions of the present disclosure comprise nasal formulations. Nasal formulations include, for instance, nasal sprays, nasal drops, nasal ointments, nasal washes, nasal injections, nasal packings, bronchial sprays and inhalers, or indirectly through use of throat lozenges, mouthwashes or gargles, or through the use of ointments applied to the nasal nares, or the face or any combination of these and similar methods of application.

In another embodiment, the pharmaceutical compositions of the present disclosure comprise a complementary agent, including one or more antimicrobial agents and/or one or more conventional antibiotics. In order to accelerate the treatment of the infection, or augment the antibacterial effect, the therapeutic agent containing the lysin-AMP polypeptides, lysin polypeptides, variants, active fragments thereof or derivatives of the present disclosure may further include at least one complementary agent that can also potentiate the bactericidal activity of the peptide. The complementary agent may be one or more antibiotics used to treat Gram-negative bacteria. In one embodiment, the complementary agent is an antibiotic or antimicrobial agent used for the treatment of infections caused by *P. aeruginosa*.

The pharmaceutical compositions of the present disclosure may be presented in unit dosage form and may be prepared by any methods well known in the art. The amount of active ingredients which can be combined with a carrier material to produce a single dosage form will vary depending upon the host being treated, the duration of exposure of the recipient to the infectious bacteria, the size and weight of the subject, and the particular mode of administration. The amount of active ingredients that can be combined with a carrier material to produce a single dosage form will generally be that amount of each compound which produces a therapeutic effect. Generally, out of one hundred percent, the total amount will range from about 1 percent to about ninety-nine percent of active ingredients, preferably from about 5 percent to about 70 percent, most preferably from about 10 percent to about 30 percent.

Dosage and Administration

Dosages administered depend on a number of factors including the activity of infection being treated, the age, health and general physical condition of the subject to be treated, the activity of a particular lysin-AMP polypeptide, lysin polypeptide, variant, active fragment thereof or derivative, the nature and activity of the antibiotic if any with which a lysin-AMP polypeptide, lysin polypeptide, variant, active fragment thereof or derivative according to the present disclosure is being paired and the combined effect of such pairing. Generally, effective amounts of the present lysin-AMP polypeptide, lysin polypeptide, variant, active fragment thereof or derivative to be administered are anticipated to fall within the range of 1-50 mg/kg (or 1 to 50 mcg/ml) administered 1-4 times daily for a period up to 14 days, e.g. about 3 mg/kg to about 30 mg/kg, in split dosages or a single dosage such as described in the examples. In some embodiments, GN370 is administered at dosages ranging from about 3 mg/ml to about 30 mg/ml. The antibiotic if one is also used will be administered at standard dosing regimens or in lower amounts in view of the synergy. All such dosages and regimens however (whether of the lysin-AMP polypeptide, lysin polypeptide, variant, active fragment thereof or derivative or any antibiotic administered in conjunction therewith) are subject to optimization. Optimal dosages can be determined by performing in vitro and in vivo pilot efficacy experiments as is within the skill of the art but taking the present disclosure into account.

It is contemplated that the present lysin-AMP polypeptides, lysin polypeptides, variants, active fragments thereof or derivatives provide a bactericidal and, when used in smaller amounts, bacteriostatic effect, and are active against a range of antibiotic-resistant bacteria and are not associated with evolving resistance. Based on the present disclosure, in a clinical setting, the present lysin-AMP polypeptides, lysin polypeptides, variants, active fragments thereof or derivatives are a potent alternative (or additive or component) of compositions for treating infections arising from drug- and multidrug-resistant bacteria alone or together with antibiotics (even antibiotics to which resistance has developed). Existing resistance mechanisms for Gram-negative bacteria should not affect sensitivity to the lytic activity of the present polypeptides.

In some embodiments, time exposure to the present lysin-AMP polypeptides, lysin polypeptides, variants, active fragments thereof or derivatives may influence the desired concentration of active polypeptide units per ml. Carriers that are classified as "long" or "slow" release carriers (such as, for example, certain nasal sprays or lozenges) could possess or provide a lower concentration of polypeptide units per ml, but over a longer period of time, whereas a "short" or "fast" release carrier (such as, for example, a gargle) could possess or provide a high concentration polypeptide units (mcg) per ml, but over a shorter period of time. There are circumstances where it may be necessary to have a much higher unit/ml dosage or a lower unit/ml dosage.

For any polypeptide of the present disclosure, the therapeutically effective dose can be estimated initially either in cell culture assays or in animal models, usually mice, rabbits, dogs, or pigs. The animal model can also be used to achieve a desirable concentration range and route of administration. Obtained information can then be used to determine the effective doses, as well as routes of administration in humans. Dosage and administration can be further adjusted to provide sufficient levels of the active ingredient or to maintain the desired effect. Additional factors which may be taken into account include the severity of the disease state, age, weight and gender of the patient; diet, desired duration of treatment, method of administration, time and frequency of administration, drug combination(s), reaction sensitivities, and tolerance/response to therapy and the judgment of the treating physician.

A treatment regimen can entail daily administration (e.g., once, twice, thrice, etc. daily), every other day (e.g., once, twice, thrice, etc. every other day), semi-weekly, weekly, once every two weeks, once a month, etc. In one embodiment, treatment can be given as a continuous infusion. Unit doses can be administered on multiple occasions. Intervals can also be irregular as indicated by monitoring clinical symptoms. Alternatively, the unit dose can be administered as a sustained release formulation, in which case less frequent administration is required. Dosage and frequency may vary depending on the patient. It will be understood by one of skill in the art that such guidelines will be adjusted for localized administration, e.g. intranasal, inhalation, rectal, etc., or for systemic administration, e.g. oral, rectal (e.g., via enema), i.m. (intramuscular), i.p. (intraperitoneal), i.v. (intravenous), s.c. (subcutaneous), transurethral, and the like.

Methods

In another aspect, the present disclosure is directed to a method of treating a bacterial infection caused by Gram-negative bacteria such as *P. aeruginosa* as described herein, comprising administering to a subject diagnosed with, at risk for, or exhibiting symptoms of a bacterial infection, a pharmaceutical composition as herein described. In one aspect, the bacterial infection is an infection of an organ or tissue in which pulmonary surfactant is present.

The terms "infection" and "bacterial infection" are meant to include respiratory tract infections (RTIs), such as respiratory tract infections in patients having cystic fibrosis (CF), lower respiratory tract infections, such as acute exacerbation of chronic bronchitis (ACEB), acute sinusitis, community-acquired pneumonia (CAP), hospital-acquired pneumonia (HAP), ventilator-associated pneumonia (VAP) and nosocomial respiratory tract infections; sexually transmitted diseases, such as gonococcal cervicitis and gonococcal urethritis; urinary tract infections; acute otitis media; sepsis including neonatal septisemia and catheter-related sepsis; and osteomyelitis. Infections caused by drug-resistant bacteria and multidrug-resistant bacteria are also contemplated.

Non-limiting examples of infections caused by *P. aeruginosa* include: A) Nosocomial infections: 1. Respiratory tract infections especially in cystic fibrosis patients and mechanically-ventilated patients; 2. Bacteraemia and sepsis; 3. Wound infections, particularly those of burn victims; 4. Urinary tract infections; 5. Post-surgery infections on invasive devises; 6. Endocarditis by intravenous administration of contaminated drug solutions; 7. Infections in patients with acquired immunodeficiency syndrome, cancer chemotherapy, steroid therapy, hematological malignancies, organ transplantation, renal replacement therapy, and other conditions with severe neutropenia. B) Community-acquired infections: 1. Community-acquired respiratory tract infections; 2. Meningitis; 3. Folliculitis and infections of the ear canal caused by contaminated water; 4. Malignant otitis externa in the elderly and diabetics; 5. Osteomyelitis of the caleaneus in children; 6. Eye infections commonly associated with contaminated contact lens; 7. Skin infections such as nail infections in people whose hands are frequently exposed to water; 8. Gastrointestinal tract infections; and 9. Muscoskeletal system infections.

In some embodiments, the Gram-negative bacteria of the present methods include *Achromobacter* spp., such as *Achromobacter xylosoxidans, Acinetobacter baumannii, Acinetobacter haemolyticus, Actinobacillus actinomycetemcomitans, Aeromonas hydrophila, Bacteroides* spp., such as, *Bacteroides fragilis, Bacteroides theataioatamicron, Bacteroides distasonis, Bacteroides ovatus, Bacteroides vulgatus, Bartonella Quintana, Bartonella hensenae, Bordetella pertussis, Brucella* spp., such as, *Brucella melitensis, Brucella abortus, Burkholderia* spp, such as, *Burkholderia cepacia, Burkholderia pseudomallei,* and *Burkholderia mallei, Campylobacter jejuni, Campylobacter fetus, Campylobacter coli, Chlamydia* spp., such as *Chlamydia psittaci, Chlamydia pneumoniae* and *Chlamydia trachomatis, Citrobacter freundii, Citrobacter koseri, Coxiella burnetii, Edwarsiella* spp., such as, *Edwarsiella tarda, Ehrlichia chafeensis, Eikenella corrodens, Enterobacter* spp., such as, *Enterobacter cloacae, Enterobacter aerogenes,* and *Enterobacter agglomerans, Escherichia coli, Francisella tularensis, Fusobacterium, Haemophilus influenzae, Haemophilus ducreyi, Helicobacter pylori, Kingella kingae, Klebsiella* spp., such as, *Klebsiella pneumoniae, Klebsiella oxytoca, Klebsiella rhinoscleromatis,* and *Klebsiella ozaenae, Legionella penumophila, Moraxella* spp., such as, *Moraxella catarrhalis, Morganella* spp., such as, *Morganella morganii, Neisseria gonorrhoeae, Neisseria meningitidis, Pandorea apista, Pseudomonas aeruginosa, Pasteurella multocida, Plesiomonas shigelloides, Prevotella corporis, Prevotella intermedia, Prevotella endodontalis, Porphyromonas asaccharolytica, Proteus mirabilis, Proteus vulgaris, Proteus penneri, Proteus myxofaciens, Providencia* spp., such as, *Providencia stuartii, Providencia rettgeri, Providencia alcalifaciens, Pseudomonas fluorescens, Ralstonia* spp., such as *Ralstonia mannitolilytica, Ricketsia prowazekii, Salmonella typhi, Salmonella typhimurium, Salmonella paratyphi, Serratia* spp., such as, *Serratia marcescens, Shigella* spp., such as, *Shigella flexneri, Shigella boydii, Shigella sonnei,* and *Shigella dysenteriae, Stenotrophomonas maltophilia, Streptobacillus moniliformis, Vibrio cholerae,*

*Vibrio parahaemolyticus, Vibrio vulnificus, Vibrio alginolyticus, Yersinia enterocolitica, Yersinia pestis,* and/or *Yersinia pseudotuberculosis.*

More typically, the Gram-negative bacteria of the present disclosure is selected from one or more of *Acinetobacter baumannii, Bordetella pertussis, Burkholderia cepacia, Burkholderia pseudomallei, Burkholderia mallei, Campylobacter jejuni, Campylobacter coli, Enterobacter cloacae, Enterobacter aerogenes, Escherichia coli, Francisella tularensis, Haemophilus influenzae, Haemophilus ducreyi, Helicobacter pylori, Klebsiella pneumoniae, Legionella pneumophila, Moraxella catarrhalis, Morganella morganii, Neisseria gonorrhoeae, Neisseria meningitidis, Pasteurella multocida, Proteus mirabilis, Proteus vulgaris, Salmonella typhi, Serratia marcescens, Shigella flexneri, Shigella boydii, Shigella sonnei, Shigella dysenteriae, Stentrophomonas maltophilia, Vibrio cholerae,* and/or *Chlamydia pneumoniae.*

Even more typically, the at least one other species of Gram-negative bacteria is selected from one or more of *Salmonella typhimurium, Salmonella typhi, Shigella* spp., *Escherichia coli, Acinetobacter baumanii, Klebsiella pneumonia, Neisseria gonorrhoeae, Neisseria meningitides, Serratia* spp. *Proteus mirabilis, Morganella morganii, Providencia* spp., *Edwardsiella* spp., *Yersinia* spp., *Haemophilus influenza, Bartonella quintana, Brucella* spp., *Bordetella pertussis, Burkholderia* spp., *Moraxella* spp., *Francisella tularensis, Legionella pneumophila, Coxiella burnetii, Bacteroides* spp., *Enterobacter* spp., and/or *Chlamydia* spp.

Yet even more typically, the one or more additional species of Gram-negative bacteria are *Klebsiella* spp., *Enterobacter* spp., *Escherichia coli, Citrobacter freundii, Salmonella typhimurium, Yersinia pestis,* and/or *Francisella tulerensis.*

In yet other embodiments, the Gram-negative bacteria include *Brucella* spp., such as, *Brucella melitensis, Brucella abortus, Burkholderia* spp, such as, *Burkholderia cepacia, Burkholderia pseudomallei,* and *Burkholderia mallei, Coxiella burnetii, Francisella tularensis* and *Yersinia pestis.*

In some embodiments, infection with Gram-negative bacteria results in a localized infection, such as a topical bacterial infection, e.g., a skin wound. In other embodiments, the bacterial infection is a systemic pathogenic bacterial infection. Common Gram-negative pathogens and associated infections are listed in Table 2 of the present disclosure. These are meant to serve as examples of the bacterial infections that may be treated, mitigated or prevented with the present lysins, active fragments thereof and lysin-AMP polypeptide constructs and are not intended to be limiting.

TABLE 2

Medically relevant Gram-negative bacteria and associated diseases.

| | |
|---|---|
| *Salmonella typhimurium* | Gastrointestinal (GI) infections-salmonellosis |
| *Shigella* spp. | shigellosis |
| *Escherichia coli* | Urinary tract infections (UTIs) |
| *Acinetobacter baumanii* | Wound infections |
| *Pseudomonas aeruginosa* | bloodstream infections and pneumonia |
| *Klebsiella pneumoniae* | UTIs, and bloodstream infections |
| *Neisseria gonorrhoeae* | Sexually transmitted disease (STD)-gonorrhea |
| *Neisseria meningitides* | Meningitis |
| *Serratia* spp. | Catheter contaminations, UTIs, and pneumonia |
| *Proteus mirabilis* | UTIs |
| *Morganella* spp. | UTIs |
| *Providencia* spp. | UTIs |
| *Edwardsiella* spp | UTIs |
| *Salmonella typhi* | GI infections-typhoid fever |
| *Yersinia pestis* | Bubonic and pneumonic plague |
| *Yersinia enterocolitica* | GI infections |
| *Yersinia pseudotuberculosis* | GI infections |
| *Haemophilus influenza* | Meningitis |
| *Bartonella Quintana* | Trench fever |
| *Brucella* spp. | Brucellosis |
| *Bordetella pertussis* | Respiratory-Whooping cough |
| *Burkholderia* spp. | Respiratory |
| *Moraxella* spp. | Respiratory |
| *Francisella tularensis* | Tularemia |
| *Legionella pneumophila* | Respiratory-Legionnaires' disease |
| *Coxiella burnetiid* | Q fever |
| *Bacteroides* spp. | Abdominal infections |
| *Enterobacter* spp. | UTis and respiratory |
| *Chlamydia* spp. | STDs, respiratory, and ocular |
| *Escherichia coli, Klebsiella pneumoniae, Acinetobacter* spp., *Proteus mirabilis* and/or *Pseudomonas aeruginosa* | Infections of implants, catheters, prosthetic joints and other medical devices |

In some embodiments, the lysin-AMP polypeptides, such as GN370 (SEQ ID NO: 44), lysin polypeptides, variants, active fragments thereof or derivatives of the present disclosure are used to treat a subject at risk for acquiring an infection due to *P. aeruginosa* and/or another Gram-negative bacterium. Subjects at risk for acquiring a *P. aeruginosa* or other Gram-negative bacterial infection include, for example, cystic fibrosis patients, neutropenic patients, patients with necrotising enterocolitis, burn victims, patients with wound infections, and, more generally, patients in a hospital setting, in particular surgical patients and patients being treated using an implantable medical device such as a catheter, for example a central venous catheter, a Hickman device, or electrophysiologic cardiac devices, for example pacemakers and implantable defibrillators. Other patient groups at risk for infection with Gram-negative bacteria including *P. aeruginosa* include without limitation patients with implanted prostheses such a total joint replacement (for example total knee or hip replacement).

In another aspect, the present disclosure is directed to a method of preventing or treating a bacterial infection comprising co-administering to a subject diagnosed with, at risk for, or exhibiting symptoms of a bacterial infection, a combination of a first effective amount of the composition containing an effective amount of a lysin-AMP polypeptide, such as GN370 (SEQ ID NO: 44), lysin polypeptide, variant, active fragment thereof or derivative as described herein, and a second effective amount of an antibiotic suitable for the treatment of Gram-negative bacterial infection.

The lysin-AMP polypeptides, such as GN370 (SEQ ID NO: 44), lysin polypeptides, variants, active fragments thereof or derivatives of the present disclosure can be co-administered with standard of care antibiotics or with antibiotics of last resort, individually or in various combinations as within the skill of the art. Traditional antibiotics used against *P. aeruginosa* are described in Table 3. Antibiotics for other Gram-negative bacteria, such as *Klebsiella* spp., *Enterobacter* spp., *Escherichia coli, Citrobacter freundii, Salmonella typhimurium, Yersinia pestis*, and *Franciscella tulerensis*, are similar to that provided in Table 3 for *P. aeruginosa*.

TABLE 3

Antibiotics used for the treatment of *Pseudomonas aeruginosa*

| Class | Agent |
| --- | --- |
| Penicillins | Ticarcillin-clavulanate |
|  | Piperacillin-tazobactam |
| Cephalosporins | Ceftazidime |
|  | Cefepime |
|  | Cefoperazone |
| Monobactams | Aztreonam |
| Fluoroquinolones | Ciprofloxacin |
|  | Levofloxacin |
| Carbapemens | Imipenem |
|  | Meropenem |
|  | Doripenem |
| Aminoglycosides | Gentamicin |
|  | Tobramycin |
|  | Amikacin |
| Polymixins | Colistin |
|  | Polymixin B |
| Macrolides | Azithromycin |
| Rifamycin | Rifampicin |
| Fosfomycin | Fosfomycin |

In more specific embodiments, the antibiotic is selected from one or more of ceftazidime, cefepime, cefoperazone, ceftobiprole, ciprofloxacin, levofloxacin, aminoglycosides, imipenem, meropenem, doripenem, gentamicin, tobramycin, amikacin, piperacillin, ticarcillin, penicillin, rifampicin, polymyxin B and colistin. In certain embodiments, the antibiotic is meropenem.

Combining lysin-AMP polypeptides, such as GN370 (SEQ ID NO: 44), lysin polypeptides, variants, active fragments thereof or derivatives of the present disclosure with antibiotics provides an efficacious antibacterial regimen. In some embodiments, the lysin-AMP polypeptides of the disclosure, such as GN370, exhibit synergy when combined with standard of care antibiotics.

In some embodiments, co-administration of lysin-AMP polypeptides, lysin polypeptides, variants, active fragments thereof or derivatives of the present disclosure with one or more antibiotics may be carried out at reduced doses and amounts of either the lysin-AMP polypeptides, lysin polypeptides, variants, active fragments thereof or derivatives or the antibiotic or both, and/or reduced frequency and/or duration of treatment with augmented bactericidal and bacteriostatic activity, reduced risk of antibiotic resistance and with reduced risk of deleterious neurological or renal side effects (such as those associated with colistin or polymyxin B use). Prior studies have shown that total cumulative colistin dose is associated with kidney damage, suggesting that decrease in dosage or shortening of treatment duration using the combination therapy with lysin-AMP polypeptides, lysin polypeptides, variants, active fragments thereof or derivatives could decrease the incidence of nephrotoxicity (Spapen et al. *Ann Intensive Care*. 1: 14 (2011), which is herein incorporated by reference in its entirety). As used herein the term "reduced dose" refers to the dose of one active ingredient in the combination compared to monotherapy with the same active ingredient. In some embodiments, the dose of the lysins, active fragments thereof and lysin-AMP polypeptide constructs or the antibiotic in a combination may be suboptimal or even subthreshold compared to the respective monotherapy.

In some embodiments, the present disclosure provides a method of augmenting antibiotic activity of one or more antibiotics against Gram-negative bacteria compared to the activity of said antibiotics used alone by administering to a subject one or more lysin-AMP polypeptides, such as GN370 (SEQ ID NO: 44), lysin polypeptides, variants, active fragments thereof or derivatives disclosed herein together with an antibiotic of interest. The combination is effective against the bacteria and permits resistance against the antibiotic to be overcome and/or the antibiotic to be employed at lower doses, decreasing undesirable side effects, such as the nephrotoxic and neurotoxic effects of polymyxin B.

The lysin-AMP polypeptides, such as GN370 (SEQ ID NO: 44), lysin polypeptides, variants, active fragments thereof or derivatives optionally in combination with antibiotics of the present disclosure can be further combined with additional permeabilizing agents of the outer membrane of the Gram-negative bacteria, including, but not limited to metal chelators, such as e.g. EDTA, TRIS, lactic acid, lactoferrin, polymyxins, citric acid (Vaara M. *Microbial Rev.* 56(3):395-441 (1992), which is herein incorporated by reference in its entirety).

In yet another aspect, the present disclosure is directed to a method of inhibiting the growth, or reducing the population, or killing of at least one species of Gram-negative bacteria, the method comprising contacting the bacteria with a composition containing an effective amount of lysin-AMP polypeptides, such as GN370 (SEQ ID NO: 44), lysin polypeptides, variants, active fragments thereof or derivatives as described herein, wherein the lysin-AMP polypeptides, lysin polypeptides, variants, active fragments thereof or derivatives inhibits the growth, or reduces the population, or kills *P. aeruginosa* and optionally at least one other species of Gram-negative bacteria.

In some embodiments, inhibiting the growth, or reducing the population, or killing at least one species of Gram-negative bacteria comprises contacting bacteria with the lysins, active fragments thereof and/or lysin-AMP polypeptide constructs such as GN370 (SEQ ID NO: 44), as described herein, wherein the bacteria are present on a surface of e.g., medical devices, floors, stairs, walls and countertops in hospitals and other health related or public use buildings and surfaces of equipment in operating rooms, emergency rooms, hospital rooms, clinics, and bathrooms and the like.

Examples of medical devices that can be protected using the lysin-AMP polypeptides, such as GN370 (SEQ ID NO: 44), lysin polypeptides, variants, active fragments thereof or derivatives described herein include but are not limited to tubing and other surface medical devices, such as urinary catheters, mucous extraction catheters, suction catheters, umbilical cannulae, contact lenses, intrauterine devices, intravaginal and intraintestinal devices, endotracheal tubes, bronchoscopes, dental prostheses and orthodontic devices, surgical instruments, dental instruments, tubings, dental water lines, fabrics, paper, indicator strips (e.g., paper indicator strips or plastic indicator strips), adhesives (e.g., hydrogel adhesives, hot-melt adhesives, or solvent-based adhesives), bandages, tissue dressings or healing devices and occlusive patches, and any other surface devices used in the medical field. The devices may include electrodes, external prostheses, fixation tapes, compression bandages, and monitors of various types. Medical devices can also include any device which can be placed at the insertion or implantation site such as the skin near the insertion or implantation site, and which can include at least one surface which is susceptible to colonization by Gram-negative bacteria.

The lysin-AMP polypeptides, such as GN370 (SEQ ID NO: 44), lysin polypeptides, variants, active fragments thereof or derivatives of the present disclosure, which can be used in vivo or in vitro as described herein may also be used to treat bacterial infections due to Gram-negative bacteria, such as *P. aeruginosa*, that are associated with biofilm formation.

For example, in some embodiments, the present lysin-AMP polypeptides, such as GN370 (SEQ ID NO: 44), lysin polypeptides, variants, active fragments thereof or derivatives may be used for the prevention, control, disruption, and/or eradication of bacterial biofilm formed by Gram-negative bacteria, such as *P. aeruginosa*. Biofilm formation occurs when microbial cells adhere to each other and are embedded in a matrix of extracellular polymeric substance (EPS) on a surface. The growth of microbes in such a protected environment that is enriched with biomacromolecules (e.g. polysaccharides, nucleic acids and proteins) and nutrients allows for enhanced microbial cross-talk and increased virulence. Biofilm may develop in any supporting environment including living and nonliving surfaces such as the mucus plugs of the CF lung, contaminated catheters, contact lenses, etc (Sharma et al. Biologicals, 42(1):1-7 (2014), which is herein incorporated by reference in its entirety). Thus, in one embodiment, the lysin-AMP polypeptides, lysin polypeptides, variants, active fragments thereof or derivatives of the present disclosure can be used for the prevention, control, disruption, eradication and treatment of bacterial infections due to Gram-negative bacteria, such as *P. aeruginosa*, when the bacteria are protected by a bacterial biofilm.

More particularly, in some aspects, the present disclosure is directed to a method for prevention, disruption or eradication of a Gram-negative bacterial biofilm comprising contacting a surface, including a biotic or abiotic surface, with a composition comprising a lysin-AMP polypeptide, such as GN370 (SEQ ID NO: 44), lysin polypeptide, variant, active fragment thereof or derivative of the present disclosure effective to kill Gram negative bacteria, wherein a biofilm is effectively prevented, disrupted or eradicated.

In some aspects, the present disclosure is directed to a method for prevention, disruption or eradication of a Gram-negative bacterial biofilm comprising administering a composition to a subject in need thereof, wherein the composition comprises a lysin-AMP polypeptide, such as GN370 (SEQ ID NO: 44), lysin polypeptide, variant, active fragment thereof or derivative of the present disclosure effective to kill Gram negative bacteria on a surface, wherein a biofilm is effectively prevented, disrupted or eradicated.

In some embodiments, the surface is a biotic surface, such as a solid biological surface, e.g., skin. In other embodiments, the surface is a non-biotic surface. In some embodiments, the surface is a surface of a medical device such as contact lenses; drug pumps, implants, including dental implants, cardiac implants such as pacemakers, prosthetic heart valves, ventricular assist devices, synthetic vascular grafts and stents; catheters including peritoneal dialysis catheters, indwelling catheters for hemodialysis and for chronic administration of chemotherapeutic agents (Hickman catheters), urinary catheters and prosthetic devices including urinary tract prostheses, prosthetic joints; orthopedic material; and tracheal and ventilator tubing.

In some embodiments, the subject is suffering from a Gram-negative bacterial infection associated with a biofilm. Such bacterial infections include tonsillitis, osteomyelitis, bacterial endocarditis, sinusitis, infections of the cornea, urinary tract infection, infection of the biliary tract, infectious kidney stones, urethritis, prostatitis, middle-ear infections, formation of dental plaque, gingivitis, periodontitis, cystic fibrosis, wound infections, in particular wounds associated with diabetes mellitus, and infections of medical devices as described herein including catheter infections and infections of joint prostheses and heart valves.

In some embodiments, the composition for treating biofilm infections comprises one or more antibiotics as described herein. In other embodiments, the present lysins or active fragments thereof or variants or derivatives thereof as described herein are administered to a subject and/or contacted to a surface simultaneously with one or more antibiotics as herein described. In other embodiments, a lysin-AMP polypeptide, lysin polypeptide, variant, active fragment thereof or derivative of the present disclosure and the one or more antibiotics as described herein are administered to a subject and/or contacted to a surface sequentially in any order. In some embodiments, the present lysin-AMP polypeptides, lysin polypeptides, variants, active fragments thereof or derivatives of the present disclosure and the one or more antibiotics as described herein may be administered to a subject and/or contacted to a surface in a single dose or multiple doses, singly or in combination.

In some embodiments, the present composition is used to prevent biofilm formation. In these embodiments, the contacted surface may contain a biofilm, may not contain a biofilm, or contains only de minimus amounts of an established biofilm. In some embodiments, de novo biofilm formation on the surface is prevented according to any mechanisms as described herein.

In some embodiments, the contacted surface comprises a biofilm and the biofilm is disrupted or eradicated. In some embodiments, eradication comprises killing bacteria in the biofilm, including persister bacteria. In other embodiments, the present lysin-AMP polypeptides, lysin polypeptides, variants, active fragments thereof or derivatives of the present disclosure not only kill bacteria within a biofilm, thus eradicating the biofilm, but also disrupt or destroy the biofilm matrix. This ability is advantageous since matrices, even in the absence of live bacteria, often become quickly re-infected.

EXAMPLES

Example 1. Activity of Gram-Negative (GN) Lysins and Lysin-AMP Polypeptide Constructs in Medium Supplemented with Human Serum Materials and Methods Gram-negative bacteria, e.g., *P. aeruginosa*, were cultured and tested in casamino acid (CAA) media (5 g/L casamino acids, Ameresco/VWR; 5.2 mM $K_2HPO_4$, Sigma-Aldrich, Inc., St. Louis, Mo.; 1 mM MgSO4, Sigma-Aldrich) supplemented with 150 mM NaCl, 2.5% human serum or 25% human serum (Type AB, male human serum, pooled from Sigma-Aldrich, Inc., referred to herein as CAA-HuS).

Determination of Minimal Inhibitory Concentrations (MIC)

MIC values were determined using a modification of the standard broth microdilution reference method defined by the Clinical and Laboratory Standards Institute (CLSI), CLSI. 2015. Methods for Dilution Antimicrobial Susceptibility Tests for Bacteria That Grow Aerobically; Approved Standard-10th Edition. Clinical and Laboratory Standards Institute, Wayne, Pa. The modification was based on the replacement of Mueller Hinton Broth with CAA medium (with or without NaCl), supplemented with 2.5% human serum (Table 4) or 25% human serum (Table 5). MIC is the minimum concentration of lysin sufficient to suppress at least 80% of bacterial growth compared to control.

Results

Table 4 provides the molecular weight and isoelectric point of the GN lysin polypeptides. By comparing the sequences and components of the various polypeptides, the effect of a particular structural modification on isoelectric point (a higher pI favors outer membrane penetration) and activity (as assessed by MIC) can be determined.

For example, Table 4 shows the effects of single point mutations on GN316 (SEQ ID NO: 22). GN394 (SEQ ID NO: 48) has a lower pI and a higher activity in CAA but a lower activity in CAA with human serum. The activity reduction in human serum is less for GN396 (SEQ ID NO: 50), whereas GN408 (SEQ ID NO: 52) is substantially more potent both in the presence and absence of human serum. On the other hand, GN418 (SEQ ID NO: 54) loses activity in unsupplemented CAA media but gains potency in the presence of human serum.

The single point mutation in GN217 (SEQ ID NO: 8) improves its potency over GN37 both in the absence and presence of human serum. The modifications to GN37 (SEQ ID NO: 84) yielding GN218 (SEQ ID NO: 10), GN223 (SEQ ID NO: 12), GN239 (SEQ ID NO: 14) and GN243 (SEQ ID NO: 16) result in very strong activity in the presence of human serum. Similar observations can be made based on comparison of the sequence and components of other polypeptides.

Table 5 shows that additional selected lysins including GN178, GN122, GN76, GN218, GN11, GN75, GN14, GN93, GN328, GN7 and GN316 were active in CAA supplemented with human serum (25%) when tested against the carbepenam-resistant clinical isolate WC-453. In contrast, the activity of GN83 (and the control T4 lysozyme and control artilysin GN126) was repressed in this medium.

Example 2. Activity of GN Lysins and Lysin-AMP Polypeptide Constructs in the Presence of Divalent Cations The activity of selected GN lysins and constructs in the presence of divalent cations was evaluated, and the impact of divalent cations at physiological concentrations was examined in the MIC assay format. Fold changes in MIC were measured in the presence of various cation concentrations (1.25 mM $CaCl_2$, 1.25 mM $CaCl_2$, 0.25 mM $CaCl_2$, 1.5 mM $MgCl_2$, 0.78 mM $MgCl_2$, 0.15 mM $MgCl_2$, and a combination of 1.25 mM $CaCl_2$ and 0.78 mM $MgCl_2$) supplemented into 25% CAA medium. The results are shown below in Table 6. It is noted that 25% CAA typically has 0.25 nM $MgSO_4$. *Pseudomonas aeruginosa* strain CFS-1292 (meropenem resistant) was used as the reporter strain. It was concluded that the GN lysins and constructs tested are active in the presence of physiological levels of calcium and magnesium.

TABLE 4

Sensitivity of selected lysins or selected lysin-AMP polypeptide constructs in human serum (2.5%).

| GN # | MW | pI | CAA MIC (mg/mL) | CAA/HuS MIC (mg/mL) |
|---|---|---|---|---|
| GN168 (SEQ ID NO: 2) | 22299.78 | 11.6 | 8 | N.D. |
| GN176 (SEQ ID NO: 4) | 19370 | 9.8 | 8 | N.D. |
| GN178 (SEQ ID NO: 6) | 19290.04 | 9.7 | 8 | 4 |
| GN217 (SEQ ID NO: 8) | 13879.91 | 9.4 | 4 | 0.125 |
| GN218 (SEQ ID NO: 10) | 16038.43 | 9.8 | 8 | 1 |
| GN223 (SEQ ID NO: 12) | 18570.35 | 10.3 | 32 | 2 |
| GN239 (SEQ ID NO: 14) | 16836.42 | 10.2 | 4 | 0.25 |
| GN243 (SEQ ID NO; 16) | 18880.02 | 10.5 | 32 | 0.5 |
| GN280 (SEQ ID NO: 18) | 17928.9 | 10.2 | 4 | 0.5 |
| GN281 (SEQ ID NO: 20) | 18188.07 | 10.2 | 2 | 0.5 |
| GN316 (SEQ ID NO: 22) | 28672.72 | 8.7 | 16 | 0.125 |
| GN329 (SEQ ID NO: 26) | 20810.83 | 8.9 | 4 | 0.25 |
| GN333 (SEQ ID NO: 28) | 20918.79 | 8.9 | 8 | 0.06 |
| GN349 (SEQ ID NO: 30) | 34169.19 | 9.5 | 16 | 1 |
| GN351 (SEQ ID NO: 32) | 33866.76 | 9.9 | 8 | 0.125 |

TABLE 4-continued

Sensitivity of selected lysins or selected lysin-AMP polypeptide constructs in human serum (2.5%).

| GN # | MW | pI | CAA MIC (mg/mL) | CAA/HuS MIC (mg/mL) |
|---|---|---|---|---|
| GN352 (SEQ ID NO: 34) | 33398.27 | 8.9 | 4 | 0.5 |
| GN353 (SEQ ID NO: 36) | 33485.42 | 8.9 | 4 | 0.25 |
| GN357 (SEQ ID NO: 38) | 30891.39 | 9.3 | 16 | 0.25 |
| GN359 (SEQ ID NO: 40) | 31094.67 | 8.7 | 8 | 0.25 |
| GN369 (SEQ ID NO: 42) | 30934.63 | 8.8 | 8 | 0.0625 |
| GN370 (SEQ ID NO: 44) | 19140.86 | 10.7 | 16 | 4 |
| GN371 (SEQ ID NO: 46) | 17530.95 | 8.7 | >32 | 0.5 |
| GN394 (SEQ ID NO: 48) | 28659.62 | 7.5 | 8 | 0.5 |
| GN396 (SEQ ID NO: 50) | 28659.62 | 7.5 | 8 | 0.25 |
| GN408 (SEQ ID NO: 52) | 28653.66 | 7.8 | 2 | 0.125 |
| GN418 (SEQ ID NO: 54) | 28659.62 | 7.5 | 32 | 0.06 |
| GN424 (SEQ ID NO: 56) | 29118.75 | 8.4 | N.D. | N.D. |
| GN425 (SEQ ID NO: 58) | 29895.81 | 7.5 | 2 | 0.25 |
| GN428 (SEQ ID NO: 60) | 28814.89 | 8.9 | 8 | 0.125 |
| GN93  (SEQ ID NO: 62) | 22959.07 | 9.6 | 128 | 8 |
| GN431 (SEQ ID NO: 64) | 28715.73 | 8.5 | 8 | 0.0625 |
| GN486 (SEQ ID NO: 66) | | 17.8 | 10.6 | 2 | 0.125 |
| GN485 (SEQ ID NO: 68) | | 8.312 | 9.8 | N.D | N.D. |

TABLE 5

Sensitivity of selected lysins and constructs in human serum (25%).

| Lysin | CAA | CAA/HuS |
|---|---|---|
| GN178 | 8 | 1 |
| GN83 | >128 | >128 |
| GN122 | 2 | 2 |
| GN76 | 64 | 8 |
| GN126 | 2 | 128 |
| GN218 | 8 | 1 |
| GN11 | 32 | 128 |
| GN75 | 8 | 8 |
| GN14 | >128 | 32 |
| GN93 | 128 | 8 |
| GN328 | 8 | 2 |
| GN7 | >128 | 128 |
| GN316 | 16 | <0.0625 |
| T4LZY | >128 | >128 |

Example 3. Time-Kill Assay of GN Lysins or Lysin-AMP Polypeptide Construct Activity An overnight culture of the carbepenam-resistant clinical isolate *P. aeruginosa* strain WC-453 was diluted 1:50 into fresh CAA media and grown for 2.5 hours at 37° C. with agitation. Exponential phase bacteria were then pelleted and resuspended in ⅕ culture volume of 25 mM HEPES, pH 7.4 before a final adjustment to an optical density corresponding to a McFarland value of 0.5. The adjusted culture was then diluted 1:50 into either 25 mM HEPES pH 7.4 or CAA supplemented with 25% human serum and the GN lysins were added at a final concentration of 10 μg/ml. Control cultures were included with the addition of no lysin (i.e., buffer control), GN65, GN126 or GN81. All treatments were incubated at 37° C. with aeration. At time points before the addition of lysin (or buffer control) and at 1 hour and 3 hours intervals thereafter, culture samples were removed for quantitative plating on CAA agar plates.

TABLE 6

Fold Increase (MIC) in presence of cations

| GN number | MIC in 25% CAA | 25% CAA supplemented with: | | | | | | |
|---|---|---|---|---|---|---|---|---|
| | | 2.5 mM CaCl$_2$ (high) | 1.25 mM CaCl$_2$ (medium) | 0.25 mM CaCl$_2$ (low) | 1.5 mM MgCl$_2$ (high) | 0.78 mM MgCl$_2$ (medium) | 0.15 mM MgCl$_2$ (low) | 1.25 mM CaCl$_2$ 0.78 mM MgCl$_2$ |
| | | | | MIC (μg/mL) | | | | |
| 108 | 4 | 1 | 0.5 | 0.5 | 0.5 | 0.5 | 0.5 | 2 |
| 121 | 1-2 | 2 | 1-2 | 0.5 | 1 | 1-2 | 0.5 | 2 |
| 123 | 2 | 1 | 1 | 1 | 1 | 1 | 1 | 1 |
| 156 | 2 | 1 | 2 | 2 | 2 | 2 | 2 | 2 |
| 316 | 4 | 1 | 1 | 1 | 1 | 1 | 1 | 1 |
| 329 | 4 | 0.5 | 0.25 | 1 | 0.5 | 0.5 | 0.5 | 2 |
| 333 | 8 | 1 | 1 | 4 | 1 | 1 | 1 | 4 |
| 351 | 1 | 1 | 1-2 | 0.5 | 2 | 1-2 | 0.25 | 2 |
| 357 | 4 | 1 | 1 | 0.5 | 1 | 1 | 1 | 0.5 |
| 428 | 4 | 1 | 1-2 | 1 | 1 | 1-4 | 1 | 1-4 |
| 370 | 4 | 1 | 1-4 | 0.5 | 1 | 1-2 | 1 | 1-4 |
| 431 | 2 | 1 | 1 | 2 | n.d. | 1 | 1 | 1 |

As shown in Tables 7 and 8, below, bactericidal activity was observed for the majority of GN lysins tested in HEPES (Table 7) and CAA/HuS (Table 8) in the time-kill format, as defined by a CFU decrease of 3-$Log_{10}$, 3 hours after the addition of lysin. For CAA/HuS, Table 8 shows that GN83, GN121, GN75, GN14, GN76, GN93, GN316, GN329, GN333, GN351, GN357, GN428, GN370 and GN431 each demonstrated bactericidal activity at a 3-hour time point after addition at a concentration of 10 µg/mL.

TABLE 7

HEPES ($Log_{10}$ CFU/mL)

| GN | 1 hr | 3 hr |
|---|---|---|
| 83 | <3.7 | <3.7 |
| 121 | <3.7 | <3.7 |
| 75 | 5.7 | <3.7 |
| 65 | 5.7 | <3.7 |
| 126 | <3.7 | <3.7 |
| 7 | 7.5 | 6.2 |
| 11 | 6.7 | <3.7 |
| 14 | <3.7 | <3.7 |
| 40 | 7.0 | 5.7 |
| 43 | 6.4 | <3.7 |
| 76 | <3.7 | <3.7 |
| 80 | 7.7 | 6.7 |
| 93 | 6.0 | <3.7 |
| 122 | 7.7 | 5.4 |
| 81 | 7.4 | 6.5 |
| Blank | 7.7 | 7.2 |

TABLE 8

CAA/HuS ($Log_{10}$ CFU/mL)

| GN | 1 hr. | 3 hr |
|---|---|---|
| 83 | 5.7 | <3.7 |
| 121 | 7.6 | <3.7 |
| 75 | 5.9 | <3.7 |
| 65 | 6.0 | <3.7 |
| 126 | 6.6 | <3.7 |
| 7 | 7.0 | 7.0 |
| 14 | 5.7 | <3.7 |
| 40 | 6.6 | 6.7 |
| 43 | 6.9 | 7.0 |
| 76 | 5.7 | <3.7 |
| 80 | 6.7 | 7.0 |
| 93 | 6.6 | <3.7 |
| 122 | 6.7 | 6.7 |
| 81 | 6.7 | 7.0 |
| 316 | 5.1 | <3.7 |
| 329 | 4.4 | <3.7 |
| 333 | 4.9 | <3.7 |
| 351 | 4.6 | <3.7 |
| 357 | 5.0 | <3.7 |
| 428 | 5.5 | <3.7 |
| 370 | 4.0 | <3.7 |
| 431 | 5.8 | <3.7 |
| Blank | 7.7 | 7.2 |

Example 4. Selected Lysins and Constructs have Potent Antibiofilm Activity

Disruption of biofilms formed by *P. aeruginosa* strain ATCC 17646 was examined in the Minimal Biofilm Eradicating Concentration (MBEC) assay as described herein. All of the selected lysins or selected lysin-AMP polypeptide constructs that were tested exhibited antibiofilm activity as depicted in Table 9, below. T4LYZ, GN126 and GN65 were included as controls.

TABLE 9

Antibiofilm Activity

| Lysin | MBEC (µg/mL) |
|---|---|
| GN76 | 0.125 |
| GN126 | 0.125 |
| GN83 | 1 |
| GN80 | 0.125 |
| GN93 | 0.125 |
| GN122 | 1 |
| GN217 | 0.5 |
| GN316 | 1 |
| GN329 | 0.5 |
| GN333 | 1 |
| GN351 | 1 |
| GN357 | 0.5 |
| GN428 | 1 |
| GN370 | 1 |
| GN431 | 1 |
| T4LYZ | >64 |

Example 5. Selected Lysins and Constructs are Active in Pulmonary Surfactant

Gram-negative bacteria, e.g., *P. aeruginosa*, were cultured and tested in CAA media, supplemented with a range of SURVANTA® concentrations (6.25%, 3.15%, 1.56%, 0.78%, 0.39%, 0.19% and 0.09% SURVANTA®) in the MIC assay format. 6.25% SURVANTA® corresponds to 1.5 mg/mL phospholipids. The physiological level of pulmonary surfactant in epithelial lining fluid is around 0.01 mg/mL.

Table 10 depicts the fold increases in MIC for selected GN lysins tested against *P. aeruginosa* isolate CFS-1292. As a positive control, the impact of SURVANTA® on daptomycin (DAP) activity against *Staphylococcus aureus* was also tested. The selected GN lysins and constructs were not inhibited by pulmonary surfactant over a wide range of concentrations, which are inhibitory to the activity of DAP.

TABLE 10

Activity of GN lysins over a range of SURVANTA ® concentrations

| GN | % SURVANTA ® | | | | | | |
|---|---|---|---|---|---|---|---|
| Clone* | 6.25 | 3.15 | 1.56 | 0.78 | 0.39 | 0.19 | 0.09 |
| 108 | 2 | 2 | 1 | 1 | 1 | 1 | 1 |
| 121 | 2 | 2 | 1-2 | 1-2 | 1 | 1 | 1 |
| 123 | 2 | 2 | 1 | 1 | 1 | 1 | 1 |
| 147 | 1 | 2 | 2 | 2 | 1 | 1 | 1 |
| 156 | 2 | 2 | 2 | 1 | 1 | 1 | 1 |
| 150 | 2 | 2 | 1 | 1 | 1 | 1 | 1 |
| 217 | 2 | 2 | 2 | 1 | 1 | 1 | 1 |
| 316 | 1 | 2 | 1 | 1 | 1 | 1 | 1 |
| 329 | 2 | 1 | 1 | 1 | 1 | 1 | 1 |
| 333 | 2 | 2 | 2 | 1 | 1 | 1 | 1 |
| 351 | 2 | 1-2 | 1-2 | 1 | 1 | 1 | 1 |
| 357 | 2 | 2 | 2 | 1 | 1 | 1 | 1 |
| 428 | 1 | 1-2 | 1 | 1 | 1 | 1 | 1 |
| 370 | 1-2 | 1-2 | 1-2 | 1 | 1 | 1 | 1 |
| 431 | 2 | 1 | 1 | 1 | 1 | 1 | 1 |
| DAP** | 256 | 128 | 128 | 64 | 64 | 32 | 32 |

Example 6. Further Characterization of GN121, GN351, GN370 and GN428 in Human Serum and Surfactant GN121, GN351, GN370 and GN428 were further characterized for activity in human serum and pulmonary surfactant against a range of isolates. Gram-negative bacteria, e.g., *P. aeruginosa*, were cultured and tested in CAA media supplemented with 12.5% human serum (Type AB, male, pooled; Sigma-Aldrich) or 6.25% SURVANTA® and a range of *P. aeruginosa* isolates were evaluated using the MIC assay. 6.25% SURVANTA® corresponds to 1.5 mg/mL phospholipids.

Tables 11 and 12 show that GN121, GN351, GN370 and GN428 are active against a variety of *P. aeruginosa* isolates in human serum (Table 11) or SURVANTA® (Table 12). GN121, GN351, GN370 and GN428 demonstrated greater or comparable activity to that of the antibiotic meropenem in either human serum or SURVANTA®. As evident in Tables 11 and 12, the MIC values for the selected lysins ranged from 0.5 to 4 mg/mL (Table 11) or 0.5 to 2 mg/mL (Table 12). In contrast, the MIC values for meropenem were 32 mg/mL or greater against certain *P. aeruginosa* isolates, e.g., CFS 1559.

TABLE 11

Activity in human serum

| P. aeruginosa Strain | Meropenem MIC (µg/mL) | CAA + 12.5% Human Serum MIC (µg/mL) | | | |
| --- | --- | --- | --- | --- | --- |
| | | GN121 | GN351 | GN370 | GN428 |
| CFS 1292 | 32 | 1 | 1 | 2 | 2 |
| CFS 1557 (PA19) | 32 | 2 | 4 | 4 | 4 |
| CFS 1558 (PA20) | 16 | 0.5 | 1 | 0.5 | 2 |
| CFS 1559 (PA21) | >32 | 1 | 2 | 2 | 2 |
| CFS 1560 (PA22) | 16 | 1 | 2 | 2 | 2 |
| CFS 1561 (PA23) | 16 | 1 | 2 | 2 | 2 |
| CFS 1562 (PA24) | >32 | 1 | 2 | 2 | 2 |
| CFS 1766 (ATCC 27853) | 1 | 2 | 2 | 4 | 4 |
| CFS 1539 (PA1) | 16 | 0.5 | 0.5 | 1 | 1 |
| CFS 1540 (PA2) | 16 | 0.5 | 0.5 | 1 | 1 |
| CFS 1541 (PA3) | 8 | 0.5 | 0.5 | 1 | 1 |
| CFS 1596 (PA26) | 0.5 | 0.5 | 1 | 1 | 1 |
| CFS 1597 (PA27) | 1 | 0.5 | 0.5 | 0.5 | 0.5 |
| CFS 1669 (PA41) | <0.25 | 1 | 1 | 2 | 2 |
| CFS 1674 (PA46) | 4 | 0.5 | 1 | 2 | 2 |
| CFS 1675 (PA47) | 4 | 0.5 | 0.5 | 1 | 1 |
| CFS 1109 (ATCC 17646) | 0.5 | 0.5 | 1 | 1 | 1 |

TABLE 12

Activity in pulmonary surfactant (SURVANTA ®)

| P. aeruginosa Strain | Fold change in MIC for CAA + 6.25% Human Serum | | | |
| --- | --- | --- | --- | --- |
| | GN121 | GN351 | GN370 | GN428 |
| CFS 1292 | 1 | 2 | 1 | 1 |
| CFS 1557 (PA19) | 2 | 1 | 0.5 | 0.5 |
| CFS 1558 (PA20) | 2 | 2 | 1 | 1 |
| CFS 1559 (PA21) | 2 | 2 | 1 | 1 |
| CFS 1560 (PA22) | 2 | 2 | 1 | 1 |
| CFS 1561 (PA23) | 1 | 1 | 1 | 1 |
| CFS 1562 (PA24) | 2 | 1 | 0.5 | 1 |
| CFS 1766 (ATCC 27853) | 1 | 1 | 1 | 2 |
| CFS 1539 (PA1) | 1 | 1 | 0.5 | 0.5 |
| CFS 1540 (PA2) | 1 | 1 | 1 | 1 |
| CFS 1541 (PA3) | 2 | 2 | 1 | 1 |
| CFS 1596 (PA26) | 2 | 2 | 1 | 1 |
| CFS 1597 (PA27) | 2 | 1 | 0.5 | 0.5 |
| CFS 1669 (PA41) | 2 | 0.5 | 0.5 | 0.5 |
| CFS 1674 (PA46) | 2 | 2 | 0.5 | 1 |
| CFS 1675 (PA47) | 1 | 0.5 | 0.5 | 0.5 |
| CFS 1109 (ATCC 17646) | 2 | 1 | 1 | 1 |

Example 7. Bactericidal Activity of GN121, GN351, GN370 and GN428 Against *Pseudomonas aeruginosa* in Human Serum and Pulmonary Surfactant Further characterization of the bacteriolytic activities of four anti-pseudomonal lysins described herein, GN121, GN351, GN370, and GN428, was evaluated using standard in vitro susceptibility testing formats that incorporate human serum or pulmonary surfactant. The mechanism of GN lysin action was further evaluated by fluorescence and transmission electron microscopy (TEM), as discussed below.

Materials and Methods:

MICs were determined by broth microdilution in media supplemented with human serum and pulmonary surfactant (SURVANTA®; Myoderm Clinical Supplies). Minimal biofilm eradicating concentrations (MBECs) were determined using standard methods. MBEC was measured using CAA supplemented with 12.5% human serum. Fluorescence microscopy was performed after LIVE/DEAD staining (ThermoFisher) and TEM was performed.

Results:

The activity of the selected GN lysins in human serum and pulmonary surfactant (SURVANTA®) was observed. Lysin MIC values were determined in the standard AST format medium (25% Casamino Acid Medium with 0.25 mM $MgSO_4$) alone and in the presence of 12.5% human serum and 0.78% SURVANTA®. The SURVANTA® concentration of 0.78% represents a physiological level of pulmonary surfactant. *Pseudomonas aeruginosa* strain CFS-1292 (meropenem resistant) was used as the reporter strain. As shown in Table 13 below, it was concluded that GN121, GN351, GN428, and GN370 are active in human serum and pulmonary surfactant. Likewise, as confirmed in Table 14 below, the lysins exhibited a potent antibiofilm effect using 12.5% human serum, with MBEC values ≤1 µg/mL, similar to those observed for MICs.

TABLE 13

MIC values for lysins in media alone (25% CAA) and supplemented with human serum or pulmonary surfactant

| Clone | Gram-negative lysin | 25% CAA MIC | MIC in human serum (12.5%) in CAA (µg/mL) | MIC in 0.78% Survanta ® (µg/mL) |
| --- | --- | --- | --- | --- |
| 1525 | GN121 | 1 | 0.5 | 2 |
| 1799 | GN351 | 1 | 0.0625 | 4 |
| 1876 | GN428 | 4 | 0.125 | 4 |
| 1818 | GN370 | 4 | 2 | 2 |

TABLE 14

MBEC values for lysins and lysin-AMP polypeptide constructs

| Lysin or Lysin-AMP polypeptide construct | MBEC (µg/mL) in CAA supplemented with 12.5% human serum |
| --- | --- |
| GN121 | 0.25 |
| GN351 | 0.5 |
| GN428 | 1 |
| GN370 | 1 |

Example 8. Ability of GN Lysins to Destabilize Bacterial Outer Membrane

Figure 2A:
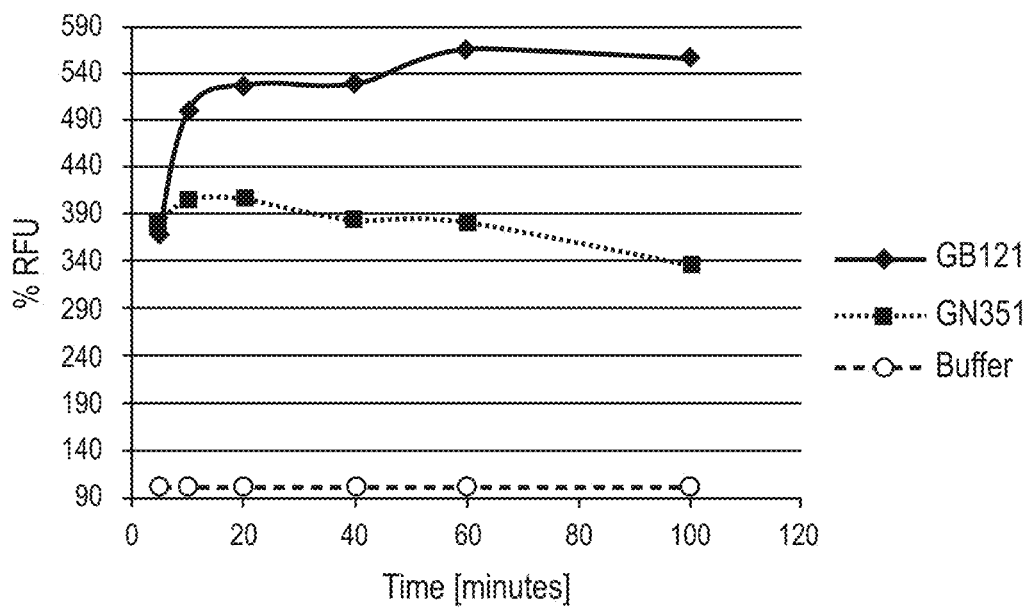
FIG. 2A is a graph showing the percent relative fluorescence unit (RFU) over time for P. aeruginosa in the presence of N-phenyl-1-napthylamine (NPN) and buffer, GN121, or GN351, as described in Example 6.
Figure 2B:
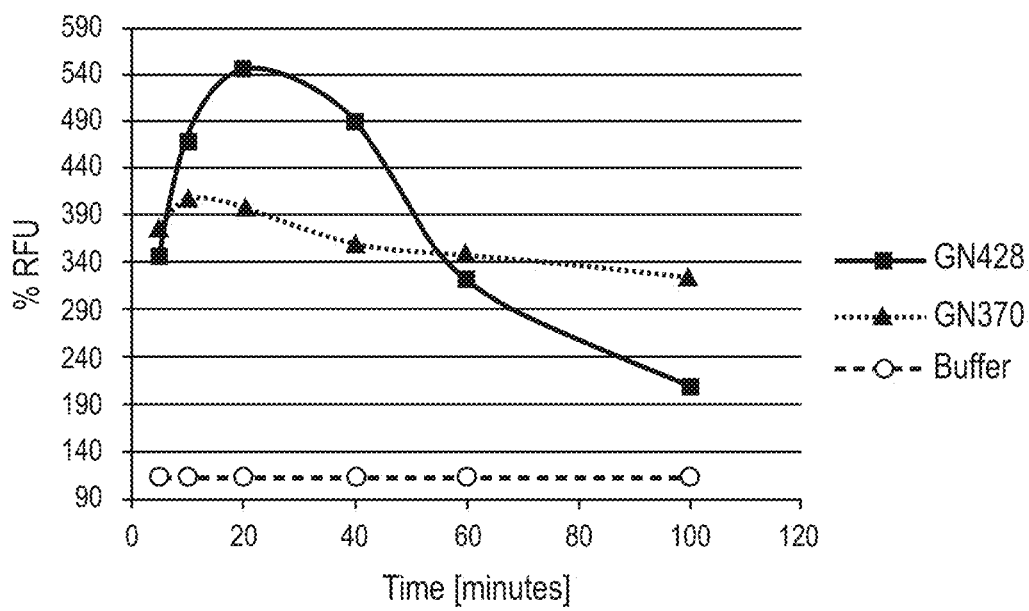
FIG. 2B is a graph showing the percent RFU over time for P. aeruginosa in the presence of NPN and buffer, GN428, or GN370, as described in Example 6.

The ability of gram-negative lysins to destabilize the outer membrane of *P. aeruginosa* was evaluated through the use of an N-phenyl-1-napthylamine (NPN) uptake assay. See Dassanayake, R. P. et al., "Antimicrobial activity of bovine NK-lysin-derived peptides on *Mycoplasma bovis*", PLOS One 2018; 9(1):e86364. Exponential *P. aeruginosa* (CFS 1292) was harvested, washed, and re-suspended in 5 mM 4-(2-hydroxyethyl)-1-piperazineethanesulfonic acid (HEPES) buffer and 5 mM glucose at pH 7.4. NPN was added to a final concentration of 10 mM. Gram-negative lysins, including GN121, GN351, GN428, and GN370, were added at a final concentration of 100 µg/well. Changes in fluorescence were recorded (excitation 1=350 nm; emission 1=420 nm) over two hours. The NPN incorporated into the membrane resulted in an increase in fluorescence. As shown in FIGS. 2A and 2B, the gram-negative lysins mediated disruption of the outer membrane of the bacterial cell wall. The data for each gram-negative lysin is shown below in Table 15.

TABLE 15

Fluorescence over time for *P. aeruginosa* exposed to NPN and gram-negative lysins

| Time in minutes | % RFU | | | | |
|---|---|---|---|---|---|
| | Buffer | GN121 | GN351 | GN428 | GN370 |
| 5 | 100 | 370 | 381 | 194 | 205 |
| 10 | 100 | 500 | 406 | 242 | 217 |
| 20 | 100 | 528 | 407 | 271 | 213 |
| 40 | 100 | 530 | 386 | 250 | 198 |
| 60 | 100 | 565 | 383 | 183 | 193 |
| 100 | 100 | 557 | 338 | 137 | 184 |

Example 9. Microscopy Shows GN Lysin Bactericidality in Serum

Figure 3:
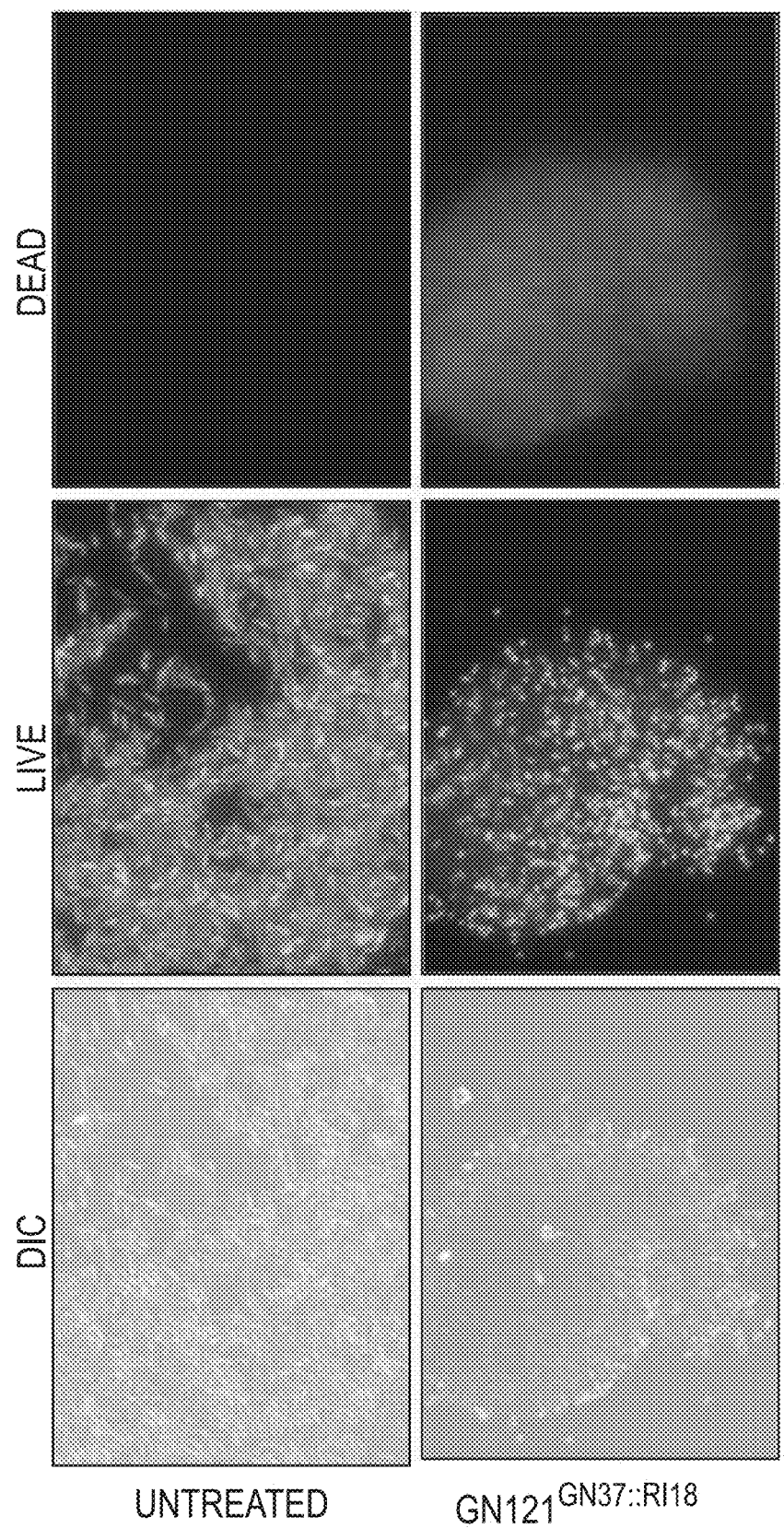
FIG. 3 is a series of photomicrographs showing microscopic analysis (×2000 magnification) of Pseudomonas aeruginosa strain 1292 treated for 15 minutes with GN121 (10 g/mL) or a buffer control ("untreated") in 100% human serum. Samples were stained using the Live/Dead Cell Viability Kit (ThermoFisher) and examined by both differential interference contrast (DIC) and fluorescence microscopy. The photomicrographs show an absence of dead bacteria in the untreated row and a reduction of live bacteria in the treated row, as described in Example 7.

*Pseudomonas aeruginosa* strain 1292 was treated for 15 minutes with GN121 (10 µg/mL) or a buffer control in 100% human serum. Samples were stained using the Live/Dead Cell Viability Kit (ThermoFisher) and examined by both differential interference contrast (DIC) and fluorescence microscopy. As depicted in FIG. 3, which shows a series of photomicrographs showing microscopic analysis (×2000 magnification), there was an absence of dead bacteria in the untreated row and a reduction of live bacteria in the treated row.

Example 10. Synergy of GN Lysins and Meropenem in Human Serum

Standard checkerboard assays were performed to assess synergy of GN lysins with meropenem in the presence of human serum. *P. aeruginosa* strains CFS 1292, 1557 (PA19), 1558 (PA20) CFS 1559 (PA21), CFS 1560 (PA22), CFS 1561 (PA23), CFS 1562 (PA24), and CFS 1766 (ATCC 27853) were suspended in a solution of 25% CAA and 12.5% human serum, and synergy was evaluated by measuring the fractional inhibitory concentration index (FICI) values. FICI values less than or equal to 0.5 were consistent with potent synergy. As shown below in Table 16, all of GN121, GN351, GN370, and GN428 exhibited synergy with meropenem for each of the three *P. aeruginosa* strains evaluated.

TABLE 16

Synergy between meropenem and gram-negative lysins in human serum

| Strain | Gram-negative lysin | FICI value (Run #1) | FICI value (Run #2) |
|---|---|---|---|
| CFS 1292 | GN121 | 0.25 | 0.292 |
| | GN351 | 0.1875 | 0.219 |
| | GN370 | 0.1875 | 0.219 |
| | GN428 | 0.1875 | 0.219 |
| CFS 1557 (PA19) | GN121 | 0.375 | 0.427 |
| | GN351 | 0.25 | 0.292 |
| | GN370 | 0.1875 | 0.240 |
| | GN428 | 0.15625 | 0.198 |
| CFS 1558 (PA20) | GN121 | 0.125 | 0.156 |
| | GN351 | 0.15625 | 0.177 |
| | GN370 | 0.09375 | 0.109 |
| | GN428 | 0.09375 | 0.135 |
| CFS 1559 (PA21) | GN121 | — | 0.229 |
| | GN351 | — | 0.177 |
| | GN370 | — | 0.438 |
| | GN428 | — | 0.396 |
| CFS 1560 (PA22) | GN121 | — | 0.313 |
| | GN351 | — | 0.323 |
| | GN370 | — | 0.198 |
| | GN428 | — | 0.229 |
| CFS 1561 (PA23) | GN121 | — | 0.198 |
| | GN351 | — | 0.240 |
| | GN370 | — | 0.240 |
| | GN428 | — | 0.323 |
| CFS 1562 (PA24 | GN121 | — | 0.214 |
| | GN351 | — | 0.177 |
| | GN370 | — | 0.240 |
| | GN428 | — | 0.198 |
| CFS 1766 (ATCC 27853) | GN121 | — | 0.229 |
| | GN351 | — | 0.109 |
| | GN370 | — | 0.156 |
| | GN428 | — | 0.156 |

Example 11. Synergy Between Antibiotics and Lysins or Lysin-AMP Polypeptide Constructs Synergy between GN76 (SEQ ID NO: 203), GN121 (SEQ ID NO: 175), GN123 (SEQ ID NO: 173), GN351 (SEQ ID NO: 32), GN370 (SEQ ID NO: 44) and GN428 (SEQ ID NO: 60) and 12 different antibiotics were examined in checkerboard assays using CAA medium, supplemented with 2.5% human serum as described herein, using the carbapenem-resistant clinical strain WC-452. Fractional inhibitor concentration index (FICI) values were determined for all combinations; values of <0.5 indicate synergy.

TABLE 17

Synergy between antibiotics and lysins or lysin-AMP polypeptide constructs

| Antibiotic | GN76 (SEQ ID NO: 203) (MIC µg/mL) | GN121 (SEQ ID NO: 175) (MIC µg/mL) | GN123 (SEQ ID NO: 173) (MIC µg/mL) | GN351 (SEQ ID NO: 32) (MIC µg/mL) | GN370 (SEQ ID NO: 44) (MIC µg/mL) | GN428 (SEQ ID NO: 60) (MIC µg/mL) |
|---|---|---|---|---|---|---|
| Amikacin | 0.281 | 0.375 | 0.250 | 0.250 | 0.125 | 0.281 |
| Azithromycin | 0.156 | 0.188 | 0.125 | 0.125 | 0.188 | 0.250 |
| Aztreonam | 0.281 | 0.625 | 0.375 | 0.125 | 0.188 | 0.156 |
| Ciprofloxacin | 0.281 | 0.313 | 0.375 | 0.375 | 0.281 | 0.125 |
| Colistin | 0.250 | 0.046 | 0.188 | 0.046 | 0.046 | 0.094 |
| Fosfomycin | 0.125 | 0.375 | 0.250 | 0.500 | 0.375 | 0.313 |
| Gentamicin | 0.313 | 0.375 | 0.375 | 0.125 | 0.250 | 0.250 |
| Imipenem | 0.254 | 0.375 | 0.188 | 0.156 | 0.094 | 0.188 |
| Meropenem | 0.375 | 0.313 | 0.125 | 0.188 | 0.125 | 0.188 |
| Pipercillan | 0.375 | 0.375 | 0.500 | 0.281 | 0.125 | 0.375 |
| Rifampicin | 0.281 | 0.313 | 0.156 | 0.250 | 0.250 | 0.500 |

TABLE 17-continued

Synergy between antibiotics and lysins or lysin-AMP polypeptide constructs

| Antibiotic | GN76 (SEQ ID NO: 203) (MIC µg/mL) | GN121 (SEQ ID NO: 175) (MIC µg/mL) | GN123 (SEQ ID NO: 173) (MIC µg/mL) | GN351 (SEQ ID NO: 32) (MIC µg/mL) | GN370 (SEQ ID NO: 44) (MIC µg/mL) | GN428 (SEQ ID NO: 60) (MIC µg/mL) |
|---|---|---|---|---|---|---|
| Tobramycin | 0.281 | 0.188 | 0.188 | 0.153 | 0.188 | 0.188 |
| Amikacin | 0.281 | 0.375 | 0.250 | 0.250 | 0.125 | 0.281 |
| Azithromycin | 0.156 | 0.188 | 0.125 | 0.125 | 0.188 | 0.250 |
| Aztreonam | 0.281 | 0.625 | 0.375 | 0.125 | 0.188 | 0.156 |
| Ciprofloxacin | 0.281 | 0.313 | 0.375 | 0.375 | 0.281 | 0.125 |
| Colistin | 0.250 | 0.046 | 0.188 | 0.046 | 0.046 | 0.094 |
| Fosfomycin | 0.125 | 0.375 | 0.250 | 0.500 | 0.375 | 0.313 |
| Gentamicin | 0.313 | 0.375 | 0.375 | 0.125 | 0.250 | 0.250 |
| Imipenem | 0.254 | 0.375 | 0.188 | 0.156 | 0.094 | 0.188 |
| Meropenem | 0.375 | 0.313 | 0.125 | 0.188 | 0.125 | 0.188 |
| Pipercillan | 0.375 | 0.375 | 0.500 | 0.281 | 0.125 | 0.375 |
| Rifampicin | 0.281 | 0.313 | 0.156 | 0.250 | 0.250 | 0.500 |
| Tobramycin | 0.281 | 0.188 | 0.188 | 0.153 | 0.188 | 0.188 |

As indicated in Table 17, below, the foregoing lysins and lysin-AMP constructs are synergistic across a broad range of antibiotics. For imipenem, the synergy is consistent with resensitization to the carbapenem antibiotic.

Example 12. Resensitization of Carbapenem-Resistant Clinical Strains Using Antibiotics in Combination with GN Lysins The ability of GN121 (SEQ ID NO: 175) or GN123 (SEQ ID NO: 173) to resensitize carbapenem-resistant *P. aeruginosa* strains to carbapenems was assessed by combining each of the foregoing lysins with two carbapenems, i.e., imipenem (IPM) or meropenem (MEM). Up to seven carbapenem-resistant isolates were assessed. Resensitization occurs in synergistic combinations in which the carbapenem MIC values fall below established breakpoints, e.g. a MIC value of ≤2 for carbapenem-sensitive isolates, a MIC value of 4 for intermediately sensitive carbapenem isolates and a MIC value of ≥8 for carbapenem-resistant isolates. See Clinical and Laboratory Standards Institute (CLSI), CLSI. 2019. M100 Performance Standards for Antimicrobial Susceptibility Testing; 29th Edition. Clinical and Laboratory Standards Institute, Wayne, Pa.

As indicated in Tables 18-21 synergistic combinations with GN123 (SEQ ID NO: 173) or GN121 (SEQ ID NO: 175) demonstrated reductions of IPM and MEM MICS to below breakpoint values for each of the seven carbapenems examined. These observations are consistent with resensitization.

TABLE 18

Gram-negative bacterial resensitization using a combination of IMIPENEM and GN123

| | IMIPENEM MIC (µg/mL) | | GN123 (µg/mL) | | |
|---|---|---|---|---|---|
| Isolate | Alone | Combination | Alone | Combination | FICI |
| PA19 | 32 (R) | 0.5 (S) | 8 | 0.125 | 0.03 |
| Analysis of additional CARBAPENEM^R isolates: | | | | | |
| PA20 | 16 (R) | 1 (S) | 16 | 2 | 0.188 |
| PA21 | 32 (R) | 0.5 (S) | 8 | 1 | 0.141 |
| PA22 | 16 (R) | 2 (S) | 16 | 1 | 0.188 |
| PA23 | 8 (R) | 0.25 (S) | 8 | 2 | 0.281 |

TABLE 18-continued

Gram-negative bacterial resensitization using a combination of IMIPENEM and GN123

| | IMIPENEM MIC (µg/mL) | | GN123 (µg/mL) | | |
|---|---|---|---|---|---|
| Isolate | Alone | Combination | Alone | Combination | FICI |
| PA24 | 32 (R) | 2 (S) | 16 | 2 | 0.188 |
| WC-452 | 16 (R) | 1 (S) | 16 | 2 | 0.188 |

(R) = resistant
(S) = sensitive

TABLE 19

Gram-negative bacterial resensitization using a combination of MEROPENEM and GN123 (SEQ ID NO: 173)

| | MEROPENEM MIC (µg/mL) | | GN123 (µg/mL) | | |
|---|---|---|---|---|---|
| Isolate | Alone | Combination | Alone | Combination | FICI |
| PA19 | 32 (R) | 0.5 (S) | 8 | 0.25 | 0.046 |
| PA20 | 16 (R) | 0.5 (S) | 16 | 1 | 0.094 |
| PA21 | 32 (R) | 1 (S) | 8 | 1 | 0.156 |
| PA22 | 16 (R) | 1 (S) | 16 | 1 | 0.125 |
| PA23 | 16 (R) | 0.5 (S) | 8 | 1 | 0.156 |
| PA24 | 32 (R) | 2 (S) | 16 | 0.5 | 0.094 |
| WC-452 | 16 (R) | 1 (S) | 16 | 1 | 0.125 |

(R) = resistant
(S) = sensitive

TABLE 20

Gram-negative bacterial resensitization using a combination of IMIPENEM and GN121 (SEQ ID NO: 175)

| | Imipenem MIC (µg/mL) | | GN121 (µg/mL) | | |
|---|---|---|---|---|---|
| Isolate | Alone | Combination | Alone | Combination | FICI |
| PA19 | 32 (R) | 1 (S) | 1 | 0.125 | 0.155 |
| PA20 | 16 (R) | 0.5 (S) | 1 | 0.25 | 0.265 |
| PA21 | 32 (R) | 1 (S) | 1 | 0.125 | 0.155 |
| PA22 | 32 (R) | 2 (S) | 2 | 0.25 | 0.188 |
| PA23 | 16 (R) | 0.125 (S) | 1 | 0.25 | 0.257 |
| PA24 | 32 (R) | 1 (S) | 1 | 0.125 | 0.155 |

(R) = resistant
(S) = sensitive

TABLE 21

Gram-negative bacterial resensitization using a combination of MEROPENEM and GN121 (SEQ ID NO: 175)

| | Meropenem MIC (µg/mL) | | GN121 (µg/mL) | | |
|---|---|---|---|---|---|
| Isolate | Alone | Combination | Alone | Combination | FICI |
| PA19 | 32 (R) | 1 | 2 | 0.5 | 0.281 |
| PA20 | 16 (R) | 1 | 2 | 0.5 | 0.313 |
| PA21 | 32 (R) | 2 | 1 | 0.125 | 0.188 |
| PA22 | 16 (R) | 1 | 1 | 0.25 | 0.313 |
| PA23 | 16 (R) | 2 | 2 | 0.5 | 0.375 |
| PA24 | 32 (R) | 1 | 1 | 0.125 | 0.156 |
| WC-452 | 16 (R) | 1 | 1 | 0.06 | 0.123 |

(R) = resistant;
(S) = sensitive

Example 13. Resensitization of Carbapenem-Resistant Clinical Strains Using Antibiotics in Combination with Additional Lysins or Lysin-AMP Constructs The ability of GN351 (SEQ ID NO: 32), GN370 (SEQ ID NO: 44) or GN428 (SEQ ID NO: 60) to resensitize carbapenem-resistant clinical strains to carbapenems was assessed by combining each of the foregoing lysins or lysin-AMP polypeptide constructs with IPM or MEM. WC-452, a carbapenem-resistant isolate, was assessed. As noted in Example 3, above, resensitization occurs in synergistic combinations in which the carbapenem MIC values fall below the previously described breakpoints.

As indicated in Table 22 synergistic combinations with GN351 (SEQ ID NO: 32), GN370 (SEQ ID NO: 44) or GN428 (SEQ ID NO: 60) demonstrated reductions of IPM and MEM MICS to below breakpoint values for WC-452. These observations are consistent with resensitization.

The findings herein indicate that the present lysins and lysin-AMP polypeptide constructs described can resensitize P. aeruginosa to carbapenem antibiotics, driving MICs below breakpoint values in vitro. This novel ability of lysins and lysin-AMP polypeptide constructs to resensitize antibiotic-resistant strains to conventional antibiotics indicates the benefit of these biologics as therapeutics to combat and reverse antimicrobial resistance.

TABLE 22

Gram-negative bacterial resensitization using combinations of MEM or IPM and GN351 (SEQ ID NO: 32), GN370 (SEQ ID NO: 44), or GN428 (SEQ ID NO: 60)

| Combinations vs. | Antibiotic MIC | | Lysin MIC | | |
|---|---|---|---|---|---|
| WC-452 | Alone | Combination | Alone | Combination | FICI |
| IPM + GN351 | 16 (R) | 0.5 (S) | 1 | 0.125 | 0.156 |
| IPM + GN370 | 16 (R) | 0.5 (S) | 2 | 0.125 | 0.094 |
| IPM + GN428 | 16 (R) | 1 (S) | 2 | 0.25 | 0.188 |
| MEM + GN351 | 16 (R) | 1 (S) | 1 | 0.125 | 0.188 |
| MEM + GN370 | 16 (R) | 0.5 (S) | 2 | 0.125 | 0.125 |
| MEM + GN428 | 16 (R) | 1 (S) | 2 | 0.25 | 0.188 |

Example 14. Low Propensity for Resistance to GN Lysins

In another experiment, it was determined that Gram-negative bacteria did not develop resistance to GN121, GN351, GN370, and GN428 in a 21-day serial passage resistance assay. An analysis of bacterial resistance was performed using P. aeruginosa (strain WC-452) over 21 days of serial passage in the presence of a GN-lysin dilution series (in duplicate). Briefly, the broth microdilution MIC format was used in which 2-fold dilution ranges of GN lysin were cultured with the bacteria $5 \times 10^6$ CFU/ml starting concentration) in CAA broth for 18 hours at 37° C. The well with the highest concentration of GN lysin in which bacterial growth was seen was then used as the inoculum for the next day's passage, and the process was repeated over a 21 day period. The MIC at each daily time-point was recorded, and resistance was measured as a step-wise increase in MIC.

Figure 4A:
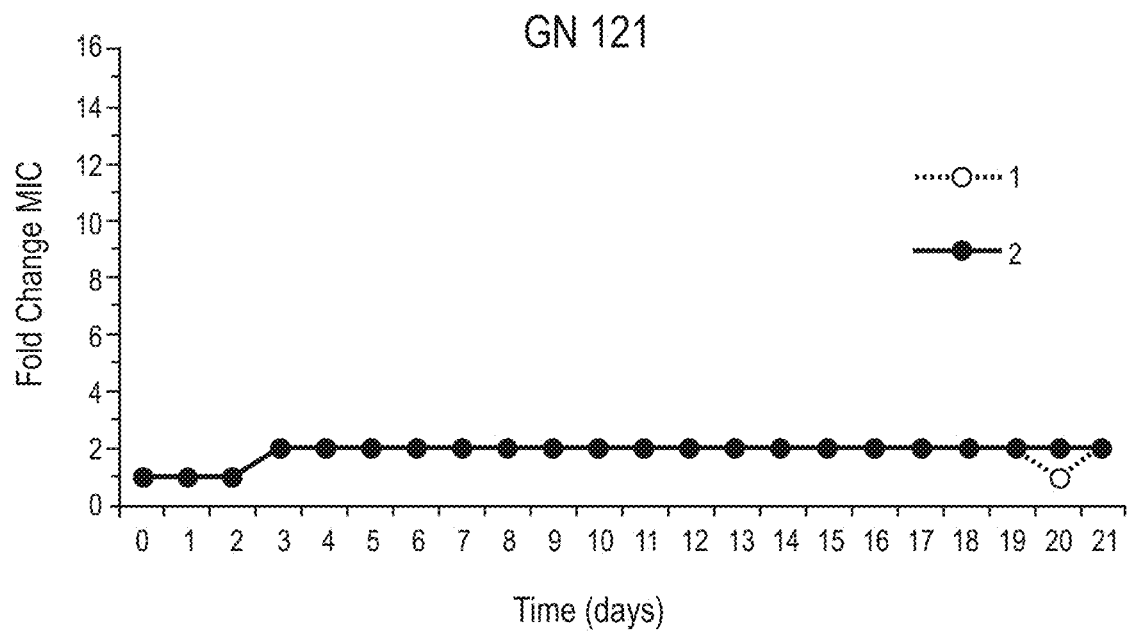
FIGS. 4A-4E show the fold change in GN lysin and Ciprofloxacin needed to achieve a Minimal Inhibitory Concentration (MIC) for P. aeruginosa (strain WC-452) over 21 day serial passage as described in Example 9: GN121 (FIG. 4A), GN351 (FIG. 4B), GN370 (FIG. 4C), GN428 (FIG. 4D) and Ciprofloxacin (FIG. 4E).
Figure 4B:
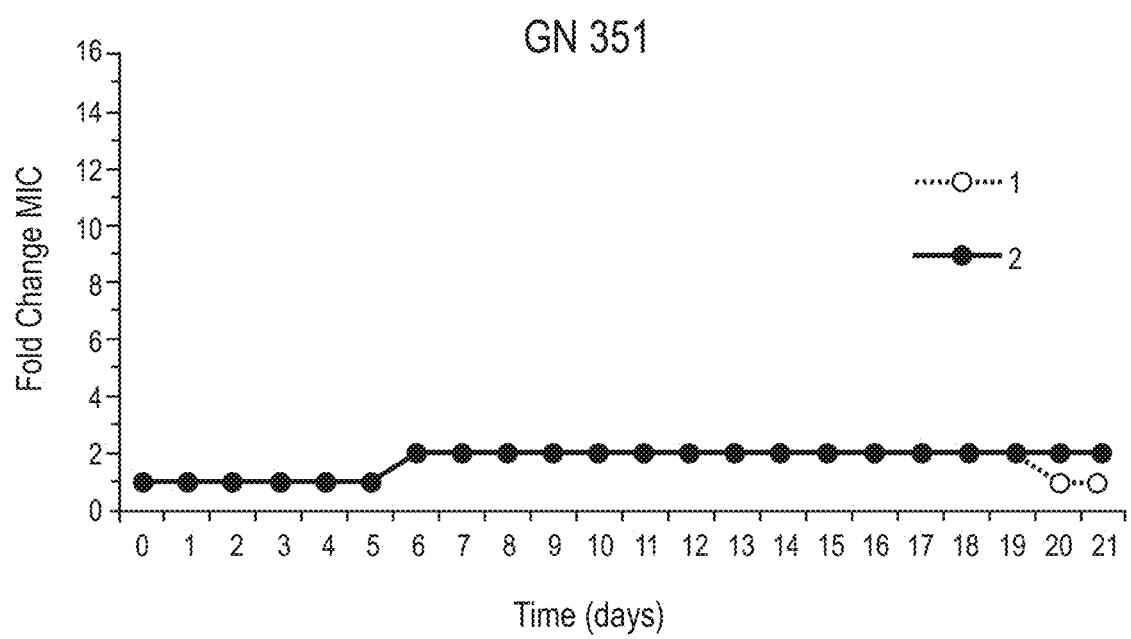
Figure 4C:
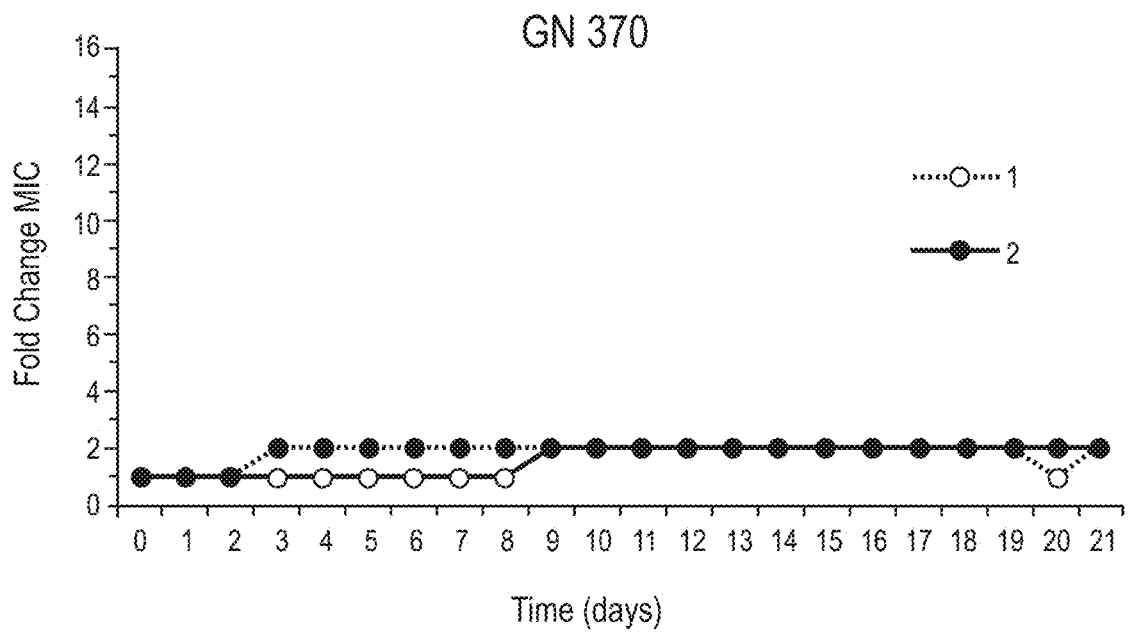
Figure 4D:
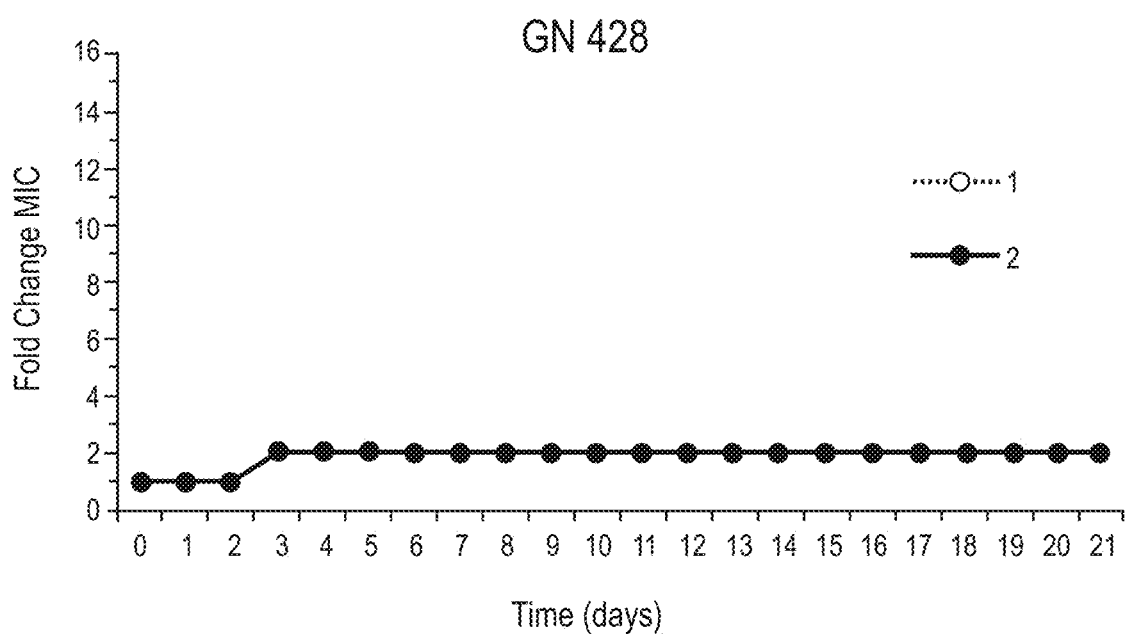
Figure 4E:
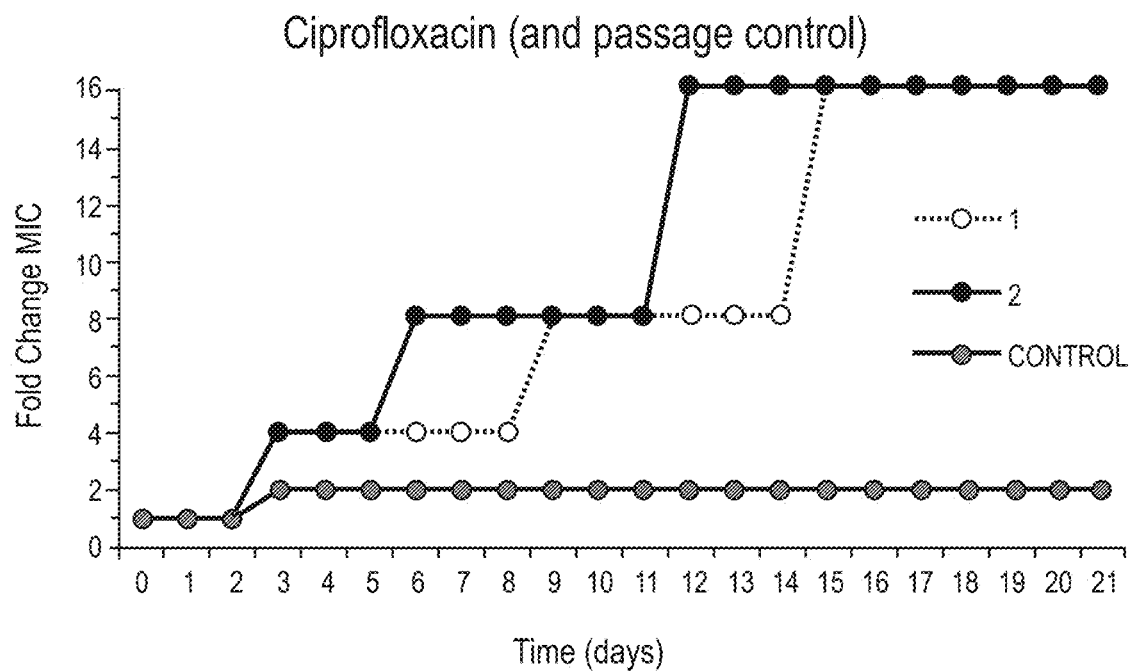

In the assay, GN121, GN351, GN370, and GN428 lysin MICs increased by up to 1-log 2 dilutions (2-fold) over 18 days, which was comparable to passage control (absence of treatment). FIGS. 4A-4D. In contrast, the Ciprofloxacin control increased 4-log 2 dilutions (16-fold) over 18 days (FIG. 4E). D'Lima et al. also found an increase in Ciprofloxacin MIC during serial passage. See D'Lima et al., 2012, *Antimicrobial Agents and Chemotherapy*, 56: 2753-2755, which reports an increase of Ciprofloxacin MIC of up to 32-fold over a 21 day serial passage. Our results are consistent with a low propensity for GN lysin resistance, which is similar to that observed with Gram-positive lysins. See, for example, PCT/US19/19638, which was filed on Feb. 26, 2019, and is herein incorporated by reference in its entirety.

Example 15. GN Lysins and Lysin-AM Constructs are not Hemolytic

The hemolytic activity of selected GN lysins and constructs was measured as the amount of hemoglobin released by the lysis of human erythrocytes (Lv et al., 2014, *PLoS One*, 9:e86364.). Briefly, 3 milliliters of fresh human blood cells (hRBGs) obtained from pooled healthy donors in a polycarbonate tube containing heparin was centrifuged at 1,000×g for 5 minutes at 4° C. The erythrocytes obtained were washed three times with PBS solution (pH 7.2) and resuspended in PBS. A 50 µL volume of the erythrocyte solution was incubated with 50 µL of each GN lysin and or construct (in PBS) in a 2-fold dilution range (from 128 µg/ml to 0.25 µg/ml) for 1 hour at 37° C. Intact erythrocytes were pelleted by centrifugation at 1,000×g for 5 minutes at 4° C., and the supernatant was transferred to a new 96-well plate. The release of hemoglobin was monitored by measuring the absorbance at 570 nm. As a negative control, hRBGs in PBS were treated as above with 0.1% Triton X-100.

Table 23 below shows the minimal hemolytic concentrations (MHCs), which result in ≥5% hemolysis compared to the Triton X-100 control. MHCs for AMPs with known hemolytic activity are shown for comparison. GN126 is also included for comparison. As indicated in the Table, the selected lysins demonstrate no hemolytic activity.

TABLE 23

Minimal Hemolytic Concentrations for selected lysins.

| Lysin | MHC (µg/mL) |
|---|---|
| GN76 | >128 |
| GN126 | >128 |
| GN83 | >128 |
| GN75 | >128 |
| GN7 | >128 |
| GN11 | >128 |
| GN14 | >128 |
| GN217 | >128 |
| GN316 | >128 |
| GN329 | >128 |
| GN333 | >128 |
| GN351 | >128 |

TABLE 23-continued

Minimal Hemolytic Concentrations for selected lysins.

| Lysin | MHC (µg/mL) |
|---|---|
| GN357 | >128 |
| GN428 | >128 |
| GN370 | >128 |
| GN431 | >128 |
| RR12 | 8 |
| RR12Polar | 4 |
| RR12hydro | 32 |

Example 16. GN Lysins and Constructs are Tolerated In Vivo

The in vivo tolerability of selected lysins was assessed in non-infected ICR mice (ca. 4-6 weeks old, 11-18 g, supplied by Charles River (Margate, UK)) by administering a single intravenous dose of each lysin to two mice at the starting doses as described in Table 24 below. The mice were monitored closely for 1 hour post dose and if there were no clinical signs of side-effects, another two mice were injected with a higher dose of each lysin (Table 24). Mice were monitored closely for 1 hour post dose and then at regular intervals until the end of study at 8 hours post dose.

TABLE 24

Study design for the tolerability study

| GN lysin | Dose (mg/kg) | Dose Volume (mL/kg) | Route | % Survival |
|---|---|---|---|---|
| GN121 | 3 and 10 | 10 | IV | 100 |
| GN150 | 30 and 85 | 10 | IV | 100 |
| GN316 | 30 and 100 | 10 | IV | 100 |
| GN370 | 30 and 100 | 10 | IV | 100 |
| GN431 | 30 an 100 | 10 | IV | 100 |

Mice were monitored at a frequency appropriate for their clinical condition. Mouse weights were recorded on days −4, −1 and 0, both to ensure animals remained within ethical limits, and to allow accurate calculation of individual dosing volumes (adjusted according to the weight of each mouse).

The mice were euthanized at 8 hours post dose and a post mortem was performed. At the designated time of euthanasia, the clinical condition and body weight of all animals was assessed, then mice were euthanized by pentobarbitone overdose.

The starting doses of all lysins were well tolerated at 1 hour post dose so the higher dose of the lysins was administered in the second cohort of mice as described earlier. The second cohort of mice were monitored closely for 1 hour post dose and subsequently all mice were regularly monitored for any clinical signs of side-effects until 8 hours post dose. Both low and high doses of the lysins were well tolerated without any clinical observations and the study was ended by euthanizing the mice at 8 hours post dose. A post mortem was carried out on all mice which showed no morphological changes to the viscera. Accordingly, the selected lysins were all well tolerated in vivo at the highest dose levels tested when administered intravenously.

Example 17. GN370 is Active Against a Wide Range of Gram-Negative Bacteria

MIC values were determined using the methodology described above, i.e., the standard broth microdilution reference method defined by CLSI. $MIC_{50}$ is the minimum concentration of peptide sufficient to suppress at least 50% of the bacterial growth compared to control, and $MIC_{90}$ is the minimum concentration of peptide sufficient to suppress at least 90% of the bacterial growth compared to control, whereas the term MIC, as described above, refers to suppression of at least 80% bacterial growth.

An antibiotic-resistant isolate bank panel was chosen from the Center for Disease Control's strain lists for use in this range study. Specifically, a panel of *Pseudomonas aeruginosa* multi-drug-resistant (MDR) and extensively antibiotic-resistant (XDR) isolates were chosen to represent a diversity of antimicrobial susceptibility results for drugs that are used to treat infections. The strains are described, for example, at wwwn.cdc.gov/ARIsolateBank/Panel/PanelDetail?ID=12 for the *Pseudomonas aeruginosa* isolates. Lab strains PAO1 and ATCC 27853 were also tested. An additional 49 *Pseudomonas aeruginosa* isolates were obtained from Weill Cornell Medical College, New York and these were also assessed. Nine (9) isolates from *Acinetobacter baumannii* and eight (8) isolates from *Klebsiella pneumoniae* were also tested.

Figure 5:
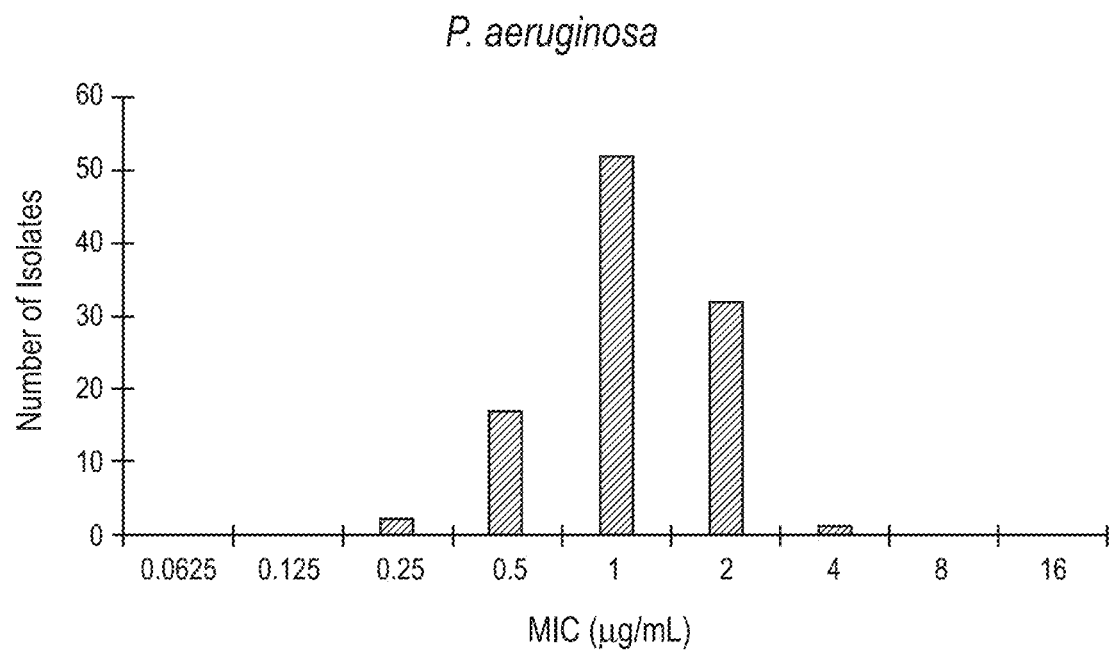
FIG. 5 depicts the MIC values for GN370 against P. aeruginosa isolates as described in Example 17.

FIG. 5 and Tables 25 and 26 show the MIC, $MIC_{50}$ and $MIC_{90}$ values for the *Pseudomonas aeruginosa* isolates. GN370 was active against all tested *Pseudomonas aeruginosa* isolates including MDR and XDR isolates (MIC values ranging from 0.25-4). Surprisingly, as shown below in Table 26, GN370 was also active against *Acinetobacter baumannii* and *Klebsiella pneumoniae* (MIC values ranging from 0.5-1 and 0.25-4, respectively).

TABLE 25

Pseudomonas aeruginosa Panel

| CDC Antibiotic-Resistant Bank No. | MIC GN370 |
|---|---|
| 0229 | 2 |
| 0230 | 1 |
| 0231 | 2 |
| 0232 | 2 |
| 0233 | 0.5 |
| 0234 | 1 |
| 0235 | 2 |
| 0236 | 0.5 |
| 0237 | 0.5 |
| 0238 | 1 |
| 0239 | 2 |
| 0240 | 2 |
| 0241 | 2 |
| 0242 | 0.5 |
| 0243 | 0.25 |
| 0244 | 2 |
| 0245 | 2 |
| 0246 | 1 |
| 0247 | 1 |
| 0248 | 1 |
| 0249 | 1 |
| 0250 | 1 |
| 0251 | 1 |
| 0252 | 1 |
| 0253 | 0.5 |
| 0254 | 1 |
| 0255 | 1 |
| 0256 | 0.5 |
| 0257 | 0.5 |
| 0258 | 1 |
| 0259 | 1 |
| 0260 | ng |
| 0261 | 1 |
| 0262 | 1 |
| 0263 | 0.5 |
| 0264 | 0.5 |

TABLE 25-continued

Pseudomonas aeruginosa Panel

| CDC Antibiotic-Resistant Bank No. | MIC GN370 |
|---|---|
| 0265 | 2 |
| 0266 | 2 |
| 0267 | 2 |
| 0268 | 2 |
| 0269 | 2 |
| 0270 | 1 |
| 0271 | 1 |
| 0272 | 2 |
| 0763 | 1 |
| 0764 | 1 |
| 0765 | 1 |
| 0766 | 0.25 |
| 0767 | 1 |
| 0768 | ng |
| 0769 | 2 |
| 0770 | 0.5 |
| 0771 | 2 |
| 0772 | 0.5 |
| 0773 | 1 |

TABLE 26

GN370 active against a range of genera

| Strain | n | $MIC_{50}$ | $MIC_{90}$ | Range |
|---|---|---|---|---|
| P. aeruginosa | 104 | 1 | 2 | 0.25-4 |
| A. baumannii | 9 | 1 | 1 | 0.5-1 |
| K. pneumoniae | 8 | 2 | 4 | 0.25-4 |

Example 18. Rat Toxicity Study

Experimental Design, Phase 1

A rat toxicity study of GN370 was conducted in two phases (Phase 1 and Phase 2). The dose escalation phase (Phase 1) of the study was conducted to determine the maximum tolerated dose (MTD) of GN370. During Phase 1, GN370 and control/vehicle (25 mM Tris, 50 mM Sodium Chloride, pH 8.0) were administered once to groups of male Sprague Dawley rats (250 g to 325 g at the onset of treatment, 7-8 weeks of age) by intravenous infusion over a period of 2 hours via the tail vein in an escalating dose fashion as described in the Table below.

The infusion rate for the animals of Groups 1 and 4 was 5 mL/kg/hour (10 mL/kg) over a two hour period. The infusion rate for Groups 2 and 3 was 2.5 mL/kg/hour (5 mL/kg), also over a two hour period. A stepwise approach was taken to ensure that each dose level used was tolerated prior to higher dose levels being tested. As such, a minimum 24 hour observation period was allowed between successive doses. All surviving animals were observed for 3, 7 or 14 days post-dose, following which they were euthanized and subjected to a necropsy examination (Study days 3, 7 or 14, post-dose).

TABLE 27

Phase 1 Design

| Group Numbers[a] | Group Designation | Dose Level (mg/kg) | Dose Concentration (mg/mL) | Dose Volume (mL/kg) | Number of Main Animals (Male) | Days of Euthanasia |
|---|---|---|---|---|---|---|
| 1 | Control* | 0 | 0 | 10 | 5 | 4 |
| | | | | | 3 | 8 |
| | | | | | 3 | 15 |
| 2 | GN370 Low Dose | 10 | 2 | 5 | 5 | 4 |
| | | | | | 3 | 8 |
| | | | | | 3 | 15 |
| 3 | GN370 Mid Dose | 50 | 10 | 5 | 5 | 4 |
| | | | | | 3 | 8 |
| | | | | | 3 | 15 |
| 4 | GN370 High Dose | 100 | 10 | 10 | 5 | 4 |
| | | | | | 3 | 8 |
| | | | | | 3 | 15 |

*The Control animals received the control/vehicle item alone
[a] = Each dose was followed by a 24-hour observation period Experimental Design, Phase 2

For Phase 2, GN370 and control/vehicle were administered to groups of rats by intravenous infusion over a period of 2 hours via tail vein for 4 consecutive days as described in the table below. The infusion rate for animals in Groups 5 and 8 was 10 mL/kg/hour (20 mL/kg) over a period of 2 hours. The infusion rate for the Group 6 animals was 2.5 mL/kg/hour (5 mL/kg), and the infusion rate for the Group 7 animals was 5 mL/kg/hour (10 mL/kg) over a period of 2 hours.

The infusion period for Group 8 was stopped on day 2 due to the effects described in the results below. On day 3, three toxicokinetic (TK) animals were infused for a period of 4 hours and subsequently dosed on days 4 and 5. The infusion rate was 5 mL/kg/hour (20 mL/kg).

All surviving animals in Groups 5, 6, and 7 were observed for 3, 7 or 14 days after the last dosing ($4^{th}$ dose), following which they were euthanized and subjected to a necropsy examination at days 7, 11 or 18, respectively. The three TK rats with the extended 4 hour infusion period were euthanized on day 8, considered as main animals, and accordingly subjected to a necropsy examination.

TABLE 28

Phase 2 Design

| Group Numbers | Group Designation | Dose Level (mg/kg/day) | Dose Concentration (mg/mL) | Dose Volume (mL/kg) | Number of Main Animals (Male) | Number of TK Animals (Male) | Days of Euthanasia |
|---|---|---|---|---|---|---|---|
| 5 | Control | 0 | 0 | 20 | — | 3 | 5 |
| | | | | | 5 | — | 7 |
| | | | | | 3 | — | 11 |
| | | | | | 3 | — | 18 |

TABLE 28-continued

Phase 2 Design

| Group Numbers | Group Designation | Dose Level (mg/kg/day) | Dose Concentration (mg/mL) | Dose Volume (mL/kg) | Number of Main Animals (Male) | Number of TK Animals (Male) | Days of Euthanasia |
|---|---|---|---|---|---|---|---|
| 6 | GN370 Low Dose | 25 | 5 | 5 | — | 6 | 5 |
|  |  |  |  |  | 5 | — | 7 |
|  |  |  |  |  | 3 | — | 11 |
|  |  |  |  |  | 3 | — | 18 |
| 7 | GN370 Mid Dose | 75 | 7.5 | 10 | — | 6 | 5 |
|  |  |  |  |  | 5 | — | 7 |
|  |  |  |  |  | 3 | — | 11 |
|  |  |  |  |  | 3 | — | 18 |
| 8 | GN370 High Dose | 200 | 10 | 20 | — | 6 | 5* |
|  |  |  |  |  | 5 | — | 3 |
|  |  |  |  |  | 3 | — | 9 |
|  |  |  |  |  | 3 | — | 16 |

*3 TK animals were euthanized on Day 8 and considered as main animals

Necropsy Procedures

The main animals were euthanized on completion of their respective observation periods following an overnight period without food. The animals were anesthetized with Isoflurane to allow for collection of blood samples for clinical pathology evaluation followed by exsanguination. Blood samples were collected from the abdominal aorta at termination. Urine was collected over a period of approximately 12 to 18 hours by placing individual rats on a wire mesh cage with a collection tray under the case or by placing the animals in metabolic cages.

For each animal, the necropsy consisted of an external examination, including reference to all clinically-recorded lesions, as well as a detailed internal examination. Organs were dissected, trimmed free of fat and weighted.

Upon completion of the gross pathology examination and selected organ weighing in both study phases, the tissues and organs were retained. Neutral buffered 10% formalin was used for fixation and preservation. For Phase 1 and 2, histopathological examination is being performed on vehicle and high dose groups (on going).

Control animals were bled at predose and 5 minutes after infusion. Each rat (unanesthetized) was bled by jugular venipuncture (as an alternate bleeding technique, the animals were bled from the sublingual vein), and the samples were collected into tubes containing the anticoagulant $K_2EDTA$. The tubes were placed on wet ice pending processing.

Following collection, the samples were centrifuged (2500 rpm for 10 minutes at approximately 4° C. within approximately 30 minutes of collection. The resulting plasma was recovered, split into 2 aliquots of approximately equal volume and stored frozen (≤60° C.) in labelled tubes. The plasma samples are analyzed for GN370 concentration using ELISA (ongoing). Non-compartmental analysis for the GN370 in the plasma data set will be performed using PHOENIX® WINNONLIN® software using default parameters.

Toxicokinetic parameters including Terminal elimination half-life ($T_{1/2}$) and Area under the plasma drug concentration time curve from the time of dosing to the last quantifiable concentration ($AUC_{0-Tlast}$) will also be assessed.

TABLE 29

Sample Collection

| | | Toxicokinetic time point (relative to end of dosing) | | | | | | | |
|---|---|---|---|---|---|---|---|---|---|
| Group No. | No. of animals | Predose | 5 min. | 15 min. | 30 min. | 1 hour | 2 hours | 4 hours | 6 hours | 24 hours |
| 6 | 3+ | ✓ |  | ✓ |  | ✓ |  | ✓ |  | ✓ |
|  | 3# |  | ✓ |  | ✓ |  | ✓ |  | ✓ |  |
| 7 | 3+ | ✓ |  | ✓ |  | ✓ |  | ✓ |  | ✓ |
|  | 3# |  | ✓ |  | ✓ |  | ✓ |  | ✓ |  |
| 8 | 3+ | ✓ |  | ✓ |  | ✓ |  | ✓ |  | ✓ |
|  | 3# |  | ✓ |  | ✓ |  | ✓ |  | ✓ |  |

+3 animals with the lowest identification numbers.
3 animals with the highest identification numbers.

Toxicokinetic Procedures

TK animals were euthanized on Day 5 and discarded without further examination following completion of sample collection. Samples were collected as follows. A series of blood samples (approximately 0.3 mL each) were collected from two cohorts of 3 TK rats/group/time-point relative to dosing on Day 1 and 4 of Phase 2 as indicated in the table below.

In addition to the above, laboratory investigations (hematology, coagulation, clinical chemistry analyses and urinalysis will be performed on all main animals at termination (both Phase 1 and Phase 2). Hematology parameters, e.g., red blood cell count, white blood cell count, coagulation parameters, e.g. prothrombin time and activated partial thromboplastin time and clinical chemistry parameters, e.g. glucose levels, total protein, will be determined from the blood samples. A urinalysis will also be conducted to assess e.g. glucose, ketone and protein levels.

Results

The Phase 1 single dose escalation study conducted as described above revealed no macroscopic findings or clinical signs of toxicity at up to 100 mg/kg GN370. The Phase 2 repeat dose study (4 days) did not reveal any clinical signs of toxicity at either 25 mg/kg or 75 mg/kg dosages. On dosing day 2, as noted above, the infusion was stopped after 1.75 hours in animals dosed at 200 mg/kg due to "swollen" nose/face. In three TK rats, as also noted above, the infusion period was extended to 4 hours (200 mg/kg) and no clinical signs or macroscopic findings indicating toxicity were observed.

Example 19. Efficacy of GN370 in Rabbit Pulmonary Model

Establishment of Model

A rabbit pulmonary model was established for use in assessing the efficacy of the GN370 lysin alone and in combination with an antibiotic (meropenem). Initially, the lowest bacterial inoculum that established robust bioburdens of *P. aeruginosa* isolate CFS 1558 (PA20) in all target tissues without excess mortality was determined. A comparison of the bioburden in target tissue at inoculums of $6 \times 10^8$ CFU, $3 \times 10^9$ CFU and $8 \times 10^9$ CFU is shown below. $3 \times 10^9$ CFU of the *P. aeruginosa* isolate was used to challenge the rabbits during the efficacy study described below.

TABLE 30

Bacterial Burden after administration of Pseudomonas inoculum

| Treatment* | Organ | | | |
|---|---|---|---|---|
| | Lung 1 | Lung 2 | Kidneys | Spleen |
| Control $6 \times 10^8$ CFU (5) | 3.24 ± 0.47 | 3.40 ± 1.12 | 1.18 ± 0.71 | 1.24 ± 0.71 |
| Control $3 \times 10^9$ CFU (3) | 7.77 ± 0.92 | 6.15 ± 0.43 | 5.22 ± 0.34 | 4.19 ± 0.40 |
| Control $8 \times 10^9$ CFU (3) | 8.51 ± 0.13 | 8.09 ± 0.93 | 6.94 ± 0.55 | 6.94 ± 0.70 |

*Number of animals in parentheses; rabbits sacrificed 5-6 hours post-endobronchial challenge.

The dosage of meropenem resulting in a static effect was also determined, i.e. a non-bactericidal effect ($<2$ $\log_{10}$ CFU/g reduction in lung and other target tissue counts versus untreated controls). To determine this dosage, the rabbits were treated with 10 mg/kg, 20 mg/kg, 30 mg/kg and 40 mg/kg of meropenem (three times a day, subcutaneous administration for two days). Meropenem therapy was started 5-6 hours after induction of pneumonia and the animals were sacrificed at 18-24 hours after the last antibiotic dose. As indicated in the table below, 20 mg/kg established a static effect.

TABLE 31

Bacterial Burden after treatment with Meropenem

| Treatment* | Organ | | | |
|---|---|---|---|---|
| | Lung 1 | Lung 2 | Kidneys | Spleen |
| Control $3 \times 10^9$ CFU | 8.06 ± 0.63 | 6.47 ± 0.47 | 4.43 ± 0.45 | 4.72 ± 0.62 |
| Meropenem 10 mg/kg (4) | 7.39 ± 0.34 | 7.42 ± 0.64 | 4.36 ± 0.43 | 4.01 ± 0.10 |
| Meropenem 20 mg/kg (3) | 6.85 ± 1.09 | 6.97 ± 1.19 | 4.51 ± 0.73 | 4.74 ± 0.57 |
| Meropenem 25 mg/kg (6) | 4.55 ± 1.65 | 3.73 ± 1.03 | 2.06 ± 0.58 | 2.15 ± 0.78 |
| Meropenem 30 mg/kg (8) | 4.83 ± 1.19 | 4.42 ± 1.14 | 2.24 ± 0.64 | 1.91 ± 0.63 |
| Meropenem 40 mg/kg (5) | 4.66 ± 0.11 | 2.95 ± 1.19 | 2.34 ± 0.65 | 1.93 ± 0.47 |

*Number of animals in parentheses; rabbits sacrificed 18-24 hours after last antibiotic dose.

Efficacy of GN370

The rabbit pulmonary model described above was used to assess the efficacy of the GN370 lysin alone and in combination with an antibiotic (meropenem). The rabbits were infected intratracheally with *P. aeruginosa* isolate CFS 1558 (PA20) ($3 \times 10^9$ CFU). Treatment commenced 6 hours post-infection. The treatment groups are shown in Table 32 below. The rabbits were sacrificed 18-24 hours after the last dose of meropenem and the bacterial burden (CFU/gram) in the lung, spleen and kidneys was assessed.

Only 40% of the infected rabbits treated with the vehicle survived through the end of the study. None of the rabbits treated with a GN370 lysin dosage of 30 mg/kg survived after 24 hours. 40% of rabbits survived 24 hours after treatment with a 30 mg/kg dosage of lysin+meropenem.

As shown in Table 33, bacterial density in all three tissues (lung, kidney, and spleen) from animals treated with GN-370 (10 mg/kg) in addition to meropenem was decreased compared to meropenem or GN370 alone, demonstrating synergy. In addition, GN370 split doses (over a 24 h period), i.e. $3 \times 3.33$ mg/kg (total dose of 10 mg/kg) and $3 \times 10$ mg/kg (total dose of 30 mg/kg) were tested. The results indicate that a single dose of GN370 at 10 mg/kg+meropenem was more effective than the split dose of $3 \times 3.33$ mg/kg+meropenem. However, splitting the 30 mg/kg in $3 \times 10$ mg/kg+meropenem was synergistic and provided significant bacterial burden reduction. There was a paradoxical increase in counts when the single lysin dose was increased to 30 mg/kg in combination with meropenam associated with excess early mortality. Normal (uninfected) rabbits given 30 mg/kg of lysin intravenously suffered no ill acute effects or subacute mortalities.

This example provides evidence that GN lysins and constructs of the instant disclosure may be used alone or in combination with antibiotics, such as meropenem, to treat pulmonary infections, such as pneumonia (including HAP and/or VAP) and cystic fibrosis exacerbations.

TABLE 32

Treatment Groups in Rabbit Pulmonary Model

| Treatment | N | Route | Dosage amount | Frequency of Dosages |
|---|---|---|---|---|
| 6 hours untreated (pre-therapy control) | 10 | N/A | N/A | N/A |
| Meropenem | 10 | Subcutaneous (SC) | 20 mg/kg | Every 8 hours (3 doses) |
| GN370 | 10 | Intravenous (IV) | 3 mg/kg | 1 dose |
| Meropenem + GN370 | 10 | SC/IV | 20 mg/kg + 3 mg/kg | Every 8 hours (3 doses)/1 dose |

TABLE 32-continued

Treatment Groups in Rabbit Pulmonary Model

| Treatment | N | Route | Dosage amount | Frequency of Dosages |
|---|---|---|---|---|
| GN370 | 10 | IV | 10 mg/kg | 1 dose |
| Meropenem + GN370 | 10 | SC/IV | 20 mg/kg + 10 mg/kg | Every 8 hours (3 doses)/1 dose |
| GN370 | 10 | IV | 30 mg/kg | 1 dose |
| Meropenem + GN370 | 10 | SC/IV | 20 mg/kg + 30 mg/kg | Every 8 hours (3 doses)/1 dose |
| Meropenem + GN370 | 9 | SC/IV | 20 mg/kg + 10 mg/kg | Every 8 hours (3 doses)/Every 8 hours (3 doses) |
| GN370 | 10 | IV | 10 mg/kg | Every 8 hours (3 doses) |
| Meropenem + GN370 | 10 | SC/IV | 20 mg/kg + 3.3 mg/kg | Every 8 hours (3 doses)/Every 8 hours (3 doses) |
| GN370 | 10 | IV | 3.3 mg/kg | Every 8 hours (3 doses) |

TABLE 33

Bacterial Burden Reduction with GN370 alone or combined with meropenem

| Treatment | Lung 1 | Lung 2 | Kidneys | Spleen |
|---|---|---|---|---|
| 6 hours untreated (pre-therapy control) | 7.28 ± 095 | 7.35 ± 1.12 | 4.61 ± 0.71 | 4.77 ± 0.83 |
| Vehicle (N = 10; 6 out of 10 rabbits died at 24 h post-infection) | 7.67 ± 0.57 | 7.92 ± 0.43 | 5.77 ± 1.14 | 5.81 ± 0.73 |
| meropenem (20 mg/kg × 3 doses) | 6.08 ± 0.86 | 6.17 ± 0.93 | 4.22 ± 0.69 | 3.74 ± 0.54 |
| GN370 (3 mg/kg, 1 dose) | 6.45 ± 1.05 | 6.59 ± 0.97 | 4.91 ± 1.11 | 5.20 ± 1.11 |
| meropenem (20 mg/kg) + GN370 (3 mg/kg, 1 dose) | 6.06 ± 1.22 | 6.27 ± 1.08 | 4.05 ± 1.11 | 4.16 ± 0.92 |
| GN370 (10 mg/kg, 1 dose) | 6.84 ± 0.88 | 5.65 ± 1.35 | 3.86 ± 0.87 | 3.90 ± 0.50 |
| meropenem (20 mg/kg) + GN370 (10 mg/kg, 1 dose) | 3.77 ± 1.48 | 4.07 ± 1.50 | 2.26 ± 1.05 | 2.26 ± 1.18 |
| GN370 (30 mg/kg, 1 dose) | 7.97 ± 0.43 | 7.79 ± 0.50 | 5.34 ± 0.48 | 5.25 ± 0.35 |
| meropenem (20 mg/kg) + GN370 (30 mg/kg, 1 dose) | 6.79 ± 0.95 | 6.70 ± 1.14 | 4.37 ± 0.78 | 4.41 ± 0.84 |
| meropenem (20 mg/kg) + GN370 (10 mg/kg × 3 dose) | 3.80 ± 1.14 | 3.60 ± 1.20 | 3.33 ± 1.00 | 3.00 ± 0.88 |
| GN370 (10 mg/kg × 3 dose) | 6.92 ± 1.61 | 6.57 ± 1.50 | 5.22 ± 1.20 | 5.35 ± 0.32 |
| meropenem (20 mg/kg) + GN370 (3.3 mg/kg × 3 dose) | 5.58 ± 1.64 | 4.99 ± 0.90 | 4.30 ± 0.98 | 4.78 ± 0.63 |
| GN370 (3.3 mg/kg × 3 dose) | 7.11 ± 1.40 | 7.34 ± 1.40 | 5.38 ± 0.74 | 5.79 ± 0.65 |

I claim:

1. A lysin-antimicrobial peptide (AMP) polypeptide construct comprising:
   (a) a first component comprising the polypeptide sequence of:
      (i) SEQ ID NO: 118; or
      (ii) a polypeptide having lytic activity and having at least 80% sequence identity with the polypeptide sequence of SEQ ID NO: 118; or
      (iii) an active fragment of SEQ. ID NO: 118; and
   (b) a second component comprising the polypeptide sequence of SEQ ID NO: 114,
   wherein the polypeptide having lytic activity and having at least 80% sequence identity with the polypeptide sequence of SEQ ID NO: 118 and the active fragment of SEQ ID NO: 118 retain an α-helix domain of the polypeptide of SEQ ID NO: 118.

2. The lysin-AMP polypeptide construct according to claim 1, wherein the construct further comprises a peptide as a stabilizing component.

3. The lysin-AMP polypeptide construct according to claim 2, wherein the peptide stabilizing component has the amino acid sequence of SEQ ID NO: 112 and/or SEQ ID NO: 116.

4. The lysin-AMP polypeptide construct according to claim 1, wherein the lysin-AMP construct is selected from (i) SEQ ID NO: 44 or (ii) a polypeptide having lytic activity and at least 80% sequence identity with the polypeptide sequence of SEQ ID NO: 44.

5. The lysin-AMP polypeptide construct according to claim 1, wherein the lysin-AMP construct comprises the polypeptide sequence of SEQ ID NO: 44.

6. A pharmaceutical composition comprising the lysin-AMP polypeptide construct of claim 1 and a pharmaceutically acceptable carrier.

7. The pharmaceutical composition according to claim 6, wherein the lysin-AMP polypeptide construct comprises the polypeptide sequence of SEQ ID NO: 44.

8. The pharmaceutical composition according to claim 6, wherein the pharmaceutical composition is formulated as a solution, a suspension, an emulsion, an inhalable powder, an aerosol, or a spray.

9. The pharmaceutical composition according to claim 6, wherein the pharmaceutical composition further comprises an antibiotic suitable for the treatment of Gram-negative bacteria.

10. A method of treating a bacterial infection caused by a Gram-negative bacteria, which method comprises:
    administering to a subject diagnosed with, at risk for, or exhibiting symptoms of a bacterial infection, the pharmaceutical composition according to claim 6.

11. The method according to claim 10, wherein the lysin-AMP polypeptide construct comprises the polypeptide sequence of SEQ ID NO: 44.

12. The method according to claim 10, wherein the bacterial infection is a topical bacterial infection.

13. The method according to claim 10, wherein the Gram-negative bacteria is *Pseudomonas aeruginosa*.

14. The method according to claim 10, wherein the Gram-negative bacteria is selected from the group consisting of *Klebsiella pneumoniae, Acinetobacter baumannii, Enterobacter cloacae, Escherichia coli, Stentrophomonas maltophilia, Achromobacter* spp., and *Pandorea apista*.

15. The method according to claim 10, further comprising administering an antibiotic to the subject.

16. The method according to claim 15, wherein the antibiotic is selected from one or more of ceftazidime, cefepime, cefoperazone, ceftobiprole, ciprofloxacin, levofloxacin, aminoglycosides, imipenem, meropenem, doripenem, gentamicin, tobramycin, amikacin, piperacillin, ticarcillin, penicillin, rifampicin, polymyxin B, and colistin.

17. The method of claim 10, wherein the bacterial infection caused by a Gram-negative bacteria is a bacterial infection of an organ or tissue in which pulmonary surfactant is present.

18. The method of claim 10, wherein the bacterial infection comprises pneumonia.

19. A method of disrupting or eradicating a Gram-negative bacterial biofilm comprising: administering the lysin-AMP polypeptide construct of claim 1 in an amount effective to kill Gram-negative bacteria in a biofilm to a subject in need thereof.

20. The method according to claim 19, wherein the lysin-AMP polypeptide construct comprises the polypeptide sequence of SEQ ID NO: 44.

* * * * *